US007838270B2

(12) United States Patent
Davydova et al.

(10) Patent No.: US 7,838,270 B2
(45) Date of Patent: Nov. 23, 2010

(54) TARGET-DEPENDENT TRANSCRIPTION USING DELETION MUTANTS OF N4 RNA POLYMERASE

(75) Inventors: Elena K. Davydova, Chicago, IL (US); Krystyna Maria Kazmierczak, Bloomington, IN (US); Lucia B. Rothman-Denes, Chicago, IL (US)

(73) Assignee: The University of Chicago, Chicago, IL (US)

(*) Notice: Subject to any disclaimer, the term of this patent is extended or adjusted under 35 U.S.C. 154(b) by 702 days.

(21) Appl. No.: 10/743,975

(22) Filed: Dec. 23, 2003

(65) Prior Publication Data

US 2004/0191812 A1 Sep. 30, 2004

Related U.S. Application Data

(63) Continuation-in-part of application No. 10/153,219, filed on May 22, 2002, now Pat. No. 7,452,705.

(60) Provisional application No. 60/292,845, filed on May 22, 2001, provisional application No. 60/436,062, filed on Dec. 23, 2002.

(51) Int. Cl.
*C12P 19/34* (2006.01)
*C12Q 1/68* (2006.01)
*C12N 9/12* (2006.01)
*C07K 14/00* (2006.01)

(52) U.S. Cl. ..................... 435/91.21; 435/6; 435/91.51; 435/194; 530/350

(58) Field of Classification Search ....................... None
See application file for complete search history.

(56) References Cited

U.S. PATENT DOCUMENTS 4,883,750 A 11/1989 Whiteley et al.
4,988,617 A 1/1991 Landegren et al.
5,021,335 A 6/1991 Tecott et al.
5,130,238 A 7/1992 Malek et al.
5,168,038 A 12/1992 Tecott et al.
5,185,243 A * 2/1993 Ullman et al. ................. 435/6
5,194,370 A 3/1993 Berninger et al.
5,242,794 A 9/1993 Whiteley et al.
5,399,491 A 3/1995 Kacian et al.
5,409,818 A 4/1995 Davey et al.
5,426,180 A 6/1995 Kool
5,427,930 A 6/1995 Birkenmeyer et al.
5,437,990 A 8/1995 Burg et al.
5,466,586 A 11/1995 Davey et al.
5,494,810 A 2/1996 Barany et al.
5,514,545 A 5/1996 Eberwine
5,521,065 A 5/1996 Whiteley et al.
5,545,522 A 8/1996 Van Gelder et al.
5,554,517 A 9/1996 Davey et al.
5,648,245 A 7/1997 Fire et al.
5,665,545 A 9/1997 Malek et al.
5,674,683 A 10/1997 Kool
5,679,524 A 10/1997 Nikiforov et al.
5,683,874 A 11/1997 Kool
5,683,888 A * 11/1997 Campbell ...................... 435/8
5,686,272 A 11/1997 Marshall et al.
5,714,320 A 2/1998 Kool
5,716,785 A 2/1998 Van Gelder et al.
5,759,773 A * 6/1998 Tyagi et al. .................... 435/6
5,792,607 A 8/1998 Backman et al.
5,795,715 A * 8/1998 Livache et al. ................. 435/6
5,807,674 A 9/1998 Tyagi
5,830,711 A 11/1998 Barany et al.
5,849,546 A * 12/1998 Sousa et al. ................ 435/91.5
5,854,033 A 12/1998 Lizardi
5,866,337 A 2/1999 Schon
5,869,252 A 2/1999 Bouma et al.
5,871,921 A 2/1999 Landegren et al.
5,872,105 A 2/1999 Kool
5,876,924 A * 3/1999 Zhang et al. ................... 435/5
5,891,636 A 4/1999 Van Gelder et al.
5,912,148 A 6/1999 Eggerding
5,952,174 A 9/1999 Nikiforov et al.
5,958,688 A 9/1999 Eberwine et al.

(Continued)

FOREIGN PATENT DOCUMENTS

EP 0320308 A2 11/1988
EP 0320308 B1 11/1988
EP 0427073 5/1991
EP 0427074 5/1991
EP 0336731 B1 5/1994

(Continued)

OTHER PUBLICATIONS

Moran et al. Non-hydrogen bonding 'terminator' nucleosides increase the 3'-end homogeneity of enzymatic RNA and DNA synthesis. Nucleic Acids Research (1996) 24(11): 2044-2052.*

Tyagi et al. Extremely sensitive, background-free gene detection using binary probes and Qb replicase. Proceedings of the National Academy of Sciences, USA (1996) 93: 5395-5400.*

Weier et al. Generation of clonal DNA templates for in vitro transcription without plasmid purification. BioTechniques (1990) 8(3): 252-254, 256, 257.*

(Continued)

*Primary Examiner*—Young J Kim
*Assistant Examiner*—Angela M Bertagna
(74) *Attorney, Agent, or Firm*—Casimir Jones, S.C.

(57) ABSTRACT

The present invention comprises novel methods, compositions and kits that use N4 vRNAP deletion mutants to detect and quantify analytes comprising one or multiple target nucleic acid sequences, including target sequences that differ by as little as one nucleotide or non-nucleic acid analytes, by detecting a target sequence tag that is joined to an analyte-binding substance. The method consists of an annealing process, a DNA ligation process, an optional DNA polymerase extension process, a transcription process, and, optionally, a detection process.

1 Claim, 29 Drawing Sheets

U.S. PATENT DOCUMENTS

| | | | | |
|---|---|---|---|---|
| 5,962,223 | A | 10/1999 | Whiteley et al. | |
| 5,976,806 | A | 11/1999 | Mahajan et al. | |
| 6,025,139 | A | 2/2000 | Yager et al. | |
| 6,027,889 | A | 2/2000 | Barany et al. | |
| 6,054,266 | A | 4/2000 | Kronick et al. | |
| 6,054,564 | A | 4/2000 | Barany et al. | |
| 6,063,603 | A | 5/2000 | Davey et al. | |
| 6,077,668 | A | 6/2000 | Kool | |
| 6,090,591 | A | 7/2000 | Burg et al. | |
| 6,096,880 | A | 8/2000 | Kool | |
| 6,100,024 | A | 8/2000 | Hudson et al. | |
| 6,130,073 | A | 10/2000 | Eggerding | |
| 6,143,495 | A | 11/2000 | Lizardi et al. | |
| 6,153,384 | A | 11/2000 | Lynch et al. | |
| 6,183,960 | B1 | 2/2001 | Lizardi | |
| 6,210,884 | B1 | 4/2001 | Lizardi | |
| 6,221,603 | B1 | 4/2001 | Mahtani | |
| 6,245,505 | B1 | 6/2001 | Todd et al. | |
| 6,268,148 | B1 | 7/2001 | Barany et al. | |
| 6,274,320 | B1 | 8/2001 | Rothberg et al. | |
| 6,280,943 | B1 * | 8/2001 | Drolet et al. | 435/6 |
| 6,287,824 | B1 | 9/2001 | Lizardi | |
| 6,291,170 | B1 | 9/2001 | Van Gelder et al. | |
| 6,312,892 | B1 | 11/2001 | Barany et al. | |
| 6,316,229 | B1 | 11/2001 | Lizardi et al. | |
| 6,323,009 | B1 | 11/2001 | Lasken et al. | |
| 6,329,150 | B1 | 12/2001 | Lizardi et al. | |
| 6,344,329 | B1 | 2/2002 | Lizardi | |
| 6,355,431 | B1 | 3/2002 | Chee et al. | |
| 6,368,802 | B1 | 4/2002 | Kool | |
| 6,410,276 | B1 | 6/2002 | Burg et al. | |
| 6,562,575 | B1 | 5/2003 | Dahl | |
| 7,452,705 | B2 * | 11/2008 | Kazmierczak et al. | 435/194 |
| 2003/0119004 | A1 * | 6/2003 | Wenz et al. | 435/6 |

FOREIGN PATENT DOCUMENTS

| | | | |
|---|---|---|---|
| EP | 0329822 | B1 | 6/1994 |
| EP | 0246864 | A2 | 7/1994 |
| EP | 0246864 | B2 | 7/1994 |
| EP | 0357336 | A2 | 10/1994 |
| EP | 0439182 | A2 | 4/1996 |
| JP | 4262799 | | 9/1992 |
| JP | 4304900 | | 10/1992 |
| WO | WO 89/06700 | | 7/1989 |
| WO | WO 89/09835 | | 10/1989 |
| WO | WO 91/18155 | | 11/1991 |
| WO | WO 92/01813 | | 2/1992 |
| WO | WO 00/11160 | | 2/2000 |
| WO | WO 00/28082 | | 5/2000 |
| WO | WO 00/56877 | | 9/2000 |
| WO | WO 00/75356 | | 12/2000 |
| WO | WO 02/11447 | | 2/2002 |
| WO | WO 02/16639 | | 2/2002 |
| WO | WO 02/065093 | | 8/2002 |
| WO | WO 02/095002 | A2 * | 11/2002 |

OTHER PUBLICATIONS

Kazmierczak et al. The phage N4 virion RNA polymerase catalytic domain is related to single-subunit RNA polymerases. The European Molecular Biology Journal (2002) 21(21): 5815-5823.*
Murakawa et al., DNA 7:287-295, 1988.
Phillips and Eberwine, Methods in Enzymol. Suppl. 10:283-288, 1996.
Ginsberg et al., Ann. Neurol. 45:174-181, 1999.
Ginsberg et al., Ann. Neurol. 48:77-87, 2000.
Van Gelder et al., PNAS 87:1663-1667, 1990.
Eberwine et al., Proc. Natl. Acad. Sci. USA 89:3010-3014, 1992.
Kwoh et al., Proc. Natl. Acad. Sci. USA 86:1173, 1989.
Fahy et al, In: PCR Methods and Applications, pp. 25-33, 1991.
Prakash, G. and Kool, E., J. Am. Chem. Soc. 114: 3523-3527, 1992.
Daubendiek, S.L. et al., J. Am. Chem. Soc. 117: 7818-7819, 1995.
Liu, D. et al., J. Am. Chem. Soc. 118: 1587-1594, 1996.
Daubendiek, S.L. and Kool, E.T., Nature Biotechnol., 15: 273-277, 1997.
Diegelman, A.M. and Kool, E.T., Nucleic Acids Res., 26: 3235-3241, 1998.
Diegelman, A.M. and Kool, E.T., Chem. Biol., 6: 569-576, 1999.
Diegelman, A.M. et al., BioTechniques 25: 754-758, 1998.
Frieden, M. et al., Angew. Chem. Int. Ed. Engl. 38: 3654-3657, 1999.
Kool, E.T., Acc. Chem. Res., 31: 502-510, 1998.
Falco, et al., Proc. Natl. Acad. Sci. (USA) 75:3220-3224, 1978.
Glucksmann-Kuis, et al., Cell, 70, 491-500, 1992.
Fire, A. and Xu, S-Q, Proc. Natl. Acad. Sci. USA, 92: 4641-4645, 1995.
Dean et al., Genome Res., 11: 1095-1099, 2001.
Nilsson et al., Nucleic Acids Res., 30 (14): e66, 2002.
Pickering et al. Nucleic Acids Res., 30 (12): e60, 2002.
Haynes, et al., Cell 41:597-605, 1985.
Falco, et al., J. Biol. Chem. 255:4339-4347, 1980.
Glucksmann-Kuis, et al., Cell 84:147-154, 1996.
Dai et al., Genes Devepmnt. 12:2782-2790, 1998.
Davidova, EK and Rothman-Denes, LB, Proc. Natl. Acad. Sci. USA 100:9250-9255, 2003.
Baner, J et al., (Nucleic Acids Research, 26:5073-5078, 1998.
Markiewicz, et al., Genes and Dev. 6:2010-2019, 1992.

* cited by examiner

Bacteriophage N4 vRNAP promoters

Plasmid name: pMini-vRNAP
Plasmid size: 7426 bp
Constructed by: K. M. Kazmierczak
Construction date: 2/2000
Comments: Insert cloned into Invitrogen pBAD B expression plasmid Purification of cloned vRNAP and mini-vRNAP Activation of N4 vRNAP transcription by *Eco* SSB at different ssDNA concentrations Effect of *Eco* SSB on transcription of vRNAP and mini-RNAP

Identification of the transcription start site by catalytic autolabeling

UV crosslinking of mutant mini-vRNAPases to promoter oligonucleotides

FIG. 16

Monopartite Target Probes

Portions of a Monopartite Target Probe

Portions of a Bipartite Target Probe

PRO (+) Single-Stranded Transcription Promoter

Target-Complementary Sequence

Signal Sequence

Transcription Termination Sequence(s)

Optional Sequences (P)- Phosphate Group

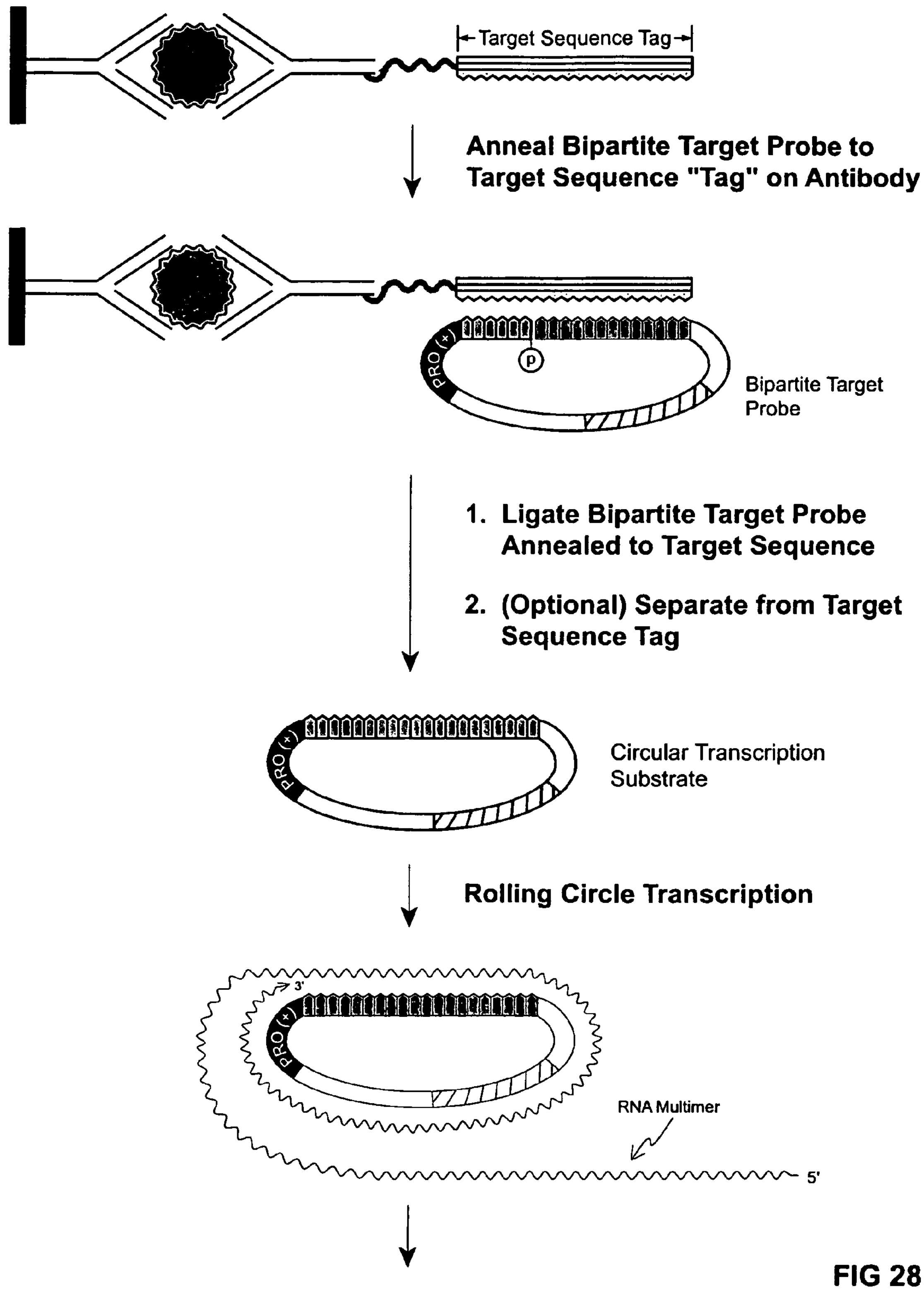
Target Sequence Tag
Anneal Bipartite Target Probe to Target Sequence "Tag" on Antibody
PRO (+)
P
Bipartite Target Probe
1. Ligate Bipartite Target Probe Annealed to Target Sequence
2. (Optional) Separate from Target Sequence Tag
PRO (+)
Circular Transcription Substrate
Rolling Circle Transcription
3'
PRO (+)
RNA Multimer
5'
FIG 28
Detect RNA Transcription Products Directly or Indir ctly

TARGET-DEPENDENT TRANSCRIPTION USING DELETION MUTANTS OF N4 RNA POLYMERASE

CROSS-REFERENCE TO RELATED APPLICATION

This application is a Continuation in Part of U.S. patent application Ser. No. 10/153,219, May 22, 2002 now U.S. Pat. No. 7,452,705, which claims priority to U.S. Provisional Patent Application Ser. No. 60/292,845, filed May 22, 2001. This application also claims priority to U.S. Provisional Patent Application Ser. No. 60/436,062 filed Dec. 23, 2002. The entire disclosure of all priority applications is specifically incorporated herein by reference.

STATEMENT REGARDING FEDERALLY SPONSORED RESEARCH OR DEVELOPMENT

The government may own rights in the present invention pursuant to grant number R01 A1 12575 from the National Institute of Health.

BACKGROUND OF THE INVENTION

I. Field of the Invention

The present invention relates to novel methods, compositions and kits for amplifying, detecting and quantifying one or multiple target nucleic acid sequences in a sample, including target sequences that differ by as little as one nucleotide. The invention has broad applicability for research, environmental and genetic screening, and diagnostic applications, such as for detecting and quantifying sequences that indicate the presence of a pathogen, the presence of a gene or an allele, or the presence of a single nucleotide polymorphism (SNP) or other type of gene mutation or variant. The invention also relates to novel methods, compositions and kits for detecting and quantifying a broad range of analytes by detecting a target sequence that is joined to an analyte-binding substance.

II. Description of Related Art

Transcription of DNA into mRNA is regulated by the promoter region of the DNA. The promoter region contains a sequence of bases that signals RNA polymerase to associate with the DNA, and to initiate the transcription of mRNA using one of the DNA strands as a template to make a corresponding complementary strand of RNA. RNA polymerases from different species typically recognize promoter regions comprised of different sequences. In order to obtain a transcription product by in vitro or in vivo transcription, the promoter driving transcription of the gene or DNA sequence must be a cognate promoter for the RNA polymerase, meaning that it is recognized by the RNA polymerase.

There are a number of methods in the art for detecting nucleic acid sequences, including point mutations. The presence of a nucleic acid sequence can indicate, for example, the presence of a pathogen, or the presence of particular genes or mutations in particular genes that correlate with or that are indicative of the presence or status of a disease state, such as, but not limited to, a cancer.

Examples of methods that involve in vitro transcription for making probes are described in: Murakawa et al., DNA 7:287-295, 1988; Phillips and Eberwine, Methods in Enzymol. Suppl. 10:283-288, 1996; Ginsberg et al., Ann. Neurol. 45:174-181, 1999; Ginsberg et al., Ann. Neurol. 48:77-87, 2000; VanGelder et al., Proc. Natl. Acad. Sci. USA 87:1663-1667, 1990; Eberwine et al., Proc. Natl. Acad. Sci. USA 89:3010-3014, 1992; U.S. Pat. Nos. 5,021,335; 5,168,038;

5,545,522; 5,514,545; 5,716,785; 5,891,636; 5,958,688; 26,291,170; and PCT Patent Applications WO 00/75356 and WO 02/065093.

Still other methods use in vitro transcription as part of a process for amplifying and detecting one or more target nucleic acid sequences in order to detect the presence of a pathogen, such as a viral or microbial pathogen, that is a causative agent for a disease or to detect a gene sequence that is related to a disease or the status of a disease for medical purposes. Examples where in vitro transcription methods have been used for medical purposes include U.S. Pat. Nos. 5,130,238; 5,194,370; 5,399,491; 5,409,818; 5,437,990; 5,466,586; 5,554,517; 5,665,545; 6,063,603; 6,090,591; 6,100,024; and 6,410,276; Kwoh et al., Proc. Natl. Acad. Sci. USA 86:1173, 1989; Fahy et al, In: PCR Methods and Applications, pp. 25-33, 1991; PCT Patent Application Nos. WO 89/06700 and WO 91/18155; and European Patent Application Nos. 0427073 A2 and 0427074 A2.

Still other methods detect sequences or mutations using methods that involve ligation of adjacently hybridizing oligonucleotide probes or ligation of non-adjacently hybridizing probes following a process such as primer extension. Ligation detection methods include those disclosed in European Patent Application Publication Nos. 0246864 A2 and 0246864 B1 of Carr; U.S. Pat. Nos. 4,883,750; 5,242,794; 5,521,065; 5,962,223; and 6,054,266 of Whiteley, N. M. et al.; U.S. Pat. No. 4,988,617 of Landegren and Hood; U.S. Pat. No. 5,871,921 of Landegren and Kwiatkowski; U.S. Pat. No. 5,866,337 of Schon; European Patent Application Publication Nos. 0320308 A2 and 0320308 B1 of Backman and Wang; PCT Publication No. WO 89/09835 of Orgel and Watt and European Patent Publication No. 0336731 B1 of Bruce Wallace; U.S. Pat. No. 5,686,272 of Marshall et al.; U.S. Pat. No. 5,869,252 of Bouma et al.; U.S. Pat. Nos. 5,494,810; 5,830,711; 6,054,564; 6,027,889; 6,268,148; and 6,312,892 of Barany et al.; U.S. Pat. Nos. 5,912,148 and 6,130,073 of F. Eggerding; U.S. Pat. No. 6,245,505 B1 of Todd and Fuery; European Patent Application Publication No. 0357336 A2 of Ullman et al.; U.S. Pat. No. 5,427,930 of Birkenmeyer et al. and U.S. Pat. No. 5,792,607 and European Patent Publication Nos. 0439182 A2 and EP 0439182 B1 of Backman et al.; U.S. Pat. Nos. 5,679,524; and 5,952,174 of Nikifoorov et al.; U.S. Pat. No. 6,025,139 of Yager and Dunn; and U.S. Pat. No. 6,355,431 B1 of Chee and Gunderson.

In addition, U.S. Pat. No. 6,153,384 of Lynch et al. discloses an assay to identify ligase activity modulators by ligation of a labeled nucleic acid to an immobilized capture nucleic acid in the presence of a potential ligase activity modulator. Furthermore, Mahajan et al., disclose in U.S. Pat. No. 5,976,806 a quantitative and functional DNA ligase assay that uses a linearized plasmid containing a reporter gene, wherein ligase activity is followed by the extent of coupled transcription-translation of the reporter gene.

Also, in U.S. Pat. No. 5,807,674 Tyagi discloses detection of RNA target sequences by ligation of the RNA binary probes, wherein a substrate for Q-beta replicase is generated.

In PCT Patent Application No. WO 92/01813, Ruth and Driver disclosed a process for synthesizing circular single-stranded nucleic acids by hybridizing a linear polynucleotide to a complementary oligonucleotide and then ligating the linear polynucleotide. They further disclosed a process for generating multiple linear complements of the circular single-stranded nucleic acid template by extending a primer more than once around the circular template using a DNA polymerase.

Japanese Patent Nos. JP4304900 and JP4262799 of Toshiya et al., disclose detection of a target sequence by ligation of a linear single-stranded probe having target-complementary 3'- and 5'-end sequences which are adjacent when the linear probe is annealed to a target sequence in the sample, followed by either rolling circle replication or in vitro transcription of the circular single-stranded template. Toshiya et al., disclose that in vitro transcription is performed by first annealing to the circular single-stranded template a complementary nucleotide primer having an anti-promoter sequence in order to form a double-stranded promoter, and then transcribing the circular single-stranded template having the annealed anti-promoter primer with an RNA polymerase that has helicase-like activity, such as T7, T3 or SP6 RNA polymerase.

In U.S. Pat. Nos. 6,344,329; 6,210,884; 6,183,960; 5,854,033; 6,329,150; 6,143,495; 6,316,229; and 6,287,824, Paul M. Lizardi also disclose the use of rolling circle replication to amplify and detect nucleic acid sequences. Lizardi further describes use of RNA polymerase protopromoters in the circular probe so that tandem-sequence single-stranded protopromoter-containing DNA products resulting from rolling circle replication can be transcribed by a cognate T7-type RNA polymerase following conversion of said DNA products to a form containing double-stranded promoters.

Furthermore, Kool et al., have disclosed synthesis of DNA or RNA multimers, meaning multiple copies of an oligomer or oligonucleotide joined end to end (i.e., in tandem) by rolling circle replication or rolling circle transcription, respectively, of a circular DNA template molecule. Rolling circle replication uses a primer and a strand-displacing DNA polymerase, such as phi 29 DNA polymerase. With respect to rolling circle transcription, it was shown these circular single-stranded DNA (ssDNA) molecules can be efficiently transcribed by phage and bacterial RNA polymerases (Prakash, G. and Kool, E., J. Am. Chem. Soc. 114: 3523-3527, 1992; Daubendiek, S. L. et al., J. Am. Chem. Soc. 117: 7818-7819, 1995; Liu, D. et al., J. Am. Chem. Soc. 118: 1587-1594, 1996; Daubendiek, S. L. and Kool, E. T., Nature Biotechnol., 15: 273-277, 1997; Diegelman, A. M. and Kool, E. T., Nucleic Acids Res., 26: 3235-3241, 1998; Diegelman, A. M. and Kool, E. T., Chem. Biol., 6: 569-576, 1999; Diegelman, A. M. et al., BioTechniques 25: 754-758, 1998; Frieden, M. et al., Angew. Chem. Int. Ed. Engl. 38: 3654-3657, 1999; Kool, E. T., Acc. Chem. Res., 31: 502-510, 1998; U.S. Pat. Nos. 5,426,180; 5,674,683; 5,714,320; 5,683,874; 5,872,105; 6,077,668; 6,096,880; and 6,368,802). Rolling circle transcription of these circular ssDNAs occurs in the absence of primers, in the absence of a canonical promoter sequence, and in the absence of any duplex DNA structure, and results in synthesis of linear multimeric complementary copies of the circle sequence up to thousands of nucleotides in length. Transcription of the linear precursor of the circular ssDNA template yielded only a small amount of RNA transcript product that was shorter than the template.

Fire and Xu (U.S. Pat. No. 5,648,245; Fire, A. and Xu, S-Q, Proc. Natl. Acad. Sci. USA, 92: 4641-4645, 1995) also disclose methods for using rolling circle replication of small DNA circles to construct oligomer concatamers.

Other researchers, including, but not limited to, Mahtani (U.S. Pat. No. 6,221,603), Rothberg et al., (U.S. Pat. No. 6,274,320), Dean et al., (Genome Res., 11: 1095-1099, 2001), Lasken et al., (U.S. Pat. No. 6,323,009), and Nilsson et al., (Nucleic Acids Res., 30 (14): e66, 2002) disclose other methods and applications of rolling circle amplification. Also, Pickering et al. (Nucleic Acids Res., 30 (12): e60, 2002) discloses a ligation and rolling circle amplification method for homogeneous end-point detection of single nucleotide polymorphisms (SNPs).

Although a number of nucleic acid amplification methods have been described in the art, there is a continuing need for methods and assays for detecting nucleic acids that are specific and accurate, yet are easier and faster than current methods. The present invention provides novel assays, methods, compositions and kits that are simple in format and very rapid to perform, but that can be used to detect and quantify any of a broad range of analytes with a high degree of specificity and sensitivity, including both nucleic acid analytes and non-nucleic acid analytes. With respect to analytes comprising a target nucleic acid, the invention provides assays, methods and kits that can detect and distinguish between target sequences, including sequences that differ even by only a single nucleotide, such as for analysis of single nucleotide polymorphisms.

All of the methods above for amplifying and detecting one or more target nucleic acid sequences use a double-stranded transcription promoter. In contrast to the methods in the art, the present invention provides methods, compositions and kits for detecting target nucleic acid sequences using an RNA polymerase that uses single-stranded DNA promoters and templates and that lacks helicase-like activity, as well as other advantages and benefits that will be clear from reading the specification below.

BRIEF SUMMARY OF THE INVENTION

The invention provides methods of using a novel N4 virion RNA polymerase (vRNAP), a mini-vRNA polymerase, and compositions and related kits. The novel polymerases are described by an isolated nucleic acid comprising a region encoding a polypeptide having the amino sequence set forth in SEQ ID NO:2, SEQ ID NO:4, SEQ ID NO:6, SEQ ID NO:8 or SEQ ID NO:15. The nucleic acid may comprise the nucleic acid sequence of SEQ ID NO: 1, SEQ ID NO:3, SEQ ID NO:5, SEQ ID NO:7, or SEQ ID NO:14. In preferred embodiments of the invention, the RNA polymerase comprises a transcriptionally active 1,106-amino acid domain of the N4 vRNAP (herein designated "mini-vRNAP"), which corresponds to amino acids 998-2103 of N4 vRNAP, as described herein. The vRNAP and mini-vRNA polymerase transcribe nucleic acid operatively linked to an N4 promoter such as a P2 promoter of SEQ ID NO:16, SEQ ID NO:19, SEQ ID NO:27, SEQ ID NO:28 or SEQ ID NO:29. The promoter of SEQ ID. NO:16 or SEQ ID NO:28 is preferred.

The current invention can use a polypeptide encoded by an isolated polynucleotide comprising a sequence identical or complementary to at least 14 contiguous nucleotides of SEQ ID NO:1. The polynucleotide may comprise at least 20, 25, 30, 35, 40, 45, 50, 60, 75, 100, 150, 200, 250, 300, 400, 600, 800, 1000, 2000, 3000, 3300 or more contiguous nucleotides of SEQ ID NO:1. The polynucleotide may comprise all contiguous nucleotides of SEQ ID NO:3 or all contiguous nucleotides of SEQ ID NO:1. Similarly, the polynucleotide may comprise at least 20, 25, 30, 35, 40, 45, 50, 60, 75, 100, 150, 200, 250, 300, 400, 600, 800, 1000, 2000, 3000, 3300 or more nucleotides complementary to at least 20, 25, 30, 35, 40, 45, 50, 60, 75, 100, 150, 200, 250, 300, 400, 600, 800, 1000, 2000, 3000, 3300 or more contiguous nucleotides of SEQ ID NO:1.

A purified N4 virion RNA polymerase of the current invention can comprise at least 20 contiguous amino acids of SEQ ID NO:2. It is preferred that the polymerase contain at least 25, 30, 35, 40, 45, 50, 60, 75, 100, 150, 200, 250, 300, 400, 600, 800, 1000 or more contiguous amino acids of SEQ ID NO:2.

In another aspect, the current invention can use a polypeptide encoded by an isolated nucleic acid comprising a region encoding at least 6 contiguous amino acids of SEQ ID NO:2, wherein the polypeptide has RNA polymerase activity under appropriate reaction conditions. It is preferred that this polypeptide comprises at least 10, 15, 20, 25, 30, 35, 40, 45, 50, 60, 75, 100, 150, 200, 250, 300, 400, 600, 800, 1000 or more contiguous amino acids of SEQ ID NO:2, SEQ ID NO:4, SEQ ID NO:6, SEQ ID NO:8, or SEQ ID NO:15. The encoded polypeptide may have at least one hexahistidine tag or other tag, or the encoded polypeptide may lack a tag. The polypeptide may be a mutant of the peptide found in SEQ ID NO:2 or SEQ ID NO:4, such as an enzyme possessing an amino acid substitution at position Y678.

An embodiment of the current invention comprises a method of making RNA. This method comprises: (a) obtaining a N4 virion RNA polymerase (i.e. the polypeptide); (b) obtaining DNA wherein the DNA preferably contains a N4 virion RNA polymerase promoter sequence; (c) admixing the RNA polymerase and the DNA; and (d) culturing the RNA polymerase and the DNA under conditions effective to allow RNA synthesis. Optionally, the method may comprise synthesizing polynucleotides containing modified ribonucleotides or deoxyribonucleotides. The DNA is preferably single-stranded DNA or denatured double-stranded DNA. Step (c) may occur in a host cell such as an *E. coli* host cell.

The amino acid sequence of the RNA polymerase is preferably the sequence essentially as set forth in SEQ ID NO:2, SEQ ID NO:4, SEQ ID NO:6, SEQ ID NO:8, SEQ ID NO:15, or a mutant form of the polymerase of SEQ ID NO:4 or SEQ ID NO:6. The mutation may be, for example, at position number Y678. The RNA transcript may contain derivatized nucleotides.

An aspect of the current invention comprises using an N4 vRNAP promoter to direct transcription. The promoter is preferentially an N4 promoter set forth in SEQ ID NO:16, SEQ ID NO:19, SEQ ID NO:20, SEQ ID NO:27, SEQ ID NO:28 or SEQ ID NO:29. The P2 promoter of SEQ ID NO:16 or SEQ ID NO:28 is preferred. The promoter sequence may be upstream of the transcription initiation site. The promoter may comprise a set of inverted repeats forming a hairpin with a 2-7 base pair long stem and 3-5 base loop having purines in the central and/or next to the central position of the loop.

The preferred conditions of the transcription method claimed herein includes a pH in step (c) of between 6 and 9, with a pH of between 7.5 and 8.5 more preferred. $Mg^{+2}$ or $Mn^{+2}$, preferably $Mg^{+2}$ may be admixed. Preferred temperatures for the reaction are 25° C. to 50° C. with the range of 30° C. to 45° C. being more preferred and the range of 32° C. to 42° C. being most preferred. The admixing may occur in vivo or in vitro.

An aspect of the current invention also includes translation of the RNA after transcription. A reporter gene such as an α-peptide of β-galactosidase may be used. It is preferred the transcription comprises admixing an *E. coli* single-stranded binding protein (EcoSSB), a SSB protein homologous to EcoSSB or another naturally occurring or chimeric SSB protein homologous to EcoSSB with the polymerase and DNA. Yet another aspect of the current invention is the transcription method in which no EcoSSB is admixed with the RNA polymerase and DNA; the product of this method is a DNA/RNA hybrid.

The DNA admixed with the RNA polymerase of the current invention may be single-stranded linear DNA or single-stranded circular DNA such as bacteriophage M13 DNA. The DNA may be denatured DNA, such as single-stranded, double-stranded linear or double-stranded circular denatured DNA. The DNA may also be double-stranded DNA under certain conditions. The RNA may be pure RNA or may contain modified nucleotides. Mixed RNA-DNA oligonucleotides may also be synthesized with the Y678F mutant mini-vRNAP (SEQ ID NO:8) of the current invention.

The synthesized RNA may comprise a detectable label such as a fluorescent tag, biotin, digoxigenin, 2'-fluoro nucleoside triphosphate, or a radiolabel such as a $^{35}S$- or $^{32}P$-label. The synthesized RNA may be adapted for use as a probe for blotting experiments or in-situ hybridization. Nucleoside triphosphates (NTPs) or derivatized NTPs may be incorporated into the RNA, and may optionally have a detectable label. Deoxynucleoside triphosphates may be incorporated into the RNA.

The RNA may be adapted for use in NMR structural determination. Short RNAs such as those between 10 and 1000 bases or between 10 and 300 bases may be used. The RNA may be adapted for use in spliceosome assembly, splicing reactions or for antisense or RNA interference experiments. Also, the RNA may be adapted for use in probing for a complementary nucleotide sequence or for use as a probe in RNase protection studies.

Yet another aspect of the current invention comprises delivering RNA into a cell after transcription of the RNA. The delivery may be by microinjection, transfection, electroporation, or other methods in the art. Another aspect of the invention comprises amplifying the RNA after transcription.

Another embodiment of the current invention comprises a method of making RNA comprising: (a) obtaining a N4 virion RNA polymerase; (b) obtaining a single-stranded DNA oligonucleotide wherein the oligonucleotide contains a N4 virion RNA polymerase promoter sequence; (c) admixing the RNA polymerase and the oligonucleotide; and (d) culturing the RNA polymerase and the oligonucleotide under conditions effective to allow RNA synthesis. The polymerase preferentially has the amino sequence set forth in SEQ ID NO:4, SEQ ID NO:6 or SEQ ID NO:8. In this embodiment, it is preferred that the DNA has between 20 and 200 bases.

Yet another embodiment of the invention comprises a method of making RNA comprising: (a) obtaining a N4 virion RNA polymerase; (b) obtaining a single-stranded DNA wherein the DNA contains a N4 virion RNA polymerase promoter sequence; (c) obtaining a ribonucleoside triphosphate (XTP) or a derivatized ribonucleoside triphosphate; (d) admixing the RNA polymerase, the DNA and the XTP; and (e) culturing the RNA polymerase and the oligonucleotide under conditions effective to allow RNA synthesis wherein the RNA is a derivatized RNA. The RNA polymerase preferentially has the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8.

One embodiment comprises a method to detect a target nucleic acid sequence, the method comprising a DNA ligation operation and a transcription operation, wherein the DNA ligation operation comprises ligation of one or more target probes comprising a promoter that that binds an RNA polymerase that can bind a single-stranded promoter and initiate transcription therefrom, wherein the ligation is dependent on hybridization of the target probes to the target nucleic acid sequence, and wherein the transcription operation comprises contacting the transcription substrate with an RNA polymerase that binds the single-stranded promoter under transcription condition to obtain a transcription product. In preferred embodiments of this aspect of the invention, the RNA polymerase comprises a transcriptionally active 1,106-amino acid domain corresponding to amino acids 998-2103 of N4 vRNAP. Preferably, the enzyme lacks a histidine or other tag. An RNA polymerase in various embodiments of the invention can also have the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8, or it can have a transcriptionally active portion of any of these sequences. In some embodiments, the target probes comprise monopartite target probes comprising a promoter target probe and a signal target probe and/or optionally, one or more simple target probes. In other embodiments, a bipartite target probe and, optionally, one or more simple target probes is used. In some embodiments, the target sequence comprises a target nucleic acid in a sample, whereas in other embodiments the target sequence comprises a target sequence tag that is joined to an analyte-binding substance that binds an analyte in the sample. In some embodiments in which a bipartite target probe is used, the transcription substrate that is transcribed remains catenated to a target nucleic acid. In other embodiments of methods in which a bipartite target probe is used, the target sequence is preferably less than about 150 to about 200 nucleotides from the 3'-end of the target nucleic acid or target sequence tag. In still other embodiments of methods in which a bipartite target probe is used and in which the target sequence is greater than about 150 to about 200 nucleotides from the 3'-end of the target nucleic acid or target sequence tag comprising the target sequence, one or more additional steps is used in order to release the catenated circular ligation product from the target sequence prior to transcription, as described elsewhere herein.

One aspect of this embodiment of the invention comprises a method for detecting a target nucleic acid sequence, the method comprising: (a) providing one or more target probes comprising linear single-stranded DNA, the target probes comprising at least two target-complementary sequences that are not joined to each other, wherein the 5'-end of a first target-complementary sequence is complementary to the 5'-end of the target nucleic acid sequence, and wherein the 3'-end of a second target-complementary sequence is complementary to the 3'-end of the target nucleic acid sequence, and wherein the target probe that comprises the first target-complementary sequence also comprises a promoter that is joined to the 3'-end of the first target complementary sequence, which promoter can bind a single-stranded promoter and initiate transcription therefrom; (b) contacting the target probes with the target nucleic acid sequence and incubating under hybridization conditions, wherein the target-complementary sequences anneal adjacently to the target nucleic acid sequence to form a complex; (c) contacting the complex with a ligase under ligation conditions to form a transcription substrate; (d) contacting the transcription substrate with an RNA polymerase that can bind the single-stranded promoter under transcription conditions to obtain a transcription product; and (e) detecting the transcription product. In preferred embodiments of this aspect of the invention, the RNA polymerase comprises a transcriptionally active 1,106-amino acid domain corresponding to amino acids 998-2103 of N4 vRNAP. Preferably, the enzyme lacks a histidine or other tag. An RNA polymerase in various embodiments of the invention can also have the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8, or it can have a transcriptionally active portion of any of these sequences. In some embodiments, the target probes comprise monopartite target probes comprising a promoter target probe and a signal target probe and/or optionally, one or more simple target probes. In other embodiments, a bipartite target probe and, optionally, one or more simple target probes is used. In some embodiments, the target sequence comprises a target nucleic acid in a sample, whereas in other embodiments the target sequence comprises a target sequence tag that is joined to an analyte-binding substance that binds an analyte in the sample. In some embodiments in which a bipartite target probe is used, the transcription substrate that is transcribed remains catenated to a target nucleic acid. In other embodiments of methods in which a bipartite target probe is used, the target sequence is preferably less than about 150 to about 200 nucleotides from the 3'-end of the target nucleic acid or target sequence tag. In still other embodiments of methods in which a bipartite target probe is used and in which the target sequence is greater than about 150 to about 200 nucleotides from the 3'-end of the target nucleic acid or target sequence tag comprising the target sequence, one or more additional steps is used in order to release the catenated circular ligation product from the target sequence prior to transcription, as described elsewhere herein.

Another aspect of this embodiment of the invention comprises a method for detecting a target nucleic acid sequence, the method comprising: (a) providing one or more target probes comprising linear single-stranded DNA, the target probes comprising at least two target-complementary sequences that are not joined to each other, wherein the 5'-end of a first target-complementary sequence is complementary to the 5'-end of the target nucleic acid sequence, and wherein the 3'-end of a second target-complementary sequence is complementary to the 3'-end of the target nucleic acid sequence, and wherein the target probe that comprises the first target-complementary sequence also comprises a promoter that is joined to the 3'-end of the first target-complementary sequence, which promoter binds an RNA polymerase that can bind a single-stranded promoter and initiate transcription therefrom; (b) contacting the target probes with the target nucleic acid sequence and incubating under hybridization conditions whereby the target probes anneal to the target nucleic acid sequence to form a complex; (c) contacting the complex with a DNA polymerase under DNA polymerization conditions to form a DNA polymerase extension product that is contiguous with the 5'-end of the first target-complementary sequence; (d) contacting the DNA polymerase extension product complex with a ligase under ligation conditions to form a transcription substrate; (e) contacting the transcription substrate with an RNA polymerase that can bind a single-stranded promoter and initiate transcription therefrom under transcription condition to obtain a transcription product; and (f) detecting the transcription product. In preferred embodiments of this aspect of the invention, the RNA polymerase comprises a transcriptionally active 1,106-amino acid domain corresponding to amino acids 998-2103 of N4 vRNAP. Preferably, the enzyme lacks a histidine or other tag. An RNA polymerase in various embodiments of the invention can also have the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8, or it can have a transcriptionally active portion of any of these sequences. In some embodiments, the target probes comprise monopartite target probes comprising a promoter target probe and a signal target probe and/or optionally, one or more simple target probes. In other embodiments, a bipartite target probe and, optionally, one or more simple target probes is used. In embodiments of methods in which a bipartite target probe is used, the target sequence is preferably less than about 150 to about 200 nucleotides from the 3'-end of the target nucleic acid or target sequence tag. In some embodiments of methods in which a bipartite target probe is used and in which the target sequence is greater than about 150 to about 200 nucleotides from the 3'-end of the target nucleic acid or target sequence tag comprising the target sequence, one or more additional steps is used in order to release the catenated circular ligation product from the target sequence prior to transcription, as described elsewhere herein. In other embodiments in which a bipartite target probe is used, the transcription substrate that is transcribed remains catenated to a target nucleic acid. In some embodiments, the target sequence comprises a target nucleic acid in a sample, whereas in other embodiments the target sequence comprises a target sequence tag that is joined to an analyte-binding substance that binds an analyte in the sample.

Another embodiment of the invention comprises a method for obtaining transcription products comprising multiple copies of a target nucleic acid sequence (target sequence) in a sample, said method comprising: (a) providing one or more target probes comprising linear single-stranded DNA, said one or more target probes having at least two different target-complementary sequences that are not joined to each other, wherein the 5'-end of a first target-complementary sequence is complementary to the 5'-end of the target sequence and the 3'-end of a second target-complementary sequence is complementary to the 3'-end of the target sequence, and wherein the target probe that comprises a target-complementary sequence that is complementary to the 5'-end of the target sequence also comprises a promoter that is 3'- of the target-complementary sequence of said target probe, which promoter is for an RNA polymerase that lacks helicase-like activity and that can bind said single-stranded promoter and initiate transcription therefrom under transcription conditions, and wherein any additional target probes, if provided, comprise simple target probes having target-complementary sequences that anneal to the target sequence between the annealing sites of the first target-complementary sequence and the second target-complementary sequence, and wherein every free 5'-end of a target-complementary sequence that anneals to a target sequence has a 5'-phosphate and is adjacent to a 3'-end of another target-complementary sequence that has a 3'-hydroxyl end; (b) contacting the target probes with the target sequence and incubating under hybridization conditions so as to permit the target-complementary sequences of said target probes to anneal adjacently to all portions of the target sequence; (c) contacting said target probes annealed to said target sequence with a ligase under ligation conditions, wherein said ligase has little or no activity in ligating blunt ends and is substantially more active in ligating ends that are adjacent when annealed to two contiguous regions of a target sequence compared to ends that are not annealed to said target sequence, so as to obtain a ligated single-stranded DNA polynucleotide that comprises a transcription substrate for an RNA polymerase that lacks helicase-like activity and that can bind the single-stranded promoter in said transcription substrate and initiate transcription therefrom under transcription conditions; and (d) obtaining said transcription substrate, wherein said transcription substrate comprises a sequence that is complementary to said target sequence; and (e) contacting said transcription substrate with the RNA polymerase that can bind said promoter and initiate transcription therefrom under transcription conditions so as to obtain transcription product that is complementary to said transcription substrate; and (f) detecting synthesis of said transcription product comprising multiple copies of the target sequence obtained from transcription of said transcription substrate under transcription conditions, wherein synthesis of said transcription product indicates the presence of the target sequence. In preferred embodiments of this aspect of the invention, the RNA polymerase comprises a transcriptionally active 1,106-amino acid domain corresponding to amino acids 998-2103 of N4 vRNAP. Preferably, the enzyme lacks a histidine or other tag. An RNA polymerase in various embodiments of the invention can also have the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8, or it can have a transcriptionally active portion of any of these sequences. In some embodiments, the target probes comprise monopartite target probes comprising a promoter target probe and a signal target probe and/or optionally, one or more simple target probes. In other embodiments, a bipartite target probe and, optionally, one or more simple target probes is used. In embodiments of methods in which a bipartite target probe is used, the target sequence is preferably less than about 150 to about 200 nucleotides from the 3'-end of the target nucleic acid or target sequence tag. In some embodiments of methods in which a bipartite target probe is used and in which the target sequence is greater than about 150 to about 200 nucleotides from the 3'-end of the target nucleic acid or target sequence tag comprising the target sequence, one or more additional steps is used in order to release the catenated circular ligation product from the target sequence prior to transcription, as described elsewhere herein. In other embodiments in which a bipartite target probe is used, the transcription substrate that is transcribed remains catenated to a target nucleic acid. In some embodiments, the target sequence comprises a target nucleic acid in a sample, whereas in other embodiments the target sequence comprises a target sequence tag that is joined to an analyte-binding substance that binds an analyte in the sample.

Another embodiment of the present invention comprises a method for obtaining a transcription product complementary to a target nucleic acid sequence (target sequence), said method comprising: (a) providing a target sequence amplification probe (TSA probe), wherein said TSA probe comprises a linear single-stranded DNA (ssDNA) comprising two end portions that are complementary to a contiguous target sequence and which end portions are connected by an intervening sequence, and wherein said TSA probe can form a TSA circle upon joining of said ends; (b) providing a primer that is complementary to the intervening sequence of said TSA probe; (c) providing a bipartite target probe, wherein said bipartite target probe comprises a linear ssDNA comprising two end portions that are complementary to a contiguous target sequence, and wherein said bipartite target probe forms a circular transcription substrate upon joining of said ends; (d) annealing said TSA probe to said target sequence under hybridization conditions; (e) ligating said TSA probe annealed to said target sequence with a ligase under ligation conditions, wherein said ligase has little or no activity in ligating blunt ends and is substantially more active in ligating said ends of said bipartite target probe if said ends are adjacent when annealed to two contiguous regions of a target sequence than if said ends are not annealed to said target sequence, so as to obtain a TSA circle; (f) annealing the primer that is complementary to the intervening sequence of the TSA probe to the TSA circle under hybridization conditions; (g) contacting said TSA circle to which said primer is annealed with a strand-displacing DNA polymerase under strand-displacing polymerization conditions so as to obtain a rolling circle replication product comprising multiple copies of the target sequence; (h) annealing said bipartite target probe to said multiple copies of the target sequence of said rolling circle replication product under hybridization conditions; (i) ligating said bipartite target probe annealed to said multiple copies of the target sequence of said rolling circle replication product with a ligase under ligation conditions, wherein said ligase has little or no activity in ligating blunt ends and is substantially more active in ligating ends that are adjacent when annealed to two contiguous regions of a target sequence than if said ends are not annealed, so as to obtain a circular ssDNA molecule that comprises a circular transcription substrate; (j) obtaining said circular transcription substrate, wherein said circular transcription substrate comprises a sequence that is complementary to said target sequence; (k) contacting said circular transcription substrate with an RNA polymerase under transcription conditions so as to obtain a transcription product that is complementary to said circular transcription substrate; (l) obtaining said transcription product that is complementary to said circular transcription substrate, wherein said transcription product indicates the presence of said target sequence. In preferred embodiments of this aspect of the invention, the RNA polymerase comprises a transcriptionally active 1,106-amino acid domain corresponding to amino acids 998-2103 of N4 vRNAP. Preferably, the enzyme lacks a histidine or other tag. An RNA polymerase in various embodiments of the invention can also have the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8, or it can have a transcriptionally active portion of any of these sequences. In some embodiments, the target sequence comprises a target nucleic acid in a sample, whereas in other embodiments the target sequence comprises a target sequence tag that is joined to an analyte-binding substance that binds an analyte in the sample. In embodiments of methods in which a TSA probe or a bipartite target probe is used, the target sequence is preferably less than about 150 to about 200 nucleotides from the 3'-end of the target nucleic acid or target sequence tag. In some embodiments, the TSA circle that is replicated remains catenated to the target nucleic acid or target sequence tag. In other embodiments of methods in which the target sequence is greater than about 150 to about 200 nucleotides from the 3'-end of the target nucleic acid or target sequence tag, then one or more additional steps is used in order to release the catenated TSA circles from the target sequence prior to rolling circle replication, as described elsewhere herein. Similarly, one or more additional steps can be used in order to release the catenated circular ssDNA ligation products that result from ligation of bipartite target probes that are annealed to target sequences in the rolling circle replication product more than about 100 nucleotides to about 150 nucleotides from the 3'-end of to the rolling circle replication product.

Yet another embodiment is a method for detecting a target sequence, said method comprising: (a) providing a first bipartite target probe, wherein said first bipartite target probe comprises a 5'-portion and a 3'-portion, wherein said 5'-portion comprises: (i) a 5'-end portion that comprises a sequence that is complementary to a target sequence, and (ii) a promoter sequence, wherein said promoter sequence is covalently attached to and 3'- of said target-complementary sequence in said 5'-portion; and wherein said 3'-portion comprises: (i) a 3'-end portion that comprises a sequence that is complementary to a target sequence, wherein said target-complementary sequence of said 3'-end portion, when annealed to said target sequence, is adjacent to said target-complementary sequence of said 5'-end portion of said first bipartite target probe, and (ii) optionally, a signal sequence, wherein said signal sequence is 5'- of said target-complementary sequence of said 3'-portion of said first bipartite target probe; (b) providing a second bipartite target probe, wherein said second bipartite target probe comprises a 5'-portion and a 3'-portion, wherein said 5'-portion comprises: (i) a 5'-end portion that comprises sequence that is complementary to said target-complementary sequence of said 3'-end portion of said first bipartite target probe, and (ii) a promoter sequence, wherein said promoter sequence in said 5'-portion of said second bipartite target probe is 3'- of said target-complementary sequence in said 5'-portion; and wherein said 3'-portion comprises: (i) a 3'-end portion that comprises sequence that is complementary to said target-complementary sequence of said 5'-end portion of said first bipartite target probe, and (ii) optionally, a signal sequence, wherein said signal sequence in said 3'-portion of said second bipartite target probe is 5'- of said target-complementary sequence in said 3'-portion; (c) annealing said first bipartite target probe to the target sequence under hybridization conditions; (d) ligating said first bipartite target probe annealed to said target sequence with a ligase under ligation conditions, wherein said ligase has little or no activity in ligating blunt ends and is substantially more active in ligating said ends of said first bipartite target probe if said ends are adjacent when annealed to two contiguous regions of a target sequence than if said ends are not annealed to said target sequence, so as to obtain a circular ssDNA molecule that comprises a first circular transcription substrate; (e) obtaining said first circular transcription substrate; (f) contacting said first circular transcription substrate with an RNA polymerase under transcription conditions so as to synthesize transcription product that is complementary to said first circular transcription substrate; (g) annealing to said transcription product that is complementary to said first circular transcription substrate a primer, wherein said primer is complementary to said transcription product; (h) contacting said transcription product to which said primer is annealed with a reverse transcriptase under reverse transcription conditions so as to obtain a first first-strand cDNA; (i) obtaining said first first-strand cDNA, wherein said first first-strand cDNA comprises a linear transcription substrate; (j) annealing to said first first-strand cDNA said second bipartite target probe under annealing conditions; (k) contacting said first first-strand cDNA to which said second bipartite target probe is annealed with a ligase under ligation conditions, wherein said ligase has little or no activity in ligating blunt ends and is substantially more active in ligating said ends of said second bipartite target probe if said ends are adjacent when annealed to two contiguous regions of said first first-strand cDNA than if said ends are not annealed to said sequence, so as to obtain a circular ssDNA molecule that comprises a second circular transcription substrate; (l) obtaining said second circular transcription substrate; (m) contacting said second circular transcription substrate with an RNA polymerase under transcription conditions so as to synthesize transcription product that is complementary to said second circular transcription substrate; (n) annealing to said transcription product that is complementary to said second circular transcription substrate a primer, wherein said primer is complementary to said transcription product; (o) contacting said transcription product to which said primer is annealed with a reverse transcriptase under reverse transcription conditions so as to obtain a second first-strand cDNA; (p) obtaining said second first-strand cDNA, wherein said second first-strand cDNA comprises a linear transcription substrate; (q) annealing to said second first-strand cDNA said first bipartite target probe under annealing conditions; (r) contacting said second first-strand cDNA to which said first bipartite target probe is annealed with a ligase under ligation conditions, wherein said ligase has little or no activity in ligating blunt ends and is substantially more active in ligating said ends of said first bipartite target probe if said ends are adjacent when annealed to two contiguous regions of said second first-strand cDNA than if said ends are not annealed to said sequence, so as to obtain a circular ssDNA molecule that comprises a third circular transcription substrate that is identical to said first circular transcription substrate; (s) obtaining said third circular transcription substrate that is identical to said first circular transcription substrate; (t) repeating steps (a) through (t); (u) detecting the synthesis of transcription products resulting from transcription of said first, second and third circular transcription substrates and from said first and second linear transcription substrates, wherein said synthesis of said transcription products indicates the presence of said target sequence comprising said target nucleic acid. In preferred embodiments of this aspect of the invention, the RNA polymerase comprises a transcriptionally active 1,106-amino acid domain corresponding to amino acids 998-2103 of N4 vRNAP. Preferably, the enzyme lacks a histidine or other tag. An RNA polymerase in various embodiments of the invention can also have the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8, or it can have a transcriptionally active portion of any of these sequences. In some embodiments, the target sequence comprises a target nucleic acid in a sample, whereas in other embodiments the target sequence comprises a target sequence tag that is joined to an analyte-binding substance that binds an analyte in the sample.

Another embodiment of the invention comprises a method for in vivo or in vitro protein synthesis comprising: (a) obtaining an RNA polymerase having the amino sequence set forth in SEQ ID NO:4, SEQ ID NO:6 or a mutant thereof; (b) obtaining DNA wherein the DNA contains a N4 virion RNA polymerase promoter sequence; (c) admixing the RNA polymerase and the DNA; (d) culturing the RNA polymerase and the DNA under conditions effective to allow RNA synthesis; and (e) culturing the RNA in vivo or in vitro under conditions effective to allow protein synthesis. Step (e) may comprise using a two plasmid system or a one plasmid system in which a reporter gene and the RNA polymerase gene are located on the same plasmid.

BRIEF DESCRIPTION OF THE SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A shows a schematic of the N4 vRNAP protein with three motifs: the T/DxxGR motif (SEQ ID NO:44) found in DNA-dependent polymerases, the P-loop, an ATP/GTP-binding motif present in some nucleotide-binding proteins, and motif B ($Rx_3Kx_{6-7}YG$) (SEQ ID NO:45), one of three motifs common to the Pol I and Pol α DNA polymerases and the T7-like RNA polymerases. FIG. 2B shows the mini-vRNAP.

FIG. 3A, SDS-PAGE analysis of the products of vRNAP digestion with trypsin. FIG. 3B N-terminal sequencing of the three initial proteolytic fragments indicated that the stable active polypeptide (mini-vRNAP) corresponds to the middle ⅓ of vRNAP, the region containing the three motifs described in FIG. 2A.

FIG. 16—Mutant mini-vRNAPases in transcription initiation (SEQ ID NOS:40-41). The initiation properties of the three enzymes were compared using catalytic autolabeling. The K670A enzyme displays significantly reduced activity with the GTP derivative. The Y678F enzyme, in contrast to wild type polymerase, incorporates dATP as efficiently as rATP in a single round of phosphodiester bond formation.

FIG. 28—A method for detecting a non-nucleic acid analyte using an analyte-binding substance that has a target sequence tag comprising a target sequence, wherein the signal for the analyte-binding substance and the analyte is generated by rolling circle transcription of a circular transcription substrate obtained by annealing and ligation of a bipartite target probe. Since the target sequence tag is designed to have a size so that a free 3'-end is less than about 150 nucleotides and preferably less than 50-100 nucleotides from the target sequence, the catenated circular transcription substrates are easily released from the target sequence tag. The analyte can be any of a broad range of analytes for which an analyte-binding substance is available or can be identified.

DETAILED DESCRIPTION OF THE INVENTION

Figure 1:
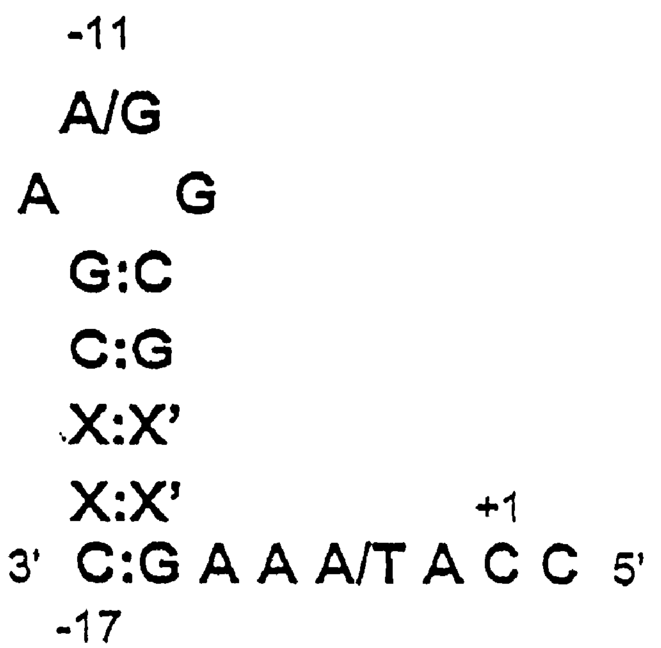
FIG. 1—Bacteriophage N4 vRNAP promoters on single-stranded templates. These promoters are characterized by conserved sequences (SEQ ID NO:43) and a 5 by stem, 3 base loop hairpin structure.

Methods are provided for using various deletion mutants of bacteriophage N4-coded, virion RNA polymerases (mini-vRNAPs), which have been developed, cloned and expressed in *E. coli*, and purified in active form. Mini-vRNAPs lack helicase-like activity. However, in the presence of *E. coli* SSB protein, mini-vRNAPs efficiently transcribe single-stranded DNA (ssDNA) transcription substrates that comprise a single-stranded DNA target sequence as a template if the template is operably joined to a sequence comprising a single-stranded 17-base promoter. The enzymes efficiently incorporate derivatized nucleoside triphosphates, and a specific amino acid mutant of mini-vRNAP (Y678F) also incorporates other nucleotides, such as 2'-deoxynucleoside triphosphates, with greater efficiency. The present invention discloses novel methods, processes, compositions, and kits for amplifying and detecting one or multiple target nucleic acid sequences in or from a sample, including target sequences that differ by as little as one nucleotide. The target sequence or target sequences can comprise at least a portion of one or more target nucleic acids comprising either RNA or DNA from any source, or a target sequence can comprise a target sequence tag that is attached to an analyte-binding substance, such as, but not limited to, an antibody, thus permitting use of the methods and compositions of the present invention to detect any analyte for which there is a suitable analyte-binding substance. The methods of the invention involve obtaining transcription products using a transcription substrate as a template, wherein the transcription substrate is made by ligating at least two different target-complementary sequences comprising one or more target probes when the target-complementary sequences are annealed adjacently on the target sequence. Since the target sequence is required for annealing and ligation of the target-complementary sequences which make the transcription substrate, obtaining the transcription product is target-dependent. Therefore, detection of the transcription products is indicative of the presence of the target sequence comprising the target nucleic acid or the target sequence tag joined to an analyte-binding substance in the sample. The invention will be understood from the description of the additional background, compositions, processes, methods and kits herein below.

I. RNA Polymerases a. Structure and Promoter Recognition of DNA-Dependent RNA Polymerases of the Prior Art Inspection of the sequences of phage, archaebacterial, eubacterial, eukaryotic and viral DNA-dependent RNA polymerases has revealed the existence of two enzyme families. The eubacterial, eukaryotic, archaebacterial, chloroplast and the vaccinia virus RNA polymerases are complex multisubunit enzymes (5-14 subunits) composed of two large subunits, one to several subunits of intermediate molecular weight (30-50-kDa) and none to several subunits of small molecular weight (<30-kDa) (Archambault and Friesen, Microbiol. Rev. 57:703-724, 1993; Record et al., Cell and Molecular Biology 1:792-821, 1995. Eubacterial RNA polymerases are the simplest with an $\beta_2\beta\beta'$ core structure. Sequence comparison of the genes coding for the different subunits of these enzymes has revealed: 1-sequence homology in eight segments (A to H) between β' and the largest subunit of other RNA polymerases, 2-sequence homology in nine segments (A to I) between β and the next largest subunit of other RNA polymerases, 3-sequence homology in 3 segments (1.1, 1.2 and 2) between a and a subunit in RNA polymerases I, II and III (Puhler, et al., Proc. Natl. Acad. Sci. USA 86:4569-4573, 1989; Sweetser, et al., Proc. Natl. Acad. Sci. USA 84:1192-1196, 1987). Not surprisingly, the crystal structures of yeast RNAP H and *E. coli* RNAP core revealed remarkable similarities (Zhang, et al., Cell 98:811-824, 1999; Cramer, et al., Sciencexpress, 19 Apr., 2001).

In contrast, members of the phage T7-like (T7, T3, SP6) family of RNA polymerases consist of a single (~100 kDa) polypeptide which catalyzes all functions required for accurate transcription (Cheetham, et al., Curr. Op. In Struc. Biol. 10:117-123, 2000). The heterodimeric bacteriophage N4 RNAP II, nuclear-coded mitochondrial, and Arabidopsis chloroplast RNA polymerases show sequence similarity to the phage RNA polymerases (Cermakian, et al., Nuc. Acids Res. 24:648-654, 1996; Hedtke, et al., Science 277:809-811, 1997; Zehring, et al., J. Biol. Chem. 258:8074-8080, 1983). Three sequence motifs—A and C, which contain the two aspartic acids required for catalysis, and motif B—are conserved in polymerases that use DNA as a template (Delarue, et al., Protein Engineering 3:461-467, 1990). The crystal structure of T7 RNAP resembles a "cupped right hand" with "palm," "fingers" and "thumb" subdomains (Sousa, et al., Nature 364:593-599, 1993). The two catalytic aspartates are present in the "palm" of the structure. This structure is shared by the polymerase domains of *E. coli* DNA polymerase I and HIV reverse transcriptase (Sousa, Trends in Biochem. Sci. 21:186-190, 1996). Genetic, biochemical and structural information indicates that T7 RNA polymerase contains additional structures dedicated to nascent RNA binding, promoter recognition, dsDNA unwinding and RNA:DNA hybrid unwinding (Cheetham, et al., Curr. Op. In Struc. Biol. 10:117-123, 2000; Sousa, Trends in Biochem. Sci. 21:186-190, 1996). This unwinding activity of T7 RNAP and T7-like RNAPs is described in Japanese Kokai Patent No. Hei 4(1992)-304,900 as "helicase-like activity."

Both Class I and Class II RNA polymerases recognize specific sequences, called promoters, on B form double-stranded DNA. Eubacterial promoters (except those recognized by $\sigma^{54}$) are characterized by two regions of sequence homology: the −10 and the −35 hexamers (Gross, et al., Cold Spring Harbor Symp. Quant. Biol. 63:141-156, 1998). Specificity of promoter recognition is conferred to the core enzyme by the σ subunit, which makes specific interactions with the −10 and −35 sequences through two distinct DNA binding domains (Gross, et al., Cold Spring Harbor Symp. Quant. Biol. 63:141-156, 1998). This modular promoter structure is also present at the promoters for eukaryotic RNA polymerases I, II and III. Transcription factors TFIIIA and TFIIIC direct recognition of RNAP III to two separate sequences (boxes A and C, separated by defined spacing) at the 5S gene promoter, while transcription factors TFIIIB and TFIIIC direct recognition of this enzyme to blocks A and B, separated by variable distance (31-74 bp) at the tRNA promoters (Paule, et al., Nuc. Acids Res. 28:1283-1298, 2000). Sequences important for RNAP I transcription initiation at the human rRNA promoters are also restricted to two regions: the "core" region located at −40 to +1 and the "upstream" region present at −160 to −107 (Paule, et al., Nuc. Acids Res. 28:1283-1298, 2000). Assembly of the initiation complex at RNAP II promoters requires several general transcription factors (TFIIA, TFIIB, TFIID, TFIIE, TFIIF and TFIIH). Recognition involves three core elements: the TATA box located at position −30 and recognized by TBP, the initiator element located near −1, and the downstream promoter element near +30 (Roeder, Trends Biochem. Sci. 21:327-335, 1996).

Promoters for the T7-like and mitochondrial RNAPs are simpler. The T7-type RNAP promoters span a continuous highly conserved 23 bp region extending from position −17 to +6 relative to the start site of transcription (+1) (Rong, et al., Proc. Natl. Acad. Sci. USA 95:515-519, 1998). The yeast mitochondrial RNAP promoters are even smaller, extending from −8 to +1 (Shadel, et al., J. Biol. Chem. 268:16083-16086, 1993). One exception are the promoters for N4 RNAP II, which are restricted to two blocks of conserved sequence: a/tTTTA at +1 and AAGACCTG present 18-26 bp upstream of +1 (Abravaya, et al., J. Mol. Biol. 211:359-372, 1990).

The activity of the multisubunit class of RNA polymerases is enhanced by activators at weak promoters. Transcription activators generally bind at specific sites on double-stranded DNA upstream of the −35 region (with the exception of the T4 sliding clamp activator), or at large distances in the cases of enhancers (Sanders, et al., EMBO Journal 16:3124-3132, 1997). Activators modulate transcription by increasing the binding (formation of closed complex) or isomerization (formation of open complex) steps of transcription through interactions with the $\alpha$ or $\sigma$ subunits of RNAP (Hochschild, et al., Cell 92:597-600, 1998). An exception is N4SSB, the activator of *E. Coli* RNAP$\sigma^{70}$ at the bacteriophage N4 late promoters, which activates transcription through direct interactions with the $\beta'$ subunit of RNAP in the absence of DNA binding (Miller, et al., Science 275:1655-1657, 1997).

Proteins that bind to ssDNAs with high affinity but without sequence specificity have been purified and characterized from several prokaryotes, eukaryotes, and their viruses (Chase, et al., Ann. Rev. Biochem. 55:130-136, 1986). These proteins (SSBs), which are required for replication, recombination and repair, bind stoichiometrically and, in many cases, cooperatively to ssDNA to cover the transient single-stranded regions of DNA that normally arise in vivo as a result of replication, repair and recombination. Binding to DNA results in the removal of hairpin structures found on ssDNA, providing an extended conformation for proteins involved in DNA metabolism. Several lines of evidence suggest that single-stranded DNA binding proteins play a more dynamic role in cellular processes. Genetic and biochemical evidence indicates that these proteins are involved in a multitude of protein-protein interactions including transcription activation (Rothman-Denes, et al., Genes Devepmnt. 12:2782-2790, 1999).

b. The Bacteriophage N4 Virion RNA Polymerase and RNA Polymerase Enzymes of the Present Invention Bacteriophage N4 virion RNA polymerase (N4 vRNAP) is present in N4 virions and is injected into the *E. coli* cell at the beginning of infection, where it is responsible for transcription of the N4 early genes (Falco, et al., Proc. Natl. Acad. Sci. (USA) 74:520-523, 1977; Falco, et al., Virology 95:454-465, 1979; Malone, et al., Virology 162:328-336, 1988). The N4 vRNAP gene maps to the late region of the N4 genome (Zivin, et al., J. Mol. Biol. 152:335-356, 1981). N4 vRNAP purified from virions is composed of a single polypeptide with an apparent molecular mass of approximately 320,000 kDa (Falco, et al., Biol. Chem. 255:4339-4347, 1980). In contrast to other DNA-dependent RNAPases, N4 vRNAP recognizes promoters on single-stranded templates (Falco, et al., Proc. Natl. Acad. Sci. (USA) 75:3220-3224, 1978). These promoters are characterized by conserved sequences and a 5 bp stem, 3 base loop hairpin structure (FIG. 1) (Haynes, et al., Cell 41:597-605, 1985; Glucksmann, et al., Cell 70:491-500, 1992). N4 vRNAP lacks unwinding or helicase-like activity on dsDNA and also lacks unwinding activity on RNA:DNA hybrids. In vivo, *E. coli* gyrase and single-stranded binding protein are required for transcription by N4 vRNAP (Falco, et al., J. Biol. Chem. 255:4339-4347, 1980; Markiewicz, et al., Genes and Dev. 6:2010-2019, 1992).

Sequencing of the N4 vRNAP gene revealed an ORF coding for a protein 3,500 amino acids in length (SEQ ID NO:1-2). Inspection of the sequence revealed no extensive homology to either the multisubunit or the T7-like families of RNA polymerases. However, three motifs are present (FIG. 2A): the T/DxxGR motif (SEQ ID NO:44) found in DNA-dependent polymerases, and Motif B ($Rx_3Kx_{6-7}YG$) (SEQ ID NO:45), one of three motifs common to the Pol I and Pol $\alpha$ DNA polymerases and the T7- like RNA polymerases.

C. Transcription Using N4 vRNAP Enzymes of the Present Invention

RNA synthesis requires RNA polymerase, a DNA template, an activated precursor (the ribonucleoside triphosphates ATP, GTP, UTP and CTP (XTP)), and divalent metal ions such as $Mg^{+2}$ or $Mn^{+2}$. The metal ion $Mg^{+2}$ is strongly preferred. Synthesis of RNA begins at the promoter site on the DNA. This site contains a sequence which the RNA polymerase recognizes and binds. The RNA synthesis proceeds until a termination site is reached. N4 vRNAP termination signals comprise a hairpin loop that forms in the newly synthesized RNA which is followed by a string of uracils (poly U). The sequence of the terminator signals for vRNAP present in the N4 genome include SEQ ID NOS:21-26. These N4 vRNAP termination signals possess all of the characteristics of eubacterial sequence-dependent terminators. The ribonucleoside triphosphate may be derivatized with, for example, biotin. Derivatized XTPs can be used for the preparation of derivatized RNA. Exemplary methods for making derivatized XTPs are disclosed in detail in Rashtchian et al., "Nonradioactive Labeling and Detection of Biomolecules," C. Kessler, Ed., Springer-Verlag, N.Y., pp. 70-84, 1992, herein incorporated by reference.

Single-stranded DNA of varying lengths can be used as a template for RNA synthesis using the N4 vRNAP or mini-vRNAP. Oligonucleotides and polynucleotides of intermediate length may be used. One particular single-stranded DNA that may be used is M13 DNA. M13 genomic DNA exists temporarily inside infected *E. coli* cells as a double-stranded DNA plasmid and is packaged as a small, single-stranded circular DNA into phage particles. M13 phage particles are secreted by an infected cell and single-stranded DNA can be purified from these particles for use as a transcription template. Initially M13 phage vectors required a working knowledge of phage biology and were primarily used for creating single-strand DNA molecules for DNA sequencing. M13-derived cloning vectors called "phagemids" take advantage of M13 replication to produce single-strand molecules, but can be propagated as conventional ColE1-based replicating double-strand plasmids.

EcoSSB is essential for N4 vRNAP transcription in vivo (Falco et al., Proc. Natl. Acad. Sci. (USA) 75:3220-3224, 1978; Glucksmann, et al., Cell 70:491-500, 1992). EcoSSB is a specific activator of N4 vRNAP on single-stranded and supercoiled double-stranded DNA templates. EcoSSB, unlike other SSBs, does not melt the N4 vRNAP promoter hairpin structure (Glucksmann-Kuis, et al., Cell 84:147-154, 1996). EcoSSB has a high specificity for N4 vRNAP and mini-vRNAP resulting from EcoSSB's ability to stabilize the template-strand hairpin, whereas the nontemplate strand hairpin is destabilized. Other single-stranded DNA binding proteins destabilize the template-strand hairpin (Glucksmann-Kuis, et al., Cell 84:147-154, 1996; Dai et al., Genes Devepmnt. 12:2782-2790, 1998). EcoSSB mediates template recycling during transcription by N4 vRNAP (Davidova, E K and Rothman-Denes, L B, Proc. Natl. Acad. Sci. USA 100: 9250-9255, 2003, incorporated herein by reference). When EcoSSB is not used in N4 vRNAP transcription in vitro, a DNA:RNA hybrid is formed, preventing template reutilization. Without being bound by theory, it appears that EcoSSB functionally replaces the N-terminal domain that is present in T7 RNAP (but absent in N4 vRNAP) that is responsible for RNA binding and unwinding, resulting in displacement of the RNA product from the template.

II. Genes and DNA Segments of RNA Polymerases of the Present Invention

Important aspects of the present invention concern isolated DNA segments and recombinant vectors encoding N4 vRNAP or more particularly mini-vRNAP or a mutant of mini-vRNAP and the creation and use of recombinant host cells through the application of DNA technology, that express a wild type, polymorphic or mutant vRNAP. Other aspects of the present invention concern isolated nucleic acid segments and recombinant vectors encoding vRNAP. Sequences of SEQ ID NO:1, 3, 5, 7, 14 and biologically functional equivalents thereof are used in the current invention. Single-stranded DNA oligonucleotides and polynucleotides can be used as DNA templates.

The present invention concerns isolated nucleic acid segments that are capable of expressing a protein, polypeptide or peptide that has RNA polymerase activity. As used herein, the term "nucleic acid segment" refers to a nucleic acid molecule that has been isolated free of total genomic DNA of a particular species. Therefore, a nucleic acid segment encoding vRNAP refers to a nucleic acid segment that contains wild-type, polymorphic or mutant vRNAP coding sequences yet is isolated away from, or purified free from, total bacterial or N4 phage genomic DNA. Included within the term "nucleic acid segment," are nucleic acid segments and smaller fragments of such segments, and also recombinant vectors, including, for example, plasmids, cosmids, phage, viruses, and the like.

Similarly, a nucleic acid segment comprising an isolated or purified vRNAP gene refers to a nucleic acid segment including vRNAP protein, polypeptide or peptide coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those of skill in the art, this functional term includes both genomic sequences, cDNA sequences and engineered segments that express, or may be adapted to express, proteins, polypeptides, domains, peptides, vRNAPs and mutants of vRNAP encoding sequences.

"Isolated substantially away from other coding sequences" means that the gene of interest, in this case the vRNAP, or more particularly mini-vRNAP genes, forms the significant part of the coding region of the nucleic acid segment, and that the nucleic acid segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

The term "a sequence essentially as set forth in SEQ ID NO:2 means, for example, that the sequence substantially corresponds to a portion of SEQ ID NO:2 and has relatively few amino acids that are not identical to, or a biologically functional equivalent of, the amino acids of SEQ ID NO:2. This applies with respect to all peptide and protein sequences herein, such as those of SEQ ID NO:4, 6, 8 and 15.

The term "biologically functional equivalent" is well understood in the art and is further defined in detail herein. Accordingly, sequences that have about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or about 99%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO:2 will be sequences that are "essentially as set forth in SEQ ID NO:2," provided the biological activity of the protein is maintained. In particular embodiments, the biological activity of a vRNAP protein, polypeptide or peptide, or a biologically functional equivalent, comprises transcription. A preferred transcriptional activity that may be possessed by a vRNAP protein, polypeptide or peptide, or a biologically functional equivalent, is RNA synthesis using single-stranded N4 vRNAP promoter-containing DNA as a template.

In certain other embodiments, the invention concerns isolated nucleic acid segments and recombinant vectors that include within their sequence a nucleic acid sequence essentially as set forth in SEQ ID NO:1. The term "essentially as set forth in SEQ ID NO:1 is used in the same sense as described above and means that the nucleic acid sequence substantially corresponds to a portion of SEQ ID NO:1 and has relatively few codons that are not identical, or functionally equivalent, to the codons of SEQ ID NO:1. Again, nucleic acid segments that encode proteins, polypeptide or peptides exhibiting RNAP activity will be most preferred.

The term "functionally equivalent codon" is used herein to refer to codons that encode the same amino acid, such as the six codons for arginine and serine, and also refers to codons that encode biologically equivalent amino acids. For optimization of expression of vRNAP in human cells, the following codons are used, with preference of use from left to right: Alanine Ala A GCC GCT GCA GCG; Cysteine Cys C TGC TGT; Aspartic acid Asp D GAG GAT; Glutamic acid Glu E GAG GAA; Phenylalanine Phe F TTC TTT; Glycine Gly G GGC GGG GGA GGT; Histidine His H CAC CAT; Isoleucine Ile I ATC ATT ATA; Lysine Lys K AAG AAA; Leucine Leu L CTG CTC TTG CTT CTA TTA; Methionine Met M ATG; Asparagine Asn N AAC AAT; Proline Pro P CCC CCT CCA CCG; Glutamine Gln Q CAG CAA; Arginine Arg R CGC AGG CGG AGA CGA CGT; Serine Ser S AGC TCC TCT AGT TCA TCG; Threonine Thr T ACC ACA ACT ACG; Valine Val V GTG GTC GTT GTA; Tryptophan Trp W TGG;

Tyrosine Tyr Y TAC TAT. Thus, the most preferred codon for alanine is "GCC," and the least is "GCG." Codon usage for various organisms and organelles can be found at the website kazusa.orjp/codon/, allowing one of skill in the art to optimize codon usage for expression in various organisms using the disclosures herein. Thus, it is contemplated that codon usage may be optimized for other animals, as well as other organisms such as a prokaryote (e.g., an eubacteria), an archaea, an eukaryote (e.g., a protist, a plant, a fungus, an animal), a virus and the like, as well as organelles that contain nucleic acids, such as mitochondria or chloroplasts, based on the preferred codon usage as would be known to those of ordinary skill in the art.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or about 99%, and any range derivable therein, such as, for example, about 50% to about 80%, and more preferably about 81% and about 90%; or even more preferably, between about 91% and about 99%; of nucleotides that are identical to the nucleotides of SEQ ID NO:1 will be sequences that are "essentially as set forth in SEQ ID NO:1".

a. Nucleic Acid Hybridization

The nucleic acid sequences disclosed herein also have a variety of uses. Contiguous sequences from vRNAP nucleic acid sequences can be used, for example, as templates to synthesize vRNAP.

Naturally, the present invention also encompasses DNA segments that are complementary, or essentially complementary, to the sequence set forth in SEQ ID NO:1, 3, 5, 7 and 14. Nucleic acid sequences that are "complementary" are those that are capable of base-pairing according to the standard Watson-Crick complementary rules. As used herein, the term "complementary sequences" means nucleic acid sequences that are complementary, as may be assessed by the same nucleotide comparison set forth above, or as defined as being capable of hybridizing to the nucleic acid segment of SEQ ID NO:1 under stringent conditions such as those described herein.

As used herein, a "DNA/RNA hybrid" is understood to mean that a single strand of RNA is hybridized to a single strand of DNA.

The term "appropriate reaction conditions" as described herein mean that temperature, pH, buffer, and other parameters are adjusted to optimize the reaction rate and yield.

As used herein, "hybridization," "hybridizes" or "capable of hybridizing" is understood to mean the forming of a double or triple stranded molecule or a molecule with partial double or triple stranded nature. The term "hybridization," "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. For example, a medium stringency condition could be provided by about 0.1 to 0.25 M NaCl at temperatures of about 37° C. to about 55° C. Under these conditions, hybridization may occur even though the sequences of probe and target strand are not perfectly complementary, but are mismatched at one or more positions. In another example, a low stringency condition could be provided by about 0.15 M to about 0.9 M salt, at temperatures ranging from about 20° C. to about 55° C. Of course, it is within the skill of one in the art to further modify the low or high stringency conditions to suit a particular application. For example, in other embodiments, hybridization may be achieved under conditions of 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 MM $MgCl_2$, at temperatures ranging from approximately 40° C. to about 72° C.

Accordingly, the nucleotide sequences of the disclosure may be used for their ability to selectively form duplex molecules with complementary stretches of genes or RNAs or to provide primers for amplification of DNA or RNA from tissues. Depending on the application envisioned, it is preferred to employ varying conditions of hybridization to achieve varying degrees of selectivity of probe towards target sequence.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a contiguous stretch of nucleotides identical to or complementary to SEQ ID NO:1, 3, 5, 7 or 14. Nucleic acid fragments for use as a DNA transcription template may also be prepared. These fragments may be short or of intermediate lengths, such as, for example, about 8, about 10 to about 14, or about 15 to about 20 nucleotides, and that are chromosome-sized pieces, up to about 35,000, about 30,000, about 25,000, about 20,000, about 15,000, about 10,000, or about 5,000 base pairs in length, as well as DNA segments with total lengths of about 1,000, about 500, about 200, about 100 and about 50 base pairs in length (including all intermediate lengths of these lengths listed above, i.e., any range derivable therein and any integer derivable therein such a range) are also contemplated to be useful.

For example, it will be readily understood that "intermediate lengths," in these contexts, means any length between the quoted ranges, such as 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 130, 140, 150, 160, 170, 180, 190, including all integers through the 200-500; 500-1,000; 1,000-2,000; 2,000-3,000; 3,000-5,000; 5,000-10,000 ranges, up to and including sequences of about 12,001, 12,002, 13,001, 13,002, 15,000, 20,000 and the like.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from I to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

The use of a hybridization probe of between 17 and 100 nucleotides in length, or in some aspect of the invention even up to 1-2 Kb or more in length, allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having complementary sequences over stretches of 20 to 30 nucleotides, or even longer where desired. Such fragments may be readily prepared by, for example, directly synthesizing the fragment by chemical means or by introducing selected sequences into recombinant vectors for recombinant production.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

b. Nucleic Acid Amplification

Nucleic acid used as a template for amplification is isolated from cells contained in the biological sample, according to standard methodologies (Sambrook et al., In: Molecular Cloning: A Laboratory Manual 2 rev.ed., Cold Spring Harbor: Cold Spring Harbor Laboratory Press, 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label, or even via a system using electrical or thermal impulse signals (Affymax technology).

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products, and the process is repeated.

A reverse transcriptase PCR amplification procedure may be performed in order to quantify the amount of mRNA amplified. Alternative methods for reverse transcription utilize thermostable, RNA-dependent DNA polymerases. These methods are described in WO 90/07641, filed Dec. 21, 1990. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Q-beta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence, which can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification method described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double-stranded DNA molecules are heat denatured again. In either case, the single-stranded DNA is made fully double-stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single-stranded DNA, which is then converted to double-stranded DNA, and then transcribed once again with an RNA polymerase such as T7 or SP6. The resulting products, whether truncated or complete, indicate target specific sequences.

Davey et al., EPA No. 329 822 disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, In: PCR Protocols: A Guide To Methods And Applications, Academic Press, N.Y., 1990).

Methods based on ligation of two (or more) oligonucleotides in the presence of nucleic acid having the sequence of the resulting "di-oligonucleotide," thereby amplifying the di-oligonucleotide, may also be used in the amplification step of the present invention.

c. Nucleic Acid Detection

In certain embodiments, it will be advantageous to employ nucleic acid sequences of the present invention such as all or part of SEQ ID NO:1, 3, 5, 7, 14 or a mutant thereof in combination with an appropriate means, such as a label, for hybridization assays, RNase protection and Northern hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In embodiments wherein nucleic acids are amplified, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., In: Molecular Cloning: A Laboratory Manual 2 rev.ed., Cold Spring Harbor: Cold Spring Harbor Laboratory Press, 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods for genetic screening to accurately detect mutations in genomic DNA, cDNA or RNA samples may be employed, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR (see above) and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of an *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase Protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild-type sequences are hybridized to complementary target regions derived from test samples. The test target generally comprises DNA (either genomic DNA or DNA amplified by cloning in plasmids or by PCR), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

Nuclease S1 analysis of reaction products can be used to measure RNA. An exemplary procedure for S1 analysis involves hybridization reaction with the RNA of interest (0.005-0.1 mg) and an excess of S1 probe which comprises a labeled oligonucleotide complementary to 20-80 or more sequential nucleotides of a specific RNA in S1 hybridization buffer (80% formamide, 0.4 M NaCl, 1 mM EDTA, 40 mM Pipes, pH 6.4). After denaturation for 4 min at 94° C., overnight hybridization at 30° C. and precipitation with ethanol, the S1 probe/RNA mixture is resuspended in S1 buffer (0.26 M NaCl, 0.05 M sodium acetate, pH 4.6, and 4.5 mM zinc sulfate). The sample is divided into two volumes and 100 units of S1 nuclease (Sigma Chemical Company) is added to one tube. The samples are incubated for 60 minutes at 37° C.; then EDTA (10 mM final concentration) and 15 g polyl-polyC RNA are added and the sample is extracted with phenol/chloroform and precipitated in ethanol. The samples are then subjected to polyacrylamide gel electrophoresis.

One method to produce a radiolabeled RNA probe with high specific activity includes admixing a radiolabeled NTP during transcription. Suitable isotopes for radiolabeling include $^{35}$S- and $^{32}$P-labeled UTP, GTP, CTP or ATP. For optimal results, a gel-purified radiolabeled RNA probe which is preferentially 300-500 bases in length, with a specific activity of 1-3×10 8 cpm/μg should be generated using the RNA polymerase of the current invention. In order to produce this in vitro transcript, it is often advisable to use a high specific activity (e.g., [$\alpha$-$^{32}$P]CTP at 3,000 Ci/mmol) NTP. To prevent background hybridization, it is important to remove plasmid template DNA by digestion which can be done with, for example, RQ1 RNase-Free DNase followed by phenol:chloroform:isoamyl alcohol extraction and ethanol precipitation.

Another method for producing radiolabeled probes includes using a riboprobe system which can produce high specific activity, radiolabeled RNA probes or microgram quantities of in vitro transcript. Riboprobes are useful with radiolabeled RNA probes in many applications including RNase protection, Northern hybridization, S1 analysis and in situ hybridization assays. The principle components of an in vitro transcription are the riboprobe, an RNA polymerase, a DNA template which includes a phage RNA polymerase promoter and ribonucleotide triphosphates.

d. Cloning vRNAP Genes

The present invention contemplates cloning vRNAP, or more particularly mini-vRNAP genes. A technique often employed by those skilled in the art of protein production today is to obtain a so-called "recombinant" version of the protein, to express it in a recombinant cell and to obtain the protein, polypeptide or peptide from such cells. These techniques are based upon the "cloning" of a nucleic acid molecule encoding the protein from a DNA library, i.e., on obtaining a specific DNA molecule distinct from other portions of DNA. This can be achieved by, for example, cloning a cDNA molecule, or cloning a genomic-like DNA molecule.

The first step in such cloning procedures is the screening of an appropriate DNA library, such as, for example, from a phage, bacteria, yeast, fungus, mouse, rat, monkey or human. The screening protocol may utilize nucleotide segments or probes that are designed to hybridize to cDNA or genomic sequences of vRNAPs from protists. Additionally, antibodies designed to bind to the expressed vRNAP proteins, polypeptides, or peptides may be used as probes to screen an appropriate viral, eubacterial, archaebacterial or eukaryotic DNA expression library. Alternatively, activity assays may be employed. The operation of such screening protocols are well known to those of skill in the art and are described in detail in the scientific literature, for example, in Sambrook et al., In: Molecular Cloning: A Laboratory Manual 2 rev.ed., Cold Spring Harbor: Cold Spring Harbor Laboratory Press, 1989, incorporated herein by reference. Moreover, as the present invention encompasses the cloning of genomic segments as well as cDNA molecules, it is contemplated that suitable genomic cloning methods, as known to those in the art, may also be used.

Encompassed by the invention are DNA segments encoding relatively small peptides, such as, for example, peptides of from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 40, about 45, to about 50 amino acids in length, and more preferably, of from about 15 to about 30 amino acids in length; as set forth in SEQ ID NO:2, 4, 6, 8 or 15 and also larger polypeptides up to and including proteins corresponding to the full-length sequences set forth in SEQ ID NO:2 and SEQ ID NO:15, and any range derivable therein and any integer derivable in such a range. In addition to the "standard" DNA and RNA nucleotide bases, modified bases are also contemplated for use in particular applications of the present invention.

III. Recombinant Vectors, Promoters, Host Cells and Expression

Recombinant vectors form an important further aspect of the present invention. The term "expression vector or construct" means any type of genetic construct containing a nucleic acid coding for a gene product in which part or all of the nucleic acid encoding sequence is capable of being transcribed. The transcript may be translated into a proteinaceous molecule, but it need not be, such as in the case of mini-vRNAP transcribing an RNA using a single-stranded DNA template. Thus, in certain embodiments, expression includes both transcription of a single-stranded DNA and translation of an RNA into the protein product. In other embodiments, expression only includes transcription of the nucleic acid. A recombinant vector can also be used for delivery of the RNA of the current invention.

Particularly useful vectors are contemplated to be those vectors in which the coding portion of the DNA segment, whether encoding a full length protein or smaller polypeptide or peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

One particularly useful vector is pBAD. The pBAD expression vectors allow for greater control of bacterial expression of recombinant proteins and allow tight regulation for turning expression on or off. pBAD vectors allow for dose dependent induction for modulation of expression levels. The pBAD expression system helps overcome two of the most common problems of heterologous protein expression in bacteria: toxicity of the recombinant protein to the host and insolubility of the recombinant protein when it is expressed at high, uncontrolled levels. In both cases, a tightly-regulated expression system is critical for maximizing recombinant protein yields. The pBAD expression system is based on the araBAD operon which controls the arabinose metabolic pathway in *E. coli* and allows for precise modulation of heterologous expression to levels that are optimal for recovering high yields of the protein of interest (Guzman et al., J. Bact. 177:4121-4130, 1995).

a. Promoters

Any promoters normally found in a host cell in the native state can be used in the present invention to drive expression of N4 vRNA or mini-vRNA polymerase. Also, promoters not normally found in the host cell in the native state that are recognized by a native, normally native host cell RNA polymerase, or non-native RNA polymerase expressed in the cell can be used in the present invention to drive expression of the RNA polymerase. Other promoters may be selected from a nucleic acid sequence database accessible to those of skill in the art, e.g., GenBank, or the promoter can be isolated by a screening method. A promoter recognized by the host cell can be operably linked to the gene or genes encoding the N4 RNA polymerase. The operable linkage can be constructed using any known techniques for DNA manipulation, as referred to herein.

Promoters are described as either constitutive or inducible. Constitutive promoters actively drive expression of genes under their control. Inducible promoters, in contrast, are activated in response to specific environmental stimuli. Both constitutive and inducible promoters can be used in the present invention for expressing non-host genes in a host cell.

Inducible promoters include, but are not limited to, trp, tac, lac, ara, reca, λPr, and λP1. These promoters and others that can be used in the present invention for expression of the N4 vRNA or mini-vRNA polymerase, in embodiments in which the host cell is *E. coli*, are described by Makrides, Microbiological Reviews 60, 512-538, 1996. Further, in embodiments of the present invention wherein the host cell is a microbe other than *E. coli*, such as *Saccharomyces, Bacillus*, and *Pseudomonas*, any inducible promoter known to those skilled in the art to be active in the host cell can be used to drive expression of the heterologous RNA polymerase. (U.S. Pat. No. 6,218,145).

The promoter may be in the form of the promoter that is naturally associated with N4 vRNA or mini-vRNA polymerase, as may be obtained by isolating the 5' non-coding sequences located upstream of the coding segment or exon, for example, using recombinant cloning and/or PCR technology, in connection with the compositions disclosed herein (PCR technology is disclosed in U.S. Pat. No. 4,683,202 and U.S. Pat. No. 4,682,195).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with N4 vRNA or mini-vRNA polymerase in its natural environment. Such promoters may include promoters normally associated with other genes, and/or promoters isolated from any other bacterial, viral, eukaryotic, protist, or mammalian cell, and/or promoters made by the hand of man that are not "naturally occurring," i e., containing different elements from different promoters, or mutations that increase, decrease, or alter expression.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. In: Molecular Cloning: A Laboratory Manual 2 rev.ed., Cold Spring Harbor: Cold Spring Harbor Laboratory Press, 1989, incorporated herein by reference. The promoters employed may be constitutive, or inducible, and can be used under the appropriate conditions to direct high level expression of the introduced DNA segment, such as is advantageous in the large-scale production of recombinant proteins, polypeptides or peptides.

At least one module in a promoter generally functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase promoter, the spacing between promoter elements can be increased to 50 base pairs apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various other embodiments, the human cytomegalovirus (CMV) immediate early gene promoter, the SV40 early promoter and the Rous sarcoma virus long terminal repeat can be used to obtain high-level expression of the instant nucleic acids. The use of other viral or mammalian cellular or bacterial phage promoters which are well-known in the art to achieve expression are contemplated as well, provided that the levels of expression are sufficient for a given purpose.

In certain embodiments of the invention, promoter sequences may be used that that are recognized specifically by a DNA-dependent RNA polymerase, such as, but not limited to, those described by Chamberlin and Ryan, In: The Enzymes. San Diego, Calif., Academic Press, 15:87-108, 1982, and by Jorgensen et al., J. Biol. Chem. 266:645-655, 1991. These promoters can be used to express a wild-type or mutant form of a miniV RNA polymerase of the invention. Several RNA polymerase promoter sequences are especially useful, including, but not limited to, promoters derived from SP6 (e.g., Zhou and Doetsch, Proc. Nat. Acad. Sci. USA 90:6601-6605, 1993), T7 (e.g., Martin, and Coleman, Biochemistry 26:2690-2696, 1987) and T3 (e.g., McGraw et al., Nucl. Acid. Res. 13:6753-6766, 1985). An RNA polymerase promoter sequence derived from *Thermus thermophilus* can also be used (see, e.g., Wendt et al., Eur. J. Biochem. 191: 467-472, 1990; Faraldo et al., J. Bact. 174:7458-7462, 1992; Hartmann et al., Biochem. 69:1097-1104, 1987; Hartmann et al., Nucl. Acids Res. 19:5957-5964, 1991). The length of the promoter sequence will vary depending upon the promoter chosen. For example, the T7 RNA polymerase promoter can be only about 25 bases in length and act as a functional promoter, while other promoter sequences require 50 or more bases to provide a functional promoter.

In other embodiments of the invention, a promoter is used that is recognized by an RNA polymerase from a T7-like bacteriophage. The genetic organization of all T7-like phages that have been examined has been found to be essentially the same as that of T7. Examples of T7-like phages according to the invention include, but are not limited to *Escherichia coli* phages T3, ΦI, ΦII, W31, H, Y, A1, 122, cro, C21, C22, and C23*; Pseudomonas putida* phage gh-1*; Salmonella typhimurium* phage SP6*; Serratia marcescens* phages IV; Citrobacter phage ViIII; and *Klebsiella* phage No. 11 (Hausmann, Current Topics in Microbiology and Immunology 75:77-109, 1976; Korsten et al., J. Gen. Virol. 43:57-73, 1975; Dunn, et al., Nature New Biology 230:94-96, 1971; Towle, et al., J. Biol. Chem. 250:1723-1733, 1975; Butler and Chamberlin, J. Biol. Chem. 257:5772-5778, 1982).

When a T7 RNA polymerase promoter, or another T7-like RNA polymerase promoter is used to express a wild-type or mutant form of a gene for a miniV RNA polymerase of the invention, the gene can be expressed in a host cell which expresses the T7 RNA polymerase, or the corresponding T7-like RNA polymerase for the promoter used, wherein the RNA polymerase for the promoter is expressed either constitutively, or more preferably, from an inducible promoter. By way of example, a T7 RNA polymerase expression system, such as, but not limited to, the expression systems disclosed in, for example, U.S. Pat. Nos. 5,693,489 and 5,869,320, the disclosures of which are incorporated herein by reference in their entirety.

b. Enhancers

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB, epd.isb-sib.ch/) could also be used to drive expression.

Eukaryotic cells can support cytoplasmic transcription from certain bacterial promoters if the appropriate bacterial polymerase is provided, either as part of the delivery complex or as an additional genetic expression construct.

Turning to the expression of the proteinaceous molecules after transcription using the vRNAP, mini-vRNAP, or mutants thereof of the present invention, once a suitable clone or clones have been obtained, whether they be cDNA based or genomic, one may proceed to prepare an expression system.

The engineering of DNA segment(s) for expression in a prokaryotic or eukaryotic system may be performed by techniques generally known to those of skill in recombinant expression. It is believed that virtually any expression system may be employed in the expression of the proteinaceous molecules of the present invention.

Both cDNA and genomic sequences are suitable for eukaryotic expression, as the host cell will generally process the genomic transcripts to yield functional mRNA for translation into proteinaceous molecules. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

c. Antisense, RNAi and Ribozymes

In some embodiments of the invention the vRNA polymerase can be used to synthesize antisense RNA, RNAi or interference RNA or ribozymes.

The term "antisense nucleic acid" is intended to refer to the oligonucleotides complementary to the base sequences of DNA and RNA. Antisense oligonucleotides, when introduced into a target cell, specifically bind to their target nucleic acid and interfere with transcription, RNA processing, transport, translation, and/or stability. Targeting double-stranded (ds) DNA with oligonucleotides leads to triple-helix formation; targeting RNA will lead to double-helix formation. An antisense nucleic acid may be complementary to SEQ ID NO:1, 3, 5, 7 or 14, complementary to a mini-vRNAP encoding sequence or to mini-vRNAP non-coding sequences. Antisense RNA constructs, or DNA encoding such antisense RNAs, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries (splice junctions) of a gene. It is contemplated that the most effective antisense constructs may include regions complementary to intron/exon splice junctions. Thus, antisense constructs with complementary regions within 50-200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vivo to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., Science 260:1510-1513, 1993).

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligonucleotides incorporating ribozyme sequences, or introduced into the cell as an expression construct encoding the desired ribozymal RNA. Ribozymes may be used and applied in much the same way as described for antisense nucleic acids. Sequences for ribozymes may be included in the DNA template to eliminate undesired 5' end sequences in RNAs generated through T7 RNA polymerase transcription.

Ribozymes are RNA-protein complexes that cleave nucleic acids in a site-specific fashion. Ribozymes have specific catalytic domains that possess endonuclease activity (Kim and Cech, Proc. Natl. Acad. Sci. USA 84:8788-8792, 1987; Gerlach et al., Nature 328:802-805, 1987; Forster and Symons, Cell 49:211-220, 1987). For example, a large number of ribozymes accelerate phosphoester transfer reactions with a high degree of specificity, often cleaving only one of several phosphoesters in an oligonucleotide substrate (Cech et al., Cell 27:487-496, 1981; Michel and Westhof, J. Mol. Biol. 216:585-610, 1990; Reinhold-Hurek and Shub, Nature 357:173-176, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, Nature 338:217-244, 1989; Cech et al., Cell 27:487-496, 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., Proc. Natl. Acad. Sci. USA 88:10591-10595, 1991; Sarver et al., Science 247:1222-1225, 1990; Sioud et al., J. Mol. Biol. 223:831-835, 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Several different ribozyme motifs have been described with RNA cleavage activity (reviewed in Symons, Annu. Rev. Biochem. 61:641-671, 1992). Examples of ribozymes include sequences from the Group I self-splicing introns including tobacco ringspot virus (Prody, et al., Science 231:1577-1580, 1986), avocado sunblotch viroid (Palukaitis, et al., Virology 99:145-151, 1979; Symons, Nucl. Acids Res. 9:6527-6537, 1981), and Lucerne transient streak virus (Forster and Symons, Cell 49:211-220, 1987). Sequences from these and related viruses are referred to as hammerhead ribozymes based on a predicted folded secondary structure.

Other suitable ribozymes include sequences from RNase P with RNA cleavage activity (Yuan, et al., Proc. Natl. Acad. Sci. USA 89:8006-8010, 1992; Yuan and Altman, Science, 263:1269-1273, 1994), hairpin ribozyme structures (Berzal-Herranz, et al., Genes and Devel. 6:129-134, 1992; Chowrira et al., Biochemistry 32:1088-1095, 1993) and hepatitis δ virus based ribozymes (Perrotta and Been, Biochemistry 31:16-21, 1992). The general design and optimization of ribozyme directed RNA cleavage activity has been discussed in detail (Haseloff and Gerlach, Nature 334:585-591, 1988; Symons, Annu. Rev. Biochem. 61:641-671, 1992; Chowrira, et al., J. Biol. Chem. 269:25856-25864, 1994; and Thompson, et al., Nature Medicine 1:277-278, 1995).

The other variable on ribozyme design is the selection of a cleavage site on a given target RNA. Ribozymes are targeted to a given sequence by virtue of annealing to a site by complementary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., Gene 113:157-163, 1992; Thompson, et al., Nature Medicine 1:277-278, 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., J. Biol. Chem. 269:25856-25864 (1994) and Lieber and Strauss, Mol. Cell. Biol. 15: 540-551 (1995), each incorporated by reference. The identification of operative and preferred sequences for use in ribozymes is simply a matter of preparing and testing a given sequence, and is a routinely practiced "screening" method known to those of skill in the art.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

d. Host Cells

Host cells may be derived from prokaryotes or eukaryotes, including yeast cells, insect cells, and mammalian cells, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryotic host cell for replication of many vector copies. Bacterial cells used as host cells for vector replication and/or expression include DH5a, BL 21, JMI09, and KCB, as well as a number of commercially available bacterial hosts such as SURE® Competent Cells and SOLOPACK Gold Cells (STRATAGENE®, La Jolla, Calif.). Alternatively, bacterial cells such as *E. coli* LE392 could be used as host cells. Appropriate yeast cells include *Saccharomyces cerevisiae, Saccharomyces pombe*, and *Pichia pastoris.*

Examples of eukaryotic host cells for replication and/or expression of a vector include HeLa, NIH3T3, Jurrat, 293, Cos, CHO, Saos, BHK, C127 and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and/or their cognate polypeptides, proteins, or peptides.

It is proposed that vRNAP, or more particularly mini-vRNAP may be co-expressed with other selected proteinaceous molecules such as EcoSSB and other proteins of interest, wherein the proteinaceous molecules may be co-expressed in the same cell or vRNAP gene may be provided to a cell that already has another selected proteinaceous molecule. Co-expression may be achieved by co-transfecting the cell with two distinct recombinant vectors, each bearing a copy of either of the respective DNAs. Alternatively, a single recombinant vector may be constructed to include the coding regions for both of the proteinaceous molecules, which could then be expressed in cells transfected with the single vector. In either event, the term "co-expression" herein refers to the expression of both the vRNAP gene and the other selected proteinaceous molecules in the same recombinant cell.

As used herein, the terms "engineered" and "recombinant" cells or host cells are intended to refer to a cell into which an exogenous DNA segment or gene, such as a cDNA or gene encoding vRNAP, mini-vRNAP or a mutant thereof, has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant vRNAP, whether mutant or wild-type, in accordance with the present invention one would prepare an expression vector that comprises a wild-type, or mutant vRNAP proteinaceous molecule-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of the chosen promoter. The "upstream" promoter directs transcription of the DNA and promotes expression of the encoded recombinant protein, polypeptide or peptide. This is the meaning of "recombinant expression" in this context.

Many standard techniques are available to construct expression vectors containing the appropriate nucleic acids and transcriptional/translational control sequences in order to achieve protein, polypeptide or peptide expression in a variety of host expression systems. Cell types available for expression include, but are not limited to, bacteria, such as *E. coli* and *B. subtilis*, transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences which are derived from species compatible with the host cell are used in connection with these hosts. The vector ordinarily carries a replication origin, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors; and pGEX vectors, for use in generating glutathione S-transferase (GST) soluble proteins for later purification and separation or cleavage.

The following details concerning recombinant protein production in bacterial cells, such as *E. coli*, are provided by way of exemplary information on recombinant protein production in general, the adaptation of which to a particular recombinant expression system will be known to those of skill in the art.

Bacterial cells, for example, *E. coli*, containing the expression vector are grown in any of a number of suitable media, for example, LB. The expression of the recombinant proteinaceous molecule may be induced, e.g., by adding IPTG or any appropriate inducer to the media or by switching incubation to a higher temperature, depending on the regulated promoter used. After culturing the bacteria for a further period, generally of between 2 and 24 hours, the cells are collected by centrifugation and washed to remove residual media.

The bacterial cells are then lysed, for example, by disruption in a cell homogenizer, by sonication or cell press and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant proteinaceous molecule is expressed in the inclusion bodies, as is the case in many instances, these can be washed in any of several solutions to remove some of the contaminating host proteins, then solubilized in solutions containing high concentrations of urea (e.g., 8M) or chaotropic agents such as guanidine hydrochloride in the presence of reducing agents, such as β-mercaptoethanol or DTT (dithiothreitol).

Under some circumstances, it may be advantageous to incubate the proteinaceous molecule for several hours under conditions suitable for the proteinaceous molecule to undergo a refolding process into a conformation which more closely resembles that of the native proteinaceous molecule. Such conditions generally include low proteinaceous molecule concentrations, less than 500 mg/ml, low levels of reducing agent, concentrations of urea less than 2 M and often the presence of reagents such as a mixture of reduced and oxidized glutathione which facilitate the interchange of disulfide bonds within the proteinaceous molecule.

The refolding process can be monitored, for example, by SDS-PAGE, or with antibodies specific for the native molecule (which can be obtained from animals vaccinated with the native molecule or smaller quantities of recombinant proteinaceous molecule). Following refolding, the proteinaceous molecule can then be purified further and separated from the refolding mixture by chromatography on any of several supports including ion exchange resins, gel permeation resins or on a variety of affinity columns.

For expression in *Saccharomyces*, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoter sequences in yeast vectors include the promoters for 3-phosphoglycerate kinase or other glycolytic enzymes, such as enolase, glyceraldehyde-3-phosphate protein, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector downstream of the sequence desired to be expressed to provide polyadenylation of the mRNA and termination.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more RNAP coding sequences.

Different host cells have characteristic and specific mechanisms for the post-translational processing and modification of proteinaceous molecules. Appropriate cells lines or host systems can be chosen to ensure the correct modification and processing of the foreign proteinaceous molecule expressed.

A number of viral-based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1, E3, or E4) will result in a recombinant virus that is viable and capable of expressing an RNA in infected hosts.

Specific initiation signals may also be used for more efficient translation using the vRNAP of the current invention. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements and transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the proteinaceous molecule at a position prior to transcription termination.

For long-term, high-yield production of a recombinant vRNAP protein, polypeptide or peptide, stable expression is preferred. For example, cell lines that stably express constructs encoding a vRNAP protein, polypeptide or peptide may be engineered. Rather than using expression vectors that contain viral origins of replication, host cells can be transformed with vectors controlled by appropriate expression control elements (e.g., promoter, enhancer sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (tk), hypoxanthine-guanine phosphoribosyltransferase (hgprt) and adenine phosphoribosyltransferase (aprt) genes, in tk-, hgprt- or aprt-cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and hygromycin (hygro), that confers resistance to hygromycin.

Large scale suspension culture of bacterial cells in stirred tanks is a common method for production of recombinant proteinaceous molecules. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor for microbial fermentation relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the vRNAP proteins, polypeptides or peptides of the invention may be "overexpressed," i.e., expressed in increased levels relative to its natural expression in cells. Such overexpression may be assessed by a variety of methods, including radio-labeling and/or proteinaceous molecule purification. However, simple and direct methods are preferred, for example, those involving SDS/PAGE and proteinaceous composition staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific proteinaceous molecule in relation to the other proteins produced by the host cell and, e.g., visible on a gel.

IV. Methods of Gene Transfer

In order to mediate the effect of transgene expression in a cell, it will be necessary to transfer the expression constructs (e.g., a therapeutic construct) of the present invention into a cell. Such transfer may employ viral or non-viral methods of gene transfer. This section provides a discussion of methods and compositions of gene or nucleic acid transfer, including transfer of antisense sequences.

The vRNAP genes are incorporated into a viral vector to mediate gene transfer to a cell. Additional expression constructs encoding EcoSSB and other therapeutic agents as described herein may also be transferred via viral transduction using infectious viral particles, for example, by transformation with an adenovirus vector of the present invention. Alternatively, a retrovirus, bovine papilloma virus, an adeno-associated virus (AAV), a lentiviral vector, a vaccinia virus, a polyoma virus, or an infective virus that has been engineered to express a specific binding ligand may be used. Similarly, nonviral methods which include, but are not limited to, direct delivery of DNA such as by injection, electroporation, calcium phosphate precipitation, liposome mediated transfection, and microprojectile bombardment may be employed. Thus, in one example, viral infection of cells is used in order to deliver therapeutically significant genes to a cell. Typically, the virus simply will be exposed to the appropriate host cell under physiologic conditions, permitting uptake of the virus.

Microinjection can be used for delivery into a cell. Microinjection involves the insertion of a substance such as RNA into a cell through a microelectrode. Typical applications include the injection of drugs, histochemical markers (such as horseradish peroxidase or lucifer yellow) and RNA or DNA in molecular biological studies. To extrude the substances through the very fine electrode tips, either hydrostatic pressure (pressure injection) or electric currents (ionophoresis) is employed.

V. Proteinaceous Compositions

In certain embodiments, the present invention concerns novel compositions or methods comprising at least one proteinaceous molecule. The proteinaceous molecule may have a sequence essentially as set forth in SEQ ID NO:2, 4, 6, 8 or 15. The proteinaceous molecule may be a vRNAP or more preferably a mini-vRNAP, or a delivery agent. The proteinaceous molecule may also be a mutated mini-vRNAP.

As used herein, a "proteinaceous molecule," "proteinaceous composition," "proteinaceous compound," "proteinaceous chain" or "proteinaceous material" generally refers to, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to the following, beginning with the corresponding abbreviation: Aad 2-Aminoadipic acid; EtAsn N-Ethylasparagine; Baad 3-Aminoadipic acid; Hyl Hydroxylysine; Bala β-alanine, β-Amino-propionic acid; AHyl allo-Hydroxylysine; Abu 2-Aminobutyric acid; 3Hyp 3-Hydroxyproline; 4Abu 4-Aminobutyric acid, piperidinic; 4Hyp 4-Hydroxy-proline acid; Acp 6-Aminocaproic acid; Ide Isodesmosine; Ahe 2-Amino-heptanoic acid; AIle allo-Isoleucine; Aib 2-Aminoisobutyric acid; MeGly N-Methylglycine, sarcosine; Baib 3-Aminoisobutyric acid; MeIle N-Methylisoleucine; Apm 2-Aminopimelic acid; MeLys 6-N-Methyllysine; Dbu 2,4-Diaminobutyric acid; MeVal N-Methylvaline; Des Desmosine; Nva Norvaline; Dpm 2,2'-Diaminopimelic acid; Nle Norleucine; Dpr 2,3-Diaminopropionic acid; Orn Omithine EtGly N-Ethylglycine.

In certain embodiments the proteinaceous composition comprises at least one protein, polypeptide or peptide, such as vRNAP or mini-vRNAP. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (ncbi.nlm.nih.gov/). The coding regions for these known genes may be amplified and/or expressed using the techniques disclosed herein or as would be known to those of ordinary skill in the art. Alternatively, various commercial preparations of proteins, polypeptides and peptides are known to those of skill in the art.

In certain embodiments, a proteinaceous compound may be purified. Generally, "purified" will refer to a specific or desired protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody. A mini-vRNAP antibody may comprise all or part of an antibody that specifically recognizes mini-vRNAP. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, $F(ab')_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that the high viscosity will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide which is derived or obtained from an organism. Organisms that may be used include, but are not limited to, a bovine, a reptilian, an amphibian, a piscine, a rodent, an avian, a canine, a feline, a fungal, a plant, or a prokaryotic organism, with a selected animal or human subject being preferred. The "autologous protein, polypeptide or peptide" may then be used as a component of a composition intended for application to the selected animal or human subject. In certain aspects, the autologous proteins or peptides are prepared, for example from whole plasma of the selected donor. The plasma is placed in tubes and placed in a freezer at about −80° C. for at least about 12 hours and then centrifuged at about 12,000 times g for about 15 minutes to obtain the precipitate. The precipitate, such as fibrinogen may be stored for up to about one year.

VI. Protein Purification

To prepare a composition comprising a vRNAP or mini-vRNAP, it is desirable to purify the components or variants thereof Purification of the mini-vRNAP (SEQ ID NO:4) can be done in two step using affinity columns. The mini-vRNAP of SEQ ID NO:6 has been modified to comprise a His tag such that purification can be done in a single step when using metal affinity columns such as those which employ nickel, cobalt or zinc. The full length vRNAP of SEQ ID NO:15 is also His tagged for purification.

According to one embodiment of the present invention, purification of a peptide comprising vRNAP can be utilized ultimately to operatively link this domain with a selective agent. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is affinity chromatography.

A tag may be used for protein or peptide purification and detection such as hexahistidine (6-His, HHHHHH) (SEQ ID NO:46), FLAG (DYKDDDDK) (SEQ ID NO:47), hemagglutinin (HA, YPYDVPDYA) (SEQ ID NO:48) and c-myc (EQKLISEEDL) (SEQ ID NO:49). Other tags also have been generated, most of which are very small, comprising only a few amino acids, and are therefore likely to have little to no effect on the conformation of the mature protein or peptide. These small tags do not require any special conformation to be recognized by antibodies. Systems for protein purification using these tags include NTA resin (6-His) or the FLAG fusion system marketed by IBI (FLAG) where the fusion protein is affinity-purified on an antibody column.

Certain aspects of the present invention concern the purification, and in particular embodiments, the substantial purification, of an encoded protein or peptide, such as a vRNAP. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition, such as the vRNAP, that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification" number. The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

Ion exchange chromatography is a preferred method of separation. Using columns resins such as the metal affinity chromatography resin TALON are also preferred. TALON resin has an enhanced resolving power for polyhistidine-tagged proteins. This results in greater purity with less effort. TALON employs cobalt, an electropositive metal with a remarkably high affinity for polyhistidine-tagged proteins and a low affinity for other proteins. Often, no discernible binding of host proteins occurs and a separate wash step is not required. The binding properties of cobalt allow protein elution under mild pH conditions that protect protein integrity.

Further concentration of the proteins can be done on an anion exchange column, such as the MONOQ column, a high resolution, anion exchange column. This column works at pressures less than 5 MPa, has a high capacity and gives very high chromatographic resolution.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography, a particularly efficient method of purifying peptides, is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature). Tags, as described herein above, can be used in affinity chromatography.

The matrix should be a substance that itself does not adsorb molecules to any significant extent and that has a broad range of chemical, physical and thermal stability. The ligand should be coupled in such a way as to not affect its binding properties. The ligand also should provide relatively tight binding, and it should be possible to elute the substance without destroying the sample or the ligand. One of the most common forms of affinity chromatography is immunoaffinity chromatography. The generation of antibodies that would be suitable for use in accordance with the present invention is discussed below.

An affinity column may have an N4 promoter which the vRNAP or mini-vRNAP proteins recognize attached to a matrix. This column would be suitable for use for the purification of polymerases with no additional tags such as histidine tags.

VII. Separation, Quantitation, and Identification Methods

Following synthesis of the RNA, it may be desirable to separate the amplification products of several different lengths from each other and from the template and the excess primer.

a. Gel Electrophoresis

In one embodiment, amplification products are separated by agarose, agarose-acrylamide or polyacrylamide gel electrophoresis using standard methods.

b. Chromatographic Techniques

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography. In yet another alternative, labeled cDNA products, such as biotin-labeled or antigen-labeled, can be captured with beads bearing avidin or antibody, respectively.

c. Microfluidic Techniques

Microfluidic techniques include separation on a platform such as microcapillaries, designed by ACLARA BioSciences Inc., or the LabChip™ "liquid integrated circuits" made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White reports an integrated micro-PCR apparatus for collection and amplification of nucleic acids from a specimen. U.S. Pat. Nos. 5,304,487 to Wilding et al., and 5,296,375 to Kricka et al., discuss devices for collection and analysis of cell containing samples and are incorporated herein by reference. U.S. Pat. No. 5,856,174 describes an apparatus which combines the various processing and analytical operations involved in nucleic acid analysis and is incorporated herein by reference.

d. Capillary Electrophoresis

In some embodiments, it may be desirable to provide an additional, or alternative means for analyzing the amplified genes. In these embodiments, micro capillary arrays are contemplated to be used for the analysis.

Microcapillary array electrophoresis generally involves the use of a thin capillary or channel which may or may not be filled with a particular separation medium. Electrophoresis of a sample through the capillary provides a size based separation profile for the sample. Microcapillary array electrophoresis generally provides a rapid method for size-based sequencing, PCR product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Typically, these methods comprise photolithographic etching of micron scale channels on a silica, silicon or other crystalline substrate or chip, and can be readily adapted for use in the present invention. In some embodiments, the capillary arrays may be fabricated from the same polymeric materials described for the fabrication of the body of the device, using the injection molding techniques described herein.

Rectangular capillaries are known as an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea or the like, to denature nucleic acids in the sample.

e. Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods known in the art can be found summarized in Methods in Enzymology, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry).

Two ionization/desorption techniques are electrospray/ionspray (ES) and matrix-assisted laser desorption/ionization (MALDI). As a mass analyzer, a quadrupole is most frequently used. The determination of molecular weights in femtomole amounts of sample is very accurate due to the presence of multiple ion peaks, which all could be used for the mass calculation.

MALDI mass spectrometry, in contrast, can be particularly attractive when a time-of-flight (TOF) configuration is used as a mass analyzer. Since, in most cases, no multiple molecular ion peaks are produced with this technique, the mass spectra, in principle, look simpler compared to ES mass spectrometry. DNA molecules up to a molecular weight of 410,000 Daltons could be desorbed and volatilized. More recently, the use of infra red lasers (IR) in this technique (as opposed to UV-lasers) has been shown to provide mass spectra of larger nucleic acids such as synthetic DNA, restriction enzyme fragments of plasmid DNA, and RNA transcripts up to a size of 2180 nucleotides.

In Japanese Patent No. 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg.

f. Energy Transfer

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed. The distance between donor and acceptor dyes at which energy transfer efficiency is 50% is referred to as the Forster distance ($R_O$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label.

Homogeneous methods employing energy transfer or other mechanisms of fluorescence quenching for detection of nucleic acid amplification have also been described. Higuchi et al., Biotechnology 10:413-417 (1992) disclose methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target.

Signal primers or detector probes which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins.

Many donor/acceptor dye pairs known in the art and may be used in the present invention. These include, for example, fluorescein isothiocyanate (FITC)/tetramethylrhodamine isothiocyanate (TRITC), FITC/TEXAS RED (Molecular Probes), FITC/N-hydroxysuccinimidyl I-pyrenebutyrate (pYB), FITC/eosin isothiocyanate (EITC), N-hydroxysuccinimidyl I-pyrenesulfonate (pYS)/FITC, FITC Rhodamine X, FITC/tetramethylrhodamine (TAMRA), and others. The selection of a particular donor/acceptor fluorophore pair is not critical. For energy transfer quenching mechanisms, it is only necessary that the emission wavelengths of the donor fluorophore overlap the excitation wavelengths of the acceptor, i.e., there must be sufficient spectral overlap between the two dyes to allow efficient energy transfer, charge transfer or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl)aminonaphthalene (EDANS). Any dye pair which produces fluorescence quenching in the detector nucleic acids of the invention are suitable for use in the methods of the invention, regardless of the mechanism by which quenching occurs. Terminal and internal labeling methods are both known in the art and may be routinely used to link the donor and acceptor dyes at their respective sites in the detector nucleic acid.

g. In Vitro Studies

The synthesized RNA of the current invention may be used for in vitro studies of spliceosome assembly, splicing reactions, or antisense experiments.

The spliceosome is a large, multisubunit complex consisting of small, nuclear ribonucleoprotein particles (snRNPs). There are a total of 5 snRNAs: U1, U2, U4, U5, and U6 which are small and uridine rich. Each snRNP has 1 or 2 of these RNAs. In addition to catalyzing the splicing reaction, the spliceosome retains intermediate products, positions splice sites for precise joining of the exons, and prevents exons from diffusing away after cleavage and before ligation. Spliceosome catalysis involves concerted cleavage/ligation reactions in which the 2'-OH of branch site A attacks the 5' splice site to form a 2'-5' phosphodiester bond with the first nucleotide of the intron. The resulting 3'-OH at the end of the 5' exon attacks the 3' splice site to release the lariat form of the intron and join the two exons together with a normal 3'-5' phosphodiester bond. At least 50 different proteins are involved in spliceosome assembly and function. In the group I and group II introns, splicing is improved (in velocity and accuracy) by protein factors.

VIII. Methods for Detecting a Target Sequence by Target-Dependent Transcription

In one aspect, the present invention comprises novel methods, compositions and kits for amplifying, detecting and quantifying one or multiple target nucleic acid sequences in a sample, including target sequences that differ by as little as one nucleotide. The target sequence or target sequences can comprise one or more target nucleic acids comprising either RNA or DNA from any source. The methods can also be used to detect an analyte of any type for which an analyte-binding substance (such as, but not limited to, an antibody) can be obtained, provided that a tag comprising a target nucleic acid sequence is coupled or linked to said analyte-binding substance. The method is useful for detecting specific nucleic acids or analytes in a sample with high specificity and sensitivity. The method also has an inherently low level of background signal. Preferred embodiments of the method consist of an annealing process, a DNA ligation process, an optional DNA polymerase extension process, a transcription process, and, optionally, a detection process. The DNA ligation joins a probe which has a first target-complementary sequence and a single-stranded transcription promoter for an RNA polymerase that lacks helicase-like activity to another probe or another section of the same probe which has a second target-complementary sequence and, optionally, a signal sequence. This step is dependent on hybridization of the target-complementary probe sequences to a target sequence and forms a transcription substrate for in vitro transcription of the second target-complementary sequence and the signal sequence, if a signal sequence is present, in an amount that is proportional to the amount of target sequence in the sample.

In vitro transcription amplifies the target-complementary sequence and the signal sequence, if present, in proportion to the amount of transcription substrate formed, permitting quantification of the amount of target sequence present. The invention comprises use of a novel RNA polymerase that lacks helicase-like activity and that synthesizes a transcription product using a single-stranded transcription promoter and a single-stranded DNA template which is operably or functionally joined or linked to the promoter using a method of the invention. Joining of the promoter to the transcription template to obtain a transcription substrate is target-dependent because joining by ligation only occurs if the different target-complementary sequences comprising the target probes are adjacent to or abut each when they anneal to a target sequence, if the target sequence is present in the sample. The methods of the invention are therefore referred to herein as "target-dependent transcription." A preferred RNA polymerase of the invention is an N4 mini-vRNAP enzyme or a mutant form of an N4 mini-vRNAP enzyme. A preferred RNA polymerase lacks a his tag or other tag sequence and comprises a transcriptionally active 1,106-amino acid domain of the N4 vRNAP (herein designated "mini-vRNAP") which corresponds to amino acids 998-2103 of N4 vRNAP. The RNA polymerase preferentially has the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8. The vRNAP and mini-vRNA polymerase transcribe nucleic acid operatively linked to an N4 promoter such as a P2 promoter of SEQ ID NO:16, SEQ ID NO:19, SEQ ID NO:27, SEQ ID NO:28 or SEQ ID NO:29. The promoter of SEQ ID NO:16 or SEQ ID NO:28 is preferred.

The amount of transcription product obtained in a given reaction time can also be increased using a coupled rolling circle replication and rolling circle transcription reaction. The rolling circle replication reaction uses a "target sequence amplification probe" (or a "TSA probe") having target-complementary sequences at each end and an intervening sequence with a primer binding site. The TSA probe anneals to the target sequence, if present in the sample, and is ligated to form a "TSA circle." After annealing a primer to the primer binding site, rolling circle replication of the TSA circle by a strand-displacing DNA polymerase under strand-displacing polymerization conditions generates multiple tandem copies the target sequence, which serve as annealing and ligation sites for a bipartite target probe. After ligation of the bipartite target probe to form a circular transcription substrate, rolling circle transcription with an RNA polymerase of the present invention generates transcription products comprising multiple copies of the target sequence. A preferred RNA polymerase of the invention is an N4 mini-vRNAP enzyme or a mutant form of an N4 mini-vRNAP enzyme. A preferred RNA polymerase lacks a his tag or other tag sequence and comprises a transcriptionally active 1,106-amino acid domain of the N4 vRNAP (herein designated "mini-vRNAP") which corresponds to amino acids 998-2103 of N4 vRNAP. The RNA polymerase preferentially has the amino sequence set forth in SEQ ID NO:4 or SEQ ID NO:6 or a mutant of the polymerase of SEQ ID NO:4 or SEQ ID NO:6, such as a mutant with a mutation at position number Y678 or the polymerase of SEQ ID NO:8. The vRNAP and mini-vRNA polymerase transcribe nucleic acid operatively linked to an N4 promoter such as a P2 promoter of SEQ ID NO:16, SEQ ID NO:19, SEQ ID NO:27, SEQ ID NO:28 or SEQ ID NO:29. The promoter of SEQ ID NO:16 or SEQ ID NO:28 is preferred.

Figure 26:
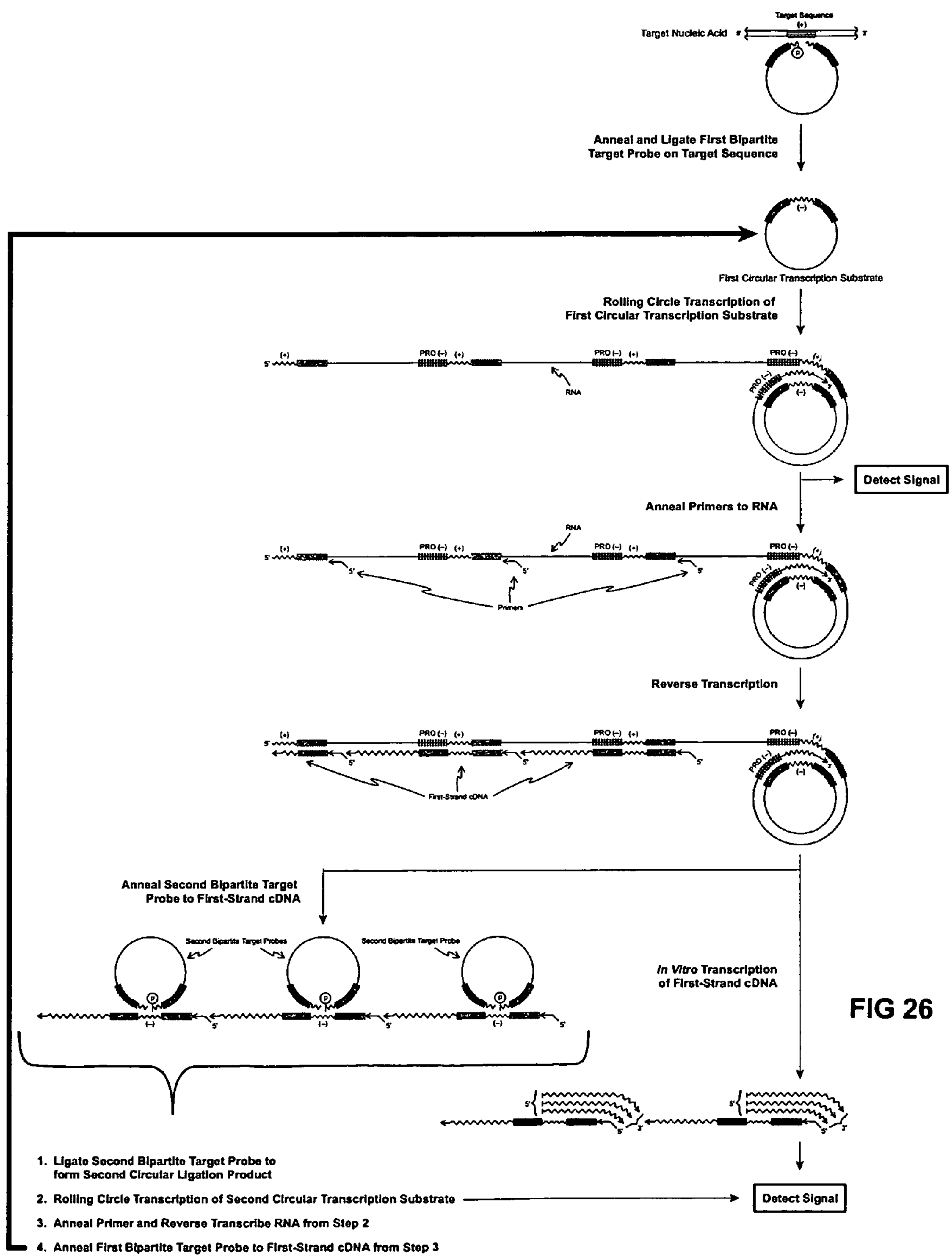
FIG. 26—A method for obtaining additional amplification of transcription products. The method uses two bipartite target probes comprising single-stranded promoters to generate circular transcription substrates for rolling circle transcription, and reverse transcription of the resulting RNA products to make additional copies of sense or anti-sense target sequences for annealing and ligation of additional first or second bipartite target probes, respectively, which in turn are used to transcribe more RNA, which is detected.

Yet another method for obtaining additional amplification of the target sequence is illustrated schematically in FIG. 26. This method generates annealing and ligation sites for a second bipartite target probe by reverse transcription of the transcription products obtained following annealing of a first bipartite target probe to a target sequence in the sample, ligation of the bipartite target probe, and in vitro transcription of the resulting circular transcription substrate.

Following in vitro transcription, RNA complementary to target-complementary probe sequences can be detected and quantified using any of the conventional detection systems for nucleic acids such as detection of fluorescent labels, enzyme-linked detection systems, antibody-mediated label detection, and detection of radioactive labels. Alternatively, the signal sequence in the transcription substrate can comprise a sequence that is amplifiable and/or detectable by another method. By way of example, but not of limitation, in some embodiments of the invention a signal sequence that encodes a substrate for an enzyme, such as, but not limited to, Q-beta replicase is used. In the latter embodiment, in vitro transcription of the ssDNA transcription substrate results in synthesis of a substrate for a replicase, which is used to rapidly and linearly amplify the signal further. Since the amplified product is directly proportional to the amount of target sequence present, quantitative measurements reliably represent the amount of a target sequence in a sample. Major advantages of this method are that the ligation process, or an optional DNA polymerase extension, can be manipulated to obtain single-nucleotide allelic discrimination, the transcription process is isothermal, and signals are strictly quantitative because the transcription reaction is linear and is catalyzed by a highly processive enzyme, and signal amplification can be obtained which is also linear and greatly enhances the sensitivity of an assay or method. In multiplex assays, the transcription promoter sequence used for in vitro transcription can be the same for all target probes.

A. Nucleic Acids and Polynucleotides of This Aspect of the Invention

A "nucleic acid" or "polynucleotide" of the invention is a polymer molecule comprising a series of "mononucleosides," also referred to as "nucleosides," in which the 3'-position of the pentose sugar of one nucleoside is linked by an internucleoside linkage, such as, but not limited to, a phosphodiester bond, to the 5'-position of the pentose sugar of the next nucleoside. A nucleoside linked to a phosphate group is referred to as a "nucleotide." The nucleotide that is linked to the 5'-position of the next nucleotide in the series is referred to as "5'- of," or "upstream of," or the "5'-nucleotide" and the nucleotide that is linked to the 3'-position of said 5' or upstream nucleotide is referred to as "3'- of," or "downstream of," or the "3'-nucleotide." When two different, non-overlapping polynucleotides or oligonucleotides hybridize or anneal to different regions of the same linear complementary nucleic acid sequence, and the 3'-end of one polynucleotide or oligonucleotide points towards the 5'-end of the other, the former may be called the "upstream" polynucleotide or oligonucleotide and the latter the "downstream" polynucleotide or oligonucleotide.

The terms "3'- of" and "5'- of" are used herein to refer to the position or orientation of a particular nucleic acid sequence or genetic element encoded by a sequence, such as, but not limited to, a transcription promoter, relative to other sequences or genetic elements.

A "portion" or "region," used interchangeably herein, of a polynucleotide or oligonucleotide is a contiguous sequence of 2 or more bases. In other embodiments, a region or portion is at least about any of 3-5, 5-10, 10-15, 15-20, 20-25, 25-50, 50-100, 100-200, 200-400, 400-600, 600-800, 800-1000, 1000-1500, or greater than 1500 contiguous nucleotides. As described above, a portion or region can be 5'- of or 3'- of another portion or genetic element or sequence. A portion or region can also comprise a 5'-end portion or a 3'-end portion, meaning it comprises a 5'-end or a 3'-end, respectively, or it can be a portion or region that is between a 5'-portion and a 3'-portion. Although a circular oligonucleotide or polynucleotide does not have an end or an end portion, it can have portions or regions that are 5'- of or 3'- of another portion or region or sequence or genetic element, which permits orientation of one portion or region or sequence or genetic element with respect to another within the circular nucleic acid strand.

Discussions of nucleic acid structure and synthesis are simplified and clarified by adopting terms to name the two complementary strands of a nucleic acid duplex. Traditionally, the strand encoding the sequences used to produce proteins or structural RNAs is designated as the "plus" or "sense" strand, and its complement is designated as the "minus" or "anti-sense" strand. It is now known that in many cases, both strands are functional, and the assignment of the designation "plus" to one and "minus" to the other must then be arbitrary. Nevertheless, the terms are useful for designating the sequence orientation of nucleic acids or for designating the specific mRNA sequences transcribed and/or expressed in a cell.

Those with knowledge in the art will understand these terms in the context of nucleic acid chemistry and structure, particularly related to the 3'- and 5'-positions of sugar moieties of canonical nucleic acid nucleotides, and in the context of enzymatic synthesis of nucleic acids in a 5'-to-3' direction. Since most descriptions of embodiments of the present invention are referring to single-stranded nucleic acids, in most cases herein the inventors use the terms "3'- of" and "5'- of" to refer to the relative position or orientation of a particular nucleic acid sequence or genetic element encoded by a sequence that is located on the same nucleic acid strand. By way of example, a transcription promoter that is "3'- of the target sequence" refers to the position of a promoter relative to a target sequence on the same strand. Those with knowledge in the art will understand that, if a first nucleic acid sequence is 3'- of a second sequence within one strand, the complement of the first sequence will be 5'- of the complement of the second sequence in the complementary strand. The description of the invention will be understood with respect to the relative position and orientation of a sequence or genetic element within a particular strand, unless explicitly stated to the contrary.

The pentose sugar of the nucleic acid can be ribose, in which case, the nucleic acid or polynucleotide is referred to as "RNA," or it can be 2'-deoxyribose, in which case, the nucleic acid or polynucleotide is referred to as "DNA." Alternatively, the nucleic acid can be composed of both DNA and RNA mononucleotides. In both RNA and DNA, each pentose sugar is covalently linked to one of four common "nucleic acid bases" (each also referred to as a "base"). Three of the predominant naturally-occurring bases that are linked to the sugars (adenine, cytidine and guanine) are common for both DNA and RNA, while one base is different; DNA has the additional base thymine, while RNA has the additional base uridine. Those in the art commonly think of a small polynucleotide as an "oligonucleotide." The term "oligonucleotide" as used herein is defined as a molecule comprised of two or more deoxyribonucleotides or ribonucleotides, preferably about 10 to 200 nucleotides, but there is no defined limit to the length of an oligonucleotide. The exact size will depend on many factors, which in turn depends on the ultimate function or use of the oligonucleotide.

Also, for a variety of reasons, a nucleic acid or polynucleotide of the invention may comprise one or more modified nucleic acid bases, sugar moieties, or internucleoside linkages. By way of example, some reasons for using nucleic acids or polynucleotides that contain modified bases, sugar moieties, or internucleoside linkages include, but are not limited to: (1) modification of the $T_m$; (2) changing the susceptibility of the polynucleotide to one or more nucleases; (3) providing a moiety for attachment of a label; (4) providing a label or a quencher for a label; or (5) providing a moiety, such as biotin, for attaching to another molecule which is in solution or bound to a surface.

In order to accomplish these or other goals, the invention does not limit the composition of the nucleic acids or polynucleotides of the invention including any target probes, detection probes, such as, but not limited to molecular beacons (U.S. Pat. Nos. 5,925,517 and 6,103,476 of Tyagi et al. and U.S. Pat. No. 6,461,817 of Alland et al., all of which are incorporated herein by reference); capture probes, oligonucleotides, or other nucleic acids used or detected in the assays or methods, so long as each said nucleic acid functions for its intended use. By way of example, but not of limitation, the nucleic acid bases in the mononucleotides may comprise guanine, adenine, uracil, thymine, or cytidine, or alternatively, one or more of the nucleic acid bases may comprise xanthine, allylamino-uracil, hypoxanthine, 2-aminoadenine, 6-methyl and other alkyl adenines, 2-propyl and other alkyl adenines, 5-halouracil, 5-halo cytosine, 5-propynyl uracil, 5-propynyl cytosine, 7-deazaadenine, 7-deazaguanine, 7-deaza-7-methyl-adenine, 7-deaza-7-methyl-guanine, 7-deaza-7-propynyl-adenine, 7-deaza-7-propynyl-guanine and other 7-deaza-7-alkyl or 7-aryl purines, N2-alkyl-guanine, N2-alkyl-2-amino-adenine, purine 6-aza uracil, 6-aza cytosine and 6-aza thymine, 5-uracil (pseudo uracil), 4-thiouracil, 8-halo adenine, 8-amino-adenine, 8-thiol adenine, 8-thiolalkyl adenines, 8-hydroxyl adenine and other 8-substituted adenines and 8-halo guanines, 8-amino-guanine, 8-thiol guanine, 8-thiolalkyl guanines, 8-hydroxyl guanine and other 8-substituted guanines, other aza and deaza uracils, other aza and deaza thymidines, other aza and deaza cytosine, aza and deaza adenines, aza and deaza guanines or 5-trifluoromethyl uracil and 5-trifluorocytosine. Still further, they may comprise a nucleic acid base that is derivatized with a biotin moiety, a digoxigenin moiety, a fluorescent or chemiluminescent moiety, a quenching moiety or some other moiety. The invention is not limited to the nucleic acid bases listed; this list is given to show the broad range of bases which may be used for a particular purpose in a method.

When a molecule comprising both a nucleic acid and a peptide nucleic acid (PNA) is used in the invention, modified bases can be used in one or both parts. For example, binding affinity can be increased by the use of certain modified bases in both the nucleotide subunits that make up the 2'-deoxyoligonucleotides of the invention and in the peptide nucleic acid subunits. Such modified bases may include 5-propynylpyrimidines, 6-azapyrimidines, and N-2, N-6 and O-6 substituted purines including 2-aminopropyladenine. Other modified pyrimidine and purine base are also expected to increase the binding affinity of macromolecules to a complementary strand of nucleic acid.

With respect to nucleic acids or polynucleotides of the invention, one or more of the sugar moieties can comprise ribose or 2'-deoxyribose, or alternatively, one or more of the sugar moieties can be some other sugar moiety, such as, but not limited to, 2'-fluoro-2'-deoxyribose or 2'-O-methyl-ribose, which provide resistance to some nucleases.

The internucleoside linkages of nucleic acids or polynucleotides of the invention can be phosphodiester linkages, or alternatively, one or more of the internucleoside linkages can comprise modified linkages, such as, but not limited to, phosphorothioate, phosphorodithioate, phosphoroselenoate, or phosphorodiselenoate linkages, which are resistant to some nucleases.

A variety of methods are known in the art for making nucleic acids having a particular sequence or that contain particular nucleic acid bases, sugars, internucleoside linkages, chemical moieties, and other compositions and characteristics. Any one or any combination of these methods can be used to make a nucleic acid, polynucleotide, or oligonucleotide for the present invention. The methods include, but are not limited to: (1) chemical synthesis (usually, but not always, using a nucleic acid synthesizer instrument); (2) post-synthesis chemical modification or derivatization; (3) cloning of a naturally occurring or synthetic nucleic acid in a nucleic acid cloning vector (e.g., see Sambrook, et al., Molecular Cloning: A Laboratory Approach Second Edition, 1989, Cold Spring Harbor Laboratory Press, Cold Spring Harbor, N.Y. and Sambrook and Russell, Molecular Cloning, A Laboratory Manual, Third Edition, 2001, Cold Spring Harbor Laboratory Press,) such as, but not limited to a plasmid, bacteriophage (e.g., M13 or lamba), phagemid, cosmid, fosmid, YAC, or BAC cloning vector, including vectors for producing single-stranded DNA; (4) primer extension using an enzyme with DNA template-dependent DNA polymerase activity, such as, but not limited to, Klenow, T4, T7, rBst, Taq, Tfl, or Tth DNA polymerases, including mutated, truncated (e.g., exo-minus), or chemically-modified forms of such enzymes; (5) PCR (e.g., see Dieffenbach, C. W., and Dveksler, eds., PCR Primer: A Laboratory Manual, 1995, Cold Spring Harbor Laboratory Press, Cold Spring Harbor, N.Y.); (6) reverse transcription (including both isothermal synthesis and RT-PCR) using an enzyme with reverse transcriptase activity, such as, but not limited to, reverse transcriptases derived from avian myeloblastosis virus (AMV), Maloney murine leukemia virus (MMLV), Bacillus stearothermophilis (rBst), or *Thermus thermophilus* (Tth); (7) in vitro transcription using an enzyme with RNA polymerase activity, such as, but not limited to, SP6, T3, or T7 RNA polymerase, Tth RNA polymerase, *E. coli* RNA polymerase, or SP6 or T7 R&DNA™

Polymerase (Epicentre Technologies, Madison, Wis., USA), or another enzyme; (8) use of restriction enzymes and/or modifying enzymes, including, but not limited to exo- or endonucleases, kinases, ligases, phosphatases, methylases, glycosylases, terminal transferases, including kits containing such modifying enzymes and other reagents for making particular modifications in nucleic acids; (9) use of polynucleotide phosphorylases to make new randomized nucleic acids; (10) other compositions, such as, but not limited to, a ribozyme ligase to join RNA molecules; and/or (11) any combination of any of the above or other techniques known in the art. Oligonucleotides and polynucleotides, including chimeric (i.e., composite) molecules and oligonucleotides with modified bases, sugars, or internucleoside linkages are commercially available (e.g., TriLink Biotechnologies, San Diego, Calif., USA or Integrated DNA Technologies, Coralville, Iowa).

The terms "hybridize" or "anneal" and "hybridization" or "annealing" refer to the formation of complexes between nucleotide sequences on opposite or complementary nucleic acid strands that are sufficiently complementary to form complexes via Watson-Crick base pairing. Where a target probe, primer, transcription substrate, or another oligonucleotide or polynucleotide "hybridizes" or "anneals" with target nucleic acid or a template or another oligonucleotide or polynucleotide, such complexes or "hybrids" are sufficiently stable to serve the function required for ligation, DNA polymerase extension, or other function for which it is intended.

With respect to nucleic acid synthesis, a "template" is a nucleic acid molecule that is being copied by a nucleic acid polymerase. The synthesized copy is complementary to the template. Both RNA and DNA are always synthesized in the 5'-to-3' direction and the two strands of a nucleic acid duplex always are aligned so that the 5'-ends of the two strands are at opposite ends of the duplex (and, by necessity, so then are the 3'-ends). In general, DNA polymerases, including both DNA-dependent (i.e, having a DNA template) and RNA-dependent (i.e., having an RNA template, which enzyme is also called a "reverse transcriptase") DNA polymerases, require a primer for synthesis of DNA. In general, RNA polymerases do not require a primer for RNA synthesis.

With respect to ligation, a "template" or a "ligation template" or a "template for ligation" is a nucleic acid molecule to which two or more complementary oligonucleotides, target probes, or other nucleic acids that are to be ligated anneal or hybridize prior to ligation, wherein the ends of said nucleic acid molecules that are to be ligated are adjacent to each other when annealed to the ligation template.

B. Samples, Analytes and Target Nucleic Acids of This Aspect of the Invention A "sample" or a "biological sample" according to the present invention is used in its broadest sense. A sample is any specimen that is collected from or is associated with a biological or environmental source, or which comprises or contains biological material, whether in whole or in part, and whether living or dead. In some embodiments of the invention a sample can also be chemically synthesized or derived in the laboratory, rather than from a natural source.

Biological samples may be plant or animal, including human, fluid (e.g., blood or blood fractions, urine, saliva, sputum, cerebral spinal fluid, pleural fluid, milk, lymph, or semen), swabs (e.g., buccal or cervical swabs), solid (e.g., stool), microbial cultures (e.g., plate or liquid cultures of bacteria, fungi, parasites, protozoans, or viruses), or cells or tissue (e.g., fresh or paraffin-embedded tissue sections, hair follicles, mouse tail snips, leaves, or parts of human, animal, plant, microbial, viral, or other cells, tissues, organs or whole organisms, including subcellular fractions or cell extracts), as well as liquid and solid food and feed products and ingredients such as dairy items, vegetables, meat and meat by-products, and waste. Biological samples may be obtained from all of the various families of domestic plants or animals, as well as wild animals or plants.

Environmental samples include environmental material such as surface matter, soil, water, air, or industrial samples, as well as samples obtained from food and dairy processing instruments, apparatus, equipment, utensils, disposable and non-disposable items. These examples are not to be construed as limiting the sample types applicable to the present invention.

In short, a sample comprises a specimen from any source that contains or may contain a target nucleic acid.

A sample on which the assay method of the invention is carried out can be a raw specimen of biological material, such as serum or other body fluid, tissue culture medium or food material. More typically, the method is carried out on a sample that is a processed specimen, derived from a raw specimen by various treatments to remove materials that would interfere with detection of a target nucleic acid or an amplification product thereof. Methods for processing raw samples to obtain a sample more suitable for the assay methods of the invention are well known in the art.

An "analyte" means a substance or a part of a substance whose presence, concentration or amount in a sample is being determined in an assay. An analyte is sometimes referred to as a "target substance" or a "target molecule" or a "target analyte" of an assay. An analyte may also be referred to more specifically. In some embodiments, the present invention pertains to analytes that are target nucleic acid sequences that comprise or are in a "target nucleic acid" or a "target polynucleotide" or a "target oligonucleotide." A composition, kit, or method of the invention can be used for an "analyte-specific reagent" to detect an analyte comprising a target nucleic acid sequence in a sample.

With respect to the present invention, an analyte is often associated with a biological entity that is present in a sample if and only if the analyte is present. Such biological entities include viroids (analyte is, e.g., a segment of a viroid nucleic acid sequence); viruses (analyte is, e.g., a sequence in the viral genome); other microorganisms (analyte is, e.g., a sequence in the genome or the RNA of the microorganism); abnormal cells, such as cancer cells (analyte is, e.g., a sequence in an oncogene); or an abnormal gene (analyte is, e.g., a sequence in a gene segment that includes the altered bases which render the gene abnormal or in a messenger RNA segment that includes altered bases as a result of having been transcribed from the abnormal gene).

However, in some embodiments of the invention an analyte can be chemically synthesized sequence or derived in the laboratory for a particular purpose, rather than from a natural source. By way of example, but not of limitation, the analyte can be a chemically synthesized oligonucleotide tag that comprises a target sequence that is covalently or non-covalently attached to an analyte-binding substance such as an antibody in order to indirectly detect another analyte in the sample which is bound by the analyte-binding substance. Alternatively, as discussed in greater detail later in the specification, the oligonucleotide tag that is attached or joined to an analyte-binding substance can be referred to as a "target sequence" or a "target sequence tag," even though it is used to detect and/or quantify a protein, lipid, carbohydrate or another analyte by detecting the analyte-binding substance to which the target sequence is joined.

From the description of analytes, it is apparent that the present invention has widespread applicability, including in applications in which nucleic acid probe hybridization assays or immunoassays are often employed. Thus, among other applications, the invention is useful in diagnosing diseases in plants and animals, including humans; and in testing products, such as food, blood, and tissue cultures, for contaminants.

A "target" of the present invention is a biological organism or material that is the reason or basis for which a diagnostic assay is performed. By way of example, but not of limitation, an assay of the present invention may be performed to detect a target that is a virus which is indicative of a present disease or a risk of future disease (e.g., HIV which is believed to result in AIDS), or a target that is a gene which is indicative of antibiotic resistance (e.g., an antibiotic resistance gene in an infectious pathogenic bacterium), or a target that is a gene which, if absent, may be indicative of disease (e.g., a deletion in an essential gene). In developing assays according to the present invention, it is important to identify target analytes that yield assay results that are sufficiently specific, accurate, and sensitive to be meaningful related to the presence or condition of the target. A target analyte that is a sequence in a "target polynucleotide" or a "target nucleic acid" comprises at least one nucleic acid molecule or portion of at least one nucleic acid molecule, whether said molecule or molecules is or are DNA, RNA, or both DNA and RNA, and wherein each said molecule has, at least in part, a defined nucleotide sequence. The target polynucleotide may also have at least partial complementarity with other molecules which can be used in an assay, such as, but not limited to, capture probes. By way of example, in one embodiment, a capture probe for this purpose is complementary to a different region of a target nucleic acid than the target sequence and may have a moiety, such as a biotin moiety, that permits immobilization of the target nucleic acid on a surface, such as a surface to which streptavidin is attached.

The target polynucleotide may be single- or double-stranded. A target sequence of the present invention may be of any length. However, it must comprise a sequence of sufficient sequence specificity and length so as to be useful for its intended purpose. By way of example, but not of limitation, a target sequence that is to be detected using target sequence-complementary target probes must have a sequence of sufficient sequence specificity and length so as remain hybridized by said target probes under assay hybridization conditions wherein sequences that are not target sequences are not hybridized. A target sequence in a target polynucleotide having sufficient sequence specificity and length for an assay of the present invention may be identified, using methods known to those skilled in the art, by comparison and analysis of nucleic acid sequences known for a target and for other sequences which may be present in the sample. For example, sequences for nucleic acids of many viruses, bacteria, humans (e.g., for genes and messenger RNA), and many other biological organisms can be searched using public or private databases, and sequence comparisons, folded structures, and hybridization melting temperatures (i.e., $T_m$'s) may be obtained using computer software known to those knowledgeable in the art.

A method of the present invention can be carried out on nucleic acid from a variety of sources, including unpurified nucleic acids, or nucleic acids purified using any appropriate method in the art, such as, but not limited to, various "spin" columns, cationic membranes and filters, or salt precipitation techniques, for which a wide variety of products are commercially available (e.g., MasterPure™ DNA & RNA Purification Kits from Epicentre Technologies, Madison, Wis., USA). Methods of the present invention can also be carried out on nucleic acids isolated from viroids, viruses or cells of a specimen and deposited onto solid supports as described by Gillespie and Spiegelman (J. Mol. Biol. 12: 829-842, 1965), including solid supports on dipsticks and the inside walls of microtiter plate wells. The method can also be carried out with nucleic acid isolated from specimens and deposited on solid support by "dot" blotting (Kafatos, et al., Nucl. Acids Res., 7: 1541-1552, 1979); White, and Bancroft, J. Biol. Chem., 257: 8569-8572, 1982); Southern blotting (Southern, E., J. Mol. Biol., 98: 503-517, 1975); "northern" blotting (Thomas, Proc. Natl. Acad. Sci. USA, 77: 5201-5205, 1980); and electroblotting (Stellwag, and Dahlberg, Nucl. Acids Res., 8: 299-317, 1980). The method can also be carried out for nucleic acids spotted on membranes, on slides, or on chips as arrays or microarrays. Nucleic acid of specimens can also be assayed by the method of the present invention applied to water phase hybridization (Britten, and Kohne, Science, 161: 527-540, 1968) and water/organic interphase hybridizations (Kohne, et al., Biochemistry, 16: 5329-5341, 1977). Water/organic interphase hybridizations have the advantage of proceeding with very rapid kinetics but are not suitable when an organic phase-soluble linking moiety, such as biotin, is joined to the nucleic acid affinity molecule.

The methods of the present invention can also be carried out on amplification products obtained by amplification of a naturally occurring target nucleic acid, provided that the target sequence in the target nucleic acid is amplified by the method used only if the target nucleic acid is present in the sample. Suitable amplification methods include, but are not limited to, PCR, RT-PCR, NASBA, TMA, 3SR, LCR, LLA, SDA (e.g., Walker et al., Nucleic Acids Res. 20:1691-1696, 1992), RCA, Multiple Displacement Amplification (Molecular Staging), ICAN.TM. or UCAN.TM.0 (TAKARA), LOOP-AMP (EIKEN), and SPIA.TM. or Ribo-SPIA.TM. (NuGEN Technologies). There are various reasons for using a nucleic acid that is a product of another amplification method as a target nucleic acid for an assay of the present invention, such as, but not limited to, for obtaining more sensitive detection of targets, greater specificity, or to decrease the time required to obtain an assay result.

The methods of the invention can also be carried out on nucleic acids isolated from specimens and deposited onto solid supports by dot-blotting, or by adsorption onto walls of microtiter plate wells or solid support materials on dipsticks, on membranes, on slides, or on chips as arrays or microarrays. The amplified target-complementary sequences of target probes of the invention can also be hybridized to oligonucleotides or nucleic acids attached to or deposited on slides, chips or other surfaces, such as, but not limited to arrays or microarrays, for detection and identification.

Still further, the methods of the invention are applicable to detecting target sequences in cellular nucleic acids in whole cells from a specimen, such as a fixed or paraffin-embedded section, or from microorganisms immobilized on a solid support, such as replica-plated bacteria or yeast. In some embodiments, the methods of the invention can be used to amplify and/or detect target nucleic acid sequences in living cells.

The invention is also not limited to detection of analytes comprising a target nucleic acid. The present invention provides assays, methods, compositions and kits for detection and quantification of an analyte of any type in a sample.

C. Target Sequences Comprising Target Nucleic Acids in a Sample or a Target Sequence Tag Joined to an Analyte-Binding Substance The term "target nucleic acid sequence" or "target sequence" refers to the particular nucleotide sequence of the target nucleic acid(s) that is/are to be detected. A "target sequence" comprises one or more sequences within one or more target nucleic acids, which target nucleic acid can be naturally occurring in a sample or a target sequence tag that is joined or attached to an analyte-binding substance.

The target nucleic acid may be either single-stranded or double-stranded and may include other sequences besides the target sequence. A target nucleic acid is sometimes referred to more specifically by the type of nucleic acid. By way of example, but not of limitation, a target nucleic acid can be a "target RNA" or an "RNA target," or a "target mRNA," or a "target DNA" or a "DNA target." Similarly, the target sequence can be referred to as "a target RNA sequence" or an "RNA target sequence", or as a "target mRNA sequence" or a "target DNA sequence," or the like. In some embodiments, the target sequence comprises one or more entire target nucleic acids. In other embodiments, which are more common, the target sequence comprises only a portion of one or more nucleic acid molecules. The term "target sequence" sometimes is also used to refer to the particular target-complementary nucleotide sequences that is/are present in the target-complementary "target probes" used in a method or assay of the invention, but more preferably, these sequences are referred to as "target-complementary sequences." The term "target sequence" refers only to that portion of the sequence of a target nucleic acid for which a complementary sequence is present in a target probe of the invention. In some embodiments of the invention, multiple target probes are used, including target probe sets that are complementary to other target sequences in a target nucleic acid, which other target sequences can be on the same or the opposite nucleic acid strand of the same target nucleic acid, or on another target nucleic acid in the sample or joined to another analyte-binding substance. In some of those embodiments, a transcription promoter is present in a target probe that is complementary to only one strand of the target sequence, and in other embodiments, a transcription promoter is present in two different target probes—one that is complementary to a target sequence on one strand, and the other that is complementary to a complementary target sequence on the other strand, wherein the transcription promoters can be the same or different in each case. In most embodiments of the invention, the target sequence in a method or assay of the invention will be a known sequence or one of a small number of known sequences, such as, but not limited to one or a small number of sequences comprising known specific mutations or single nucleotide polymorphisms (SNPs), or one of known sequences that are specific for and identify a particular organism or group of closely-related organisms. In some embodiments, wherein a method or assay of the invention is used to distinguish between two or more target sequences that differ by a single nucleotide, we sometimes refer to the specific nucleotide that differs between otherwise identical sequences as a "target nucleotide." A "target nucleotide" is part of a target sequence and comprises the nucleotide position that differs between "wild-type" or "normal" alleles and single-base "mutant" alleles, or the nucleotide that differs between different "wild-type" alleles that comprise different single-nucleotide polymorphisms (SNPs) for a particular nucleotide position in a target nucleic acid.

A target nucleic acid of the present invention comprising a target sequence to be detected and/or quantified includes nucleic acids from any source in purified or unpurified form. As discussed in greater detail herein above, target nucleic acids can be any DNA, including, but not limited to, dsDNA and ssDNA, such as mitochondrial DNA, chloroplast DNA, chromosomes, plasmids or other episomes, the genomes of bacteria, yeasts, viruses, viroids, mycoplasma, molds, or other microorganisms, or genomes of fungi, plants, animals, or humans, or target nucleic acids can be any RNA, including, but not limited to, tRNA, mRNA, rRNA, mitochondrial RNA, chloroplast RNA, or target nucleic acids can be mixtures of DNA and RNA, including, but not limited to, mixtures of the above nucleic acids or fragments thereof or DNA-RNA hybrids. The target nucleic acid can be only a minor fraction of a complex mixture such as a biological sample and can be obtained from various biological materials by procedures known in the art. As discussed herein above, methods for purification of a target nucleic, if further purification is necessary, are also known in the art.

An initial step prior to amplification of a target nucleic acid sequence is rendering the target nucleic acid single-stranded. If the target nucleic acid is a double-stranded DNA (dsDNA), the initial step is target denaturation. The denaturation step may be thermal denaturation or any other method known in the art, such as alkali treatment. Thus, in some embodiments of the invention in which the target nucleic acid in a sample is DNA, the ssDNA target sequence comprises either ssDNA that is present in a biological sample or ssDNA that is obtained by denaturation of dsDNA in the sample.

In other embodiments, the ssDNA target sequence comprises ssDNA that is obtained as a result of a "primer extension reaction," meaning an in vitro or in vivo DNA polymerization reaction using either ssDNA or denatured dsDNA that is present in the sample as a template and an oligonucleotide as a primer under DNA polymerization reaction conditions. In some embodiments the target nucleic acid in the sample or the primer extension product, or both, are made into smaller DNA fragments by methods known in the art in order to generate a DNA target sequence for use in the methods of the invention.

If a target nucleic acid is RNA, the initial step may be the synthesis of a single-stranded cDNA. Techniques for the synthesis of cDNA from RNA are known in the art. Thus, in some embodiments of the invention, which are preferred embodiments, the ssDNA target sequence comprises first-strand cDNA obtained by reverse transcription of the RNA target, meaning an in vitro reaction that utilizes an RNA present in a sample as a template and a nucleic acid oligonucleotide that is complementary to at least a portion of a sequence of the RNA template as a primer in order to synthesize ssDNA using an RNA-dependent DNA polymerase (i.e., reverse transcriptase) under reaction conditions. In some embodiments, a first-strand cDNA for use in methods of the invention is synthesized in situ in cells or tissue in a tissue section using methods such as those described in U.S. Pat. Nos. 5,168,038; 5,021,335; and 5,514,545, which are incorporated herein by reference.

D. Target Probes of the Invention; Simple Target Probes; Promoter Target Probes; Signal Target Probes; Monpartite Target Probes; Bipartite Target Probes A "target probe" of the present invention is a linear single-stranded oligonucleotide that comprises at least one sequence that is "a target-complementary sequence," meaning a sequence that is complementary to a portion of a target sequence comprising a target nucleic acid or a target sequence tag, and wherein the target probe is used in an assay or method of the invention.

The size and composition of a target-complementary sequence can vary. However, the target-complementary sequences of all target probes of the invention must be of sufficient length and nucleotide composition so as to anneal with specificity to a complementary target sequence with which it is perfectly based-paired under the conditions used in the assay or method for annealing of target probes to the target sequence and for ligation of the target probes that are annealed to the target sequence, under which conditions, target probes that are not complementary to the target sequence do not remain annealed and, if not perfectly base-paired at the ligation junction, do not ligate. In order to meet these conditions, those with knowledge in the art will understand that the length of a target-complementary sequence can vary based in part on its sequence and on the $T_m$ of that sequence, and on the temperature and other reaction conditions that are used for annealing of the target probes and ligation of the target probes on the target sequence. In general, a target-complementary sequence of a target probe will comprise at least four nucleotides if the target-complementary sequences are annealed to the target sequence and ligated at a temperature that is less than or equal to about 30 degrees C, or at least about eight nucleotides if the target-complementary sequences are annealed to the target sequence and ligated at a temperature that is greater than about 30 degrees C. Preferably, a target-complementary sequence of a target probe that is complementary to the 5'-end or to the 3'-end of the target sequence comprises about 10 to about 100 nucleotides, and most preferably, about 10 to about 50 nucleotides. However, based on this description of the invention, those with knowledge in the art will know how to empirically determine the optimal lengths of target-complementary sequences for target probes for particular target sequences, and under the particular conditions, which conditions can vary with respect to factors such as but not limited to temperature, ionic strength, concentration of co-solvents such as but not limited to betaine, or other factors.

Further, the length of one target-complementary sequence of a bipartite target probe can be different than the other. Also, the length of a target-complementary sequence of one monopartite target probe can be different than the lengths of target-complementary sequences of other monopartite target probes used in the assay or method.

In general, the sequence of a target probe that is complementary to the 3'-end of a target sequence is designed to be longer than the sequence of a target probe that is joined to a sense promoter sequence and that is complementary to the 5'-end of the target sequence, although the sequence of a target probe that is complementary to the 3'-end of the target sequence need not be longer, and can be about the same size or even shorter than the sequence that is complementary to the 5'-end of the target sequence. However, by using a target probe with a longer sequence that is complementary to the 3'-end of the target sequence, the hybridization complex between that target probe and the target sequence will be more stable so that the ability to form a ligation junction will be more dependent on the annealing of the target-complementary sequence that is joined to the sense promoter sequence and that anneals to the 5'-end of the target sequence.

It is preferable that the length of the target-complementary sequence that is joined to the sense promoter sequence comprises a sufficient number of nucleotides so as anneal to the 5'-end of the target sequence with specificity under the conditions of the assay or method, but is optimized so that transcription of said target-complementary sequence is minimized unless and until it is ligated to another target-complementary sequence that is adjacently annealed on the target sequence. Without being bound by theory, it appears that the optimal length of the target-complementary sequence that is joined to the sense promoter sequence can vary for different RNA polymerases. N4 mini-vRNAP, unlike T7 RNAP, does not have RNA:DNA hybrid unwinding activity and EcoSSB Protein appears to be responsible for displacing the RNA transcript from the template strand. The amount of EcoSSB-activated displacement appears to vary with the total length of the template strand and the length of the transcript (Davidova, E. and Rothman-Denes, Proc. Natl. Acad. Sci. USA, 100: 9250-9255, 2003). Therefore, if a target probe comprises an N4 vRNAP promoter, the length of the target-complementary sequence that is joined to the N4 promoter sequence is designed, based on the information of Davidova et al., so that a transcript made by an N4 mini-vRNAP will either not be displaced or at least, EcoSSB-activated displacement is minimized from the target-complementary sequence unless and until this sequence is ligated to an adjacent target-complementary sequence that is annealed to the target sequence to make a transcription substrate of the invention. This differs from RNA polymerases, such as T7-like RNAPs, which have RNA:DNA hybrid unwinding activity and displace both long and very short transcripts from the template. Thus, target probes can be designed for N4 mini-vRNAP enzymes so that background transcription from an unligated N4 promoter-containing target probe is less than from an unligated T7 sense promoter-containing target probe under transcription conditions in the presence of the respective cognate RNA polymerase.

If there is a gap between target-complementary sequences of a bipartite target probe or between target-complementary sequences of a promoter target probe and another monopartite target probe when annealed to the 5'-end and the 3'-end, respectively, of the target sequence, and one or more simple target probes is used in the assay or method to fill the gap, then the simple target probe(s) that is/are used to fill the gap can be of any length so long as they provide suitable ligation junctions for joining to the target-complementary sequences that are annealed to the 3'- and 5'-ends of the target sequence.

In general, target probes comprise deoxyribonucleotides having canonical nucleic acid bases and internucleoside linkages, although modified sugars, bases or internucleoside linkages can be used for a particular purpose as discussed elsewhere herein.

One type of target probe of the invention, which is called a "simple target probe," comprises a linear single-stranded oligonucleotide comprising only a sequence that is complementary to one continuous portion of a target sequence.

Another embodiment of a target probe of the invention is a "promoter target probe." A "promoter target probe" comprises a 5'-portion and a 3'-portion, wherein, said 5'-portion comprises a sequence that is complementary to the most 5'-portion of a target sequence, and said 3'-portion comprises a sequence that serves as a functional transcription promoter for an RNA polymerase that synthesizes RNA under transcription conditions using said single-stranded transcription promoter and ssDNA that is 5'- of said promoter (with respect to the same strand) as a template. Optionally, a promoter target probe can also comprise other "optional sequences" that do not comprise a target-complementary sequence or a promoter sequence, which optional sequences, if present, are 3'- of said promoter sequence in said promoter target probe. Such optional sequences in said promoter target probe can serve other functions in a method or assay of the invention.

In embodiments of the invention that result in linear transcription substrates rather than circular transcription substrates, as discussed below, another embodiment of a target probe of the invention that can be used, but which is optional, is a "signal target probe." A "signal target probe" comprises a 3'-portion and a 5'-portion, wherein, the 3'-end portion of said signal probe comprises a sequence that is complementary to the most 3'-portion of a target sequence, and said 5'-portion comprises a "signal sequence," wherein said signal sequence comprises a sequence that is detectable in some way, directly or indirectly, following transcription of said signal sequence that is joined, in the presence of a target sequence, to a target-complementary sequence and a single-stranded promoter sequence during an assay or method of the present invention. In vitro transcription of the signal sequence results in synthesis of RNA that is complementary to said signal sequence, which in turn is detectable in some way (depending on what the signal sequence encodes) in an assay or method of the invention. A signal target probe can also comprise other "optional sequences" that do not comprise the signal sequence, which sequences can serve another function in a method or assay of the invention, or they can have no function, other than to connect the signal sequence to one or more other sequences.

Figure 18:
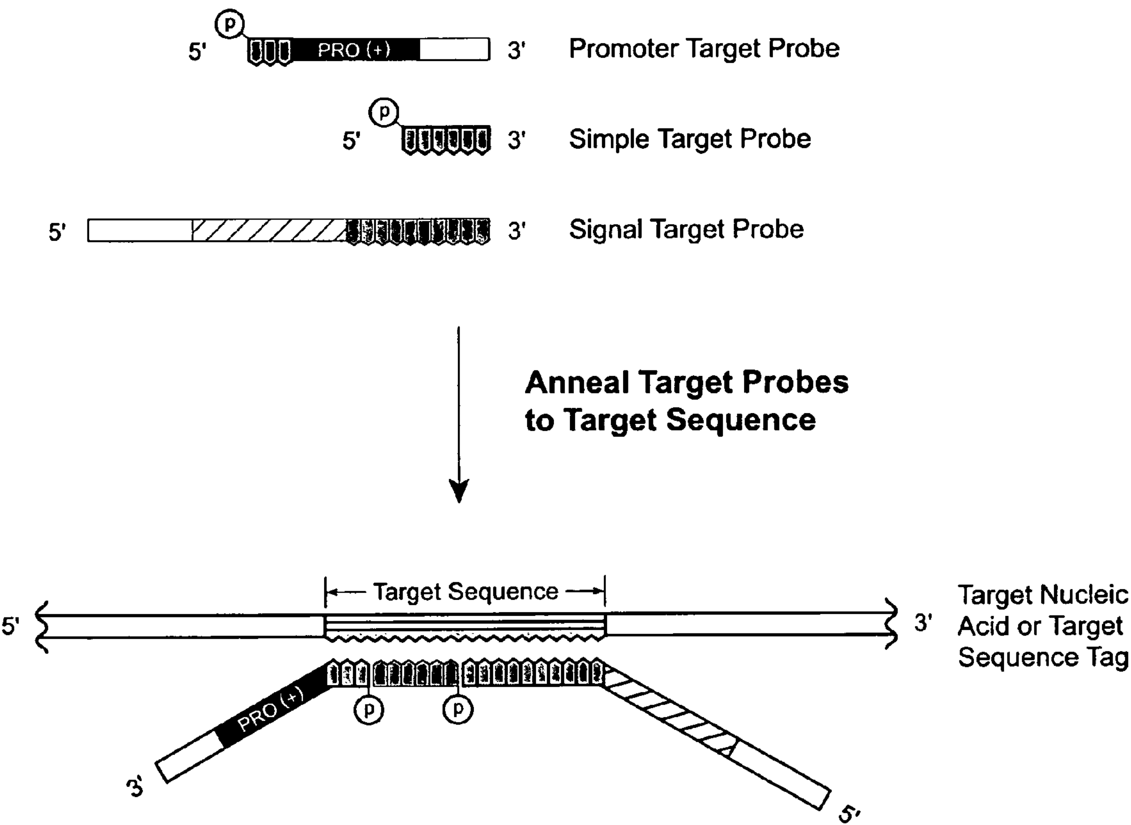
FIG. 18—Examples of different monopartite target probes of the invention.
Figure 18:
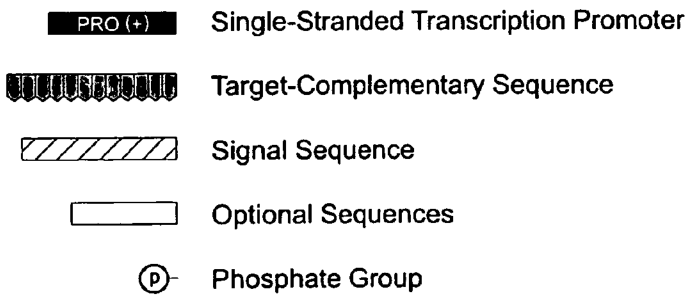

"Monopartite target probes" of the present invention are target probes that comprise only one sequence that is complementary to one portion of a target sequence. The target-complementary sequence in a monopartite target probe is not interrupted by any other sequence that is not complementary to the target sequence. Promoter target probes and signal target probes are monopartite target probes that are used to generate linear transcription substrates in some embodiments of assays and methods of the invention. Simple target probes are monopartite target probes that can be used in embodiments of the invention to generate either linear transcription substrates or circular transcription substrates, as discussed herein below. Simple target probes are monopartite target probes that are used in embodiments of the invention in order to fill at least a portion of a gap region between target-complementary sequences of other target probes that are not contiguous when annealed to a target sequence. For example, one or more simple target probes can be used in methods and assays of the invention that generate a linear transcription substrate by annealing to a target sequence between the sequences of the target sequence to which the target-complementary sequences of a promoter target probe and a signal target probe anneal. FIG. 18 illustrates monopartite target probes and shows one embodiment of how monopartite target probes are oriented when annealed to a target sequence. In still other embodiments of the invention, the target-complementary sequences of the promoter target probe and the signal target probe are contiguous or adjacent when they are annealed to a target sequence and a simple target probe is not used. In still another embodiment, the target-complementary sequences of the promoter target probe and the signal target probe are not contiguous when they are annealed to a target sequence, but rather than using a simple target probe to anneal to the gap region on the target sequence between the target-complementary sequences of the promoter target probe and the signal target probe, the gap is "filled" by DNA polymerase extension from the 3'-end of the signal target probe.

One or more simple target probes can also be used in embodiments of methods and assays of the invention that generate a circular transcription substrate, in which case, the simple target probe(s) anneal to a target sequence between the regions of the target sequence to which the target-complementary sequences at the ends of a bipartite target probe anneal.

Thus, other embodiments of the invention, which are preferred embodiments, use a bipartite target probe and generate a circular transcription substrate. A "bipartite target probe" is referred to as "bipartite" because it comprises two different target-complementary sequences, each of which is complementary to a different portion of a target sequence, which target-complementary sequences are separated within the bipartite target probe by other sequences that are not complementary to the target sequence. Thus, the target-complementary sequences in a bipartite target probe are in two parts or "bipartite." A bipartite target probe comprises a ssDNA that has a 5'-end that resembles a promoter target probe and a 3'-end that resembles either a simple target probe or a signal target probe. Thus, the 5'-end of a bipartite target probe has a sequence that is complementary to the most 5'-portion of a target sequence and, then on the same strand, 3'- of the target-complementary sequence, a functional transcription promoter for an RNA polymerase that can synthesize RNA under transcription conditions using said single-stranded transcription promoter and ssDNA that is covalently joined 5'- of said promoter as a template. The 3'-end of a bipartite target probe comprises a sequence that is complementary to the most 3'-end portion of said target sequence. If it is used, a signal sequence can be 5'- of the target-complementary sequence at the 3'-end of a bipartite target probe, although a signal sequence does not need to be contiguous with or immediately adjacent to the target-complementary sequence at the 3'-end of a bipartite target probe. Other sequences that can have other functions or that have no function other than to join the two sequences can be between a target-complementary sequence at the 3'-end and a signal sequence of a bipartite target probe. The target-complementary sequences of a bipartite target probe need not be contiguous or immediately adjacent when they are annealed to a target sequence. If the bipartite target-complementary sequences are not contiguous or immediately adjacent when they are annealed to a target sequence, then one or more simple target probes that are complementary to the portions of the target sequence between the target-complementary sequences of the bipartite target probe can be used in some embodiments of methods or assays of the invention.

Alternatively, in other embodiments of the invention in which the bipartite target-complementary sequences are not contiguous or immediately adjacent when they are annealed to a target sequence, a DNA polymerase can be used to "fill in" where there is no target probe annealed to the target sequence by primer-extending from the 3'-hydroxyl end of a bipartite target probe that is annealed to a target sequence using the target sequence as a template.

Figure 19:
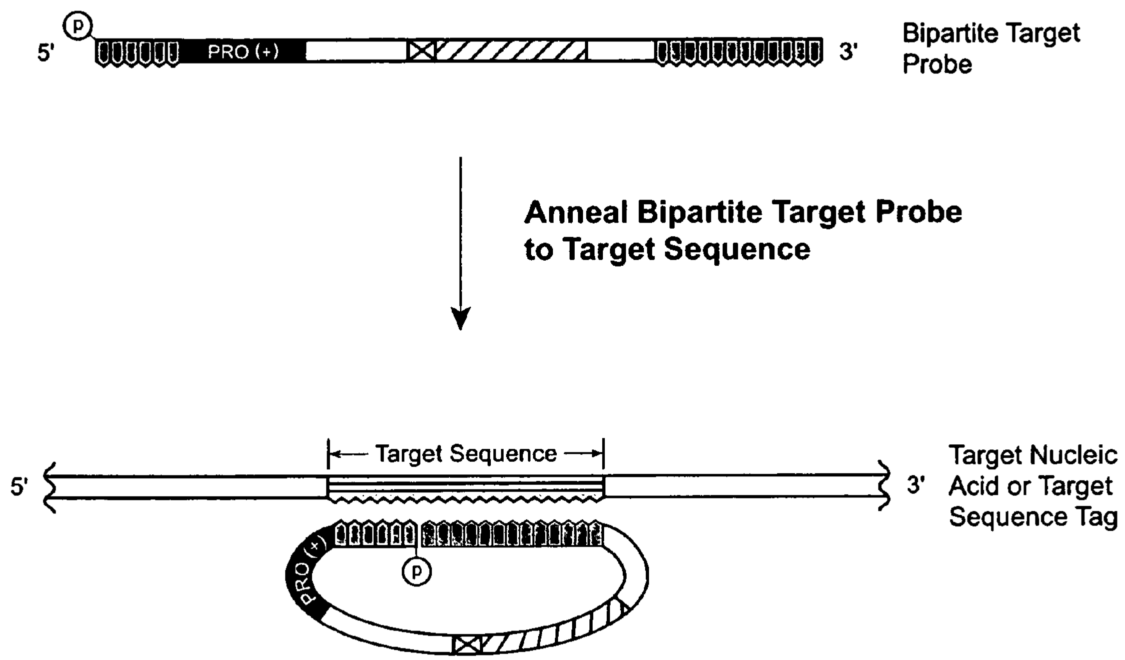
FIG. 19—An example of a bipartite target probe of the invention.

FIG. 19 illustrates a bipartite target probe of the invention and shows how different sequence portions of a bipartite target probe are oriented with respect to each other when said bipartite target probe is free in solution and when it is annealed to a target sequence. The embodiment illustrated in FIG. 19 shows a bipartite target probe comprising target-complementary sequences at each end that are contiguous or adjacent when annealed to a target sequence. As discussed above, the invention also comprises other embodiments of bipartite target probes wherein the target-complementary sequences at each end that are not contiguous or adjacent when annealed to a target sequence. In those embodiments, the "gap" between the target-complementary sequences of the bipartite target probe can be "filled" using one or more simple target probes or by DNA polymerase extension from the 3'-end of the bipartite target probe using the target sequence as a template.

In general, all target probes of the invention, including both monopartite and bipartite target probes that are joined with a ligase in a method or assay of the invention, will have a phosphate group at their 5'-end and a hydroxyl group at their 3'-end. The 5'-ends of target probes that are not joined with a ligase to the 3'-end of another target probe in a method or assay of the invention do not have a phosphate group on their 5'-ends. The only exceptions will be in those embodiments that use another joining method, such as, but not limited to a chemical joining method or a topoisomerase-mediated joining method.

In some embodiments of the invention, such as, but not limited to the embodiment illustrated in FIG. 26, secondary or additional amplification of a target sequence and/or a signal sequence is obtained by using a "second target probe," which second target probe can comprise either: (i) "second monopartite target probes" comprising a "second promoter target probe" and either a "second signal target probe," if a signal sequence is present, or a "second simple target probe," and one or more additional "second simple target probes; or (ii) a "second bipartite target probe." If a second target probe is used, then the target probes that are complementary to the target sequence are referred to as "first target probes." A second target probe is generally identical to a first target probe except with respect to the target-complementary sequence of said target probe. Thus, the sequence at the 5'-end of a second promoter target probe or at the 5'-end of a second bipartite target probe, rather than being complementary to a target sequence, is complementary to the target-complementary sequence at the 3'-end of the first signal target probe or to the target-complementary sequence at the 3'-end of the bipartite target probe, respectively. Similarly, the sequence at the 3'-end of a second signal target probe or at the 3'-end of a second bipartite target probe, rather than being complementary to a target sequence, is complementary to the target-complementary sequence at the 5'-end of the first promoter target probe or to the target-complementary sequence at the 5'-end of the bipartite target probe, respectively. A second simple target probe, rather than being complementary to a target sequence, is complementary to a first target probe. A second target probe can also be referred to as an "target amplification probe," which can comprise either: (i) "monopartite target amplification probes" comprising a "promoter target amplification probe" and either a "signal target amplification probe," if a signal sequence is present, or a "simple target amplification probe," and one or more additional "simple target amplification probes; or (ii) a "bipartite target amplification probe."

E. Design of Target Probes of the Invention for Detection of Mutations, Including Single Nucleotide Polymorphisms (SNP's)

In embodiments of a method or assay of the invention to distinguish between two or more target sequences that differ by a single nucleotide, wherein the specific nucleotide that differs between otherwise identical sequences is referred to as a "target nucleotide," the target probes used in said assay or method are designed in order to be able to distinguish said target nucleotide(s). In preferred embodiments of assays and methods to detect a single-nucleotide difference in a target sequence, the nucleotide of a target probe of the invention that is complementary to the target nucleotide comprises either the 5'-end of a promoter target probe if the assay or method generates a linear transcription substrate, or the nucleotide at the 5'-end of a bipartite target probe if the assay or method generates a circular transcription substrate. Then, if a target nucleotide is present in a target sequence in a sample, the complementary nucleotide at the 5'-end of the respective promoter target probe or the bipartite target probe will anneal thereto and will be ligated, respectively, either to the 3'-end of an adjacently-annealed monopartite target probe or to an adjacently-annealed 3'-end of the bipartite target probe. If the 5'-end of the promoter target probe or the 5'-end of the bipartite target probe is not complementary to the target nucleotide, it will not anneal thereto, and said 5'-end will not be ligated to the 3'-end of an adjacently-annealed monopartite target probe or the 3'-end of the bipartite target probe, respectively, during the ligation process. That is, the non-complementarity of the 5'-end of a target probe with a target nucleotide in a target sequence, when the target probes of an assay or method are annealed to the target sequence prevents ligation of said 5'-end with a 3'-hydroxyl end, so that a transcription substrate is not formed. Although the preferred nucleotide of a target probe of the invention that is complementary to the target nucleotide comprises either the 5'-end of a promoter target probe if the assay or method generates a linear transcription substrate, or the nucleotide at the 5'-end of a bipartite target probe if the assay or method generates a circular transcription substrate, the invention also comprises other embodiments of target probes in which the nucleotide that is complementary to the target nucleotide comprises a different nucleotide in a monopartite or bipartite target probe. Thus, in embodiments of assays or methods using monopartite target probes in which there is no "gap" between the sites on the target sequence to which a promoter target probe and a signal target probe if a signal sequence is present, or a simple target probe if a signal sequence is not present, then the nucleotide that is complementary to the target nucleotide can comprise either the 3'-end of the signal target probe if a signal sequence is present, or the 3'-end of the simple target probe if a signal sequence is not used. Similarly, in embodiments of assays or methods using a bipartite target probe in which there is no "gap" between the sites on the target sequence to which the 5'-end and the 3'-end of said bipartite target probe anneal, then the nucleotide that is complementary to the target nucleotide can comprise the 3'-end of said bipartite target probe. In embodiments of assays or methods using monopartite target probes in which there is a gap between the sites on the target sequence to which a promoter target probe and a signal target probe if a signal sequence is present, or a simple target probe if a signal sequence is not present, wherein one or more simple target probes are used to "fill the gap," then the nucleotide that is complementary to the target nucleotide can comprise a nucleotide at either the 3'-end or the 5'-end of one of said simple target probes that is used to fill the gap. Preferably, the nucleotide that is complementary to the target nucleotide comprises a nucleotide at either the 3'-end or the 5'-end of a simple target probe used to fill the gap that anneals to the target sequence adjacent to the promoter target probe, and most preferably, the nucleotide that is complementary to the target nucleotide comprises a nucleotide at the 3'-end of said simple target probe. In embodiments of assays or methods using bipartite target probes in which there is a gap between the sites on the target sequence to which the ends of the bipartite target probe anneal, wherein one or more simple target probes are used to fill the gap, then the nucleotide that is complementary to the target nucleotide can comprise a nucleotide at either the 3'-end or the 5'-end of one of said simple target probes that is used to fill the gap. Preferably, the nucleotide that is complementary to the target nucleotide comprises a nucleotide at either the 3'-end or the 5'-end of a simple target probes used to fill the gap that anneals to the target sequence adjacent to the 5'-end of said bipartite target probe, and most preferably, the nucleotide that is complementary to the target nucleotide comprises a nucleotide at the 3'-end of said simple target probe. It will be understood by those with knowledge in the art that one or more 5'-terminal or 3'-terminal nucleotide positions of a target probe used in an assay or method to detect a particular target nucleotide in a target sequence may not comprise a sequence that will anneal with specificity to said target sequence, such as, when said target nucleotide is part of a target sequence that has a low $T_m$ with respect to said target-complementary sequence of said target probe. In such cases, those with knowledge in the art will know how to evaluate and, without undue experimentation, how to choose which of those possible 5'-terminal and 3'-terminal nucleotide positions of all of the target probes used in said method or assay comprises the "best nucleotide" to be complementary to said target nucleotide, wherein said best nucleotide results in the greatest specificity and sensitivity in said assay or method.

F. Signal Sequences in Signal Target Probes or Bipartite Target Probes of the Invention A method or assay of the invention does not need to use a signal sequence. The use of a signal sequence or a signal target probe in a method or assay of the invention is optional. If a signal sequence is used in an embodiment, the invention is not limited with respect to particular signal sequences that can be used in signal target probes or bipartite target probes of the invention. A signal sequence can comprise any sequence that generates a detectable signal or that enables sensitive and specific detection, whether directly or indirectly, of the generation of an RNA transcription product encoded by the signal sequence. Preferably, a signal sequence encodes an RNA product that results in additional amplification or more sensitive detection.

By way of example, but not of limitation, one signal sequence that can be used in a signal target probe or a bipartite target probe of the present invention is a sequence that encodes a substrate for a replicase, such as, but not limited to, Q-beta replicase or a partial or interrupted sequence for a substrate for a replicase, such as, but not limited to, Q-beta replicase. Q-beta replicase substrates and methods that can be used for making and using signal sequences that encode a partial or interrupted replicase substrate for signal target probes are described in U.S. Pat. No. 6,562,575, incorporated herein by reference. A complete sequence for a replicase substrate is preferred in a signal probe of the present invention, but a sequence of a partial or interrupted replicase substrate is used in embodiments that require reduced background signal (or "noise") and greater sensitivity. If the time for appearance of a signal in an assay or method is shortened by amplifying the amount of transcription product using other methods described herein, it is less likely that a sequence for a partial or interrupted replicase substrate, rather than for a complete replicase substrate, is needed to obtain a good signal to noise ratio in the assay or method. Once an RNA that is a substrate for Q-beta replicase is synthesized, incubation of said RNA substrate with Q-beta replicase results in replication of the substrate, thereby resulting in additional amplification of the signal and more sensitive, though indirect, detection of the presence of a target sequence.

A "replicase" according to the invention is an enzyme that catalyzes exponential synthesis (i.e., "replication") of an RNA substrate. The replicase can be from any source for which a suitable exponentially replicatable substrate can be obtained for use in the invention. Preferably, the replicase is an RNA-directed RNA polymerase. In preferred embodiments, the replicase is a bacteriophage replicase, such as Q-beta replicase, MS2 replicase, or SP replicase. In the most preferred embodiment, the replicase is Q-beta replicase. In other preferred embodiments, the replicase is isolated from eucaryotic cells infected with a virus, such as, but not limited to, cells infected with brome mosaic virus, cowpea mosaic virus, cucumber mosaic virus, or polio virus. In another embodiment, the replicase is a DNA-directed RNA polymerase, in which case, a T7-like RNA polymerase (as defined in U.S. Pat. No. 4,952,496) is preferred, and T7 RNA polymerase (Konarska, M. M., and Sharp, P. A., Cell, 63: 609-618, 1990) is most preferred. The replicase can be prepared from cells containing a virus or from cells expressing a gene from a bacteriophage or a eukaryotic virus cloned into a plasmid or other vector.

If Q-beta replicase is used, replication of a Q-beta replicase substrate can be carried out substantially according to the protocol of Kramer et al. (J. Mol. Biol., 89: 719-736, 1974). Briefly, an RNA substrate is incubated at 37° C. in a reaction mixture containing about 20-50 micrograms of Q-beta replicase per ml, 40-100 mM Tris-HCl (pH 7-8), about 10-12 mM $MgCl_2$, and about 200-400 micromolar each of ATP, CTP, UTP and GTP. If desired, one of the NTPs can be labeled with a fluorescent or other dye, or the replication products can be detected using another method, such as but not limited to by detection of fluorescence that results from intercalation of a dye such as ethidium bromide.

In embodiments that use Q-beta replicase, it is preferred that the sequence of the recombinant substrate or template be derived from the sequence of an RNA in the following group: midivariant RNA (MDV-1 RNA), microvariant RNA, nanovariant RNA, CT RNA, RQ135 RNA, RQ120 RNA, and other variants or Q-beta RNA, which are known in the art. Once a substrate for a replicase is identified, improved substrates can be obtained, if desired, by serial transfer and selection of higher yielding products from successive reactions, including prolonged reactions. Further, improved substrates can be obtained by random or site-directed modification of a known substrate, followed by serial transfer and selection to select new substrates that result in greater incorporation of UTP during replication.

Another signal sequence that can be used is an expressable gene for an enzyme that has a substrate that results in a colored or fluorescent or otherwise detectable product. By way of example, but not of limitation, a gene for a green fluorescent protein (GFP) can be used. In that case, in vitro transcription of a transcription substrate generated by target-dependent annealing and ligation of target probes results in an RNA transcript that encodes a GFP. In the presence of an in vitro translation system, a detectable GFP is synthesized. There are many other genes that encode enzymes that can be used to generate detectable signals following coupled or step-wise in vitro transcription and translation. By way of example, but not of limitation, signal sequences comprising genes for phosphatases or beta-galactosidases can be used, together with a suitable substrate that generates a colored, fluorescent or chemiluminescent product. A large number of enzymes and coenzymes, as well as enzyme combinations that are useful in a signal producing system are indicated In U.S. Pat. No. 4,275,149 and U.S. Pat. No. 4,318,980, which disclosures are incorporated herein in their entirety by reference. Still further, a signal sequence can comprise a binding site for another molecule, such as, but not limited to, a molecular beacon that results in a signal. Those with knowledge in the art will know many other ways to design a signal sequence for use in target probes of the invention, all of which are part of the present invention.

G. Other Optional Sequences in Target Probes of the Invention

A monopartite or a bipartite target probe of the present invention can optionally comprise other "optional sequences." Optional sequences, if present, can be 5'- of the target-complementary sequence at the 3'-end and 3'- of the promoter sequence in the 5'-portion of a bipartite target probe. Optional sequences, if present in a monopartite target probe, can be 5'- of the target-complementary sequence in a signal target probe or 3'- of the promoter sequence in a promoter target probe. By way of example, but not of limitation, other optional sequences can comprise one or more transcription termination sequences, one or more capture sequence sites, one or more detection sequence sites, one or more address tag sites, one or more priming sites, one or more sequences for another specific purpose, or one or more intervening sequences that have no function other than to link one portion of a target probe to another portion. A capture sequence site can be a site that is complementary to another oligonucleotide, such as, but not limited to an oligo with a biotin group, that facilitates capture of a target sequence to a surface, such as a surface to which streptavidin is bound. A detection sequence site can be a sequence that is complementary to an oligo used for detection, such as, but not limited to, a molecular beacon. An address tag can be a sequence that is complementary to an oligonucleotide or a polynucleotide that is attached to a surface, such as, but not limited to, a dipstick or a spot on an array or microarray. A priming site can be for a sequence that is complementary to an oligonucleotide primer, such as, but not limited to a primer for use in reverse transcription of an RNA transcript product of an assay or method of the invention. These optional sequences can be of any length that permits stable and specific hybridization for the intended purpose and that does not hinder the performance of an assay or method of the invention.

H. Transcription Substrates of the Invention

Circular Transcription Substrates and Linear Transcription Substrates

As used herein, a "transcription substrate" according to the present invention comprises a ssDNA comprising: (i) a sequence that serves as a functional transcription promoter for an RNA polymerase that lacks helicase-like activity and that can use said promoter to initiate transcription of a ssDNA sequence that is 5'- of said single-stranded promoter in the same strand under transcription conditions; and (ii) a sequence that comprises a contiguous target-complementary sequence that results from covalent joining in the presence of a target sequence of either: (a) at least two portions of a target-complementary sequence comprising at least two monopartite target probes; or (b) at least two target-complementary portions of a sequence comprising a bipartite target probe; and wherein said transcription promoter is 3'- of said contiguous target-complementary sequence to which it is joined. Optionally, a transcription substrate of the invention can also have additional nucleic acid sequences, such as, but not limited to, detectable "signal sequences," that are in the same DNA strand and 5'- of said contiguous target-complementary sequence, which in turn is in the same DNA strand and 5'- of said transcription promoter sequence, wherein, in the absence of a transcription terminator sequence, both said contiguous target-complementary sequence, and said additional nucleic acid sequences, if present in said transcription substrate, are transcribed by said RNA polymerase that recognizes said transcription promoter under transcription conditions. However, a transcription substrate of the invention is not required to have said additional nucleic acid sequences.

A transcription substrate typically has a transcription initiation site at the 5'-end of the promoter sequence. A transcription substrate of the invention can also have one or more other sequences that are 5'- of the target-complementary sequence. By way of example, but not of limitation, a transcription substrate can have one or more transcription termination sequences, one or more sites for DNA cleavage to permit controlled linearization of a circular transcription substrate, and/or other sequences or genetic elements for a particular purpose, including, but not limited to, sequences that are transcribed by the RNA polymerase so as to provide additional regions of complementarity in the RNA transcription products: (i) for annealing of primers for reverse transcription in order to make cDNA for additional rounds of amplification; or (ii) for annealing of additional target probes for generation of additional transcription substrates by means of additional joining reactions using the RNA transcription product as a ligation template (e.g., by using a different joining enzyme or joining method on the RNA ligation template than the joining enzyme or joining method that was used in the initial joining reaction of target probes on the target sequence).

I. Hybridization or Annealing Processes of the Invention

"Hybridization" or "annealing" refers to the "binding" or "pairing" of complementary nucleic acid bases in one single-stranded nucleic acid, peptide nucleic acid (PNA), or linked nucleic acid-PNA molecule with another single-stranded nucleic acid, PNA, or linked nucleic acid-PNA molecule under "binding" or "annealing" or "hybridization" conditions." The ability of two polymers of nucleic acid and/or PNA containing complementary sequences to find each other and anneal through base pairing interaction is a well-recognized phenomenon. The initial observations of the "hybridization" process by Marmur and Lane (Proc. Nat. Acad. Sci. USA, 46: 453, 1960) and Doty, et al. (Proc. Nat. Acad. Sci. USA, 46: 461, 1960) have been followed by the refinement of this process into an essential tool of modern biology. Hybridization occurs according to base pairing rules (e.g., adenine pairs with thymine or uracil and guanine pairs with cytosine). Those with skill in the art will be able to develop and make conditions which comprise binding conditions or hybridization conditions for a particular target nucleic acid analytes or target sequence tag joined to a non-nucleic acid analyte and target probes of an assay or method of the invention. In developing and making binding conditions for particular target nucleic acid analytes or target sequence tags joined to non-nucleic acid analytes with target probes an assay of the invention, as well as in developing and making hybridization conditions for other oligonucleotides or polynucleotides which can be used, such as, but not limited to capture probes, or detection probes such as molecular beacons, certain additives can be added in the hybridization solution. By way of example, but not of limitation, dextran sulfate or polyethylene glycol can be added to accelerate the rate of hybridization (e.g., Chapter 9, Sambrook, et al., Molecular Cloning: A Laboratory Manual, 2nd Edition, Cold Spring Harbor Laboratory Press, 1989), or betaine can be added to the hybridization solution to eliminate the dependence of $T_m$. on basepair composition (Rees, W. A., et al., Biochemistry, 32, 137-144, 1993). However, other hybridization conditions that do not use such additives can also be used in an assay or method of the invention.

The terms "degree of homology" or "degree of complementarity" refer to the extent or frequency at which the nucleic acid bases on one strand (e.g., of the affinity molecule) are "complementary with" or "able to pair" with the nucleic acid bases on the other strand (e.g., the analyte). Complementarity may be "partial," meaning only some of the nucleic acid bases are matched according to base pairing rules, or complementarity may be "complete" or "total." The length (i.e., the number of nucleic acid bases comprising the nucleic acid and/or PNA affinity molecule and the nucleic acid analyte), and the degree of "homology" or "complementarity" between the affinity molecule and the analyte have significant effects on the efficiency and strength of binding or hybridization when the nucleic acid bases on the affinity molecule are maximally "bound" or "hybridized" to the nucleic acid bases on the analyte. The terms "melting temperature" or "$T_m$" are used as an indication of the degree of complementarity. The $T_m$ is the temperature at which a population of double-stranded nucleic acid molecules becomes half dissociated into single strands under defined conditions. Based on the assumption that a nucleic acid molecule that is used in hybridization will be approximately completely homologous or complementary to a target polynucleotide, equations have been developed for estimating the $T_m$ for a given single-stranded sequence that is hybridized or "annealed" to a complementary sequence. For example, a common equation used in the art for oligodeoxynucleotides is: $T_m$=81.5° C.+0.41(% G+C) when the nucleic acid is in an aqueous solution containing 1 M NaCl (see e.g., Anderson and Young, Quantitative Filter Hybridization, in Nucleic Acid Hybridization, 1985). Other more sophisticated equations available for nucleic acids take nearest neighbor and other structural effects into account for calculation of the $T_m$. Binding is generally stronger for PNA affinity molecules than for nucleic acid affinity molecules. For example the $T_m$ of a 10-mer homothymidine PNA binding to its complementary 10-mer homoadenosine DNA is 73° C., whereas the $T_m$ for the corresponding 10-mer homothymidine DNA to the same complementary 10-mer homoadenosine DNA is only 23° C. Equations for calculating the $T_m$ for a nucleic acid are not appropriate for PNA. Preferably, a $T_m$ that is calculated using an equation in the art, is checked empirically and the hybridization or binding conditions are adjusted by empirically raising or lowering the stringency of hybridization as appropriate for a particular assay.

As used herein the term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids that are not completely complementary to one another be hybridized or annealed together.

With regard to complementarity, it is important for some assays of the invention to determine whether the hybridization represents complete or partial complementarity. For example, where it is desired to detect simply the presence or absence of pathogen DNA (such as from a virus, bacterium, fungi, mycoplasma, protozoan), it is only important that the hybridization method ensures hybridization when the relevant sequence is present. In those embodiments of the invention, conditions can be selected where both partially complementary probes and completely complementary probes will hybridize.

However, the invention can also be used for assays to detect mutations, or genetic polymorphisms, or single nucleotide polymorphisms (SNPs). These embodiments of the invention require that the hybridization and other aspects of the method distinguish between partial and complete complementarity. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence. Thus, some embodiments of the invention are used for assays that can detect and distinguish even as small a difference as a single basepair in a target nucleic acid analyte.

J. Ligases and Ligation Processes of the Invention

In general, "ligation" refers to the joining of a 5'-phosphorylated end of one nucleic acid molecule with the 3'-hydroxyl end of another nucleic acid molecule by an enzyme called a "ligase," although in some methods of the invention, the ligation can be effected by another mechanism. With respect to ligation, a region, portion, or sequence that is "adjacent to" or "contiguous to" or "contiguous with" another sequence directly abuts that region, portion, or sequence.

The invention is not limited to a specific ligase. However, preferably the ligase is not active in ligating blunt ends and is highly selective for ligation of a deoxyribonucleotide having a 5'-phosphate and a deoxyribonucleotide having 3'-hydroxyl group when these respective 5'- and 3'-nucleotides are adjacent to each other when annealed to a target sequence of a target nucleic acid. Ampligase® Thermostable DNA Ligase Tth DNA ligase, and Tfl DNA Ligase (Epicentre Technologies, Madison, Wis., USA), or Tsc DNA Ligase (Prokaria Ltd., Reykjavik, Iceland) are NAD-dependent thermostable ligases that are not active on blunt ends and that ligate the 5'-phosphate and 3'-hydroxyl termini of DNA ends that are adjacent to one another when annealed to a complementary DNA molecule; these enzymes are preferred ligases in embodiments of the invention wherein a target sequence comprises DNA. Another DNA ligase that can be used in the methods of the invention for target sequences comprising DNA is Pfu DNA ligase as described by Mathur et al. (U.S. Pat. Nos. 5,700,672 and 6,280,998). Thermostable DNA ligases are preferred in some embodiments because they can be cycled through multiple annealing-ligation-melting cycles, permitting multiple target probe ligations for every target sequence present in a sample, and thus, increasing the sensitivity of the assay or method. However, the invention is not limited to the use of a particular ligase, or to the use of a thermostable ligase and other suitable ligases that function in the assays and methods of the invention can also be used. For example, T4 DNA ligase can be used in some embodiments of the invention for target sequences that comprise DNA. In addition, Faruqui discloses in U.S. Pat. No. 6,368,801 that T4 RNA ligase can efficiently ligate DNA ends of nucleic acids that are adjacent to each other when hybridized to an RNA strand. Thus, T4 RNA ligase is a preferred ligase of the invention in embodiments in which DNA ends are ligated on a target sequence that comprises RNA. However, because of the high potential for "background" ligation reactions, T4 RNA ligase is not preferred when high specificity and/or high sensitivity is desired. Other ligases that ligate DNA ends of nucleic acids that are adjacent to each other when hybridized to an RNA strand are also preferred for target nucleic acids comprising RNA. The invention is also not limited to the use of a ligase for covalently joining target probe ends in the various embodiments of the invention. By way of example, other ligation methods such as, but not limited to, topoisomerase-mediated ligation (e.g., U.S. Pat. No. 5,766,891, incorporated herein by reference) can be used, although topoisomerase-mediated ligation is not preferred in most embodiments because of the high potential for background ligation. In some other embodiments, chemical ligation methods can be used, such as, but not limited to, the use of a target probe with a 5'-end sequence that comprises a 5'-iodo-nucleotide and a 3'-end comprising a nucleotide with phosphorothioate, as disclosed by Xu, Y., and Kool, E. T. (Nucleic Acids Res., 27: 875-881, 1999), which is incorporated herein by reference. The invention is not limited with respect to the ligation method used except that the ligation should occur efficiently in the presence of a target sequence to which the target probes anneal contiguously and ligation should occur rarely or not at all in the absence of a target sequence. As used herein, "ligation" refers to any suitable method for joining adjacent 5'- and 3'-ends of target probes that are adjacent or contiguous to each other when annealed to a target sequence. In preferred ligation processes of the present invention, all of the target probes that anneal to a target sequence have a similar melting temperature ($T_m$) with respect to the target sequence, and the lowest temperature at which a ligation process is performed is near the $T_m$ of the target probe having the lowest $T_m$ when it is annealed to the target sequence.

K. Releasing Circular ssDNA Molecules that are Catenated to a Target Sequence Following Ligation Using the Target Sequence as a Ligation Template Bipartite probes that are ligated when annealed to a target sequence create circular DNA molecules catenated to the target sequence (Nilsson, M. et al., Science, 265:2085-2088, 1994, incorporated herein by reference). Nilsson et al. showed that, if the target sequence was less than about 150-200 nucleotides from the 3'-end of the target nucleic acid, the catenated circular ssDNA molecules obtained by ligation of a linear probe on a target sequence were able to slip off of the target strand during denaturing washes, whereas circular molecules catenated on the target sequence 850 nucleotides from the 3'-end of the target nucleic acid were not removed during denaturing washes.

The present invention comprises some embodiments in which a TSA circle is replicated by rolling circle replication while catenated to target nucleic acid or a target sequence tag using a DNA polymerase, such as but not limited to IsoTherm™ DNA polymerase (EPICENTRE Technologies, Madison, Wis.), Bst DNA polymerase large fragment, or another DNA polymerase that can efficiently replicated catenated templates. The present invention also comprises embodiments in which circular transcription substrates are transcribed by rolling circle transcription while they are catenated to a target nucleic acid or target sequence tag so long as the assay or method functions for its intended purpose. It can be beneficial that the respective molecules remain catenated to the target nucleic acid, and it is beneficial if the number of steps and the time to perform an assay is kept to the minimum to obtain the information for which the assay or method was intended.

However, in other embodiments, it can be desirable for a variety of reasons that circular ssDNA ligation products obtained using a method of the invention does not remain catenated to a target nucleic acid or target sequence tag comprising the target sequence following ligation. By way of example, but not of limitation, catenation of a TSA circle obtained by annealing and ligation of a target sequence amplification probe (TSA probe) on a target sequence or catenation of a circular transcription substrate obtained by annealing and ligation of a bipartite target probe on a target sequence and annealing of an anti-sense promoter oligo may limit the amount of rolling circle replication product (e.g., see Baner, J. et al., Nucleic Acids Research, 26: 5073-5078, 1998) or rolling circle transcription product, respectively, if the catenated circular molecules remain catenated to the target nucleic acid or target sequence tag comprising the target sequence following ligation.

However, the affect of catenation on the target nucleic acid should be determined empirically in view of the results of Kuhn et al. (Nucleic Acids Res., 30: 574-580, 2002), incorporated herein by reference. Kuhn et al. showed that, although rolling circle replication was limited on catenated circular ssDNA molecules using phi29 DNA polymerase (which was used by Baner et al., Nucleic Acids Research, 26: 5073-5078, 1998), the amount of rolling circle replication product obtained using catenated circular ssDNA molecules was not affected when Bst DNA polymerase large fragment, Sequenase® DNA polymerase (USB, Cleveland, Ohio), or Vent (exo-minus) DNA polymerase (New England Biolabs, Beverly, Mass.) was used. Whether or not it is necessary to release catenated circular ssDNA molecules from the target nucleic acid prior to rolling circle replication depends on the DNA polymerase used, indicating that the need to release catenated circular transcription substrates from the target nucleic acid may also depend on the particular RNA polymerase used for rolling circle transcription.

Therefore, if a target nucleic acid comprising a target sequence does not have a free 3'-end that is less than about 150-200 nucleotides from the target sequence, the present invention comprises empirically determining if catenation of a ligation product obtained from ligation of a TSA probe or a bipartite target probe on the target sequence results in a reduction in the amount of product obtained during rolling circle replication or rolling circle transcription, respectively, compared to the amount of product obtained on an oligodeoxyribo-nucleotide comprising only the target sequence. If the amount of product obtained is found to be decreased by catenation, then an assay or method of the invention will either use additional steps to release the catenated circular ssDNA molecule from the target nucleic acid for the particular assay or method, such as but not limited to one of the methods to release catenated molecules described herein below, or will use a different polymerase for which the amount of replication product or transcription product is not affected by catenation.

In general, for this reason, a target sequence tag of the present invention will comprise a sequence that has a 3'-end that is less than about 150-200 nucleotides from the target sequence. Preferably, the 3'-end of the target sequence tag is less than 100 nucleotides from the target sequence and most preferably, the 3'-end of the target sequence tag is less than 50 nucleotides from the target sequence.

With respect to a target sequence comprising a target nucleic acid in a sample, if the target sequence is more than about 150-200 nucleotides from the 3'-end of the target nucleic acid, it is obvious to a person with knowledge in the art that there are a number of methods for breaking or cutting or shortening the target nucleic acid in order to obtain a fragmented target nucleic acid comprising the target sequence and any suitable method can be used to obtain a target nucleic acid for an assay or method of the present invention. Preferably, the target nucleic acid is fragmented to a size that has a 3'-end that is less than about 150-200 nucleotides from the target sequence prior to use of the target nucleic acid in an assay or method of the invention.

By way of example, but not of limitation, a DNA in a sample comprising a dsDNA molecule or a ssDNA molecule to which an appropriate complementary DNA oligo is annealed can be digested with a restriction endonuclease, provided that a suitable restriction site is present within less than about 150-200 nucleotides from the 3'-end of the target sequence and no restriction sites for the enzyme are present within the target sequence. Alternatively, if a suitable restriction site is not present on the target nucleic acid, one or more DNA oligonucleotides having a double-stranded segment that contains a FokI restriction enzyme site and a single-stranded segment that binds to the desired cleavage site on a first-strand cDNA can be used. As is well known in the art, this type of oligonucleotide can be used with the restriction enzyme FokI to cut a single-stranded DNA at almost any desired sequence (Szybalski, W., Gene 40:169-173, 1985; Podhajska A. J. and Szybalski W., Gene 40:175, 1985, incorporated herein by reference).

Still further, either RNA or DNA nucleic acids of known sequence can be cleaved at specific sites using a 5'-nuclease or Cleavase™ enzyme and specific oligonucleotides, as described by Kwiatkowski, et al., (Molecular Diagnosis 4:353-364, 1999) and in U.S. Pat. No. 6,001,567 and related patents assigned to Third Wave Technologies (Madison, Wis., USA), which are incorporated herein by reference.

If the target nucleic acid is first-strand cDNA obtained by reverse transcription of RNA using a primer, the RNA can be cleaved with RNase H at a site to which a DNA oligo is annealed in order to define the 3'-end of the reverse transcription product that is obtained. Alternatively, the length of the reverse transcription product can be kept within a desired size range by limiting the time of the reverse transcription reaction, which reverse transcription reaction can be optimized for the particular primer, template sequence and reaction conditions used to obtain a target nucleic acid comprising a target sequence, if present in the sample.

Still another method that can be used is to incorporate dUMP randomly into the first-strand cDNA during reverse transcription or primer extension to prepare a target nucleic acid comprising a target sequence. In these embodiments, dUTP (deoxyribo-uridine triphosphate) is used in place of a portion of the dTTP (thymidine triphosphate) in the reaction. Also, dUTP can be incorporated in place of a portion of the dTTP in rolling circle replication of TSA circles that are used to increase the number of target sequences available for annealing and ligation of target probes for target-dependent transcription. As discussed elsewhere herein, TSA circles are obtained by annealing and ligation of target sequence amplification probes (TSA probes) on a target sequence in a sample. When dUTP is used in a reverse transcription, primer extension or rolling circle replication reaction in addition to dTTP, dUMP will be incorporated randomly in place of dTMP at a frequency based on the ratio of dUTP to dTTP. Then, the respective first-strand cDNA, primer extension product or rolling circle replication product can be cleaved at sites of dUMP incorporation by treatment (e.g., see U.S. Pat. No. 6,048,696, incorporated herein by reference) with uracil-N-glycosylase (UNG) and endonuclease IV (endo IV), which are available from EPICENTRE Technologies (Madison, Wis., USA). UNG hydrolyzes the N-glycosidic bond between the deoxyribose sugar and uracil in single- and double-stranded DNA that contains uracil in place of thymidine. UNG has no activity on dUTP or in cleaving uracil from UMP residues in RNA. Endo IV cleaves the phosphodiester linkage at the abasic site. It may be useful to use a thermolabile UNG (e.g., HK™-UNG from EPICENTRE Technologies, Madison, Wis., USA) for some applications. (Also, incorporation of dUMP at one or more specific sites within a synthetic oligonucleotide introduces a specific cleavage site which can be used at any time to cleave a resulting nucleic acid which contains the site by treatment with UNG and endo IV.)

Further, the 3'-end of a first-strand cDNA that is to become the template sequence for a transcription reaction can be defined by first amplifying the target nucleic acid sequence using any suitable amplification method, such as but not limited to PCR or RT-PCR, that delimits the end sequence.

If a 3'-end of a target sequence need not be at an exact location, and can be random or imprecise, which is the case in some embodiments of the invention, there are a number of other methods that can be used for making smaller fragments of a DNA molecule, whether for a target nucleic acid, a target sequence, or otherwise. By way of example, but not of limitation, a target nucleic acid can be fragmented by physical means, such as by movement in and out of a syringe needle or other orifice or by sonication. If desired, the ends of physically fragmented double-stranded DNA can be made blunt prior to denaturation and use in an assay or method of the present invention using a T4 DNA polymerase or a kit, such as the End-It™ DNA End Repair Kit (EPICENTRE Technologies, Madison, Wis., USA).

Although it is preferred that a target nucleic acid comprising a target sequence is short enough so that its 3'-end will easily be released from the catenated circular molecules that result from ligation of a bipartite target probe annealed to the target sequence, the present invention also includes embodiments of methods, assays, compositions and kits for detecting target sequences comprising larger target nucleic acids, wherein the catenated ligation product is not substantially released from the target nucleic acid. In those embodiments, the invention comprises additional steps for release of the catenated circular ligation product after annealing and ligation on the target sequence.

Baner, J. et al. (Nucleic Acids Research, 26: 5073-5078, 1998, incorporated herein by reference) showed that ligation of a linear DNA having two target-complementary end sequences that anneal adjacently on a target sequence resulted in a catenated molecule that was not efficiently replicated by rolling circle replication using phi29 DNA polymerase unless there was a free 3'-end of the target nucleic acid near the ligation site. Baner et al. showed that, in order to obtain efficient rolling circle replication by phi29 DNA polymerase of circular ssDNA molecules that had been ligated on a target sequence, the topological link of the circular DNA with the target molecules needed to be released. U.S. Pat. No. 6,558,928, incorporated herein by reference, provided methods for release of catenated circular DNA molecules in order to improve the efficiency of rolling circle replication reactions. The present invention comprises the use of the methods described in U.S. Pat. No. 6,558,928, which methods are incorporated herein by reference, in order to release catenated circular ligation products for rolling circle transcription as described herein.

In some embodiments, the circular ssDNA ligation product is released from catenation with the target sequence by digestion with an exonuclease after ligation of the bipartite probe on the target sequence. Preferred exonucleases are those that digest single-stranded DNA and that do not have endonuclease activity. One enzyme that can be used is exonuclease I (exo I) (EPICENTRE Technologies, Madison, Wis.), which has 3'-to-5' single-stranded exonuclease activity in the presence of $Mg^{2+}$ cations. Another enzyme that can be used is exonuclease VII (exo VII) (EPICENTRE Technologies, Madison, Wis.), which has both 3'-to-5' and 5'-to-3' single-stranded exonuclease activity. Exo VII is active in the absence of $Mg^{2+}$ cations, which makes it a preferred embodiment for many applications. Rec J nuclease (EPICENTRE Technologies, Madison, Wis.), which has 5'-to-3' single-stranded exonuclease activity in the presence of $Mg^{2+}$ cations, can also be used in some embodiments. Still further, it is preferable to also use a double-stranded exonuclease, such as but not limited to exonuclease III (exo III) in addition to a single-stranded exonuclease, such as but not limited to exo I, in order to release catenated circular DNA molecules from a target nucleic acid comprising a target sequence. In some embodiments, the target sequence that has been digested with an exonuclease can prime rolling circle replication after exonuclease removal of the non-base-paired 3' end. Other methods in the art for releasing a catenated circular DNA molecule can also be used.

L. DNA Polymerases and Processes of the Invention for Filling "Gaps" Between Target Probes DNA polymerases are used in some embodiments of the present invention in order to fill by DNA polymerase extension one or more "gaps" between non-contiguous target-complementary sequences of target probes that are annealed to a target sequence. The invention is not limited to a particular DNA polymerase to accomplish this purpose, and the invention includes use of any DNA polymerase that is active in filling a gap under suitable reaction conditions. A suitable DNA polymerase fills the gap by DNA polymerase extension from the 3'-hydroxyl end of one target-complementary target probe to the 5'-end of the next target-complementary target probe, without strand-displacement of the target-complementary 5'-end portion of a target probe. The "strand displacement" activity of a DNA polymerase is an operational definition and depends on reaction conditions, such as, but not limited to, reaction temperature, buffer, salt concentration, pH, $Mg^{2+}$ concentration, use of cosolvents such as DMSO, or DNA polymerase enhancers such as betaine, as well as on the intrinsic properties of a DNA polymerase. Thus, even though a particular DNA polymerase may have strand-displacement activity under certain reaction conditions, it may not have significant strand-displacement activity under other reaction conditions. Thus, it is preferred that a DNA polymerase is evaluated for strand-displacement activity under the desired reaction conditions of an assay or method of the invention. Strand displacement and DNA polymerase processivity can be assayed using methods described in Kong et al., (J. Biol. Chem., 268: 1965-1975, 1993), which is incorporated herein by reference. Preferred DNA polymerases lack 5'-to'3' and 3'-to-5' exonuclease activity under the reaction conditions used. It is also important that the DNA polymerase used to fill a gap lacks a 5' structure-dependent nuclease, such as Cleavase™ or Invader™ nucleases used by Third Wave Technologies (Madison, Wis.) because these enzymes could cleave off an unpaired nucleotide, especially at the 5'-end of a sequence that is partially annealed to a target sequence 3'- of another target probe, and then the DNA polymerase could fill in the gap formed. Therefore, a DNA polymerase with 5' structure-dependent nuclease activity could result in inaccurate results in the assay. Most preferred DNA polymerases are thermostable so that activity is more consistent during the course of a method or assay of the invention and in order to be more easily stored without loss of polymerase activity. A preferred DNA polymerase of the invention for filling gaps between target probes annealed to a target sequence is T4 DNA polymerase. Another DNA polymerase that can be used is T7 DNA polymerase (Epicentre Technologies, Madison, Wis., USA).

M. Transcription Processes of the Invention

The target-complementary sequence at the 5'-end of a bipartite target probe or the 5'-end of a promoter target probe is a template for transcription by the cognate RNA polymerase that recognizes the promoter. However, since the target-complementary sequence at the 5'-end of a bipartite target probe of a promoter target probe is short, comprising only about 4-100 nucleotides, preferably about 8-30 nucleotides, the reaction conditions of the method of the invention can be adjusted so that RNA that is complementary to the target-complementary sequence at the 5'-end of a bipartite target probe or a promoter target probe, if it is synthesized by the RNA polymerase, forms an RNA:DNA hybrid and the RNA is not displaced from the DNA template under the transcription reaction conditions used. Thus, in the absence of a target sequence that permits ligation of the target-complementary sequence at the 5'-end of a bipartite target probe or a promoter target probe to the 3'-end of a second target-complementary sequence, only a maximum of about one RNA copy of the target-complementary sequence at the 5'-end of the bipartite target probe or promoter target probe is synthesized by the RNA polymerase and no RNA copy is synthesized that is complementary to a target-complementary sequence or a signal sequence of a signal target probe or the 3'-end of a bipartite target probe, since these latter sequences are not joined to the promoter. Therefore, a method of the present invention detects, directly or indirectly, synthesis of RNA that is complementary to the target-complementary sequence at the 3'-end of a bipartite target probe or that is 5'- of a promoter target probe, i.e., that is, complementary to a simple target probe or a signal target probe. In preferred embodiments of the invention, a target sequence is detected, directly or indirectly, by transcription of a signal sequence portion of a circular or linear transcription substrate. A preferred signal sequence portion of the invention comprises a sequence that encodes a substrate for a replicase, and the target sequence is detected by contacting the RNA replicase substrate encoded by the signal sequence portion with a replicase that replicates the transcribed RNA that is a replicase substrate under replication conditions. However, the invention also comprises other embodiments that use other signal sequences or no signal sequence, as discussed herein above.

Paul Lizardi discusses the optional use of a transcription promoter in an open circle probe ("OCP") for use in rolling circle amplification ("RCA"), as disclosed in U.S. Pat. Nos. 6,344,329; 6,210,884; 6,183,960; 5,854,033; 6,329,150; 6,143,495; 6,316,229; 6,287,824. However, in contrast to the methods of the present invention, Lizardi disclosed that a promoter portion can be included in an open circle probe so that RNA transcripts can be generated from tandem sequence DNA ("TS-DNA"), which is a product of rolling circle amplification. In contrast, in the methods of the present invention, the RNA transcripts are primary amplification products and are synthesized by in vitro transcription of transcription substrates obtained by target-dependent joining of target probes. Thus, the RNA transcripts of the present invention are complementary to the target probes used in an assay or method. Preferred promoters in the methods of Lizardi are T7 or SP6 RNA polymerase promoters, which are double-stranded promoters, and the cognate polymerase for the promoter is used for transcriptional amplification. Thus, in embodiments of Lizardi's invention that contain a promoter sequence, Lizardi's open circle probes actually contain a protopromoter sequence, to which a complementary sequence must be annealed or a second DNA strand needs to be synthesized in order to obtain a functional promoter. Lizardi further states that a promoter on an open circle probe, if present, is preferably immediately adjacent to the left target probe (i.e., the promoter is 5'- of the target-complementary sequence on the 3'-end of the open circle probe) and is oriented to promote transcription toward the 3'-end of the open circle probe so the orientation results in transcripts that are complementary to TS-DNA. Thus, the position and orientation of a promoter sequence in the methods disclosed by Lizardi are completely different and would not be workable for the methods of the present invention. As discussed elsewhere herein, a single-stranded promoter of the present invention must be located 3'- of the target-complementary sequence at the 5'-end of a bipartite target probe or must be located 3'- of the target-complementary sequence at the 5'-end of a monopartite promoter target probe in order to function in the assays and methods of the invention. In short, promoters, if present at all, are included in open circle probes for the methods of Lizardi in order to obtain secondary amplification of DNA replication products, rather than for the purpose of primary amplification as is the case in the methods and assays of the present invention. Also, the RNA polymerases of the present invention have not been used for amplification methods in the prior art. The RNA polymerases of the present invention lack helicase-like activity and use single-stranded promoters and templates for transcription, whereas the T7-type RNA polymerases, such as T7 RNAP and SP6 RNAP, used by Lizardi and others have helicase-like activity for unwinding of dsDNA. Therefore, Lizardi and others were not able to envision embodiments of the present invention that use single-stranded promoters and templates.

The present invention also differs from and provides significant advantages over the methods disclosed in Japanese Patent Nos. JP4304900 and JP4262799 of Aono Toshiya et al. First, the method of Toshiya et al. disclosed use of an RNA polymerase with helicase-like activity, such as T7, T3 or SP6 RNA polymerase. In contrast, the novel mini-vRNA polymerases disclosed in the present invention lack helicase-like activity. Mini-vRNAP enzymes use single-stranded DNA templates and are unable to unwind or transcribe double-stranded DNA. Mini-vRNAP enzymes also are unable to displace the RNA product from the RNA: DNA hybrid obtained from transcription of linear templates. The RNA product from in vitro transcription using mini-vRNAP is displaced from linear templates only in the presence of EcoSSB Protein. This lack of helicase-like activity and lack of activity in displacing the transcription product results in low background transcription of the linear target probes in an assay or method of the current invention.

Still further, the method of Toshiya et al. requires annealing a complementary nucleotide primer having an anti-promoter sequence in order to form a functional double-stranded promoter for the RNA polymerase. In contrast, the RNA polymerases disclosed in the present invention use single-stranded promoters and single-stranded templates. Therefore, the present invention does not use a step for annealing of an "anti-promoter" sequence. As shown in Example 8, although we observed a high level of rolling circle transcription product using mini-vRNAP with a circular single-stranded transcription substrate having a P2 promoter, we did not detect mini-vRNAP transcription products using the unligated precursor comprising a linear single-stranded oligonucleotide having a P2 promoter sequence. Also, no transcription was detected with a circular single-stranded oligonucleotide that either lacked a P2 promoter or had an anti-sense P2 promoter instead of the sense P2 promoter.

It is known that large amounts of transcription product are obtained by in vitro transcription of short DNA sequences that are joined to a functional double-stranded T7 RNAP promoter (Milligan, J F et al., Nucleic Acids Res., 15: 8783-8798, 1987). Therefore, using the method of Toshiya et al., the amount of transcription product obtained during in vitro transcription in the presence of unligated linear probe to which the anti-promoter primer was annealed would be significant and would seriously limit the sensitivity of the method. Still further, based on the schematic diagrams provided in Japanese Patent Nos. JP4304900 and JP4262799, it did not appear that the double-stranded promoter sequence in the method disclosed was positioned close to the 5'-end of the linear probe in order to minimize transcription of the linear template upon annealing of the anti-promoter primer.

These problems may explain why the methods disclosed in Japanese Patent Nos. JP4304900 and JP4262799 did not appear to have been pursued. The inventors believe that the methods of the present invention that use novel mini-vRNAP enzymes and completely single-stranded transcription substrates having single-stranded promoters solve these problems.

N. Amplification and Detection Processes of the Invention

Amplifying a Target Sequence and Amplifying a Signal Sequence

The terms "amplifying a target" or "amplifying a target nucleic acid" or "amplifying a target nucleic acid sequence" or "amplifying a target sequence" herein mean increasing the number of copies of that portion of the sequence of a target nucleic acid for which a complementary sequence is present in a target probe of the invention, including, but not limited to, a target-complementary sequence that is present in a target probe that also comprises a sequence for a transcription promoter for an RNA polymerase. An "amplified target" or an "amplified target sequence" comprises only that portion of the sequence of a target nucleic acid for which a complementary sequence is present in a target probe of the invention. The use of the terms "amplifying a target" or "amplifying a target nucleic acid" or "amplifying a target nucleic acid sequence" or "amplifying a target sequence" herein is not intended to imply that all of the sequence of a target nucleic acid is amplified. The use of these terms is also not intended to imply that the amplification of that portion of the sequence of a target nucleic acid for which a complementary sequence is present in a target probe of the invention is actually directly observed or detected in a method or assay of the invention. The invention comprises embodiments in which the amplified target sequence is directly detected, such as, but not limited to, embodiments in which the target sequence is detected by measuring a fluorescent signal following annealing of a transcript-complementary detection probe such as, but not limited to a molecular beacon. The invention also comprises embodiments in which the amplified target sequence is detected only indirectly by generation of another signal, such as, but not limited to, embodiments in which a signal is generated as a result of transcription of another DNA sequence that is covalently attached to a target-complementary sequence and that is transcribed along with a target-complementary sequence. By way of example, but not of limitation, in one embodiment, which is a preferred embodiment, the amplification of a target sequence is detected by detecting a substrate for Q-beta replicase. The substrate is replicated by Q-beta replicase using replication conditions well known in the art following synthesis of said RNA substrate by transcription of a signal sequence portion of a target probe that encodes said Q-beta substrate. The term "amplification signal" as used herein is intended to describe the output or result of any method, whether direct or indirect, for detecting if amplification of a target sequence has occurred. By way of example, but not of limitation, an amplification signal can comprise a fluorescent signal that results from annealing of a molecular beacon to an RNA transcript that is complementary to a target probe, or an amplification signal can comprise a Q-beta substrate that is replicated by Q-beta replicase following transcription of a DNA portion of a target probe that encodes said Q-beta substrate. As discussed previously with respect to signal sequences, the invention comprises any signal sequence and any detection method that detects target-dependent transcription of a target sequence or a signal sequence.

O. Reverse Transcriptases and Reverse Transcription Processes of the Invention In some embodiments in which a target nucleic acid in a sample comprises RNA, reverse transcription is used to obtain a target sequence comprising DNA. Also, some embodiments of methods and assays of the present invention use reverse transcription processes in conjunction with other processes in order to obtain additional amplification of a target sequence and/or a signal sequence. These embodiments use a reverse transcriptase. A "reverse transcriptase" or "RNA-dependent DNA polymerase" is an enzyme that synthesizes a complementary DNA copy ("cDNA") from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates. Examples of reverse transcriptases that can be used in methods of the present invention include, but are not limited to, AMV reverse transcriptase, MMLV reverse transcriptase, Tth DNA polymerase, rBst DNA polymerase large fragment, also called IsoTherm™ DNA Polymerase (Epicentre Technologies, Madison, Wis., USA), and BcaBEST™ DNA polymerase (Takara Shuzo Co, Kyoto, Japan). In some cases, a mutant form of a reverse transcriptase, such as, but not limited to, an AMV or MMLV reverse transcriptase that lacks RNase H activity can be used. In other embodiments, a wild-type enzyme is preferred. In some embodiments of the invention, a separate RNase H enzyme, such as but not limited to, *E. coli* RNase H or Hybridase™ Thermostable RNase H (Epicentre Technologies, Madison, Wis. 53713, USA). can also be used in reverse transcription reactions. MMLV reverse transcriptase (wild-type, RNase H-positive) is preferred for some embodiments of the invention in which it can be used without a separate RNase H enzyme. In some other embodiments, IsoTherm™ DNA polymerase or AMV reverse transcriptase can be used. The processes of the invention include conducting experiments to determine the effects on amplification of RNase H activity of a reverse transcriptase and/or separate RNase H enzyme(s) used, including, but not limited to, AMV reverse transcriptase, IsoTherm DNA polymerase, and both RNase H-plus and RNase H-minus MMLV reverse transcriptase, and *E. coli* RNase H or thermostable RNase H enzymes that are stable for more than 10 minutes at 70° C. (U.S. Pat. Nos. 5,268,289; 5,459,055; and 5,500,370), such as, but not limited to, Hybridase™ thermostable RNase H, Tth RNase H, and Tfl RNase H (Epicentre Technologies, Madison, Wis., USA), or by different combinations of a reverse transcriptase and a separate RNase H. Kacian et al. (U.S. Pat. No. 5,399,491), incorporated herein by reference, discloses information related to the effects of adding different amounts of a separate RNase H enzyme to transcription-mediated amplification assays that used T7 RNAP and dsDNA templates and either MMLV or AMV reverse transcriptase, which information is useful in suggesting how to vary and evaluate reaction conditions related to use of reverse transcriptases and RNase H enzymes in methods and assays of the present invention.

P. Strand-Displacing DNA Polymerases for Rolling Circle Replication Processes of the Invention Some DNA polymerases are able to displace the strand complementary to the template strand as a new DNA strand is synthesized by the polymerase. This process is called "strand displacement" and the DNA polymerases that have this activity are referred to herein as "strand-displacing DNA polymerases." If the DNA template is a single-stranded circle, primed DNA synthesis proceeds around and around the circle, with continual displacement of the strand ahead of the replicating strand, a process called "rolling circle replication." Rolling circle replication results in synthesis of tandem copies of the circular template. The suitability of a DNA polymerase for use in an embodiment of the invention that comprises rolling circle replication can be readily determined. By way of example, but not of limitation, the ability of a polymerase to carry out rolling circle replication can be determined by using the polymerase in a rolling circle replication assay as described by Fire and Xu (Proc. Natl. Acad. Sci. USA, 92: 4641-4645, 1995), incorporated herein by reference. It is preferred that a DNA polymerase be a strand displacing DNA polymerase and lack a 5'-to-3' exonuclease activity for strand displacement polymerization reactions using both linear or circular templates since a 5'-to-3' exonuclease activity, if present, might result in the destruction of the synthesized strand. It is also preferred that DNA polymerases for use in the disclosed strand displacement synthesis methods are highly processive. The ability of a DNA polymerase to strand-displace can vary with reaction conditions, in addition to the particular enzyme used. Strand displacement and DNA polymerase processivity can also be assayed using methods described in Kong et al (J. Biol. Chem., 268: 1965-1975, 1993 and references cited therein, all of which are incorporated herein by reference).

Preferred strand displacing DNA polymerases of the invention are RepliPHI™ phi29 DNA polymerase (EPICENTRE Technologies, Madison, Wis., USA), phi29 DNA polymerase, rBst DNA polymerase large fragment (also called IsoTherm™ DNA polymerase (EPICENTRE Technologies, Madison, Wis., USA), BcaBEST™ DNA polymerase (Takara Shuzo Co., Kyoto, Japan), and SequiTherm™ DNA polymerase (EPICENTRE Technologies, Madison, Wis., USA). Other strand-displacing DNA polymerases which can be used include, but are not limited to phage M2 DNA polymerase (Matsumoto et al., Gene, 84: 247, 1989), phage phi PRD1 DNA polymerase (Jung et al., Proc. Natl. Acad. Sci. USA, 84: 8287, 1987), VENT® DNA polymerase (Kong et al., J. Biol. Chem. 268: 1965-1975, 1993), Klenow fragment of DNA polymerase I (Jacobsen et al., Eur. J. Biochem. 45: 623-627, 1974), T5 DNA polymerase (Chatterjee et al., Gene 97:13-19, 1991), PRD1 DNA polymerase (Zhu and Ito, Biochim. Biophys. Acta, 1219: 267-276, 1994), or T7 DNA polymerase in the presence of a T7 helicase/primase complex (Tabor and Richardson, Abstact No. 11, presented at the meeting "New Horizons in Genomics," Mar. 30-Apr. 1, 2003 in Santa Fe, N. Mex., sponsored by the DOE Joint Genome Institute. Strand displacing DNA polymerases are also useful in some embodiments of the invention for strand displacement replication of linear first-strand cDNA, and in other embodiments, for rolling circle replication of circular first-strand cDNA.

In general, it is desirable that the amount of strand-displacing DNA polymerase in the reaction be as high as possible without inhibiting the reaction. By way of example, but without limitation, RepliPHI™ phi29 DNA Polymerase can be used at about one microgram of protein in a 20-microliter reaction and IsoTherm™ DNA Polymerase can be used at about 50 units to about 300 units in a 50-microliter reaction. Since definitions for units vary for different DNA polymerases and even for similar DNA polymerases from different vendors or sources, and also because the activity for each enzyme varies at different temperatures and under different reaction conditions, it is desirable to optimize the amount of strand-displacing DNA polymerase and reaction conditions for each target sequence and particular assay or method of the invention.

Although not required for all DNA polymerases, strand displacement can be facilitated for some DNA polymerases through the use of a strand displacement factor, such as a helicase. It is considered that any DNA polymerase that can perform rolling circle replication in the presence of a strand displacement factor is suitable for use in embodiments of the invention that comprise rolling circle replication, even if the DNA polymerase does not perform rolling circle replication in the absence of such a factor. Strand displacement factors useful in rolling circle replication include, but are not limited to, BMRF1 polymerase accessory subunit (Tsurumi et al., J. Virology, 67: 7648-7653, 1993), adenovirus DNA-binding protein (Zijderveld and van der Vliet, J. Virology, 68: 1158-1164, 1994), herpes simplex viral protein ICP8 (Boehmer and Lehman, J. Virology, 67: 711-715, 1993); Skaliter and Lehman, Proc. Natl. Acad. Sci. USA, 91: 10,665-10,669, 1994), single-stranded DNA binding proteins (SSB; Rigler and Romano, J. Biol. Chem., 270: 8910-8919, 1995), and calf thymus helicase (Siegel et al., J. Biol Chem., 267: 13,629-13,635, 1992).

Q. Methods and Assays of the Invention for Detecting a Target Sequence

Figure 20:
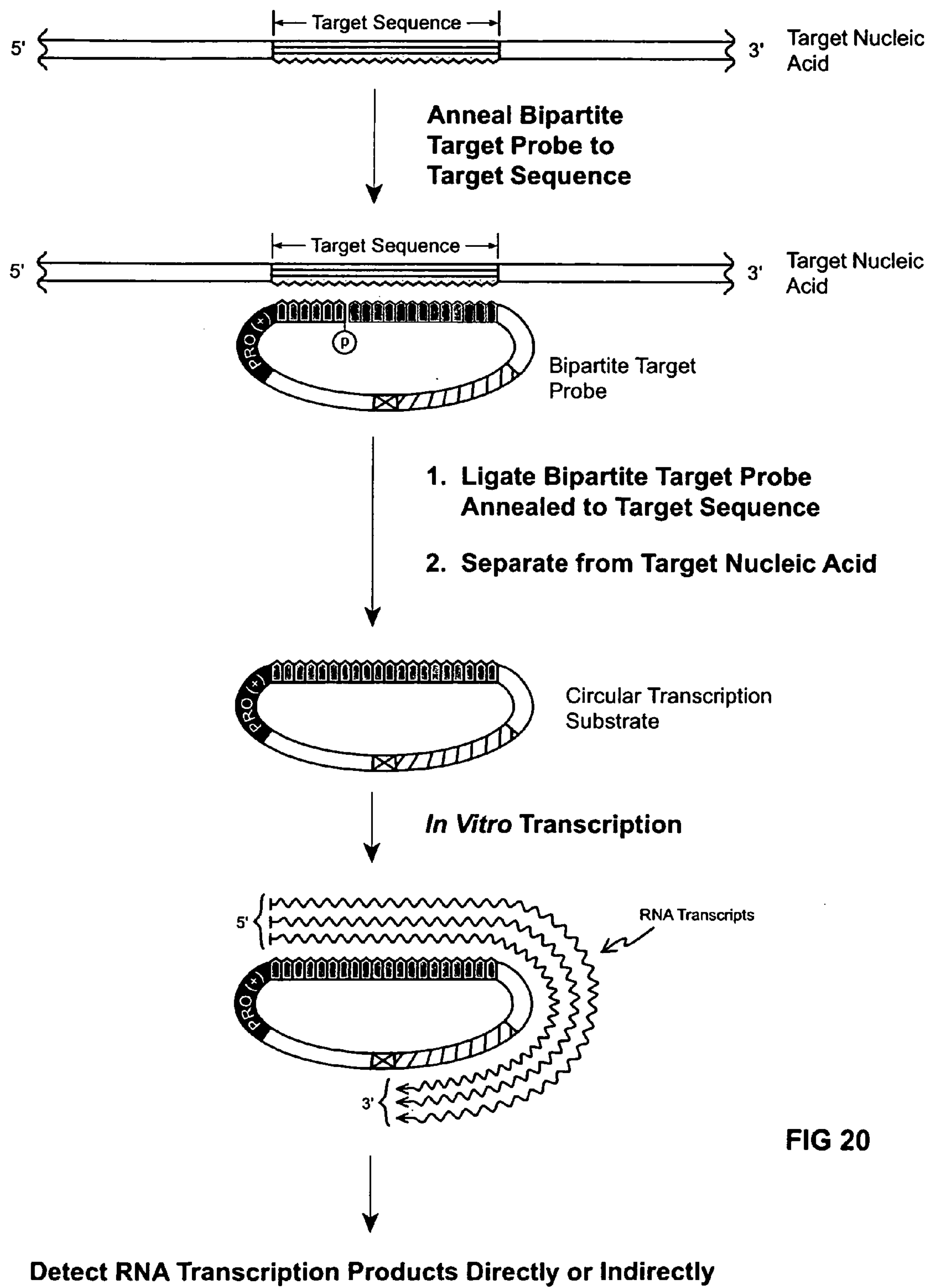
FIG. 20—A basic embodiment of the invention for detecting a target sequence using a bipartite target probe having target-complementary sequences that are contiguous when annealed to a target sequence comprising a target nucleic acid or a target sequence tag that is joined to an analyte-binding substance.

The present invention comprises methods, compositions and kits for detecting one or multiple specific target sequences in a sample by target-dependent transcription. FIG. 20 shows one basic embodiment of a method of the present invention. This embodiment uses a bipartite target probe. A bipartite target probe is a linear single-stranded DNA molecule that has sequences on both ends of the probe that are complementary to different portions of a target sequence. In the embodiment shown in FIG. 20, the target-complementary sequences of the bipartite target probe are contiguous or adjacent or abut to each other when annealed to the target sequence. The sequence at the 5'-end of the bipartite target probe preferably has a 5'-phosphate group or is phosphorylated by a polynucleotide kinase during the course of a method of the invention. The 5'-portion of the bipartite target probe also has a sequence for a single-stranded transcription promoter that is a functional promoter for a DNA-dependent RNA polymerase that can bind to this single-stranded promoter and initiate transcription of RNA therefrom in a 5'-to-3' direction using single-stranded DNA that is 5'- of and covalently linked to the promoter as a template. The promoter is oriented within the single-stranded DNA of the bipartite target probe 3'- of the target-complementary sequence at the 5'-end of the 5'-portion. The sequence at the 3'-end of the bipartite target probe preferably has a 3'-hydroxyl group.

Referring to FIG. 20, in the presence of a target sequence comprising a single-stranded DNA target or one strand of a double-stranded DNA target, a bipartite target probe anneals to the target sequence under hybridization conditions, wherein the 5'-phosphorylated end of the bipartite target probe is adjacent to its 3'-hydroxyl end. Then, the ends of the bipartite target probe are ligated under ligation conditions by contacting the target-complementary ends annealed to a target sequence with a ligase that has little or no activity in ligating free ends that are not annealed to a complementary sequence but is active in joining a 5'-phosphorylated end to a 3'-hydroxylated end when the ends are adjacent when annealed to a complementary DNA sequence. Ligation of the ends of the bipartite target probe generates a "circular transcription substrate," meaning a circular single-stranded DNA molecule that is a template for transcription by an RNA polymerase that recognizes a promoter sequence in said circular transcription substrate.

Thus, again referring to FIG. 20, one embodiment of the present invention comprises a method for detecting a target sequence, said method comprising:

a. providing a bipartite target probe, wherein said bipartite target probe comprises a linear single-stranded DNA (ssDNA) comprising two end portions that are complementary to a contiguous target sequence, and wherein said bipartite target probe forms a circular transcription substrate upon joining of said ends;

b. annealing said bipartite target probe to said target nucleic acid comprising said target sequence under hybridization conditions;

c. ligating said bipartite target probe annealed to said target nucleic acid under ligation conditions with a ligase, wherein said ligase has little or no activity in ligating blunt ends and is substantially more active in ligating said ends of said bipartite target probe if said ends are adjacent when annealed to two contiguous regions of a target sequence than if said ends are not annealed to said target sequence, so as to obtain a circular ssDNA molecule that comprises a circular transcription substrate;

d. obtaining said circular transcription substrate, wherein said circular transcription substrate comprises a sequence that is complementary to said target sequence;

e. contacting said circular transcription substrate with an RNA polymerase under transcription conditions so as to synthesize RNA that is complementary to said circular transcription substrate; and f. detecting the synthesis of RNA resulting from transcription of said circular transcription substrate, wherein said synthesis of said RNA indicates the presence of said target sequence comprising said target nucleic acid.

Also, since transcription of said circular transcription substrate increases the number of copies of the target sequence, the invention also comprises a method for amplifying a target sequence, said method comprising:

a. providing a bipartite target probe, wherein said bipartite target probe comprises a linear single-stranded DNA (ssDNA) comprising two end portions that are complementary to a contiguous target sequence, wherein said bipartite target probe forms a circular transcription substrate upon joining of said ends;

b. annealing said bipartite target probe to said target nucleic acid comprising said target sequence under hybridization conditions;

c. ligating said bipartite target probe annealed to said target nucleic acid under ligation conditions with a ligase, wherein said ligase has little or no activity in ligating blunt ends and is substantially more active in ligating said ends of said bipartite target probe if said ends are adjacent when annealed to two contiguous regions of a target sequence than if said ends are not annealed to said target sequence, so as to obtain a circular ssDNA molecule that comprises a circular transcription substrate;

d. obtaining said circular transcription substrate, wherein said substrate comprises a sequence that is complementary to said target sequence;

e. contacting said circular transcription substrate with an RNA polymerase under transcription conditions so as to synthesize RNA that is complementary to said circular transcription substrate; and f. obtaining RNA transcripts comprising multiple copies of said target sequence.

Figure 21:
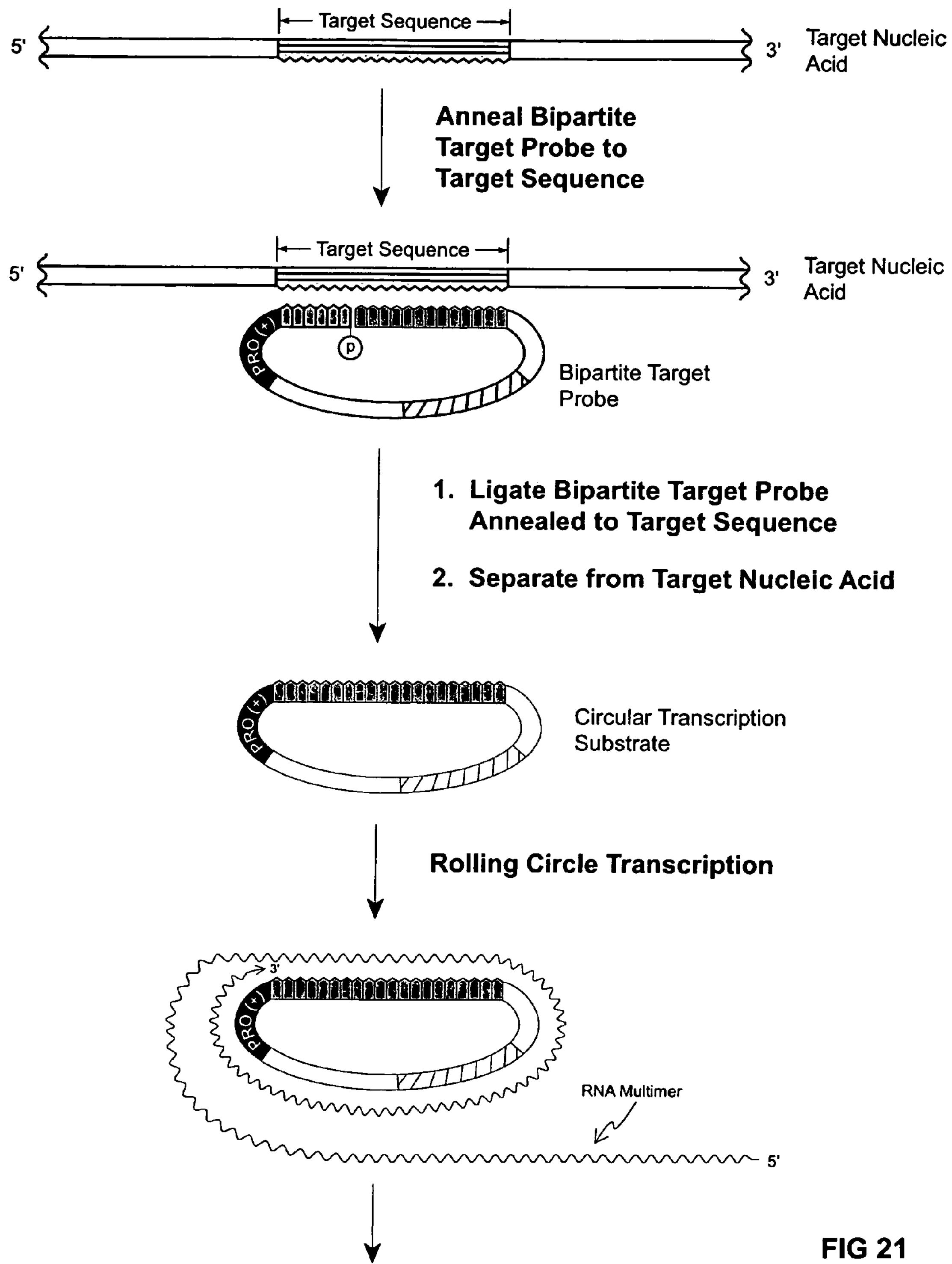
FIG. 21—An embodiment where a circular transcription substrate is used to obtain a multimeric transcription product by rolling circle transcription.

FIG. 21 shows an embodiment of a method or assay of the invention that is similar to the embodiment shown in FIG. 20 except that the bipartite target probe used in the method shown in FIG. 21 does not have a transcription termination sequence and transcription of the circular transcription substrate resulting therefrom generates a transcription product comprising an RNA multimer by rolling circle transcription.

Thus, referring to FIG. 21, one embodiment of the present invention comprises a method for detecting a target sequence, said method comprising:

a. providing a bipartite target probe, wherein said bipartite target probe comprises a linear single-stranded DNA comprising two end portions that are complementary to a contiguous target sequence, and wherein said bipartite target probe forms a circular transcription substrate upon joining of said ends;

b. annealing said bipartite target probe to said target nucleic acid comprising said target sequence under hybridization conditions;

c. ligating said bipartite target probe annealed to said target nucleic acid under ligation conditions with a ligase, wherein said ligase has little or no activity in ligating blunt ends and is substantially more active in ligating said ends of said bipartite target probe if said ends are adjacent when annealed to two contiguous regions of a target sequence than if said ends are not annealed to said target sequence, so as to obtain a circular ssDNA molecule that comprises a circular transcription substrate;

d. obtaining said circular transcription substrate, wherein said circular transcription substrate comprises a sequence that is complementary to said target sequence;

e. contacting said circular transcription substrate with an RNA polymerase under rolling circle transcription conditions so as to synthesize RNA multimers, wherein an RNA multimer comprises multiple tandem copies of an oligomer that is complementary to one copy of said circular transcription substrate; and f. detecting the synthesis of said RNA resulting from rolling circle transcription of said circular transcription substrate, wherein said synthesis of said RNA indicates the presence of said target sequence comprising said target nucleic acid.

Figure 22A:
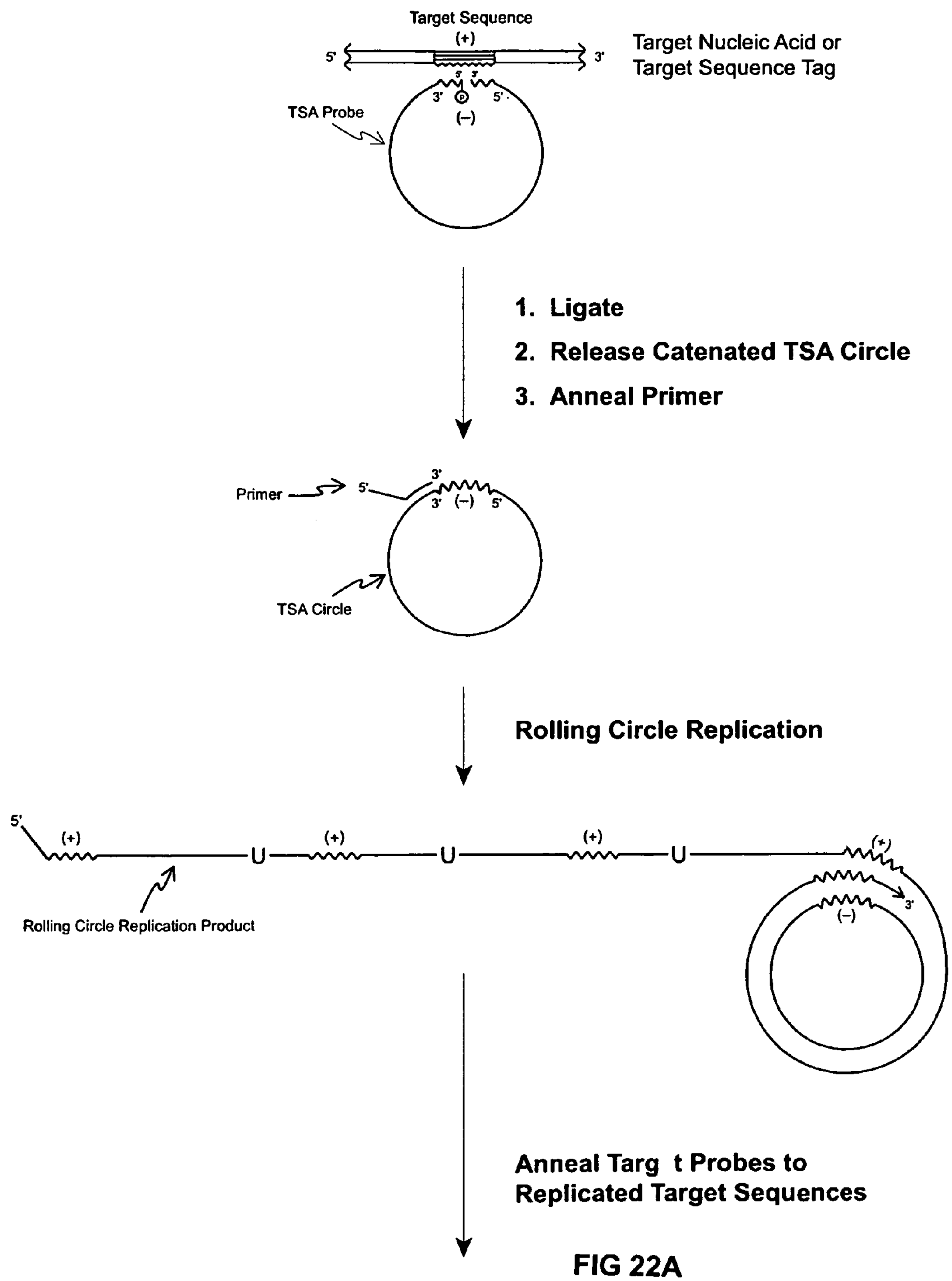
FIGS. 22A+B—An embodiment that uses coupled target-dependent rolling circle replication and rolling circle transcription to amplify the amount of transcription product obtained. The copies of the target sequence in the rolling circle replication product are identical to the target sequence in the sample and provide additional sites for annealing and ligation of bipartite target probes in order to obtain more circular transcription substrates. Ligation of the bipartite target probe catenates the circular transcription substrate to the rolling circle replication product comprising the replicated target sequence. The catenated circular transcription substrates must be released from the rolling circle replication product to achieve efficient rolling circle transcription. The method for releasing the catenated circular transcription substrates illustrated here is to include a quantity of dUTP in the rolling circle replication reaction mix in addition to dTTP so that a dUMP residue is incorporated randomly about every 100-400 nucleotides. Uracil-N-glycosylase and endonuclease N, which cleave the DNA strand wherever dUMP is incorporated, is also included in the reaction mixture. Once the rolling circle replication product is cleaved so that, on average, most of the replicated target sequences are within about 150-200 nucleotides from a free 3'-end, the catenated circular transcription substrates will be released during rolling circle transcription.
Figure 22B:
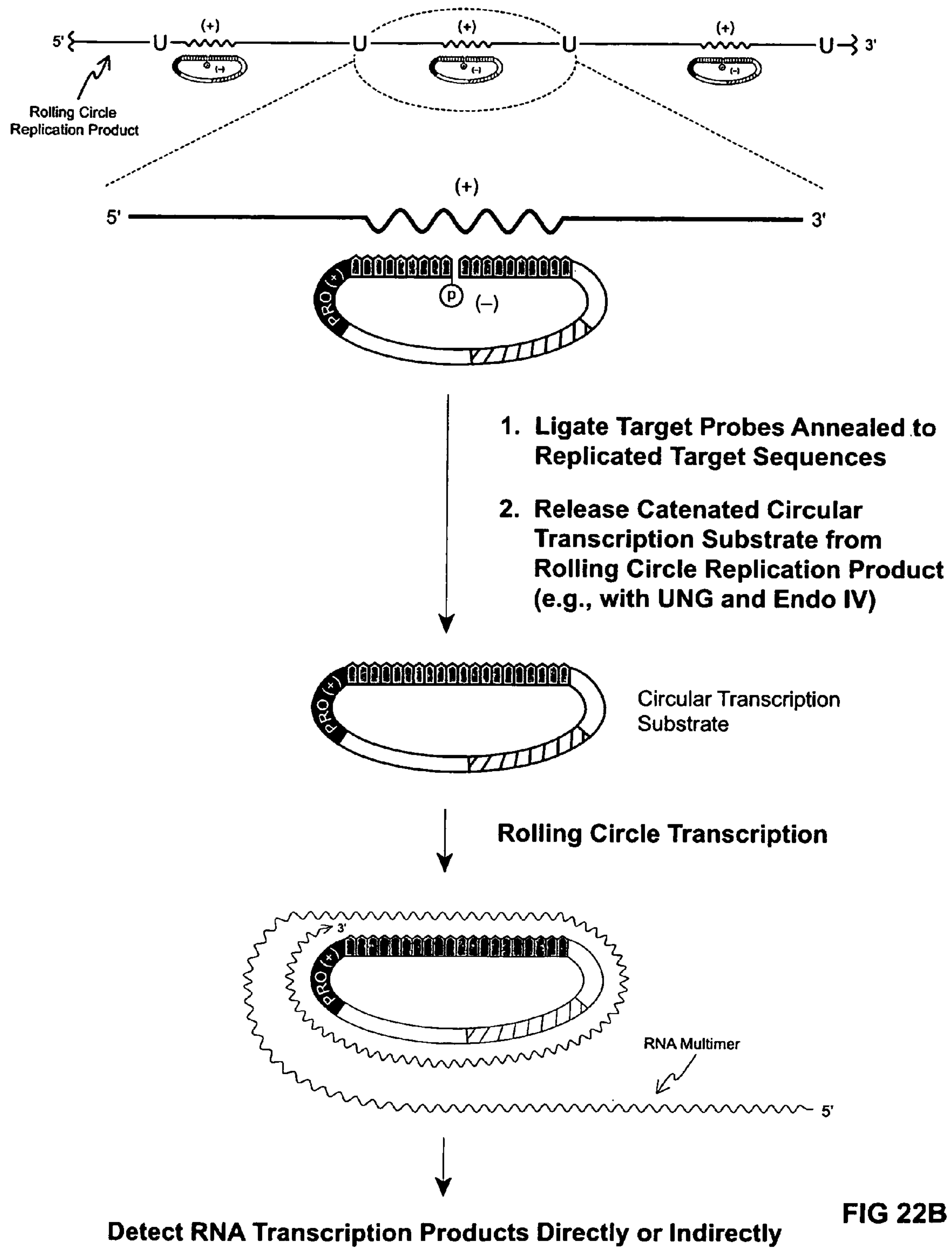

Other embodiments of the present invention, as shown in FIG. 22, comprise compositions, methods and kits for detecting one or multiple specific target sequences in a sample by coupled target-dependent rolling circle replication (RCR) and rolling circle transcription (RCT). These embodiments use bipartite target probes to generate circular transcription substrates as shown in either FIG. 20 or FIG. 21, which result in circular transcription substrate either with a transcription terminator or lacking a transcription terminator, respectively. If the circular transcription substrate lacks a transcription terminator sequence, transcription comprises rolling circle transcription as described elsewhere herein. In addition to using a bipartite target probe, these embodiments also use a “bipartite target sequence amplification probe,” which is also referred to as a “bipartite TSA probe” or simply as a “TSA probe” herein. The purpose of a TSA probe in an assay or method is to obtain a target-dependent amplification of the number of copies of the target sequence and thereby, to provide additional sites for annealing and ligation of the bipartite target probe.

A TSA probe is a linear single-stranded DNA molecule that comprises two target-complementary sequences that are connected by an intervening sequence that is not complementary to the target sequence. The target-complementary portions on the ends are complementary to different portions of a target sequence in a target nucleic acid or a target sequence tag of an analyte-binding substance. Each of the 5' and 3' target-complementary sequences in a TSA probe for a particular assay or method is identical to the corresponding target-complementary sequence at the 5'-end or the 3'-end of a bipartite target probe used in the assay or method. That is, the 5'-end of a TSA probe anneals to the same nucleotides in the target sequence as the 5'-end of the corresponding bipartite target probe that is used to obtain a circular transcription substrate and similarly, the 3'-end of the TSA probe anneals to the same nucleotides of the target sequence as the 3'-end of the bipartite target probe. Thus, as shown in FIG. 22, the target-complementary sequences of the TSA probe are adjacent to each other when annealed to the target sequence in exactly the same manner as described previously for bipartite target probes. Similarly, the sequence at the 5'-end of the TSA probe preferably has a 5'-phosphate group or is phosphorylated by a polynucleotide kinase during the course of a method of the invention and the sequence at the 3'-end of a TSA probe preferably has a 3'-hydroxyl group. After annealing to a target sequence, if present in a sample, the adjacent target-complementary sequences of a TSA probe are ligated in a method of the invention with a ligase that has little or no activity in ligating blunt ends and that is substantially more active in ligating said ends that are adjacent when annealed to two contiguous regions of a target sequence than if said ends are not so annealed. Ligation of a TSA probe results in formation of a "TSA circle," which, upon annealing to a primer, is a substrate for rolling circle replication.

The target-complementary sequences of a TSA probe are connected by an intervening sequence. The sequence and nucleotide composition of the intervening sequence can vary, but it should comprise a sequence of sufficient length and sequence specificity to provide a primer-binding site for specific priming by a primer for rolling circle replication. The intervening sequence should also be of sufficient length to permit the target-complementary sequences of the TSA probe to anneal to the target sequence with specificity. In addition, the length of the intervening sequence should be optimized to obtain the optimal target-dependent ligation efficiency with the ligase and the maximum rolling circle replication rate and maximum end-point level of RCR product with the strand-displacing DNA polymerase under the assay conditions used. Although a bipartite target probe could also be used as a TSA probe, it is preferable that the TSA probe is not a bipartite target probe. Preferably, a TSA probe does not have a transcription promoter sequence, a transcription termination sequence, or a signal sequence, and preferably the primer-binding site in a TSA probe for a strand-displacing DNA polymerase primer used for rolling circle replication is not present in the corresponding bipartite target probe. The lack of a promoter sequence in the TSA probe or the resulting TSA circle permits maximum rolling replication because there is no promoter to bind an RNA polymerase or initiate transcription. Similarly, the lack of a primer-binding site for priming by a strand-displacing DNA polymerase on the bipartite target probe or the resulting circular transcription substrate permits maximum transcription because there is not site for priming a competitive rolling circle transcription reaction.

Referring to FIG. 22, in the presence of a target sequence, a TSA probe anneals to the target sequence under hybridization conditions, wherein the 5'-phosphorylated end of the TSA probe is adjacent to its 3'-hydroxyl end. Then, the ends of the TSA probe are ligated under ligation conditions by contacting the target-complementary ends annealed to a target sequence with a ligase that has little or no activity in ligating free ends that are not annealed to a complementary sequence but is active in joining a 5'-phosphorylated end to a 3'-hydroxylated end when the ends are adjacent when annealed to a complementary DNA sequence. Ligation of the ends of the TSA probe generates a TSA circle. Upon annealing of a primer to the TSA circle and contacting the resulting complex with a strand-displacing DNA polymerase under strand-displacing polymerization conditions, rolling circle replication occurs, thereby generating multiple tandem copies of the target sequence to which the target-complementary sequences of a bipartite target probe can anneal under hybridization conditions. The adjacent 5'-phosphorylated end and the 3'-hydroxyl end of the bipartite target probes annealed to the tandem target sequences of the rolling circle replication products are ligated by the ligase under ligation conditions, thereby generating a circular transcription substrate. Transcription products are obtained by contacting the circular transcription substrates with an RNA polymerase that can bind the single-stranded promoter and initiate transcription therefrom using a single-stranded template, and the transcription products are obtained or detected by a suitable means.

Thus, again referring to FIG. 22, one embodiment of the present invention comprises a method for obtaining a transcription product complementary to a target nucleic acid sequence (target sequence), said method comprising:

a. providing a TSA probe, wherein said TSA probe comprises a linear single-stranded DNA (ssDNA) comprising two end portions that are complementary to the contiguous target sequence that are connected by an intervening sequence, and wherein said TSA probe can form a TSA circle upon joining of said ends;

b. providing a primer that is complementary to the intervening sequence of said TSA probe;

c. providing a bipartite target probe, wherein said bipartite target probe comprises a linear ssDNA comprising two end portions that are complementary to a contiguous target sequence, and wherein said bipartite target probe forms a circular transcription substrate upon joining of said ends;

d. annealing said TSA probe to said target sequence under hybridization conditions;

e. ligating said TSA probe annealed to said target sequence under ligation conditions with a ligase, wherein said ligase has little or no activity in ligating blunt ends and is substantially more active in ligating said ends of said bipartite target probe if said ends are adjacent when annealed to two contiguous regions of a target sequence than if said ends are not annealed to said target sequence, so as to obtain a TSA circle;

f. annealing the primer that is complementary to the intervening sequence of the TSA probe to the TSA circle under hybridization conditions;

g. contacting said TSA circle to which said primer is annealed with a strand-displacing DNA polymerase under strand-displacing polymerization conditions so as to obtain a rolling circle replication product comprising multiple copies of the target sequence;

h. annealing said bipartite target probe to said multiple copies of the target sequence of said rolling circle replication product under hybridization conditions;

i. ligating said bipartite target probe annealed to said multiple copies of the target sequence of said rolling circle replication product with a ligase under ligation conditions, wherein said ligase has little or no activity in ligating blunt ends and is substantially more active in ligating ends that are adjacent when annealed to two contiguous regions of a target sequence than if said ends are not annealed, so as to obtain a circular ssDNA molecule that comprises a circular transcription substrate;

j. obtaining said circular transcription substrate, wherein said circular transcription substrate comprises a sequence that is complementary to said target sequence;

k. contacting said circular transcription substrate with an RNA polymerase under transcription conditions so as to obtain a transcription product that is complementary to said circular transcription substrate; and l. obtaining said transcription product that is complementary to said circular transcription substrate, wherein said transcription product indicates the presence of said target sequence.

Preferably, only one ligase is used in this embodiment for ligating both the TSA probe and the bipartite target probe. Preferably, the ligase has little or no activity in ligating blunt ends and is substantially more active in ligating ends that are adjacent when annealed to two contiguous regions of a target sequence compared to ends that are not annealed to the target sequence. One suitable ligase that can be used is Ampligase® Thermostable DNA Ligase (EPICENTRE Technologies, Madison, Wis.). A preferred strand-displacing DNA polymerase that can be used is IsoTherm™ DNA Polymerase (EPICENTRE Technologies, Madison, Wis.). Another suitable strand-displacing DNA polymerase that can be used is RepliPHI™ phi29 DNA polymerase (EPICENTRE Technologies, Madison, Wis.). Some preferred RNA polymerases are T7 RNAP, T3 RNAP, SP6 RNAP or another T7-like RNA polymerase or a mutant form of one of these T7-like RNA polymerases. Preferably, AmpliScribe T7-Flash™ Transcription Kit is used for in vitro transcription of the transcription substrate (EPICENTRE Technologies, Madison, Wis.).

In some embodiments, the target sequence comprises a target nucleic acid in a sample, whereas in other embodiments the target sequence comprises a target sequence tag that is joined to an analyte-binding substance that binds an analyte in the sample. In some embodiments, the TSA circle that is replicated remains catenated to a target nucleic acid. Preferably, the target sequence is less than about 150 to about 200 nucleotides from the 3'-end of the target nucleic acid or target sequence tag. In other embodiments of methods in which the target sequence is greater than about 150 to about 200 nucleotides from the 3'-end of the target nucleic acid or target sequence tag, then one or more additional steps is used in order to release the catenated TSA circles from the target sequence prior to rolling circle replication, as described elsewhere herein. Similarly, one or more additional steps can be used in order to release the catenated circular ssDNA ligation products (which are circular transcription substrates) that result from ligation of bipartite target probes that are annealed to target sequences in the rolling circle replication product more than about 150 nucleotides to about 200 nucleotides from the 3'-end of to the rolling circle replication product. In one preferred embodiment, rolling circle replication is carried out using a ratio of dUTP to dTTP that results in incorporation of a dUMP residue about every 100-400 nucleotides and a composition comprising uracil-N-glycosylase and endonuclease IV is used to release catenated DNA molecules that are ligated on the linear rolling circle replication product following annealing of bipartite target probes to the replicated target sequences.

Figure 23:
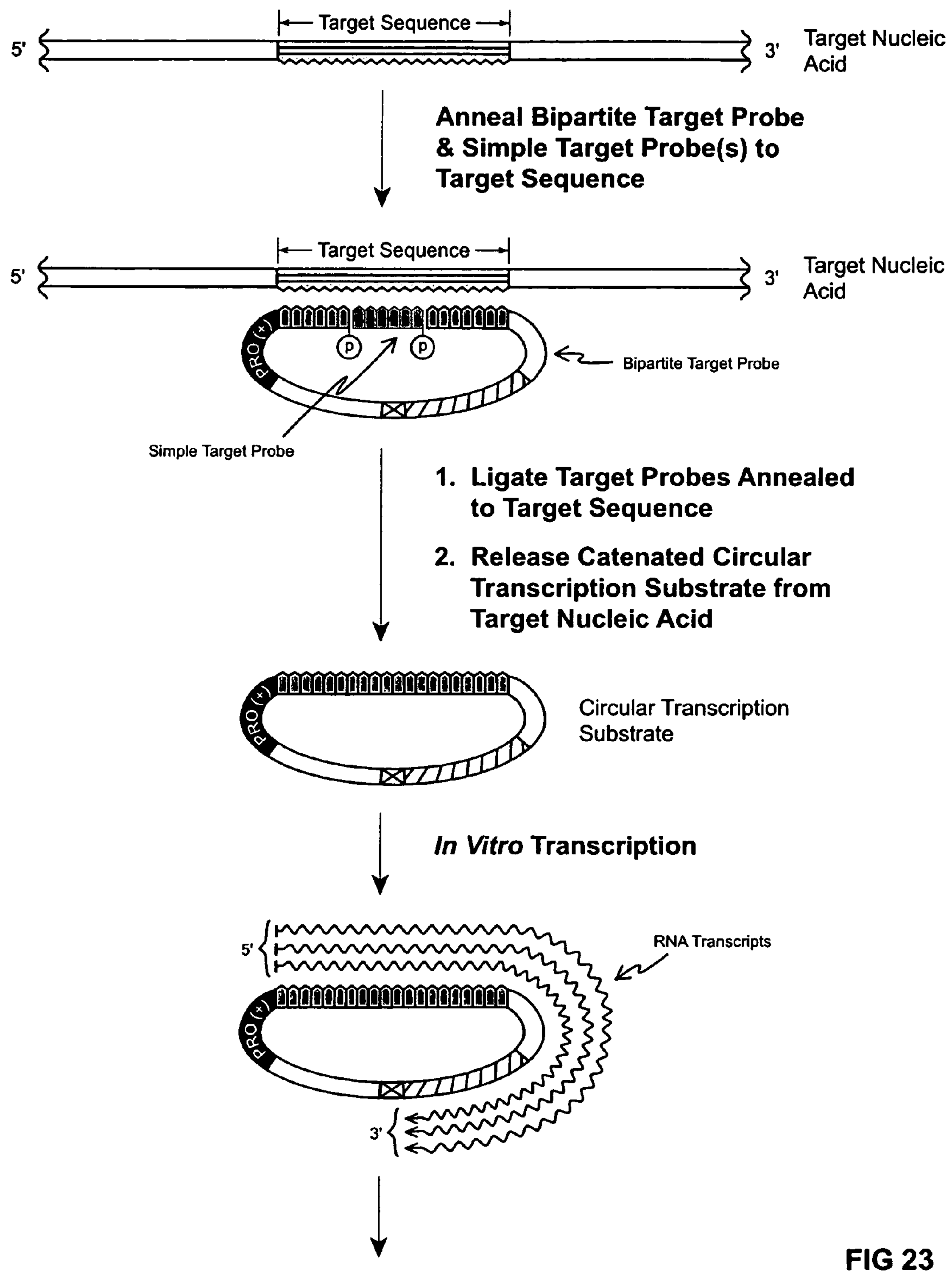
FIG. 23—An embodiment in which target-complementary sequences of the bipartite target probe are not contiguous when annealed to a target sequence and the gap between the target-complementary sequences is filled using simple target probes. In the embodiment illustrated here, the circular transcription substrate has a transcription termination sequence so that only one copy of the transcription product is obtained, rather than a multimer of tandem oligomers as obtained from rolling circle transcription.

FIG. 23 shows one aspect of another embodiment of a method of the present invention. This embodiment also uses a bipartite target probe that is similar to a bipartite target probe used in the method shown in FIG. 20, except that the target-complementary sequences of the bipartite target probe used in the embodiment shown in FIG. 23 are not contiguous or adjacent to each other when annealed to the target sequence. Rather, the target-complementary sequences of a bipartite target probe of this embodiment are separated from each other when they are annealed to the target sequence. The gap between the two target-complementary sequences can comprise from about four nucleotides to about 1000 nucleotides or more. Although the invention is not limited to a particular distance between the target-complementary sequences when annealed to a target sequence, preferably the gap in this embodiment of the invention comprises from about six nucleotides to about 100 nucleotides, and most preferably, the gap comprises from about six nucleotides to about 25 nucleotides. As in the previous embodiments, the 5'-end of the bipartite target probe in the embodiment in FIG. 23 preferably has a 5'-phosphate group or is phosphorylated by a polynucleotide kinase during the course of a method of the invention, and the 3'-end preferably has a 3'-hydroxyl group. Also as in previously discussed embodiments, the 5'-portion of the bipartite target probe in the embodiment of FIG. 23 has sequence for a single-stranded transcription promoter that is a functional promoter for a DNA-dependent RNA polymerase that can bind to this single-stranded promoter and initiate transcription of RNA therefrom in a 5'-to-3' direction using single-stranded DNA which is 5'- of and covalently linked to the promoter. The promoter is oriented within the single-stranded DNA of a bipartite target probe 3'- of the target-complementary sequence at the 5'-end of the 5'-portion.

In the aspect of the embodiment of the method shown in FIG. 23, the gap between the target-complementary sequences of a bipartite target probe annealed to a target sequence is filled by also annealing one or more simple target probes comprising target-complementary sequences that anneal to the target sequence between portions of the target to which the target-complementary sequences of the bipartite target probe anneal. The simple target probes used anneal to the target sequence so as to fill the gap completely so as to abut with or to be contiguous with each other and with the target-complementary sequences of the bipartite target probe. All 5'-ends of simple target probes and of the bipartite target probe have a 5'-phosphate group and all 3'-ends have hydroxyl groups. Thus, ligation of the bipartite target probe and simple target probes that are annealed to a target sequence with a ligase, which ligase has little or no activity in ligating free ends that are not annealed to a complementary sequence but is active in joining a 5'-phosphorylated end to an adjacent 3'-hydroxylated end when the ends are annealed to a complementary DNA sequence, generates a circular transcription substrate. Transcription of the circular transcription substrate results in synthesis of RNA that is complementary to the circular transcription substrate and that can be used to detect the presence of the target sequence.

Thus, again referring to FIG. 23, one embodiment of the present invention comprises a method for detecting a target sequence, said method comprising:

a. providing a bipartite target probe, wherein said bipartite target probe comprises a linear single-stranded DNA (ssDNA) comprising two end portions that are complementary to different non-contiguous 5'- and 3'-end portions of a target sequence;

b. providing one or more simple target probes, wherein said simple target probes are complementary to the target sequence so as to anneal to said target sequence in the gap between the target-complementary sequences of said bipartite target probe so as to completely fill said gap and so that each of the ends of said simple target probes are contiguous with an end of a simple target probe or with an end of said bipartite target probe;

c. annealing said bipartite target probe and said simple target probes to said target sequence comprising said target nucleic acid under hybridization conditions;

d. ligating said bipartite target probe and said simple target probes annealed to said target sequence under ligation conditions with a ligase, wherein said ligase has little or no activity in ligating blunt ends and is substantially more active in ligating said ends of said simple target probes and said ends of said bipartite target probe if said ends are adjacent when annealed to two contiguous regions of a target sequence than if said ends are not annealed to said target sequence, so as to obtain a circular ssDNA molecule that comprises a circular transcription substrate;

e. obtaining said circular transcription substrate, wherein said substrate comprises a sequence that is complementary to said target sequence;

f. contacting said circular transcription substrate with an RNA polymerase under transcription conditions so as to synthesize RNA that is complementary to said circular transcription substrate; and g. detecting the synthesis of RNA resulting from transcription of said circular transcription substrate, wherein said synthesis of said RNA indicates the presence of said target sequence comprising said target nucleic acid.

Figure 24:
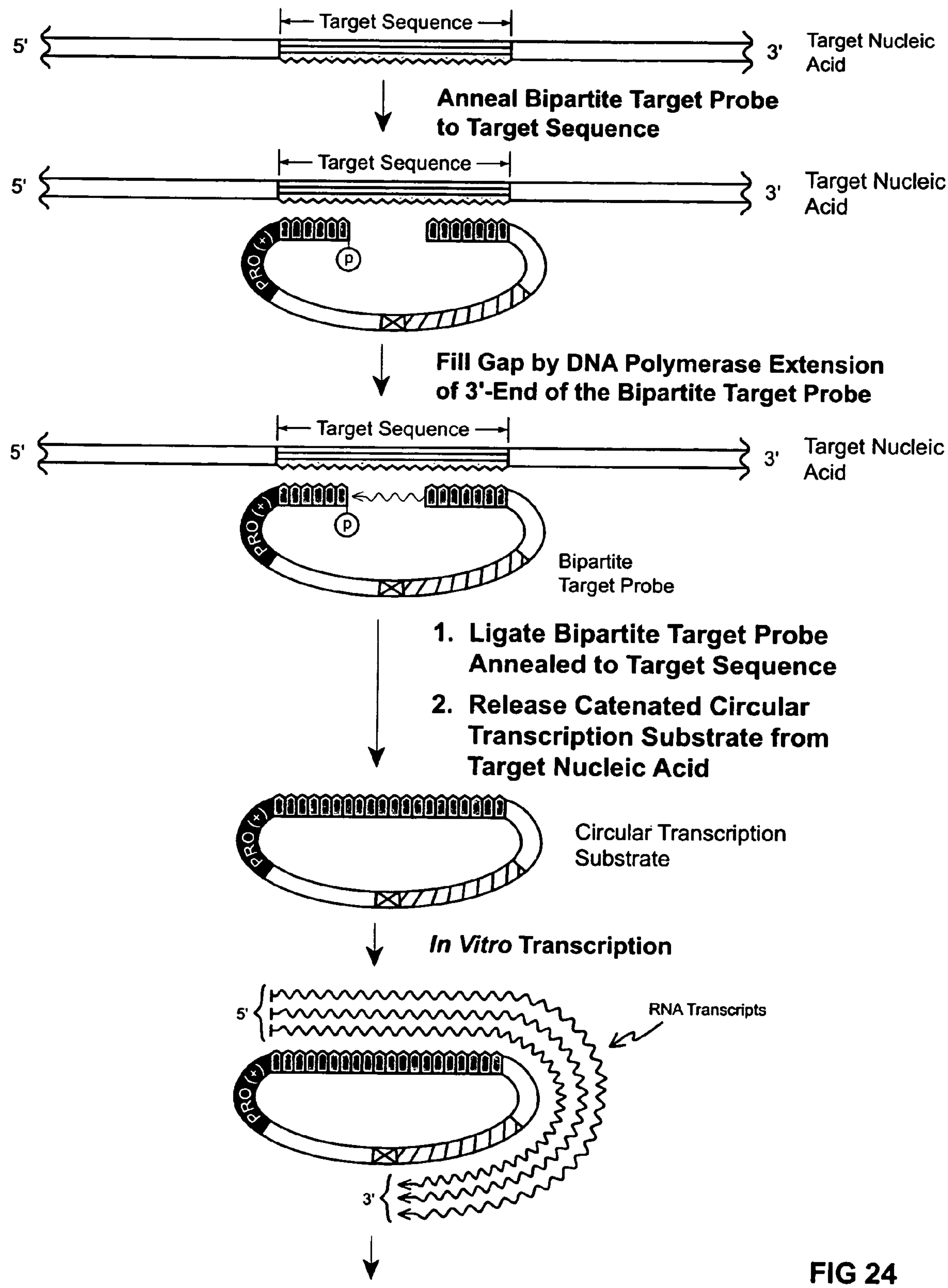
FIG. 24—An embodiment in which target-complementary sequences of the bipartite target probe are not contiguous when annealed to a target sequence and the gap between the target-complementary sequences is filled by DNA polymerase extension.

FIG. 24 shows another aspect of an embodiment of a method of the present invention that uses a bipartite target probe that comprises target-complementary sequences that are separated from each other when they are annealed to a target sequence. However, in this embodiment, the gap between the target-complementary sequences of a bipartite target probe annealed to a target sequence is filled by primer extension using a DNA polymerase and subsequently joined by ligation with a ligase if and only if both the 3'-end of the target probe that is annealed to the target sequence 3'- of the gap and the target probe that is annealed to the target sequence 5'- of the gap are complementary to and correctly basepaired with the target sequence. If the 3'-end of the target probe that is 3'- of the gap is not annealed to the target sequence, then the DNA polymerase will be unable to fill the gap by primer extension. Also, if the 5'-end of the target probe that is 5'- of the gap is not annealed to the target sequence, then the 3'-end of the primer extension product will not be adjacent to a 5'-end on the target sequence and it will not be possible to join the 3'-end of the primer-extended target probe with the 5'-phosphorylated end of the target probe annealed 5'- of the gap.

The gap between the two target-complementary sequences can comprise from one nucleotide to about 1000 nucleotides or more. Although the invention is not limited to a particular distance between the target-complementary sequences when annealed to a target sequence, preferably the gap comprises from one nucleotide to about 100 nucleotides, and most preferably, the gap in most embodiments comprises from one nucleotide to about 25 nucleotides. The 5'-end of a bipartite target probe in the embodiment in FIG. 24 preferably has a 5'-phosphate group or is phosphorylated by a polynucleotide kinase during the course of a method of the invention, and the 3'-end preferably has a 3'-hydroxyl group. Also, the 5'-portion of the bipartite target probe in the embodiment of FIG. 24 has sequence for a single-stranded transcription promoter that is a functional promoter for a DNA-dependent RNA polymerase that can bind to this single-stranded promoter and initiate transcription of RNA therefrom in a 5'-to-3' direction using single-stranded DNA which is 5'- of and covalently linked to the promoter. The promoter is oriented within the single-stranded DNA of a bipartite target probe 3'- of the target-complementary sequence at the 5'-end of the 5'-portion.

In the embodiment of a method shown in FIG. 24, the gap between the target-complementary sequences of a bipartite target probe annealed to a target sequence is filled by contacting the target sequence to which a bipartite target probe is annealed with a DNA polymerase under polymerization conditions. Then, the 5'-phosphorylated end of a bipartite target probe annealed to a target sequence is joined to the 3'-end of the DNA polymerase-extended 3'-end of said bipartite target probe with a ligase, which ligase has little or no activity in ligating free ends that are not annealed to a complementary sequence but is active in joining a 5'-phosphorylated end to an adjacent 3'-hydroxylated end when the ends are annealed to a complementary DNA sequence, generates a circular transcription substrate. Transcription of the circular transcription substrate results in synthesis of RNA that is complementary to the circular transcription substrate and that can be used to detect the presence of the target sequence.

Thus, referring to FIG. 24, one embodiment of the present invention comprises a method for detecting a target sequence, said method comprising:

a. providing a bipartite target probe, wherein said bipartite target probe comprises a linear single-stranded DNA (ssDNA) comprising two end portions that are complementary to different non-contiguous 5'- and 3'-end portions of a target sequence;

b. annealing said bipartite target probe to said target nucleic acid comprising said target sequence under hybridization conditions;

c. contacting said complex comprising said bipartite target probe annealed to said target nucleic acid with a DNA polymerase under non-strand-displacing DNA polymerization conditions so as to obtain a DNA polymerase extension product that is complementary to the target sequence between the target-complementary sequences of said annealed bipartite target probe so as to completely fill said gap and so that the 3'-end of said synthesized DNA is contiguous with the 5'-end of said bipartite target probe;

d. ligating the 5'-end of said bipartite target probe annealed to said target nucleic acid with the 3'-end of said DNA polymerase extension product under ligation conditions with a ligase, wherein said ligase has little or no activity in ligating blunt ends and is substantially more active in ligating said ends of said simple target probes and said ends of said bipartite target probe if said ends are adjacent when annealed to two contiguous regions of a target sequence than if said ends are not annealed to said target sequence, so as to obtain a circular ssDNA molecule that comprises a circular transcription substrate;

e. obtaining said circular transcription substrate, wherein said substrate comprises a sequence that is complementary to said target sequence;

f. contacting said circular transcription substrate with an RNA polymerase under transcription conditions so as to synthesize RNA that is complementary to said circular transcription substrate; and g. detecting the synthesis of RNA resulting from transcription of said circular transcription substrate, wherein said synthesis of said RNA indicates the presence of said target sequence comprising said target nucleic acid.

In addition to the embodiments disclosed above for filling a gap between target-complementary sequences of a bipartite target probe that are not contiguous when annealed to a target sequence, the invention also comprises methods that use a combination of both one or more simple target probes and DNA polymerase extension in order to fill the gap so as to obtain adjacent target-complementary sequences prior to the ligation step.

Figure 25:
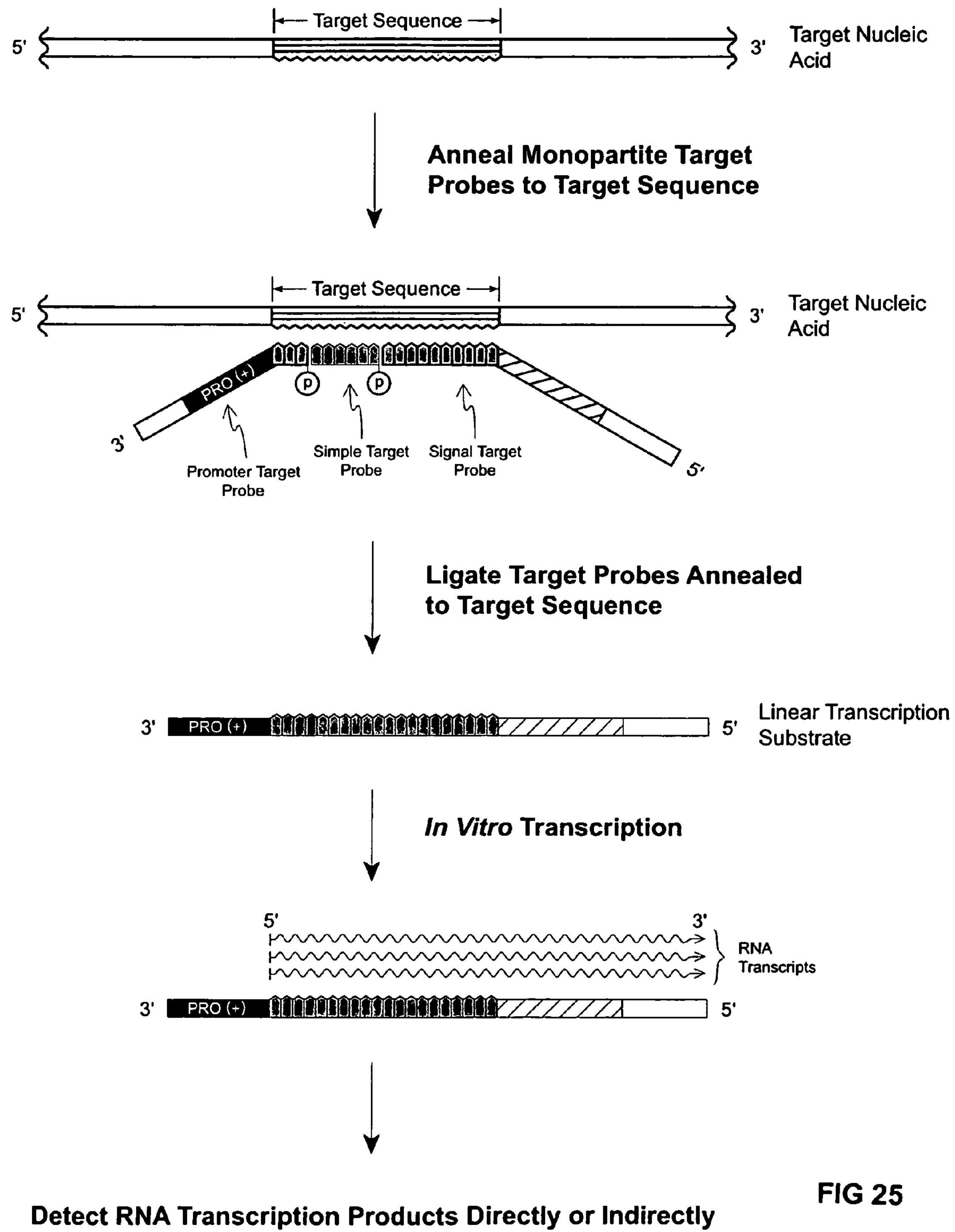
FIG. 25—An embodiment for detecting a target sequence by generating a linear transcription substrate using monopartite target probes.

Other embodiments of methods of the invention generate a linear transcription substrate for amplifying, detecting and quantifying one or multiple target nucleic acid sequences in a sample, including target sequences that differ by as little as one nucleotide. FIG. 25 shows a basic embodiment of a method that generates a linear transcription substrate. This embodiment uses only monopartite target probes. A monopartite target probe is a single-stranded DNA molecule that comprises only one target-complementary sequence, although a monopartite target probe can comprise other sequences that are not complementary to a target sequence. By way of example, but not of limitation, a method of the invention that generates a linear transcription substrate always uses a monopartite target probe called a "promoter target probe." A "promoter target probe" has a 5'-portion and a 3'-portion. The 5'-portion of a promoter target probe comprises a sequence that is complementary to the most 5'-portion of a target sequence, and the 3'-portion of a promoter target probe comprises a sequence that serves as a functional transcription promoter for a DNA-dependent RNA polymerase that can bind to this single-stranded promoter and initiate transcription of RNA therefrom in a 5'-to-3' direction under transcription conditions using single-stranded DNA that is 5'- of (with respect to the same strand) and covalently linked to the promoter as a template. The sequence at the 5'-end of the promoter target probe preferably has a 5'-phosphate group or is phosphorylated by a polynucleotide kinase during the course of a method of the invention. The embodiment of the method shown in FIG. 25 also uses another monopartite target probe called a "signal target probe." A "signal target probe" has a 3'-portion and a 5'-portion. At least the 3'-end portion of a signal target probe comprises a sequence that is complementary to the most 3'-portion of a target sequence. As shown in the embodiment in FIG. 25, the 3'-end of the signal target probe has a 3'-hydroxyl group. The 5'-portion of a signal target probe comprises a "signal sequence." A signal sequence is a sequence that is detectable in some way following its transcription during a method of the invention. The invention does not require the use of a signal target probe having a signal sequence. By way of example, but not of limitation, a simple target probe could be used in an assay of the invention in place of a signal target probe. If a signal target probe is used in a method of the invention, the signal sequence can comprise any sequence that is detectable following transcription. By way of example, but not of limitation, a signal sequence can comprise a sequence that is detectable using a molecular beacon as described by Tyagi et al. (U.S. Pat. Nos. 5,925,517 and 6,103,476 of Tyagi et al. and 6,461,817 of Alland et al., all of which are incorporated herein by reference). A preferred signal sequence of the invention is a sequence that results in an additional amplification of the signal following its transcription, thus making the detection of a target sequence more sensitive. The signal target probe used in the method shown in FIG. 25 can be, for example, a signal sequence that encodes a substrate for Q-beta replicase (EPICENTRE Technologies, Madison, Wis.), which permits additional amplification of the signal by incubating the transcription product with Q-beta replicase under replication conditions. However, as discussed elsewhere herein, many other signal sequences can be used in a signal target probe, all of which are incorporated as part of the present invention.

Thus, again referring to FIG. 25, one embodiment of the present invention comprises a method for detecting a target, said method comprising:

- a. providing a promoter target probe, wherein said promoter target probe comprises a linear single-stranded DNA (ssDNA) comprising a 5'-end portion that is complementary to the most 5'-portion of said target sequence and, 3'- of said target-complementary portion, a transcription promoter for an RNA polymerase that can bind to said single-stranded promoter and initiate transcription of RNA therefrom in a 5'-to-3' direction using single-stranded DNA that is 5'- of and covalently linked to said promoter as a template;
- b. providing a signal target probe, wherein said signal target probe comprises a linear ssDNA comprising a 3'-end portion that is complementary to the most 3'-portion of said target sequence and a 5'-portion comprising a signal sequence;
- c. optionally, provided said target-complementary sequences of said promoter target probe and said signal target probe are not contiguous when annealed to said target sequence, providing one or more simple target probes, wherein said simple target probes are complementary to said target sequence so as to anneal to said target sequence in the gap between the target-complementary sequences of said promoter target probe and said signal target probe so as to completely fill said gap and so that each of the ends of said simple target probes are contiguous with an end of a simple target probe or with a 5'-end of said promoter target probe or a 3'-end of said signal target probe;
- d. annealing said promoter target probe, said simple target probes, if present, and said signal target probe to said target nucleic acid comprising said target sequence under hybridization conditions;
- e. ligating said promoter target probe, said simple target probes, if present, and said signal target probe that are annealed to said target nucleic acid under ligation conditions with a ligase, wherein said ligase has little or no activity in ligating blunt ends and is substantially more active in ligating said ends of said target probes if said ends are adjacent when annealed to two contiguous regions of a target sequence than if said ends are not annealed to said target sequence, so as to obtain a linear ssDNA molecule that comprises a linear transcription substrate;
- f. obtaining said linear transcription substrate, wherein said linear transcription substrate comprises a sequence that is complementary to said target sequence;
- g. contacting said linear transcription substrate with an RNA polymerase under transcription conditions so as to synthesize RNA that is complementary to said target-complementary sequence and said signal sequence of said linear transcription substrate; and
- h. detecting the synthesis of RNA resulting from transcription of said linear transcription substrate, wherein said synthesis of said RNA indicates the presence of said target sequence comprising said target nucleic acid.

In addition to the embodiment shown in FIG. 25 in which a simple target probe is used to fill a gap on a target sequence between the target-complementary sequences of a promoter target probe and a signal target probe, the invention also comprises embodiments in which a DNA polymerase is used to fill the gap between a promoter target probe and a signal target probe, wherein said target probes are not adjacent when annealed to a target sequence. The invention further comprises use of a combination of a promoter target probe, one or more simple target probes, a signal target probe and DNA polymerase extension of the 3'-hydroxyl end of said signal target probe or of one or more simple target probes so that said target probes, including said DNA polymerase-extended target probes, completely fill the gap on a target sequence between the target-complementary portions of said promoter probe and said signal target probe. Thus any combination of simple target probes and DNA polymerase extension can be used to fill the gap between the target-complementary portions of the promoter probe and the signal target probe so as to obtain adjacent target-complementary sequences prior to the ligation step.

The invention also comprises methods for obtaining secondary or additional amplification by using the RNA products synthesized by transcription of a circular transcription substrate or a linear transcription substrate as a template for ligation of the same or different bipartite or monopartite target probes, thus generating additional circular transcription substrates or linear transcription substrates, respectively. By way of example, but not of limitation, one embodiment of a method of the invention for obtaining secondary amplification uses bipartite target probes and two ligases—one ligase that can ligate target-complementary sequences of a bipartite target probe annealed to a DNA target sequence to form a first circular transcription substrate, and one that can ligate the same target-complementary sequences of said bipartite target probe annealed to an RNA transcript resulting from transcription of said first circular transcription substrate. By way of example, but not of limitation, one ligase that can be used in a method of the present invention for ligation of contiguous DNA molecules annealed to an RNA ligation template is T4 RNA ligase (Epicentre Technologies, Madison, Wis., USA), as disclosed by Faruqi in U.S. Pat. No. 6,368,801 B1. The invention also comprises embodiments that use similar secondary amplification methods with two ligases using monopartite target probes and that generate linear transcription substrates.

In addition to comprising embodiments of methods wherein bipartite target probes are used that anneal to both the target sequence and to the same sequence in the RNA transcripts resulting from transcription of a first circular transcription substrate, the invention also comprises other embodiments of methods and assays wherein a second bipartite target probe is used that anneals to a sequence in the RNA transcript that is complementary to a signal sequence or an optional sequence of the first circular transcription substrate rather than annealing to the target sequence or the identical sequence in the RNA transcript.

In still other embodiments, the invention also comprises use of a reverse transcriptase process to obtain additional amplification of a target sequence and/or a signal sequence in an assay or method of the invention. An example of an embodiment of the invention that uses a reverse transcriptase process is shown in FIG. 26. This example illustrates a number of aspects of the invention that result in improvements over the methods and assays of the prior art.

The first part of the assay or method in FIG. 26 is similar to the embodiment shown in FIG. 21. Thus, a first circular transcription substrate is generated by ligation of a first bipartite target probe annealed to a target sequence in a sample. Then, in vitro transcription of the first circular transcription substrate amplifies the target sequence and the signal sequence, if present. In the example, shown in FIG. 26, rolling circle transcription is used to synthesize RNA comprising multimeric copies of an RNA oligomer that is complementary to the first circular transcription substrate. In contrast to run-off transcription of linear transcription substrates, as is used for methods in the prior art such as, but not limited to, NASBA or TMA, rolling circle transcription synthesizes RNA tht has sequences that are complementary to the single-stranded transcription promoter in a circular transcription substrate. As discussed below, the presence of these promoter-complementary sequences in the RNA transcription product from rolling circle transcription permits generation of additional single-stranded transcription promoters that can initiate additional in vitro transcription reactions and thereby further amplify the target sequence and/or signal sequence.

Thus, one or more oligonucleotide primers anneal to the multimeric RNA transcription products and first-strand cDNA is synthesized by extension of said primers by a reverse transcriptase under reverse transcription reaction conditions. In the example shown in FIG. 26, only one reverse transcription primer is used that anneals to the same sequence in different repeated sites on the multimeric RNA. However, the invention also comprises embodiments that use multiple reverse transcription primers, each of which is complementary to a different sequence of an RNA oligomer that is, in turn, complementary to a circular transcription substrate. The sequence to which a reverse transcription primer anneals in an RNA multimer can also vary. Preferably, a reverse transcription primer anneals to a sequence in the RNA multimer in a region that is complementary to an optional sequence portion of a circular transcription substrate and that is 3'- of a signal sequence-complementary sequence, if present. The reverse transcription primer shown in FIG. 26 anneals to the RNA multimer at a site that is 3' of a signal sequence-complementary sequence of each oligomer of the multimer. The reverse transcription primer shown in FIG. 26 has a 5'-portion comprising a "tail" that is a sequence that is not complementary to the RNA transcript. The use of a tail is optional and is not required for methods and assays of the invention.

Again referring to FIG. 26, following reverse transcription of the RNA multimer, the first-strand cDNA is available in the reaction mixture for at least two subsequent functions. First, the first-strand cDNA has a functional single-stranded transcription promoter and is used as a linear transcription substrate for synthesis of RNA using the RNA polymerase that initiates transcription from said promoter under transcription conditions. Synthesis of RNA corresponding to the target sequence and/or the signal sequence in these linear transcription substrates can be detected according to the detection method used in the particular embodiment of an assay or method of the invention. Second, the first strand cDNA can be used as a ligation template for ligation of a second bipartite target probe under ligation conditions. In the embodiment shown in FIG. 26, the second bipartite target probe is identical to the first bipartite target probe except that with respect to the target-complementary sequences at the 3'- and 5'-ends of said second bipartite target probe. The 5'-end portion of the second bipartite target probe comprises a sequence that is complementary to the target-complementary sequence at the 3'-end portion of the first bipartite target probe, and this sequence is in turn covalently attached and 5'- of a promoter sequence in the 5'-portion of the second bipartite target probe. The 3'-end portion of the second bipartite target probe comprises a sequence that is complementary to the target-complementary sequence at the 5'-end portion of the first bipartite target probe, and this sequence is in turn covalently attached and 3'- of a signal sequence in the 3'-portion of the second bipartite target probe, if a signal sequence is present. Thus, the sequences at the 3'- and 5'-ends of said second bipartite target probe are identical to the target sequence and are complementary to the target-complementary sequences in both the first circular transcription substrate and in the first-strand cDNA obtained by reverse transcription of RNA transcripts from said first circular transcription substrate, both of which thus serve as ligation templates for ligation of the second bipartite target probe by a ligase under ligation conditions. Ligation of a second bipartite target probe generates a second circular transcription substrate.

The second circular transcription substrate is then a substrate for rolling circle transcription, generating a complementary RNA multimer transcript. The RNA multimer transcript resulting from rolling circle transcription is then a substrate for reverse transcription by a reverse transcriptase under reverse transcription conditions. Since, in the embodiment shown in FIG. 26, the second circular transcription substrate is identical to the first circular transcription substrate in all portions except for the target-complementary portion, the same reverse transcription primer can be used to generate first-strand cDNA that is complementary to the RNA multimer from the second circular transcription substrate. The resulting first-strand cDNA is a second linear transcription substrate. In vitro transcription of said second linear transcription substrate by an RNA polymerase that initiates transcription using said single-stranded transcription promoter under transcription conditions generates RNA transcripts that can be detected in the assay or method. The sequence corresponding to a target sequence in said first-strand cDNA also serves as a template for ligation of a first bipartite target probe by a ligase under ligation conditions. Ligation of another first bipartite target probe forms another first circular transcription substrate. Thus, the various annealing, ligation, rolling circle transcription, reverse transcription, and linear run-off transcription processes of this embodiment of an assay or method of the invention can continue, with continual generation of RNA that can be detected according to the particular assay or method until one or more of the reaction components are exhausted. The repeating cycles of processes of this embodiment of an assay or method results in high sensitivity and shorter reaction times, while retaining a high degree of specificity.

Thus, again referring to FIG. 26, one embodiment of the present invention comprises a method for detecting a target sequence, said method comprising:

a. providing a first bipartite target probe, wherein said first bipartite target probe comprises a 5'-portion and a 3'-portion, wherein said 5'-portion comprises: (i) a 5'-end portion that comprises a sequence that is complementary to a target sequence, and (ii) a promoter sequence, wherein said promoter sequence is covalently attached to and 3'- of said target-complementary sequence in said 5'-portion; and wherein said 3'-portion comprises: (i) a 3'-end portion that comprises a sequence that is complementary to a target sequence, wherein said target-complementary sequence of said 3'-end portion, when annealed to said target sequence, is adjacent to said target-complementary sequence of said 5'-end portion of said first bipartite target probe, and (ii) optionally, a signal sequence, wherein said signal sequence is 5'- of said target-complementary sequence of said 3'-portion of said first bipartite target probe;

b. providing a second bipartite target probe, wherein said second bipartite target probe comprises a 5'-portion and a 3'-portion, wherein said 5'-portion comprises: (i) a 5'-end portion that comprises sequence that is complementary to said target-complementary sequence of said 3'-end portion of said first bipartite target probe, and (ii) a promoter sequence, wherein said promoter sequence in said 5'-portion of said second bipartite target probe is 3'- of said target-complementary sequence in said 5'-portion; and wherein said 3'-portion comprises: (i) a 3'-end portion that comprises sequence that is complementary to said target-complementary sequence of said 5'-end portion of said first bipartite target probe, and (ii) optionally, a signal sequence, wherein said signal sequence in said 3'-portion of said second bipartite target probe is 5'- of said target-complementary sequence in said 3'-portion;

c. annealing said first bipartite target probe to said target nucleic acid comprising said target sequence under hybridization conditions;

d. ligating said first bipartite target probe annealed to said target nucleic acid under ligation conditions with a ligase, wherein said ligase has little or no activity in ligating blunt ends and is substantially more active in ligating said ends of said first bipartite target probe if said ends are adjacent when annealed to two contiguous regions of a target sequence than if said ends are not annealed to said target sequence, so as to obtain a circular ssDNA molecule that comprises a first circular transcription substrate;

e. obtaining said first circular transcription substrate;

f. contacting said first circular transcription substrate with an RNA polymerase under transcription conditions so as to synthesize RNA that is complementary to said first circular transcription substrate;

g. annealing to said RNA that is complementary to said first circular transcription substrate a primer, wherein said primer is complementary to said RNA;

h. contacting said RNA to which said primer is annealed with a reverse transcriptase under reverse transcription conditions so as to obtain a first first-strand cDNA;

i. obtaining said first first-strand cDNA;

j. annealing to said first first-strand cDNA said second bipartite target probe under annealing conditions;

k. contacting said first first-strand cDNA to which said second bipartite target probe is annealed with a ligase, wherein said ligase has little or no activity in ligating blunt ends and is substantially more active in ligating said ends of said second bipartite target probe if said ends are adjacent when annealed to two contiguous regions of said first first-strand cDNA than if said ends are not annealed to said sequence, so as to obtain a circular ssDNA molecule that comprises a second circular transcription substrate;

l. obtaining said second circular transcription substrate;

m. contacting said second circular transcription substrate with an RNA polymerase under transcription conditions so as to synthesize RNA that is complementary to said second circular transcription substrate;

n. annealing to said RNA that is complementary to said second circular transcription substrate a primer, wherein said primer is complementary to said RNA;

o. contacting said RNA to which said primer is annealed with a reverse transcriptase under reverse transcription conditions so as to obtain a second first-strand cDNA;

p. obtaining said second first-strand cDNA;

q. annealing to said second first-strand cDNA said first bipartite target probe under annealing conditions;

r. contacting said second first-strand cDNA to which said first bipartite target probe is annealed with a ligase, wherein said ligase has little or no activity in ligating blunt ends and is substantially more active in ligating said ends of said first bipartite target probe if said ends are adjacent when annealed to two contiguous regions of said second first-strand cDNA than if said ends are not annealed to said sequence, so as to obtain a circular ssDNA molecule that comprises a third circular transcription substrate that is identical to said first circular transcription substrate;

s. obtaining said third circular transcription substrate that is identical to said first circular transcription substrate;

t. repeating steps a through t; and u. detecting the synthesis of RNA resulting from transcription of said first, second and third circular transcription substrates and from said first and second linear transcription substrates, wherein said synthesis of said RNA indicates the presence of said target sequence comprising said target nucleic acid.

The methods and assays of the embodiment of the invention shown in FIG. 26 can be performed in a stepwise manner or, more preferably, in a single reaction mixture in a continuous manner. Thus, one embodiment of the present invention comprises a method for detecting a target sequence, said method comprising:

1. providing a reaction mixture comprising:

a. a first bipartite target probe, wherein said first bipartite target probe comprises a 5'-portion and a 3'-portion, wherein said 5'-portion comprises: (i) a 5'-end portion that comprises a 5'-phosphate group and a sequence that is complementary to a target sequence, and (ii) a promoter sequence, wherein said promoter sequence is covalently attached to and 3'- of said target-complementary sequence in said 5'-portion; and wherein said 3'-portion comprises: (i) a 3'-end portion that comprises a sequence that is complementary to a target sequence, wherein said target-complementary sequence of said 3'-end portion, when annealed to said target sequence, is adjacent to said target-complementary sequence of said 5'-end portion of said first bipartite target probe, and (ii) optionally, a signal sequence, wherein said signal sequence is 5'- of said target-complementary sequence of said 3'-portion of said first bipartite target probe;

b. a second bipartite target probe, wherein said second bipartite target probe comprises a 5'-portion and a 3'-portion, wherein said 5'-portion comprises: (i) a 5'-end portion that comprises a 5'-phosphate group and sequence that is complementary to said target-complementary sequence of said 3'-end portion of said first bipartite target probe, and (ii) a promoter sequence, wherein said promoter sequence in said 5'-portion of said second bipartite target probe is 3'- of said target-complementary sequence in said 5'-portion; and wherein said 3'-portion comprises: (i) a 3'-end portion that comprises sequence that is complementary to said target-complementary sequence of said 5'-end portion of said first bipartite target probe, and (ii) optionally, a signal sequence, wherein said signal sequence in said 3'-portion of said second bipartite target probe is 5'- of said target-complementary sequence in said 3'-portion;

c. a ligase, wherein said ligase has little or no activity in ligating blunt ends and is substantially more active in ligating the ends of a bipartite target probe if said ends are adjacent when annealed to two contiguous regions of a complementary sequence than if said ends are not annealed to said complementary sequence, so as to obtain a circular ssDNA molecule that comprises a circular transcription substrate;

d. a reverse transcriptase and one or more primers, wherein at least the 3'-portion of one said primer comprises a sequence that is complementary to a sequence of said first bipartite target probe and of said second bipartite target probe and wherein said complementary portion of said primer is not complementary to said target sequence or the complement of said target sequence;

e. an RNA polymerase, wherein said RNA polymerase recognizes said single-stranded transcription promoters of said first and second bipartite target probes and synthesizes RNA therefrom using as a template single-stranded DNA to which said promoters are functionally attached;

f. optionally, a single strand binding protein;

g. optionally, a detection oligo, wherein said detection oligo anneals to an RNA transcript sequence that is complementary to a signal sequence of said first and/or second bipartite target probe; and h. reaction conditions wherein said ligase, said reverse transcriptase, and said RNA polymerase are optimally active in combination and wherein said target-complementary sequences of said first bipartite target probe anneal to said target sequence, if present, with specificity, and;

2. contacting said reaction mixture from step 1 above with a sample comprising a target nucleic acid comprising a target sequence, if present, wherein said reaction mixture containing said sample is maintained at a temperature wherein said ligase, said reverse transcriptase, and said RNA polymerase are optimally active in combination and wherein said target-complementary sequences of said first bipartite target probe anneal to said target sequence, if present, with specificity, and wherein said temperature of said reaction mixture is maintained for a time sufficient to permit synthesis of RNA transcription products complementary to circular transcription substrates obtained from said bipartite target probes if said target sequence is present in said sample; and 3. detecting the synthesis of RNA resulting from transcription of said circular transcription substrates, wherein said synthesis of said RNA indicates the presence of said target sequence comprising said target nucleic acid.

In preferred embodiments of the above methods or assays for detecting a target sequence, said ligase comprises a ligase chosen from among Ampligase® thermostable DNA Ligase, Tth DNA Ligase, Tfl DNA Ligase, Tsc DNA Ligase, or Pfu DNA Ligase.

In preferred embodiments of the above methods or assays for detecting a target sequence, said reverse transcriptase is a reverse transcriptase that has RNase H activity, wherein said reverse transcriptase is chosen from among MMLV reverse transcriptase, AMV reverse transcriptase, another retroviral reverse transcriptase, or a reverse transcriptase encoded by a thermostable phage. In other embodiments of the above methods or assays, said reverse transcriptase comprises a DNA polymerase chosen from among IsoTherm™ DNA polymerase, Bst DNA polymerase large fragment, BcaBEST™ DNA polymerase, and Tth DNA polymerase.

In preferred embodiments of the above methods or assays for detecting a target sequence, said RNA polymerase is N4 mini-vRNAP.

R. Methods and Assays for Detecting and Quantifying Non-Nucleic Acid Analytes Using Target Sequence Tags Comprising or Attached to Analyte-Binding Substances The present invention includes methods, compositions and kits that use an analyte-binding substance for detecting an analyte in a sample. An "analyte-binding substance" is a substance that binds an analyte that one desires to detect in an assay or method of the invention. An analyte-binding substance is also referred to as an "affinity molecule," an "affinity substance," a "specific binding substance," or a "binding molecule" for an analyte. Usually, an analyte molecule and an analyte-binding substance or affinity molecule for the analyte molecule are related as a specific "binding pair", i.e., their interaction is only through non-covalent bonds such as hydrogen-bonding, hydrophobic interactions (including stacking of aromatic molecules), van der Waals forces, and salt bridges. Without being bound by theory, it is believed in the art that these kinds of non-covalent bonds result in binding, in part due to complementary shapes or structures of the molecules involved in the binding pair.

The term “binding” according to the invention refers to the interaction between an analyte-binding substance or affinity molecule and an analyte as a result of non-covalent bonds, such as, but not limited to, hydrogen bonds, hydrophobic interactions, van der Waals bonds, and ionic bonds.

In most embodiments of the invention, target probes are used to detect an analyte comprising a target sequence in a target nucleic acid. Following annealing and joining of target probes in the presence of a target sequence in a sample, the resulting transcription substrate is amplified by transcription using an RNA polymerase, and the presence of an RNA complementary to the transcription substrate indicates that the target sequence was present in the sample.

However, a nucleic acid can also be used in a method of the present invention as an analyte-binding substance to detect an analyte that does not comprise a nucleic acid. By way of example, but not of limitation, a method termed “SELEX,” as described by Gold and Tuerk in U.S. Pat. No. 5,270,163, which is incorporated herein by reference, can be used to select a nucleic acid for use as an analyte-binding substance in a method of the invention for detecting an analyte comprising almost any molecule in a sample. SELEX permits selection of a nucleic acid molecule that has high affinity for a specific analyte from a large population of nucleic acid molecules, at least a portion of which have a randomized sequence. For example, a population of all possible randomized 25-mer oligonucleotides (i.e., having each of four possible nucleic acid bases at every position) will contain $4^{25}$ (or $10^{15}$) different nucleic acid molecules, each of which has a different three-dimensional structure and different analyte binding properties. SELEX can be used, according to the methods described in U.S. Pat. Nos. 5,270,163; 5,567,588; 5,580,737; 5,587,468; 5,683,867; 5,696,249; 5723,594; 5,773,598; 5,817,785; 5,861,254; 5,958,691; 5,998,142; 6,001,577; 6,013,443; and 6,030,776, all of which are incorporated herein by reference, in order to select an analyte-binding nucleic acid with high affinity for a specific analyte that is not a nucleic acid or polynucleotide for use in a method or assay of the invention. Once selected using SELEX, analyte-binding substances or affinity molecules comprising nucleic acid molecules can be made for use in the methods of the present invention by using any of numerous in vivo or in vitro techniques known in the art, including, by way of example, but not of limitation, automated nucleic acid synthesis techniques, PCR, or in vitro transcription. A nucleic acid molecule that is an analyte-binding substance that has been selected using SELEX can be detected using bipartite or monopartite target probes in a similar way to how such target probes are used to detect a target sequence in a target nucleic acid analyte, as described elsewhere herein. Since an analyte-binding substance that is selected using SELEX comprises a nucleic acid, a continuous sequence within the analyte-binding substance can be used as a “target sequence” and target probes can be designed, wherein the target-complementary sequences in said target probes are complementary to said continuous sequence in said analyte-binding substance. Another important aspect of these embodiments of the invention is that said target sequence in said analyte-binding substance that was selected using SELEX should be capable of annealing to said target probes when said analyte-binding substance is also bound to an analyte; i.e., the binding to the analyte does not block annealing of target probes to the target sequence.

Thus, another embodiment of the present invention is a method for detecting an analyte in a sample, wherein said analyte comprises a biomolecule that is not a nucleic acid, said method comprising:

a. providing an analyte-binding substance comprising a nucleic acid, wherein said nucleic acid binds with selectivity and high affinity to said analyte;
b. providing target probes comprising either (i) a promoter target probe and one or more additional target probes chosen from among a signal target probe and simple target probe; or (ii) a bipartite target probe and, if said target-complementary sequences of said bipartite target probe are not contiguous when annealed to said target sequence in said analyte-binding substance, optionally, one or more simple target probes; wherein said target probes of (i) or (ii) comprise sequences that are complementary to adjacent regions of a target sequence in said analyte-binding substance;
c. contacting said analyte-binding substance to an analyte in a sample;
d. separating said analyte-binding substance molecules that are bound to said analyte from said analyte-binding substance molecules that are not bound to said analyte;
e. contacting said analyte-binding substance molecules that are bound to said analyte with said target probes provided in step b(i) or step b(ii) above under hybridization conditions that permit said target probes that are complementary to said target sequences in said analyte-binding substance to anneal thereto;
f. ligating said adjacent target probes that are annealed to said target sequence of said analyte-binding substance with a ligase under ligation conditions so as to obtain a transcription substrate;
g. obtaining said transcription substrate;
h. contacting said transcription substrate with an RNA polymerase under transcription conditions so as to synthesize RNA that is complementary to said transcription substrate;
i. optionally, repeating steps a through i; and
j. detecting the synthesis of RNA resulting from transcription of said transcription substrate, wherein said synthesis of said RNA indicates the presence of said analyte in said sample.

Thus, the use of an analyte-binding substance comprising a nucleic acid selected using SELEX permits the methods of the present invention to be used to detect other analyte molecules that are not nucleic acids.

The nucleic acid molecules that contain a randomized sequence that are used to generate a library of molecules for selection of an analyte-binding substance using SELEX can also be made using methods similar to those described by Ohmichi et al. (Proc. Natl. Acad. Sci. USA, 99: 54-59, 2002), incorporated herein by reference. Thus, random sequence circular DNA molecules comprising about 103 nucleotides, of which about 40 nucleotides comprise randomized sequence are repeatedly selected for binding to an analyte by: binding the circular DNAs to an analyte attached to a surface; washing away the unbound circular DNA molecules; recovering the circular DNAs bound to the analyte; obtaining RNA complementary to the recovered circular DNA molecules by rolling circle transcription; amplifying the RNA by RT-PCR using one 5'-biotinylated primer; immobilizing the RT-PCR product on a surface with streptavidin; obtaining the strand of the RT-PCR product that does not contain biotin; and then ligating the single-stranded RT-PCR strand (using a ligation splint) to obtain the first round of selected circular DNA molecules. The first round of circular DNA molecules is then bound to an analyte as just described, and the whole process is again repeated for a total of about 15 rounds of selection of circular DNA molecules for analyte binding. The selected circular DNA molecules are then analyzed for analyte binding in order to obtain an analyte-binding substance for use in an assay or method of the present invention. As described above related to SELEX, a target sequence in the selected analyte-binding substance can be detected using monopartite or bipartite target probes as described elsewhere herein. Thus, an analyte-binding substance is used to bind an analyte in a sample and then, after removing unbound analyte-binding substance (if the analyte-binding substance is attached to a surface or becomes attached to a surface during a process of the assay or method), the analyte-binding substance is detected using target probes that are complementary to a target sequence in the analyte-binding substance. A method for detecting an analyte-binding substance can comprise a step comprising ligation of target probes of the invention as described in the embodiments of the method immediately above herein for detecting a target sequence in an analyte-binding substance that is bound to an analyte. However, in some other embodiments for detecting an analyte-binding substance that is bound to an analyte, a ligation step is omitted and the analyte-binding substance:analyte complex is detected by annealing to said complex a transcription substrate that contains a sequence that is complementary to a target sequence in said analyte-binding substance. After removing unhybridized transcription substrates, transcription substrates that are annealed to said analyte-binding substance: analyte complex are detected by synthesis of RNA resulting from in vitro transcription of the complex-bound transcription substrate.

A "peptide nucleic acid (PNA)" or a molecule comprising both a nucleic acid and a PNA, as described in U.S. Pat. Nos. 5,539,082; 5,641,625; 5,700,922; 5,705,333; 5,714,331; 5,719,262; 5,736,336; 5,773,571; 5,786,461; 5,817,811; 5,977,296; 5,986,053; 6,015,887; and 6,020,126, which are incorporated herein by reference, can also be used in methods of the present invention as an analyte-binding substance for a non-nucleic acid analyte. In general, a PNA molecule is a nucleic acid analog consisting of a backbone comprising, for example, N-(2-aminoethyl)glycine units, to each of which a nucleic acid base is linked through a suitable linker, such as, but not limited to an aza, amido, ureido, or methylene carbonyl linker. The nucleic acid bases in PNA molecules bind complementary single-stranded DNA or RNA according to Watson-Crick base-pairing rules. However, the $T_m$'s for PNA/DNA or PNA/RNA duplexes or hybrids are higher than the $T_m$'s for DNA/DNA, DNA/RNA, or RNA/RNA duplexes. In these embodiments, a "PNA target sequence" is present in said analyte-binding substance comprising PNA, to which, target-complementary sequences of monopartite or bipartite target probes (or transcription substrates) can anneal, permitting detection as described above for analyte-binding molecules selected using SELEX. Thus, PNA used as an analyte-binding substance in an assay or method of the present invention provides tighter binding (and greater binding stability) for target-complementary sequences in target probes or transcription substrates (e.g., see U.S. Pat. No. 5,985,563). Also, since PNA is not naturally occurring, PNA molecules are highly resistant to protease and nuclease activity. PNA for use as an analyte binding substance can be prepared according to methods known in the art, such as, but not limited to, methods described in the above-mentioned patents, and references therein. Antibodies to PNA/analyte complexes can be used in the invention for capture, recognition, detection, identification, or quantitation of nucleic acids in biological samples, via their ability to bind specifically to the respective complexes without binding the individual molecules (U.S. Pat. No. 5,612,458).

The invention also contemplates that a combinatorial library of randomized peptide nucleic acids prepared by a method such as, but not limited to, the methods described in U.S. Pat. Nos. 5,539,083; 5,831,014; and 5,864,010, can be used to prepare analyte-binding substances for use in assays for analytes of all types, including analytes that are nucleic acids, proteins, or other analytes, without limit. As is the case for the SELEX method with nucleic acids, randomized peptide or peptide nucleic acid libraries are made to contain molecules with a very large number of different binding affinities for an analyte. After selection of an appropriate affinity molecule for an analyte from a library, the selected affinity molecule can be used in the invention as an analyte-binding substance in the second portion of the reporter probe.

An analyte-binding substance can also be an oligonucleotide or polynucleotide with a modified backbone that is not an amino acid, such as, but not limited to modified oligonucleotides described in U.S. Pat. Nos. 5,602,240; 6,610,289; 5,696,253; or 6,013,785.

The invention also contemplates that an analyte-binding substance can be prepared from a combinatorial library of randomized peptides (i.e., comprising at least four naturally-occurring amino acids). One way to prepare the randomized peptide library is to place a randomized DNA sequence, prepared as for SELEX, downstream of a phage T7 RNA polymerase promoter, or a similar promoter, and then use a method such as, but not limited to, coupled transcription-translation, as described in U.S. Pat. Nos. 5,324,637; 5,492,817; or 5,665,563, or stepwise transcription, followed by translation. Alternatively, a randomized DNA sequence, prepared as for SELEX, can be cloned into a site in a DNA vector that, once inserted, encodes a recombinant MDV-1 RNA containing the randomized sequence that is replicatable by Q.beta. replicase (e.g., between nucleotides 63 and 64 in MDV-1 (+) RNA; see U.S. Pat. No. 5,620,870). The recombinant MDV-1 DNA containing the randomized DNA sequence is downstream from a T7 RNA polymerase promoter or a similar promoter in the DNA vector. Then, following transcription, the recombinant MDV-1 RNA, containing the randomized sequence can be used to make a randomized peptide library comprising at least four naturally occurring amino acids by coupled replication-translation as described in U.S. Pat. No. 5,556,769. An analyte-binding substance can be selected from the library by binding peptides in the library to an analyte, separating the unbound peptides, and identifying one or more peptides that is bound to analyte by means known in the art. Alternatively, high throughput screening methods can be used to screen all individual peptides in the library to identify those that can be used as analyte-binding substances. Although the identification of an analyte-binding peptide by these methods is difficult and tedious, the methods in the art are improving for doing so, and the expenditure of time and effort required may be warranted for identifying analyte-binding substances for use in assays of the invention that will be used routinely in large numbers.

In embodiments of the present invention in which an analyte-binding substance comprises a peptide, a protein, including, but not limited to an antibody, streptavidin, or another biomolecule, a nucleic acid sequence can be attached to said analyte-binding substance, wherein said nucleic acid serves as a "tag" comprising a target sequence that can be detected using target probes or transcription substrates of the invention. In this way, the methods and assays of the invention can be used for sensitive and specific detection of analytes that are not nucleic acids.

Analyte-binding substances for particular analytes and methods of preparing them are well known in the art. Naturally occurring nucleic acid or polynucleotide sequences that have affinity for other naturally occurring molecules such as, but not limited to, protein molecules, are known in the art, and nucleic acid molecules comprising these sequences can be used, both as analyte-binding substances and as tags comprising target sequences for detection using target probes or transcription substrates of the invention. Examples include, but are not limited to certain nucleic acid sequences such as operators, promoters, origins of replication, sequences recognized by steroid hormone-receptor complexes, restriction endonuclease recognition sequences, ribosomal nucleic acids, and so on, which are known to bind tightly to certain proteins. For example, in two well-known systems, the lac repressor and the bacteriophage lambda repressor each bind to their respective specific nucleic acid sequences called "operators" to block initiation of transcription of their corresponding mRNA molecules. Nucleic acids containing such specific sequences can be used in the invention as analyte-binding substances for the respective proteins or other molecules for which the nucleic acid has affinity. In these cases, the nucleic acid with the specific sequence is used as the analyte-binding substance in assays for the respective specific protein, glycoprotein, lipoprotein, small molecule or other analyte that it binds. One of several techniques that is generally called "footprinting" (e.g., see Galas, D. and Schmitz, A, Nucleic Acids Res., 5: 3161, 1978) can be used to identify sequences of nucleic acids that bind to a protein. Other methods are also known to those with skill in the art and can be used to identify nucleic acid sequences for use as specific analyte-binding substances for use in the invention.

A variety of other analyte-binding substances can also be used. For an antigen analyte (which itself may be an antibody), antibodies, including monoclonal antibodies, are available as analyte-binding substances. For certain antibody analytes in samples which include only one antibody, an antibody binding protein such as *Staphylococcus aureus* Protein A can be employed as an analyte-binding substance. For an analyte, such as a glycoprotein or class of glycoproteins, or a polysaccharide or class of polysaccharides, which is distinguished from other substances in a sample by having a carbohydrate moiety that is bound specifically by a lectin, a suitable analyte-binding substance is the lectin. For an analyte that is a hormone, a receptor for the hormone can be employed as an analyte-binding substance. Conversely, for an analyte that is a receptor for a hormone, the hormone can be employed as the analyte-binding substance. For an analyte that is an enzyme, an inhibitor of the enzyme can be employed as an analyte-binding substance. For an analyte that is an inhibitor of an enzyme, the enzyme can be employed as the analyte-binding substance.

Based on the definition for "binding," and the wide variety of affinity molecules and analytes that can be used in the invention, it is clear that "binding conditions" vary for different specific binding pairs. Those skilled in the art can easily determine conditions whereby, in a sample, binding occurs between affinity molecule and analyte that may be present. In particular, those skilled in the art can easily determine conditions whereby binding between affinity molecule and analyte that would be considered in the art to be "specific binding" can be made to occur. As understood in the art, such specificity is usually due to the higher affinity of affinity molecule for analyte than for other substances and components (e.g., vessel walls, solid supports) in a sample. In certain cases, the specificity might also involve, or might be due to, a significantly more rapid association of affinity molecule with analyte than with other substances and components in a sample.

Figure 27:
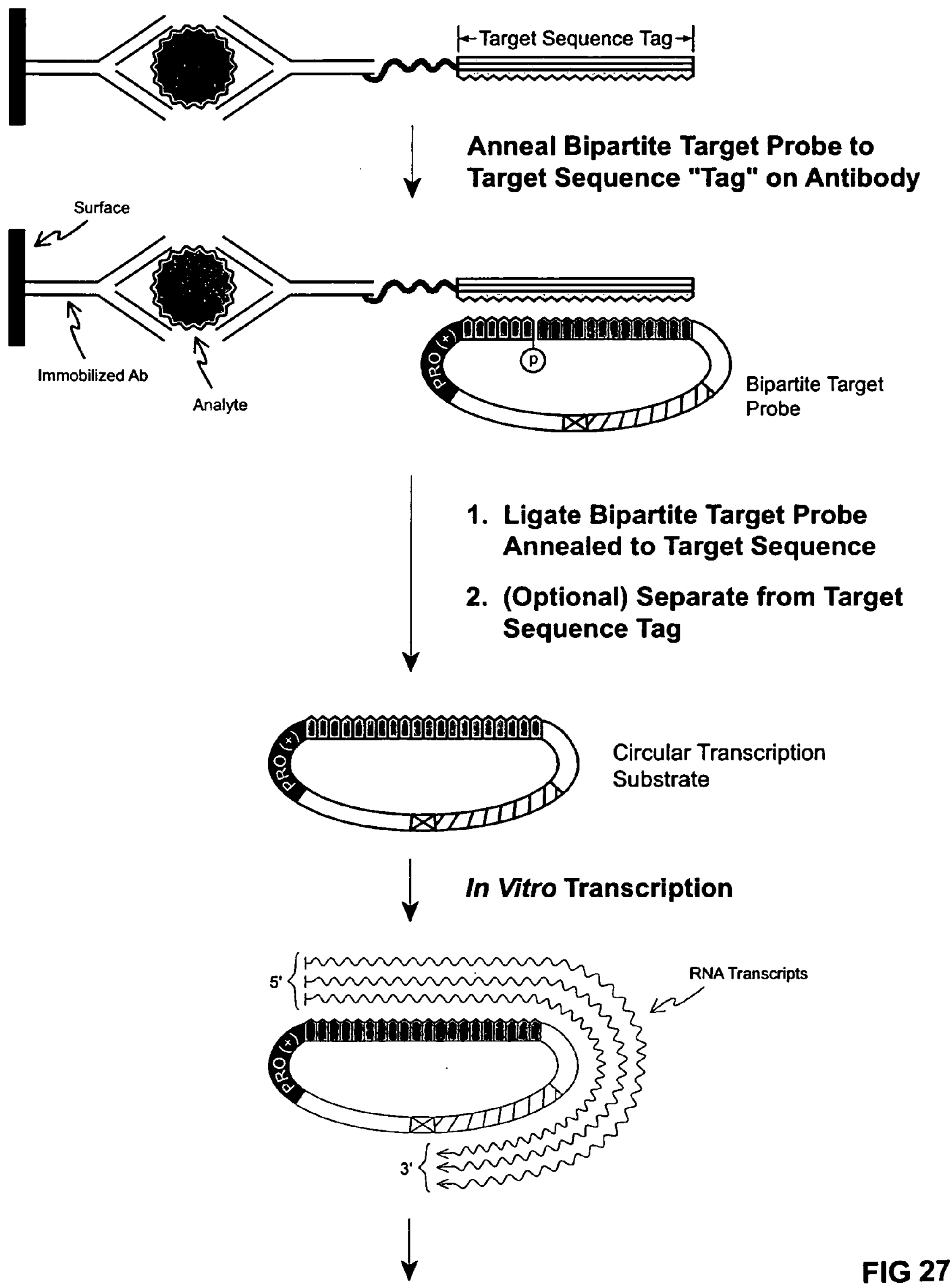
FIG. 27—A method for detecting a non-nucleic acid analyte using an analyte-binding substance comprising an antibody that has a covalently—(e.g., chemically) or non-covalently—(e.g., using biotin and streptavidin) attached target sequence tag comprising a target sequence. In the embodiment illustrated here, the signal for detection of the analyte-binding substance and the analyte is generated by transcription of a circular transcription substrate obtained by annealing and ligation of a bipartite target probe. In this particular embodiment, the circular transcription substrate has a transcription termination sequence so that multiple single RNA copies are obtained, rather than multimeric tandem copies of an oligomeric RNA as obtained by rolling circle transcription.

In general, any of the methods and assays described herein to detect and quantify an analyte comprising a target sequence in a target nucleic acid can also be used to detect and quantify a target sequence that comprises a target sequence tag that is attached to an analyte-binding substance for a non-nucleic acid analyte by adjusting the reaction conditions of said assay or method to accommodate the specific analyte and analyte-binding substance. Thus, the methods and assays of the invention permit detection and quantification of any analyte for which there is a suitable analyte-binding substance that either comprises or to which a target sequence tag can be attached. Two methods for detecting an analyte using an analyte-binding substance comprising an antibody having a target sequence tag are illustrated in FIGS. 27 and 28.

S. Use of Transcription Substrates and RNA Polymerases of the Invention as Signaling Systems The invention also comprises methods, compositions and kits for using ssDNA transcription substrates and RNA polymerases that can transcribe said ssDNA transcription substrates as a signaling system for an analyte of any type, including analytes such as, but not limited to, antigens, antibodies or other substances, in addition to an analyte that is a target nucleic acid.

Thus, the invention comprises a method for detecting an analyte in or from a sample, said method comprising:

1. providing a transcription signaling system, said transcription signaling system comprising a ssDNA comprising: (a) a 5'-portion comprising a sequence for a promoter for an RNA polymerase that can synthesize RNA using a ssDNA transcription substrate chosen from among N4 vRNAP, N4 mini-vRNAP, and N4 mini-vRNAP Y678F enzymes or another enzyme that can use a promoter having similar properties; and (b) a signal sequence, wherein said signal sequence, when transcribed by said RNA polymerase, is detectable in some manner;
2. joining said transcription signaling system, either covalently or non-covalently, to an analyte-binding substance, wherein said joining to said substance is not affected by the conditions of the assay and wherein said joining to said substance does not affect the ability of said transcription signaling system to be transcribed using said RNA polymerase under transcription conditions;
3. contacting said analyte-binding substance to which said transcription signaling system is joined with a sample under binding conditions, wherein said analyte, if present in said sample, binds to said analyte-binding substance so as to form a specific binding pair;
4. removing said specific binding pair from said sample so as to separate it from other components in said sample;
5. incubating said specific-binding pair under transcription conditions with an RNA polymerase, wherein said RNA polymerase can synthesize RNA that is complementary to said signal sequence in said ssDNA transcription signaling system under said transcription conditions;
6. obtaining an RNA synthesis product that is complementary to said signal sequence in said ssDNA transcription signaling system; and 7. detecting said RNA synthesis product or a substance that results from said RNA synthesis product.

An analyte or an analyte-binding substance of this aspect of the invention can be any of those described in U.S. Pat. No. 6,562,575, which is incorporated herein by reference. By way of example, but not of limitation, an analyte-binding substance can be an antibody and the analyte an antigen, or an analyte-binding substance can be a nucleic acid and the analyte can be another complementary nucleic acid. A large number of other substances exist for which a specific-binding pair can be found. Also the signal sequence can vary greatly. By way of example, but not of limitation, a signal sequence can comprise a substrate for Q-beta replicase, which is detectable in the presence of said replicase under replication conditions. It can also comprise a sequence that encodes a protein, such as green fluorescent protein, that is detectable following translation of the signal sequence. Without limitation, it can also comprise a sequence that is detectable by a probe, such as, but not limited to a molecular beacon, as described by Tyagi et al. (U.S. Pat. Nos. 5,925,517 and 6,103,476 of Tyagi et al. and 6,461,817 of Alland et al., all of which are incorporated herein by reference). The present invention with regard to signaling systems also comprises uses such as those for methods described by Zhang et al. (Proc. Natl. Acad. Sci. USA, 98: 5497-5502, 2001, incorporated herein by reference) or by Hudson et al. in U.S. Pat. No. 6,100,024, incorporated herein by reference.

T. Modes of Performance of Methods and Assays of the Invention for Detecting a Target Sequence Depending on the application and its requirements and constraints, the methods of the invention can be performed in a stepwise fashion, with one set of reactions being performed, followed by purification of a reaction product or removal of reagents or inactivation of enzymes or addition of reagents before proceeding to the next set of reactions. Alternatively, the methods of the invention can be performed in a preferred embodiment as a continuous set of multiple reactions in a single reaction mixture. The invention also comprises methods or assays in which multiple target probes or target probe sets are used in a single reaction mixture in order to detect and/or quantify multiple target sequences in one or multiple target nucleic acids. Thus, the compositions, kits, methods and assays of the invention can be used in a multiplex format.

The invention also comprises parts or subsets of the methods and compositions of the invention. Thus, the invention comprises all of the individual steps of the methods of the invention that are enabled thereby, in addition to the overall methods.

U. Kits and Compositions of the Invention for Detecting a Target Sequence in a Target Nucleic Acid Analyte or a Target Sequence Tag Comprising or Attached to an Analyte-Binding Substance The present invention also comprises kits and compositions for carrying out the methods of the invention. A kit of the invention comprises one or, preferably, multiple components or compositions for carrying out the various processes of a method. Different embodiments of kits and compositions of the present invention can comprise one or more of the following:

1. A bipartite target probe for an assay or method for detecting a particular target sequence, and, optionally if the target-complementary sequences of said bipartite target probe are not contiguous when annealed to a target sequence, a monopartite target probe, all of which target probes preferably have a 5'-phosphate group.
2. A set of monopartite target probes for an assay or method for detecting a particular target sequence, wherein said set of monopartite target probes comprises a promoter target probe, preferably having a 5'-phosphate group, and either a signal target probe or a simple target probe and one or more additional simple target probes, which if present, preferably each have a 5'-phosphate group.
3. A ligase, wherein said ligase has little or no activity in ligating blunt ends and is substantially more active in ligating the ends of target probe if said ends are adjacent when annealed to two contiguous regions of a complementary sequence than if said ends are not annealed to said complementary sequence. In preferred embodiments of the above methods or assays for detecting a target sequence, said ligase comprises a ligase chosen from among Ampligase® thermostable DNA Ligase, Tth DNA Ligase, Tfl DNA Ligase, Tsc DNA Ligase, or Pfu DNA Ligase.
4. An RNA polymerase preparation, wherein said RNA polymerase recognizes a single-stranded transcription promoter and initiates transcription therefrom using as a template single-stranded DNA to which said promoter is functionally attached. In some embodiments, said RNA polymerase preparation comprises a single strand binding protein, which is preferably EcoSSB Protein. In preferred embodiments of the above methods or assays for detecting a target sequence, said RNA polymerase is N4 mini-vRNAP. In some embodiments that incorporate non-canonical 2'-modified nucleotides, the N4 mini-vRNAP Y678F mutant enzyme is preferred.
5. A reverse transcriptase, for embodiments that use a reverse transcription process in order to obtain additional amplification of a target sequence and/or a signal sequence. In preferred embodiments, said reverse transcriptase has RNase H activity and is chosen from among MMLV, AMV or another retroviral reverse transcriptase, or a reverse transcriptase encoded by a thermostable phage. In other embodiments, said reverse transcriptase comprises a DNA polymerase chosen from among IsoTherm™, Bst large fragment, BcaBEST™, and Tth DNA polymerase. Embodiments that use a reverse transcription process also use one or more primers, which can also comprise a composition or kit of the invention.
6. A DNA polymerase, for embodiments that use DNA polymerase extension to fill a gap between target probes. Any DNA polymerase that does not strand displace a downstream target probe can be used in a composition or kit of the invention.
7. An analyte-binding substance that either comprises or has an attached target sequence tag for embodiments of the invention for detecting and/or quantifying an analyte in a sample.
8. Compositions of the invention and kits comprising the same for detecting an RNA transcript that is complementary to a target sequence and/or a signal sequence. By way of example, but not of limitation, a composition or kit can comprise a detection oligo, such as a molecular beacon. Alternatively, a composition or kit can comprise an enzyme, such as Q-beta replicase, if the signal sequence encodes a Q-beta replicase substrate. The invention comprises kits comprising any suitable detection composition.
9. Controls, including quantification standards. Controls are used in assays and methods of the invention in order to verify that the assay or method produces the required specificity and sensitivity, or, in other words, to determine the frequency and conditions that lead to "false positive" and/or "false negative" results. Thus, controls comprise important compositions and kits for assays and methods of the invention. By way of example, but not of limitation, a positive control might be a sample containing a known quantity of a target sequence. A negative control would lack the target sequence. For an assay or method to detect a target nucleotide that is a single nucleotide polymorphism or SNP, positive controls might comprise sample that contain either the mutant or the predominant allele or other known alleles for that nucleotide position in the target sequence. In general, quantification of a target analyte in a sample using an assay or method of the invention, including an analyte comprising a target sequence, is achieved by using controls containing different known quantities of said analyte as a standard. Provided that the control sample is as close in performance as possible to a "real world" sample using the methods or assays of the invention, the amount of the analyte in the sample can be standardized against the results obtained using quantification controls. A composition or kit can also, for example, comprise a control comprising an antigen for an assay or method that uses an analyte-binding substance comprising an antibody with a bound target sequence tag or a molecule selected using SELEX. Most of the embodiments for detecting a target sequence are linear and the side-by-side results obtained compared to quantification standards will be proportional to the amount of said analyte in a sample. However, special care will need to be taken in trying to quantify the amount of analyte in a sample when an embodiment of an assay or method that comprises secondary or additional amplification processes, such as, the embodiments illustrated in FIG. 26.

In general, a kit of the invention will also comprise a description of the components of said kit and instructions for their use in a particular process or method or methods of the invention. In general, a kit of the present invention will also comprise other components, such as, but not limited to, buffers, ribonucleotides and/or deoxynucleotides, including modified nucleotides in some embodiments, DNA polymerization or reverse transcriptase enhancers, such as, but not limited to betaine (trimethylglycine), and salts of monovalent or divalent cations, such as but not limited to potassium acetate or chloride and/or magnesium chloride, enzyme substrates and/or cofactors, such as, but not limited to, ATP or NAD, and the like which are needed for optimal conditions of one or more reactions or processes of a method or a combination of methods for a particular application. A kit of the invention can comprise a set of individual reagents for a particular process or a series of sets of individual reagents for multiple processes of a method that are performed in a stepwise or serial manner, or a kit can comprise a multiple reagents combined into a single reaction mixture or a small number of mixtures of multiple reagents, each of which perform multiple reactions and/or processes in a single tube. In general, the various components of a kit for performing a particular process of a method of the invention or a complete method of the invention will be optimized so that they have appropriate amounts of reagents and conditions to work together in the process and/or method.

V. Additional Embodiments of the Invention

Some of the additional embodiments of the invention described below use a ligation splint or a ligation splint oligo. A "ligation splint" or a "ligation splint oligo" is an oligo that is used to provide an annealing site or a "ligation template" for joining two ends of one nucleic acid (i.e., "intramolecular joining") or two ends of two nucleic acids (i.e., "intermolecular joining") using a ligase or another enzyme with ligase activity. The ligation splint holds the ends adjacent to each other and "creates a ligation junction" between the 5'-phosphorylated and a 3'-hydroxylated ends that are to be ligated.

1. Obtaining a Circular Transcription Substrate by Circularizing a Ligation Product Obtained Using Monopartite Target Probes In some embodiments of the present invention, a circular transcription substrate is obtained using monopartite target probes rather than a bipartite target probe. In these embodiments, the monopartite target probes anneal to the target sequence and are ligated in the presence of a target sequence to form a linear ligation product as described previously. However, in these embodiments, the linear ligation product is denatured from the target sequence and subsequently circularized by ligation of its 3'-end to its 5'-end. The 5'-end of the linear ligation product has a 5'-phosphate group or is phosphorylated using a kinase, such as but not limited to T4 polynucleotide kinase, in the presence of ATP. This 5'-phosphorylated linear ligation product is then complexed with a ligation splint oligo that has ends that are complementary to the 3'-end and the 5'-end of the linear ligation product and the ends are ligated under ligation conditions with a ligase that has little or no activity in ligating blunt ends and that is substantially more active in ligating ends that are adjacent when annealed to a contiguous complementary sequence than if the ends are not annealed to the complementary sequence, such as but not limited to Ampligase® DNA Ligase (EPICENTRE Technologies, Madison, Wis.). The use of a ligation splint and a ligase, such as Ampligase® DNA Ligase, that is not active in ligating blunt ends or non-homologous ligation minimizes "background," such as background rolling circle transcription that could result from a circular molecule obtained by intramolecular ligation of a promoter target probe if a non-homologous ligase were used. Preferably, the same ligase is used both for ligation of the target probes annealed to the target sequence and for subsequent ligation of the 3'-end to the 5'-end of the ligation product using a ligation splint. After annealing an anti-sense promoter oligo to the circularized ligation product, a circular transcription substrate of the invention is obtained.

One reason to circularize a linear ligation product obtained from monopartite target probes is because rolling circle transcription is often more efficient and generates more transcription product than transcription of linear transcription substrates. Since initiation of transcription (rather than elongation) is usually a rate-limiting step for transcription, the efficiency of transcription of circular versus linear transcription substrates is particularly increased for small transcription substrates. Still further, transcription is also greatly enhanced for circular transcription substrates in embodiments that use an N4 mini-vRNAP because the transcription product is not efficiently displaced from linear transcription substrates (Davidova, E K and Rothman-Denes, L B, Proc. Natl. Acad. Sci. USA 100:9250-9255, 2003), whereas the transcription product of rolling circle transcription of small circular transcription substrates by an N4 min-vRNAP is displaced and transcription is therefore much more efficient and productive.

2. Use of Probes Lacking a Target-Complementary Sequence

The invention also comprises embodiments in which a circular transcription substrate comprising a target-complementary sequence is generated even if there is no target-complementary sequence at either the 3'-end or the 5'-end or at both ends of an "open circle probe" (the word "target" is removed from the name of the probe here because there are no target-complementary sequences). In these embodiments, simple target probes that can anneal to the target sequence can be used and then, following ligation of these simple target probes on the target sequence, the resulting target-complementary sequence generated by ligation of the simple target probes can be joined directly to an open circle probe by using two ligation splints, each of which has a portion complementary to a respective end of the open circle probe and to an appropriate end of the target-complementary sequence. One ligation splint oligo is used to join a sense promoter of an open circle probe to the 3'-end of a polynucleotide ligation product that was previously obtained by ligation of two or more simple target probes that were annealed to a target sequence. This first ligation splint oligo has a 3'-sequence that is complementary to the 3'-end of the polynucleotide and a second adjacent 5'-sequence that is complementary to the 5'-end of a the 5'-phosphorylated sense promoter sequence of the open circle probe. The second ligation splint oligo has a 5'-sequence that is complementary to the 5'-end of the polynucleotide and a second adjacent 3'-sequence that is complementary to the 3'-end of the open circle probe. Ligases that can be used to ligate suitable ends that are annealed to a ligation splint comprising DNA include, but are not limited to, Ampligase® DNA Ligase (EPICENTRE Technologies, Madison, Wis.), Tth DNA ligase, Tfl DNA ligase, Tsc DNA ligase (Prokaria, Ltd., Reykjavik, Iceland), or T4 DNA ligase. These ligases can be used for both intermolecular and intramolecular ligations when a ligation splint comprising DNA is used to bring the respective ends adjacent to each other. If a ligation splint comprising RNA is used, T4 DNA ligase can be used to join the ends that are annealed to the ligation splint. These embodiments of the invention remove all background transcription that could result from run-off transcription of the small target-complementary sequence at the 5'-end of a bipartite target probe.

The invention also comprises similar embodiments for generating linear transcription substrates of the invention, meaning, for example, that simple target probes can be used without using a promoter target probe, and/or a signal target probe, and then, the resulting target-complementary sequence can be joined to a suitable sense promoter and a signal sequence, if used, by means of ligation splints and a ligase under ligation conditions.

Still further, in other embodiments, simple target probes that anneal adjacently on a target sequence are ligated, then denatured from the target sequence, then ligated to an oligo comprising a sense promoter sequence using a ligation splint that is complementary to the most 3'-end of the target-complementary target probes and to the 5'-end of a sense promoter sequence, and finally circularized by non-homologous intramolecular ligation of a 5'-phosphorylated end with a 3'-hydroxyl end to obtain a circular transcription substrate. Circularization of a linear single-stranded DNA without a ligation splint can be carried out using ThermoPhage™ RNA Ligase II (Prokaria, Ltd., Reykjavik, Iceland). A reason to circularize a linear ligation product is to obtain a circular transcription substrate for more efficient transcription by a rolling circle transcription mechanism, rather than by linear transcription. This embodiment is used only if steps are taken to assure that only ligation products derived from the target-complementary sequences that were ligated in the presence of the target sequence are circularized by the ligase that catalyzes non-homologous ligation, or that the other non-target-dependent transcription products will not be detected in the assay or method.

3. Use of Circular Transcription Substrates to Synthesize Double-Stranded RNA by Rolling Circle Transcription that can be Used for RNA Interference If a target sequence in a target nucleic acid is present in a sample, the methods of the invention that use a bipartite target probe, as disclosed herein, can be used to generate a circular transcription substrate of the present invention. This circular transcription substrate can be used as a substrate for rolling circle transcription by an RNA polymerase that binds to a single-stranded promoter and synthesizes RNA therefrom in order to synthesize double-stranded RNA (dsRNA) that can be used to silence a gene by RNA interference. That is the dsRNA is used as RNAi. By way of example, but not of limitation, dsRNA for use as RNAi can be synthesized using the embodiment of the invention illustrated in FIG. 26. If the target sequence comprises a target nucleic acid that is encoded by a pathogen or by an oncogene, for example, the dsRNA can be a therapeutic composition.

In another embodiment, a new circular transcription substrate is prepared for synthesis of dsRNA for use as RNAi, wherein each oligomer of the RNA multimer transcription product obtained using said circular transcription substrate for rolling circle transcription comprises a self-complementary double-stranded hairpin structure with a non-complementary loop between the self-complementary regions, such that each oligomer corresponds to the desired RNAi and the loop structure. Preferably, said circular transcription substrate is designed so that said RNA oligomers can be cleaved from the RNA multimer obtained from rolling circle transcription.

Preferred RNA polymerases for rolling circle transcription comprise the N4 mini-vRNAP and the N4 mini-vRNAP-Y678F enzymes and the promoter is an N4. Most preferred embodiments of this aspect of the invention use an enzyme chosen from among N4 mini-vRNAP Y678F mutant enzyme, These most preferred embodiments use an N4 promoter in circular transcription substrates for N4 mini-vRNAP Y678F mutant enzyme. Most preferred embodiments of this aspect of the invention synthesize RNA containing 2'-fluoro-pyrimidine nucleotides by using 2'-fluoro-dCTP and 2'-fluoro-dUTP, in addition to ATP and GTP in the rolling circle transcription reaction. Modified RNA molecules that contain 2'-F-dCMP and 2'-F-dUMP are resistant to RNase A-type ribonucleases (Sousa et al., U.S. Pat. No. 5,849,546), included herein by reference. Capodici et al, (J. Immunology, 169: 5196-5201, 2002) showed that 2'-fluoro-containing dsRNA molecules made using the DuraScribe™ Transcription Kit (Epicentre Technologies, Madison, Wis., USA) did not require transfection reagents for delivery into cells, even in the presence of serum. Kakiuchi et al. (J. Biol. Chem., 257: 1924-1928, 1982) showed that use of $[(2'\text{-F-dI})_n\text{: }(2'\text{-F-dC})_n$ duplexes were 40-100 times less antigenic than $[(rI)_n:(rC)_n]$ duplexes, and did not induce an interferon response like $[(rI)_n:(rC)_n]$ duplexes.

Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of a Transcriptionally Active Domain of N4 Virion RNA Polymerase To determine the minimal domain possessing RNA polymerase activity, controlled proteolysis was performed followed by catalytic (transcriptional) autolabeling (Hartmann, et al., 1988). Upon incubation of RNA polymerase with a benzaldehyde derivative of the initiating nucleotide, the benzaldehyde group forms a Schiff-base with the ϵ-amino group of lysines located within 12 Å of the nucleotide-binding site. The crosslinking step was performed in the presence of DNA template because it stimulates binding of the initiating nucleotide. The unstable Schiff-base is converted to a stable secondary amine by reduction under mild conditions with sodium borohydride, with concomitant reduction of any non-reacted benzaldehyde derivative. Addition of the next template-directed $\alpha$-$^{32}$P labeled NTP leads to phosphodiester bond formation and catalytic autolabeling of the transcriptionally active polypeptide. Controlled trypsin proteolysis of vRNAP was performed, followed by catalytic autolabeling and analysis on SDS-PAGE (FIG. 3A). Initially, three proteolytic fragments are generated, of which the smaller two are catalytically active. Upon further incubation with trypsin, a single stable, transcriptionally active product approximately 1,100 amino acids in length remains. N-terminal sequencing of the three initial proteolytic fragments (FIG. 3B) indicated that the stable active polypeptide (mini-vRNAP) corresponds to the middle ⅓ of vRNAP, the region containing the three motifs described above (FIG. 2A, SEQ ID NOS:3-4).

Example 2

Cloning and Purification of N4 Mini-vRNAP

Figure 4:
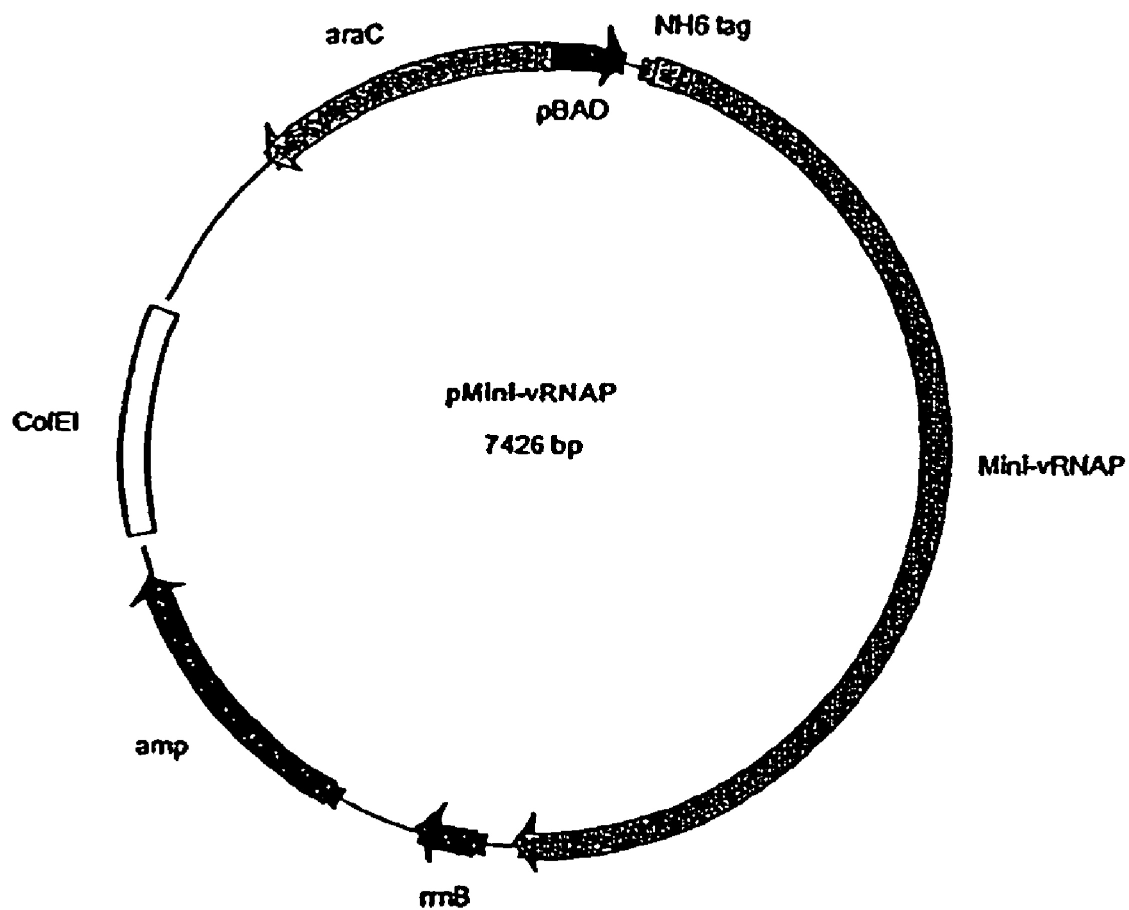
FIG. 4—ORFs for full length polymerase, mini-vRNAP and mutants thereof were cloned under pBAD control with an N-terminal hexahistidine tag. In other experiments, ORFs for mini-vRNAP and the Y678F mutant thereof, both of which lacked an N-terminal hexahistidine tag, were cloned in *E. coli* under pT7 control in cells which inducibly express T7 RNAP; the polypeptides obtained showed similar activities to the polypeptides with hexahistidine tags shown in this figure.
Figure 5:
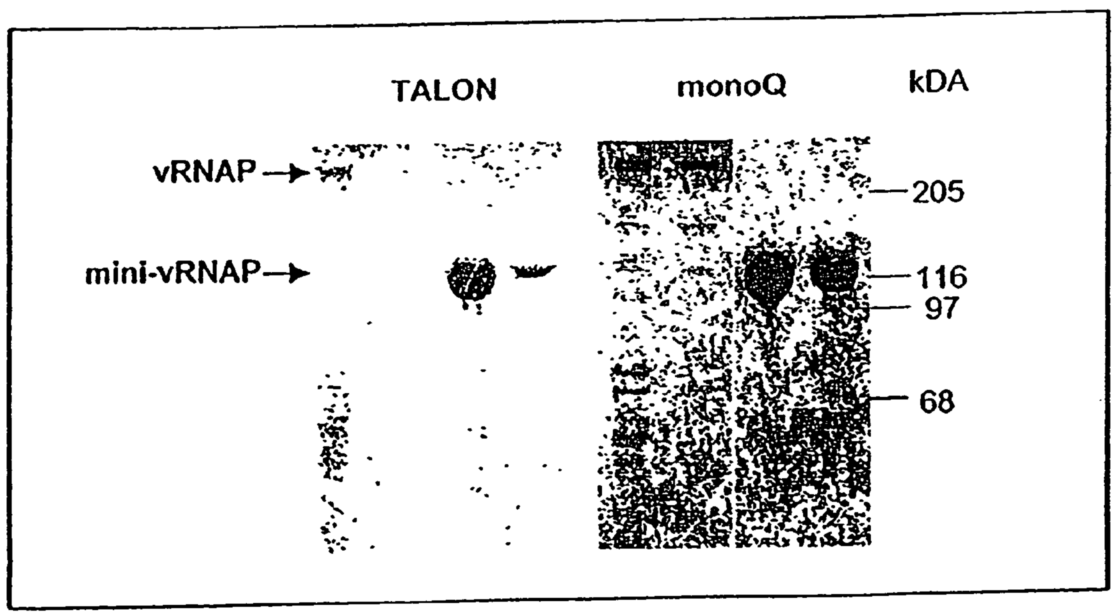
FIG. 5—Purification of cloned vRNAP and mini-vRNAP. The left hand side shows the relative amounts of full size and mini-vRNAP proteins purified on TALON columns from the same volume of induced cells. Further concentration on a MONOQ column reveals that, in contrast to full size vRNAP, mini-vRNAP is stable after induction (right).

The full-size vRNAP and the mini-vRNAP (SEQ ID NOS:6 and 15) ORFs were cloned under pBAD control with an N-terminal hexahistidine tag (FIG. 4). The mini-vRNAP domain was cloned into the pBAD B expression plasmid, which was purchased from Invitrogen. Five restriction enzyme sites within pBAD B have been altered; the SnaI site was converted to a HpaI site, and the PflMI and EcoRV sites were destroyed, all by site-directed mutagenesis. The BstBI and HindIII sites were destroyed by enzyme digestion followed by Klenow treatment and re-ligation. FIG. 5 (left) shows the relative amounts of full-length and mini-vRNAP proteins purified on TALON columns from the same volume of *E. coli* BL21 induced cells. Cloned mini-vRNAP is expressed at 100-fold higher levels than cloned full size vRNAP. Further concentration on a MONOQ column reveals that, in contrast to full size vRNAP, mini-vRNAP is stable after induction (FIG. 5, right). At least 10 mg of mini-vRNAP at a 20 mg/ml concentration are obtained from 1 L of induced cells in just two purification steps: TALON and MONOQ minicolumns. A non-histagged version of mini-vRNAP has also been cloned (SEQ ID NO:4). In this case, the enzyme is purified from a crude extract of induced cells in two steps: a promoter DNA-affinity column and MONOQ.

Mini-vRNAP possesses a high binding affinity (Kd=1 nM) for N4 promoter-containing DNA oligonucleotides. This property was used for purification of non-his tagged mini-vRNAP (SEQ ID NO:4) on a DNA-affinity column. The column was prepared by adsorbing a 5' biotinylated N4 promoter-containing DNA oligonucleotide onto the matrix of a 1 ml HiTrap Streptavidin column (Pharmacia/Amersham Cat.#17-5112-01) according to the manufacturer's instructions. A debris-free sonicate of bacterial cells expressing mini-vRNAP was passed through the column. To bind mini vRNAP to the DNA-affinity column, the pH in the extract and binding/washing buffer should be between 5 to 9, and the NaCl concentration should be between 50 mM and 2M. Nucleases in the extract are inhibited by addition of 2 mM EDTA. After washing the column, mini-vRNAP was eluted with warm (25° C.) water; the elution temperature was raised from 4° C. to 25° C. to increase mini-vRNAP recovery. For complete elution, the temperature can be raised up to 43° C. without significant change in the quality of the preparation. Elution under these conditions occurs due to the removal of metal ions and consequent melting of the promoter hairpin and dissociation of mini-vRNAP. Different DNA oligonucleotides containing variants of the P2 promoter (SEQ ID NOS: 16-19), were used in DNA-affinity columns and tested in mini-vRNAP affinity purification. The best yield was achieved using the DNA oligonucleotide of SEQ ID NO:16. However, the DNA oligonucleotides of SEQ ID NOS:19-20 require a lower temperature than the DNA oligonucleotide of SEQ ID NO:16 for complete elution of the protein, in agreement with the lower thermal stability of the respective promoter hairpins.

Up to 1 mg of mini-vRNAP of 90% purity is obtained from a crude extract of 100 ml *E. coli* culture expressing mini-vRNAP in a single purification step using a 1 ml DNA-affinity column. The binding capacity of the DNA-affinity column was not detectably decreased by multiple use.

Example 3

Effect of EcoSSB on Transcription of Single-Stranded Templates

Figure 6:
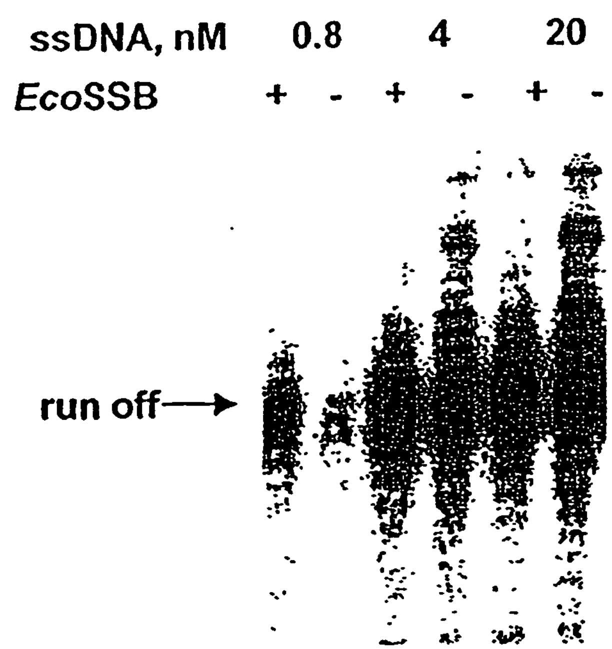
FIG. 6—Activation of N4 vRNAP transcription by EcoSSB at three different ssDNA concentrations. The extent of EcoSSB activation is template-concentration dependent, with highest activation at low DNA template concentration.

Inventors have previously shown that EcoSSB is required for N4 vRNAP transcription in vivo (Glucksmann, et al., Cell 70:491-500, 1992). EcoSSB is unique in that, unlike other SSBs whose effect on vRNAP transcription was tested, it does not melt the promoter hairpin structure (Glucksmann-Kuis, et al., Cell 84:147-154, 1996). Recently, inventors have reinvestigated the effect of EcoSSB on vRNAP transcription of single-stranded templates. FIG. 6 shows transcription in the absence and presence of Eco SSB at three different ssDNA template concentrations. The extent of EcoSSB activation is template-concentration dependent, with highest activation at low DNA template concentration. These results suggest that EcoSSB overcomes template limitation on ssDNA templates.

Figure 7:
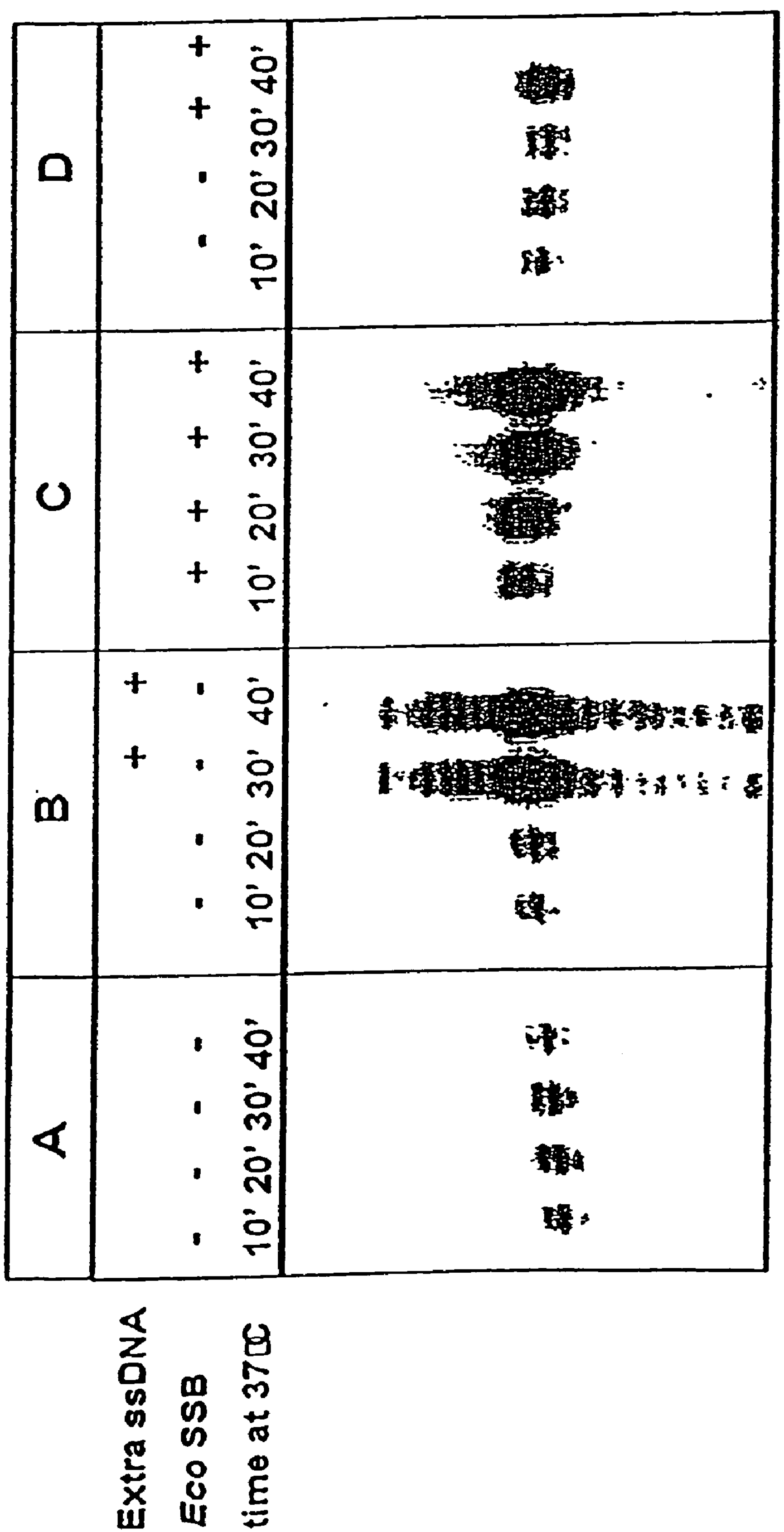
FIG. 7A, FIG. 7B, FIG. 7C, and FIG. 7D—Effect of EcoSSB on ssDNA template recycling. In the absence of EcoSSB, no increase in transcription was observed beyond 10 min of incubation (FIG. 7A). Addition of template at 20 min to the reaction carried out in the absence of EcoSSB led to a dramatic increase in RNA synthesis (FIG. 7B). RNA synthesis increased linearly throughout the period of incubation (FIG. 7C). Addition of EcoSSB at 20 min led to a slow rate of transcriptional recovery (FIG. 7D).

To further explore this hypothesis, the effect of addition of template or EcoSSB to transcription reactions after 20 min incubation in the absence of EcoSSB was tested. The transcription reaction mixtures (5-50 μl) contained 20 mM Tris-HCl (pH 7.9 at 25° C.), 10 mM $MgCl_2$, 50 mM NaCl, 1 mM dithiothreitol, 0.01-1 μM mini-vRNAP, 1-100 nM ssDNA template (30-100 nt long, synthesized by Integrated DNA Technologies), 1 mM each of 3 non-labeled NTPs, 0.1 mM $\alpha$-$^{32}$P NTP (1-2 Ci/mmol, NEN), and 1-10 μM *E. coli* SSB. Incubation was for 1 to 80 min at 37° C. at the indicated temperature. In the presence of EcoSSB, RNA synthesis increased linearly throughout the period of incubation (FIG. 7C). In the absence of EcoSSB, no increase in transcription was observed beyond 10 min of incubation (FIG. 7A). Addition of template at 20 min to the reaction carried out in the absence of EcoSSB led to a dramatic increase in RNA synthesis (FIG. 7B). Addition of EcoSSB at 20 min led to a slow rate of transcriptional recovery (FIG. 7D). These results suggest that EcoSSB converts the template from a transcriptionally inactive RNA:DNA hybrid to transcriptionally active single-stranded DNA.

To test this hypothesis, the physical states of the DNA template and the RNA product were analyzed by native gel electrophoresis in the absence and in the presence of EcoSSB. In order to have effective transcription in the absence of EcoSSB, transcription was performed at an intermediate (5 nM) DNA concentration, at which only a 2-fold effect of EcoSSB is observed.

Figure 8:
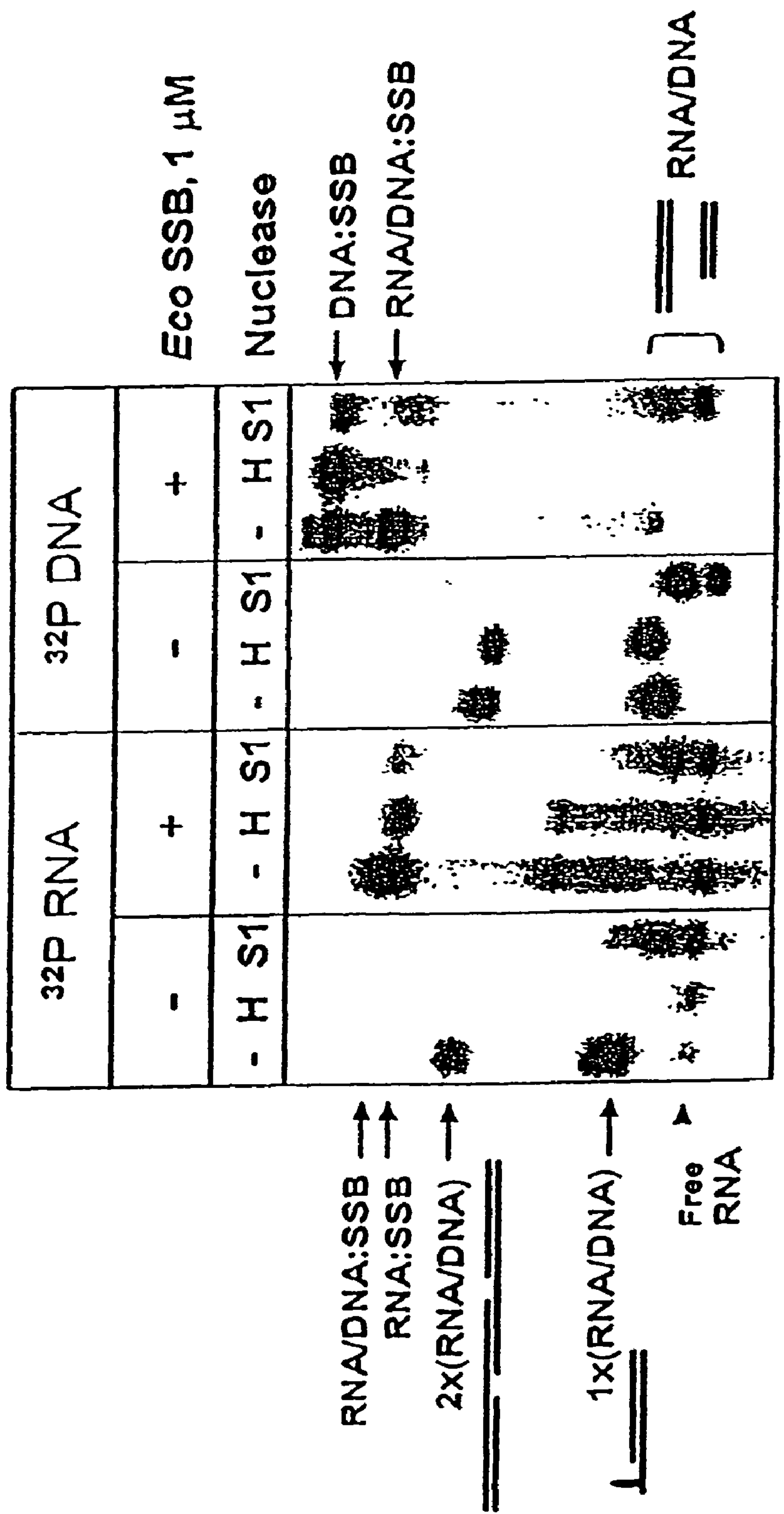
FIG. 8—Effect of EcoSSB on the state of template DNA and product RNA in vRNAP transcription. Native gel electrophoresis was carried out in the absence and in the presence of EcoSSB. Transcription was performed at an intermediate (5 nM) DNA concentration, at which only a 2-fold effect of EcoSSB is observed. Either $^{32}P$-labeled template (right panel) or labeled NTPs (left panel) were used to analyze the state of the template (right panel) or RNA product (left panel) in the absence or presence of EcoSSB.

The results of this experiment are shown in FIG. 8. Either $^{32}$P-labeled template (right panel) or labeled NTPs (left panel) were used to analyze the state of the template (right panel) or RNA product (left panel) in the absence or presence of EcoSSB. After transcription, the mixtures were split further into 3 samples: a control sample with no additions, a sample to which RNase H was added to specifically degrade RNA in RNA:DNA hybrids, and a third sample to which Nuclease S1 was added to degrade single-stranded nucleic acids. In the absence of EcoSSB, both the DNA template and the RNA product are in RNA:DNA hybrids, since the RNA product is RNase H sensitive while the DNA-containing bands show altered mobility after RNase H treatment. In the presence of EcoSSB, a significant portion of the RNA product is RNase H resistant and therefore free, although an RNase sensitive band is present that corresponds to an intermediate RNA:DNA:SSB complex. Under these conditions, the DNA is in an SSB:DNA complex. These results indicate that EcoSSB stimulates transcription through template recycling.

To define regions of EcoSSB essential for vRNAP transcription activation on single-stranded templates, the inventors have tested the effect of human mitochondrial SSB (HmtSSB), which shows extensive sequence and structural homology to EcoSSB. The N-terminus of EcoSSB contains DNA binding and tetramerization determinants while the C-terminus is involved in interaction with other replication proteins. Hmt SSB has no effect on vRNAP transcription although it does not melt the promoter hairpin. Interestingly, preliminary results using mutant EcoSSBs and EcoSSB-Hmt SSB chimeras suggest that the C-terminal region of EcoSSB is essential for vRNAP transcriptional activation.

Example 4

Characterization of Mini-vRNAP Transcription Properties

Figure 9:
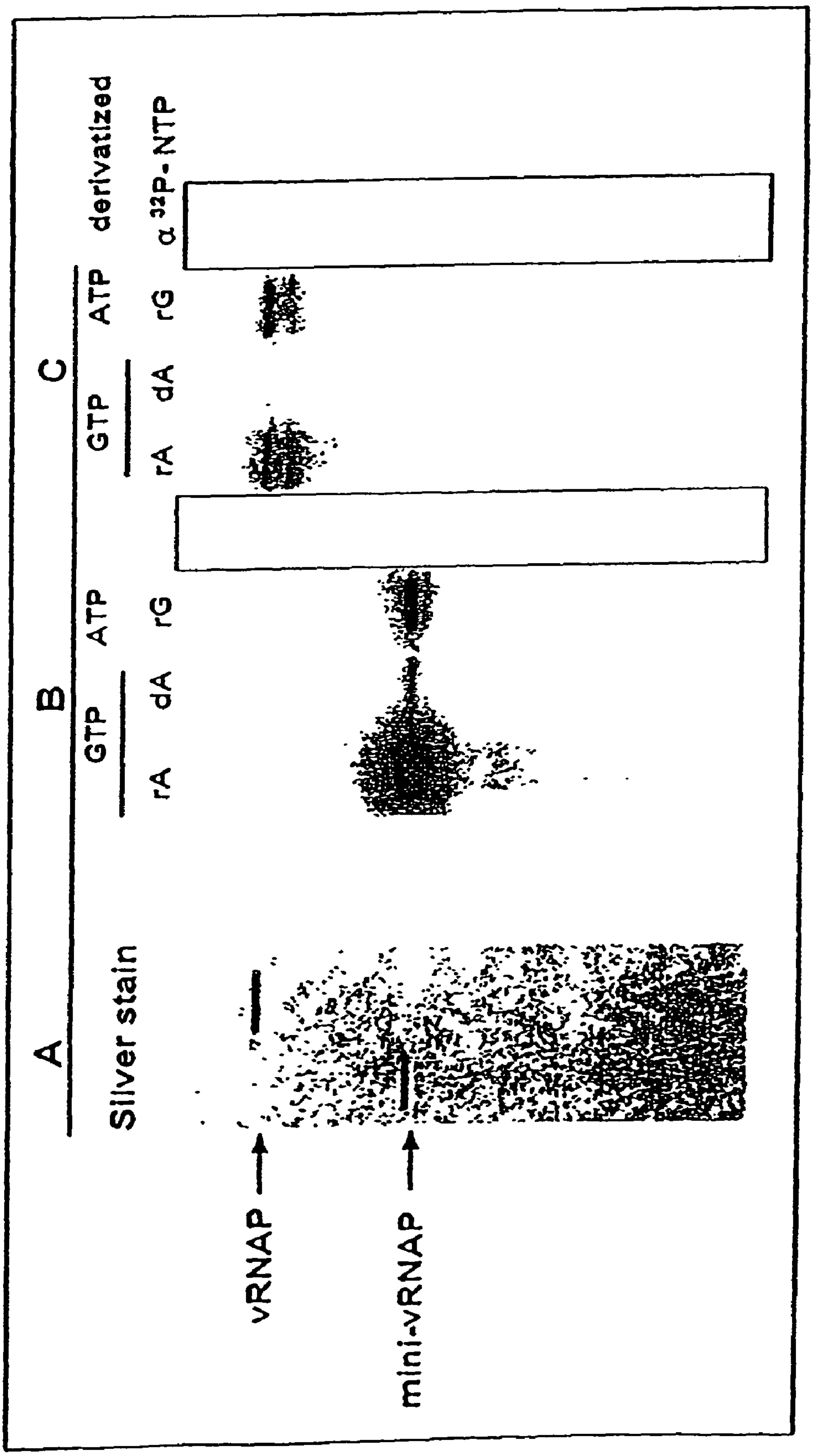
FIG. 9A, FIG. 9B, and FIG. 9C—Transcription initiation by vRNAP and mini-vRNAP. The initiation properties of the full length and mini-vRNA polymerases were compared at similar molar concentrations (FIG. 9A) using the catalytic autolabeling assay and two reaction conditions: using a template containing +1C, the benzaldehyde derivative of GTP and $\alpha$-$^{32}P$-ATP, or a template containing +1T, the benzaldehyde derivative of ATP and $\alpha$-$^{32}P$-GTP. Comparison of the results in FIGS. 9B and 9C demonstrates that mini-vRNAP exhibits initiation properties similar to full size vRNAP.

The initiation properties of the full length RNA polymerase and mini-vRNAP were compared at similar molar concentrations (FIG. 9A) using the catalytic autolabeling assay and two reaction conditions: 1-using a template containing +1C, the benzaldehyde derivative of GTP and $\alpha^{32}$P-ATP, or 2- a template containing +1T, the benzaldehyde derivative of ATP and $\alpha^{32}$P-GTP. Comparison of the results in FIGS. 9B and 9C demonstrates that mini-vRNAP exhibits initiation properties similar to full-length vRNAP. In addition, both enzymes discriminate against DATP incorporation to the same extent. Mini-vRNAP does not synthesize abortive products when the first four nucleotides of the transcript are comprised of 50% or more G or C nucleotides.

Figure 10:
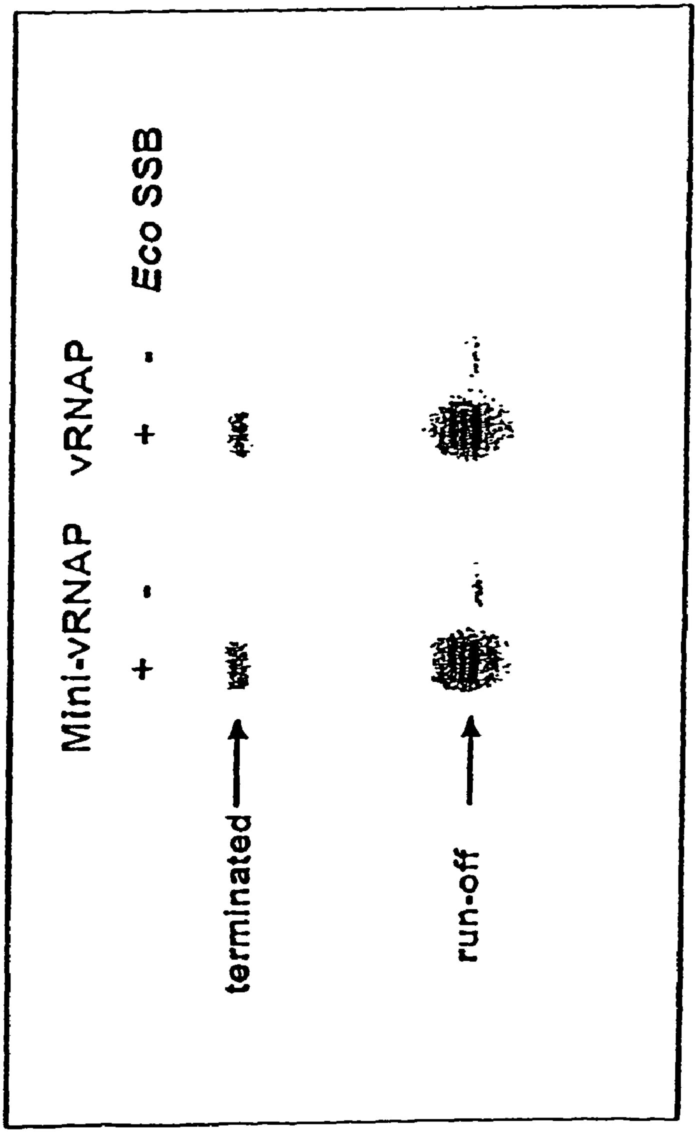
FIG. 10—Effect of EcoSSB on transcription of vRNAP and mini-vRNAP. The elongation and termination properties of vRNAP and mini-vRNAP are compared.

The elongation and termination properties of both enzymes are compared in FIG. 10. Similar run-off and terminated transcripts are synthesized. Moreover, EcoSSB activates transcription by both enzymes to the same levels. This result indicates that, if there are any sites of specific contact between vRNAP and EcoSSB, they reside in the mini-vRNAP domain.

The sequence of the terminator signals for vRNAP present in the N4 genome include SEQ ID NOS:21-26. The signals of SEQ ID NO:21 and 22 have been tested in vitro on single-stranded templates.

The rate of mini-vRNAP transcription has been compared to the rate of T7 RNA polymerase under the same conditions using the same DNA template. The template used was linearized pET11 containing the original T7 promoter and the N4 vRNAP P2 promoter that was introduced through cloning. The DNA template was denatured before performing transcription using N4 mini-vRNAP. The concentrations of T7 RNAP (Promega, Cat.#P2075) and mini-vRNAP were compared using SDS-PAGE. Transcription reactions contained 50 nM of polymerase, 100 nM of DNA template, 5× transcription buffer provided with the T7 RNAP, and 1 mM of each ATP, GTP and CTP and 0.1 mM of [$^{32}$p]-UTP (1 Ci/mmol). Each reaction mixture was split in two, and *E. coli* SSB was added to one half. The mixtures were incubated at 37° C. and aliquots were taken at different time points. Transcription products were electrophoresed on a 6% sequencing gel and the amount of radioactively-labeled RNA was quantitated by phosphoimaging. The results showed that: (a) transcription of T7 RNAP was not affected by the presence of *E. coli* SSB and (b) N4 mini-vRNAP synthesized 1.5 to 5 fold more RNA in the presence of EcoSSB than T7 RNAP at different time points of incubation.

The optimal temperature for mini-vRNAP transcription is 37° C. It exhibits 70% activity at 30° C., 65% at 45° C., and only 20% at 50° C.

The average error frequency was estimated by determining the misincorporation frequency of each of four [$^{32}$P]-$\alpha$ NTPs into RNA products using template ssDNAs missing the corresponding template nucleotide in the transcribed region. The following values were obtained: $\frac{1}{5}\times10^4$ for misincorporation of G and U using "no C" (SEQ ID NO:10) and "no A" (SEQ ID NO:11) ssDNA templates, respectively; $\frac{1}{4}10^4$ for misincorporation of C using the "no G" (SEQ ID NO:12) template, and $\frac{1}{2}\times10^4$ for misincorporation of A using the "no T" (SEQ ID NO:13) template. For comparison, the average error frequency for T7 RNAP is $\frac{1}{2}10^4$ (Huang, et al., 2000). Using the method for detection of mispair formation described by Huang, et al. (2000), no misincorporation by mini-vRNAP was detected.

The ability of mini-vRNAP to incorporate derivatized nucleotides was measured. Transcription by mini-vRNAP in the presence of 0.1-1 mM Digoxigenin-11-UTP (cat#1209256, Roche), Biotin-16-UTP (cat#1388908, Roche) or underivatized UTP, yielded comparable amounts of product RNA using "control" ssDNA (SEQ ID NO:9) as a transcription template. The product RNAs synthesized in the presence of derivatized UTP have higher molecular mass than those synthesized in the presence of underivatized UTP, and the difference corresponds to the mass difference of the UTPs used. Several derivatives (i.e. 2'Fluoro-ribonucleoside triphosphates, dideoxynucleoside triphosphates) are being tested. The fluorescent analog Fluorescein-12-UTP (Roche catalog #1427857) has been tested using a template which encodes a 51 nucleotide transcript containing a run of 4 Us, and a nucleotide mix containing ATP, CTP, GTP and Fluorescein-12-UTP only. Transcription was only 3% of that achieved with UTP, biotin-6-UTP or digoxigenin-11-UTP under the same reaction conditions. However, incorporation of the fluorescent analog at higher yields is expected to occur in the presence of underivatized UTP or on templates with other sequence compositions.

Example 5

Sequence Determinants of Mini-vRNAP Promoter Binding

The three N4 early promoters present in the N4 genome contain a pair of Cs separated by 4 nucleotides from the base of the 5 bp promoter stem. In the preferred promoter P2, these 4 bases are As and the Cs are followed by a T. Preferably, mini-vRNAP uses a 17 nucleotide promoter sequence located immediately upstream of the transcription initiation site. Promoters for N4 vRNA polymerase are described by Haynes et al., Cell 41:597-605 (1985) and Dai et al., Genes Devepmnt. 12:2782-2790 (1998), herein incorporated by reference. vRNAP-promoter recognition and activity require specific sequences and a hairpin structure on the template strand. The vRNAP promoters of SEQ ID NOS:27-29 assume a hairpin structure comprised of a 5-7 bp stem and 3 b purine-containing loop. The −11 position corresponds to the center of the loop; +1 indicates the transcription start site. Thus, promoter sequences of the invention include, but are not limited to:

```
                                  SEQ ID NO:27
-11 +1 P1 3'-CAACGAAGCGTTGAATACCT-5'

                                  SEQ ID NO:28
-11 +1 P2 3'-TTCTTCGAGGCGAAGAAAACCT-5',
and

                                  SEQ ID NO:29
-11 +1 P3 3'-CGACGAGGCGTCGAAAACCA-5'
```

Other possible vRNAP promoters of the current invention include a set of any inverted repeats forming a hairpin with a 2-7 bp long stem and 3-5 b loop having purines in the central and/or next to the central position of the loop.

Figure 11:
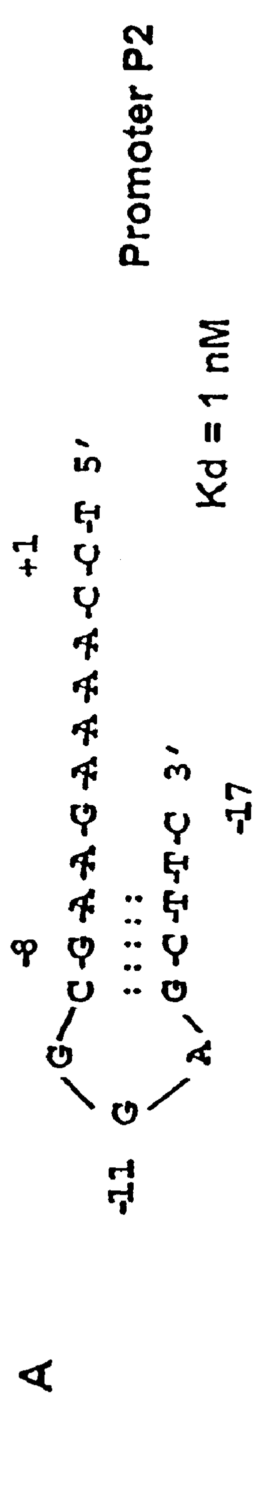
FIG. 11A and FIG. 11B—Determination of mini-vRNAP promoter contacts. A 20-base oligonucleotide (SEQ ID NO:30) containing wild type promoter P2 sequence binds with a 1 nM Kd (FIG. 11A). Most oligonucleotides substituted with 5-Iodo-dU at specific positions showed close to wild type affinity except for the oligonucleotides substituted at positions −11 (at the center of the loop) and −8, indicating that these positions are essential for promoter recognition (FIG. 11B). UV crosslinking indicates that mini-vRNAP primarily contacts the −11 position.
Figure 11:
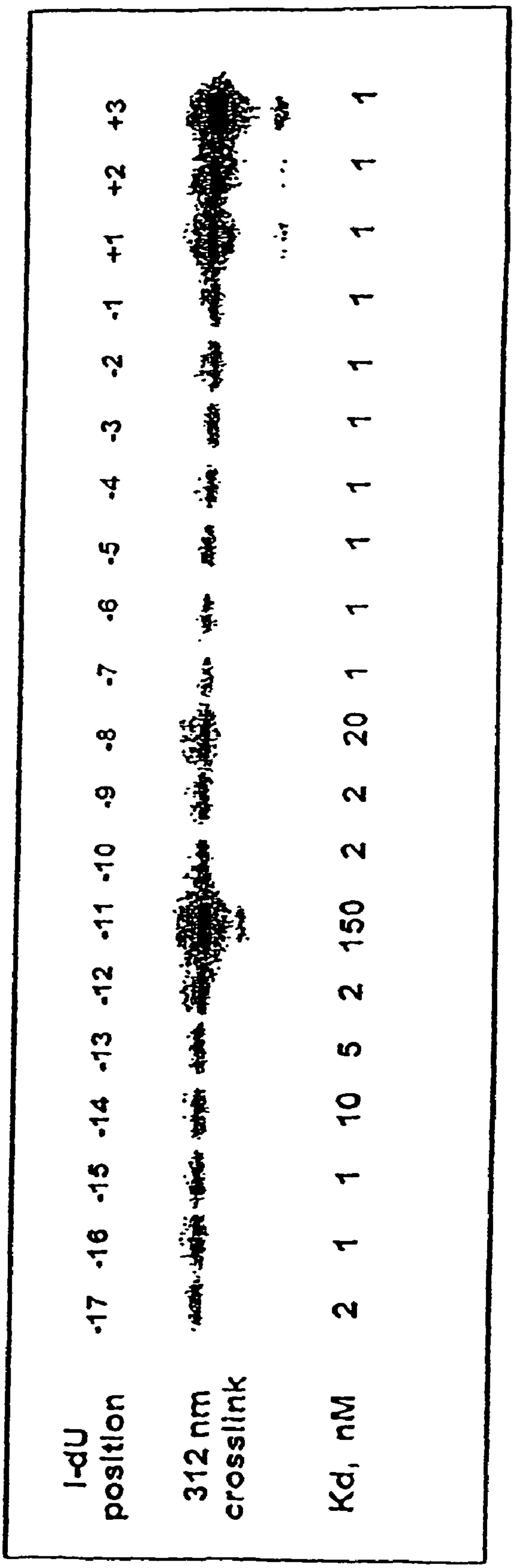

To study the sequence determinants of promoter binding, 20 base-long promoter oligonucleotides, containing the wild-type vRNAP promoter P2 sequence and substituted at every position with a single 5-Iodo-dU, were used. Whenever substitutions were made in the stem, the corresponding pairing base was changed to A. These oligonucleotides were $^{32}P$ end-labeled and used to determine the enzyme's affinity for promoter DNAs by a filter binding assay and the ability to crosslink to mini-vRNAP upon UV irradiation at 320 nm. A 20-base oligonucleotide with wild type promoter P2 sequence binds with a 1 nM Kd. Most oligonucleotides showed close to wild type affinity except for the oligonucleotides substituted at positions −11 (at the center of the loop) and −8, indicating that these positions are essential for promoter recognition (FIG. 11). Surprisingly, UV crosslinking was most effective at position −11, in spite of the low binding affinity, indicating a specific contact at this position to mini-vRNAP. Crosslinking was also observed to positions +1, +2 and +3, indicating non-specific contacts with this region of the template, since 5-Iodo-dU substituted oligonucleotides at these positions showed wild-type binding affinity.

Figure 12:
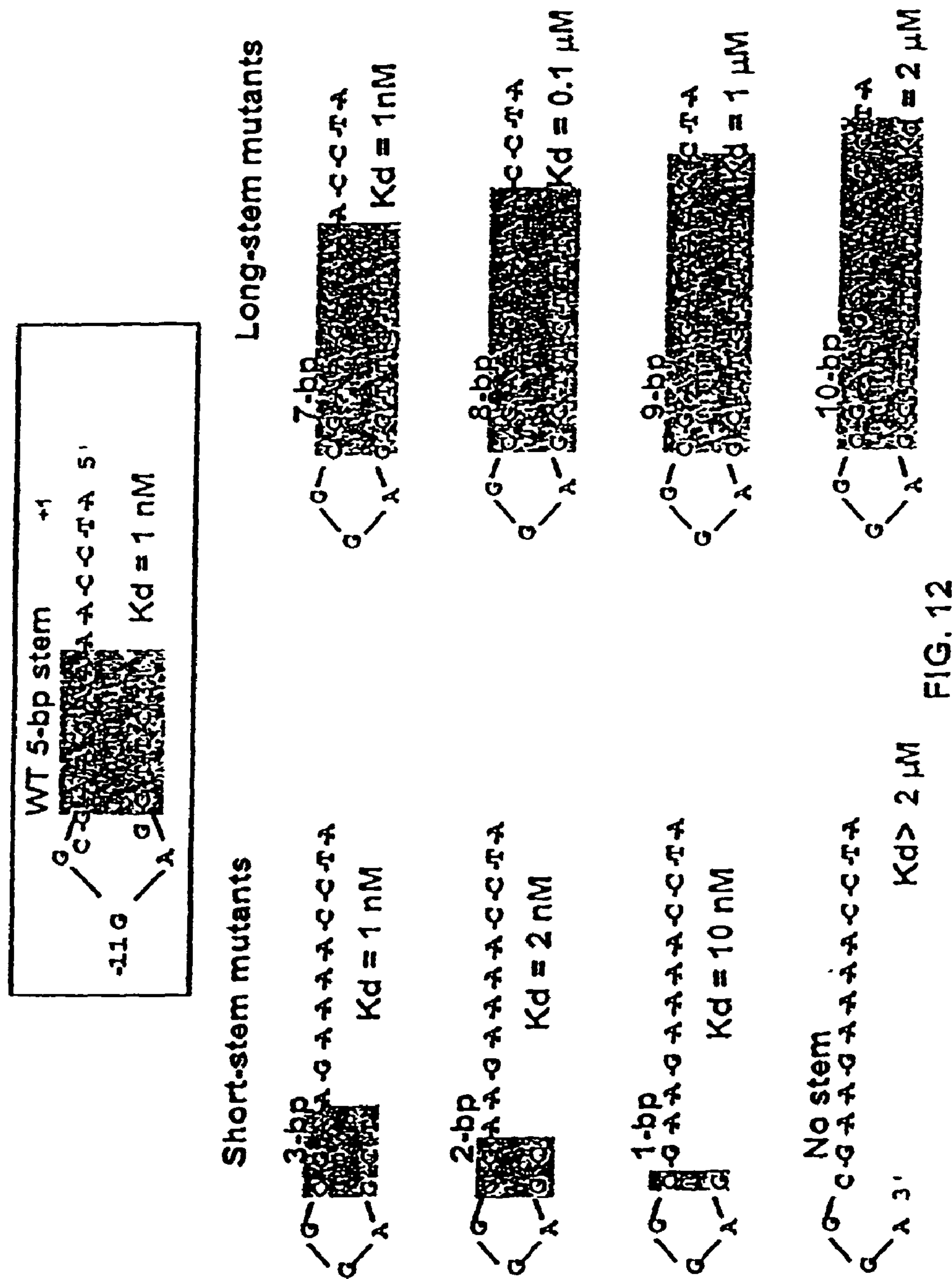
FIG. 12—Binding affinities of stem-length promoter mutants. Wild type promoter P2 with a 5 bp stem has a Kd of 1 nM (top) (SEQ ID NO:31). The stem was shortened by removal of 3' bases (left) (SEQ ID NOS:32-35). The stem can be shortened by two base pairs without change in the binding affinity. The effect of lengthening the stem by addition of 3' bases is shown (right) (SEQ ID NOS:36-39). The stem can be lengthened by two base pairs without change in the binding affinity.

The effect of changes in the stem length of the hairpin on the ability of mini-vRNAP to bind P2 promoter DNA was analyzed. As shown above, wild type promoter P2 with a 5 bp stem has a Kd of 1 nM (FIG. 12, top). The stem was shortened by removal of 3' bases as shown in FIG. 12 (left). The stem can be shortened by two base pairs without change in the binding affinity. If two or one loop-closing base pairs remain, the binding affinity of templates is still substantial (2-10 nM). This result, although surprising, is not unexpected since it has been shown that the oligonucleotide 3'd(CGAGGCG)5' forms an unusually stable minihairpin (Yoshizawa, et al., Biochemistry 36, 4761-4767, 1997). No binding is observed if one more nucleotide is removed and the loop cannot form. These results indicate that formation of a loop is essential for vRNAP-promoter recognition.

The effect of lengthening the stem by addition of 3' bases is shown in FIG. 12 (right). The stem can be lengthened by two base pairs without change in the binding affinity. On the other hand, base pairing at −2 reduces binding affinity by two orders of magnitude, with a further one order of magnitude reduction caused by base pairing at −1 and +1. These results indicate that single-strandedness of the template at positions −2, −1 and +1 is required for efficient template binding.

Figure 13:
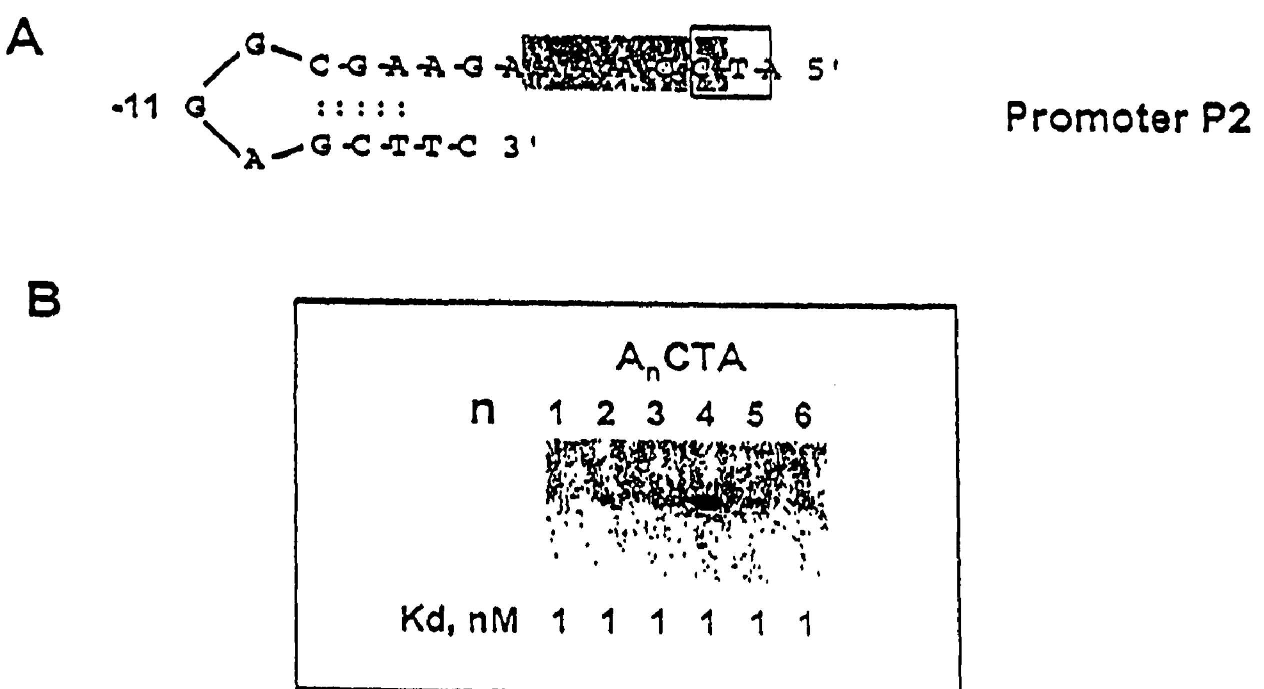
FIG. 13A and FIG. 13B—Identification of the transcription start site by catalytic autolabeling. A series of templates were constructed with a single C placed at different distances from the center of the hairpin (position −11) by addition or deletion of the tract of As present at promoter P2 (FIG. 13A) (SEQ ID NO:31). The affinity of mini-vRNAP for these promoters was measured by filter binding, and transcription initiation was measured by catalytic autolabeling of mini-vRNAP. All templates showed similar binding affinities. However, only the template with a C positioned 12 bases downstream from the center of the hairpin was able to support transcription initiation (FIG. 13B).

All three N4 early promoters present in the N4 genome contain a pair of Cs separated by 4 nucleotides from the base of the 5 bp promoter stem. In promoter P2, these 4 bases are As and the Cs are followed by a T. To identify the determinants of the site of transcription initiation, a series of templates were constructed with a single C placed at different distances from position −11 of the hairpin by addition or deletion of the tract of As present at promoter P2 (FIG. 13). The affinity of mini-vRNAP for these promoters was measured by filter binding and transcription initiation was measured by catalytic autolabeling of mini-vRNAP. All templates showed similar binding affinities. However, only the template with a C positioned 12 bases downstream from the center of the hairpin was able to support transcription initiation. This result indicates that mini-vRNAP utilizes this position as the transcription start site (+1).

Example 6

Identification of Sequence Motifs Essential for Mini-vRNAP Activity

Figure 2:
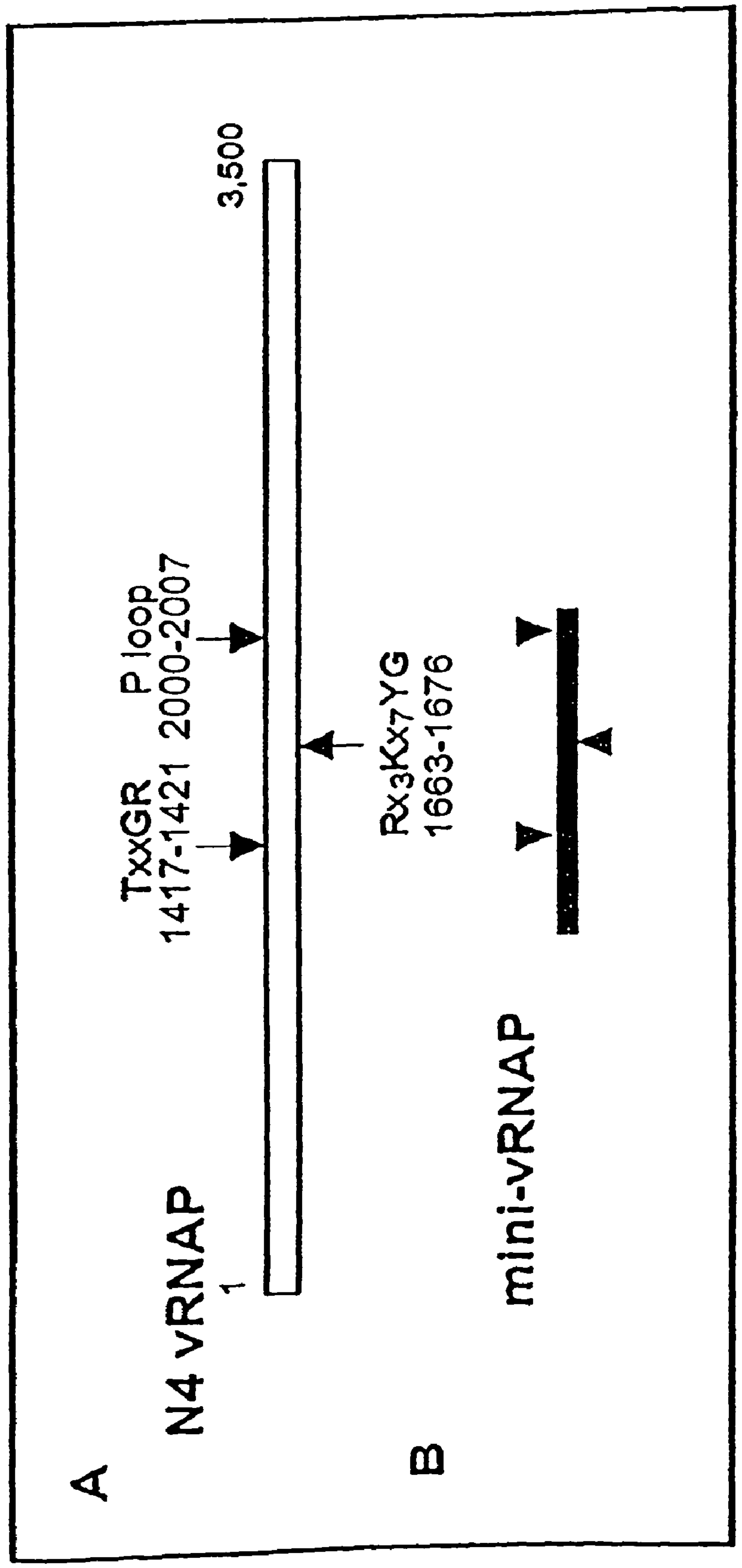
FIG. 2A and FIG. 2B—N4 vRNAP and generation of mini-vRNAP.
Figure 3:
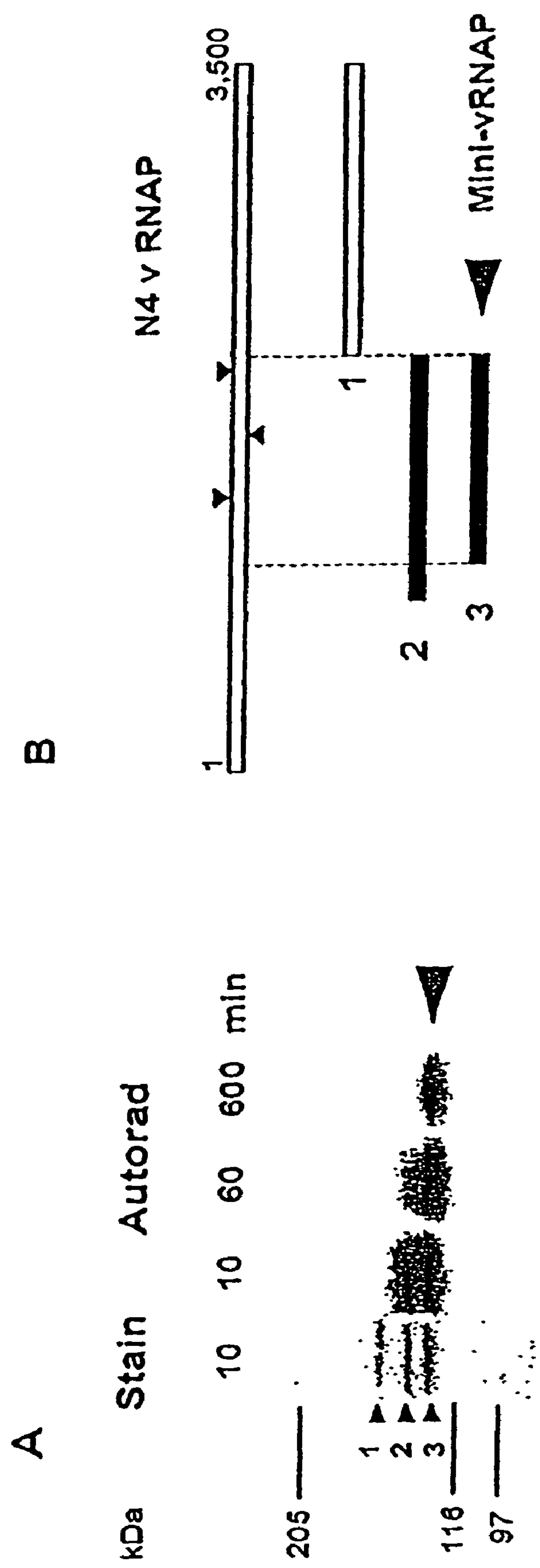
FIG. 3A and FIG. 3B—Identification of the minimal transcriptionally active domain of N4 vRNAP by proteolytic cleavage.

As shown in FIG. 2A, vRNAP contains the sequence $Rx_3Kx_{6-7}YG$ (SEQ ID NO:45), designated Motif B in the Pol I and Pol α DNA polymerases and the T7-like RNA polymerases. To determine the relevance of this motif to vRNAP activity, two mutants K670A and Y678F (SEQ ID NO:8) (position numbers in mini-vRNAP) were constructed by site-specific mutagenesis of mini-vRNAP. These two positions were chosen because, in T7-like RNA polymerases, the lysine is involved in nucleotide binding and the tyrosine in discrimination against deoxynucleoside triphosphates (Maksimova, et al., Eur. J Biochem. 195:841-847, 1991; Bonner, et al., EMBO J. 11:3767-3775, 1992; Osumi-Davis, et al., J. Mol Biol. 226:37-45, 1992). The His-tagged Y678F mini-vRNAP gene (SEQ ID NO:7) differs from that of the mini-vRNAP domain sequence (SEQ ID NO:3) at two positions: nucleotide 2033 (A) was changed to a T, and nucleotide 2034 (T) was changed to a C.

Figure 14:
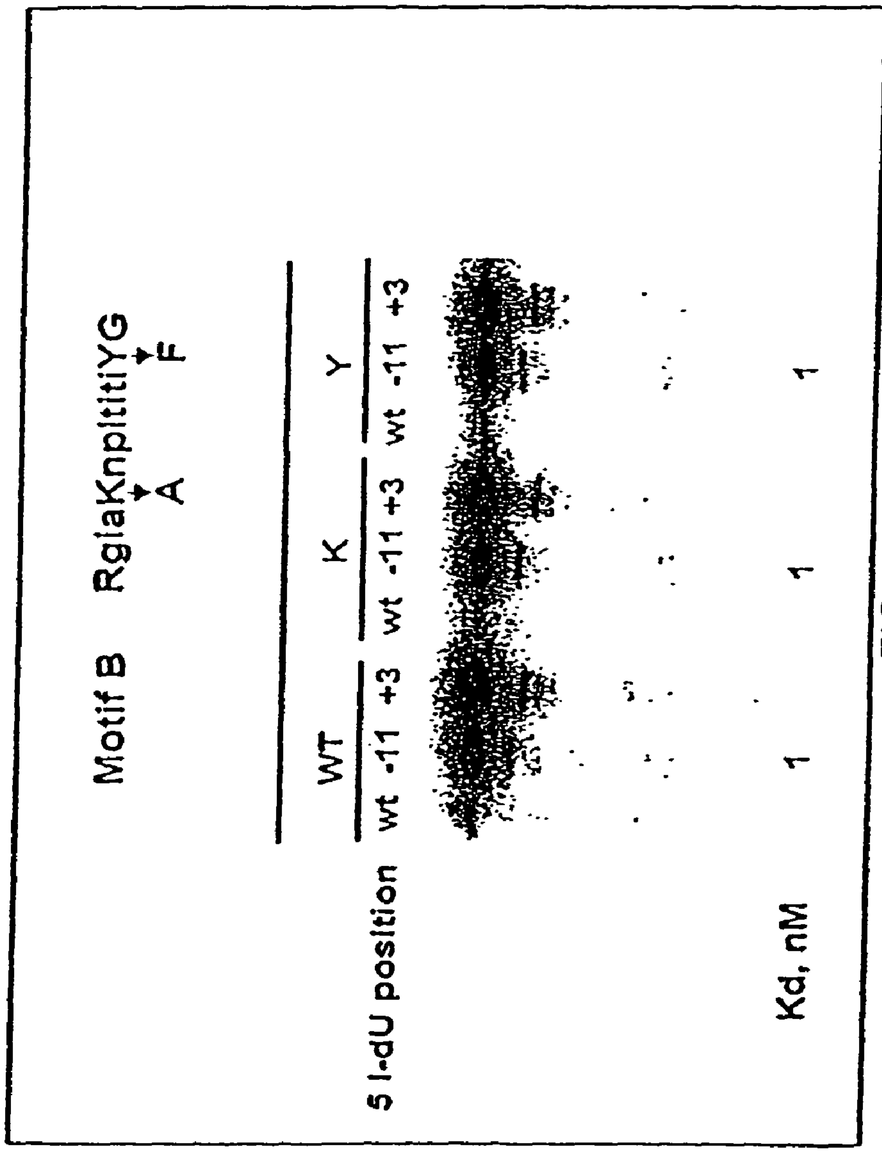
FIG. 14—UV crosslinking of mutant mini-vRNAPases to promoter oligonucleotides (SEQ ID NOS:40-41). Two mutants (K670A and Y678F) were tested for their ability to bind to wild type promoters. Both mutant RNA polymerases bound to promoter DNA with wild type affinities and crosslinked to 5-Iodo-dU substituted P2 DNA templates at positions −11 and +3 as well as the wild type enzyme, indicating that these polymerase mutations do not affect promoter binding.

These RNA polymerase mutants were cloned under pBAD control, purified and tested for their ability to bind to wild type promoters. Both mutant polymerases bound to promoter DNA with wild type affinities and crosslinked to 5-Iodo-dU substituted P2 DNA templates at positions −11 and +3 with wild-type affinities (FIG. 14), indicating that these mutations do not affect promoter binding.

Figure 15:
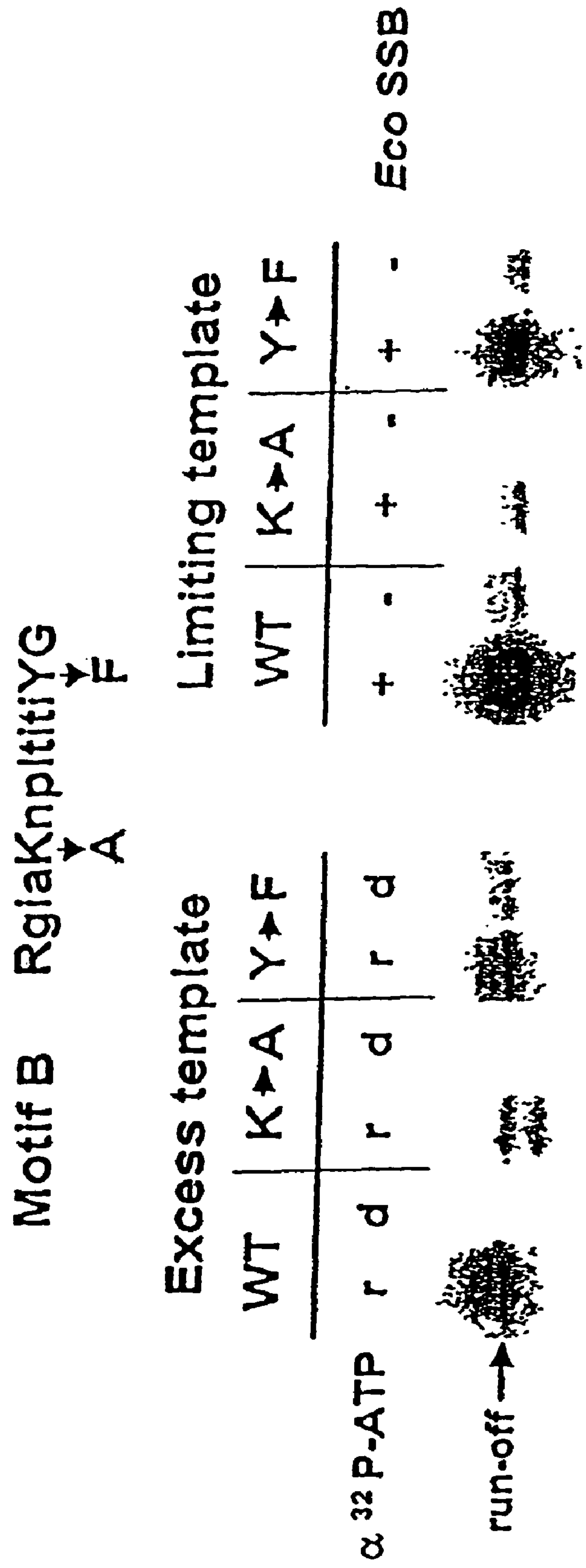
FIG. 15—Run-off transcription by mutant mini-vRNAPases (SEQ ID NOS:40-41). The wild type and Y678F (SEQ ID NO:8) enzymes displayed similar activities at both template excess and template-limiting conditions, while the K670A enzyme exhibited decreased activity under both conditions. Under limiting template conditions, all three enzymes were activated by EcoSSB (right panel). However, the Y678F enzyme showed reduced discrimination between incorporation of ribo- and deoxyribonucleoside triphosphates.

The mutant enzymes were tested for their ability to support run-off transcription. The wild-type enzyme and Y678F enzyme (SEQ ID NO:8) displayed similar activities at both template excess and template-limiting conditions, while the K670A enzyme exhibited decreased activity under both conditions (FIG. 15). Under limiting template conditions, all three enzymes were activated by Eco SSB (right panel). However, the Y678F enzyme showed reduced discrimination between ribo- and deoxyribonucleoside triphosphates.

Figure 16:
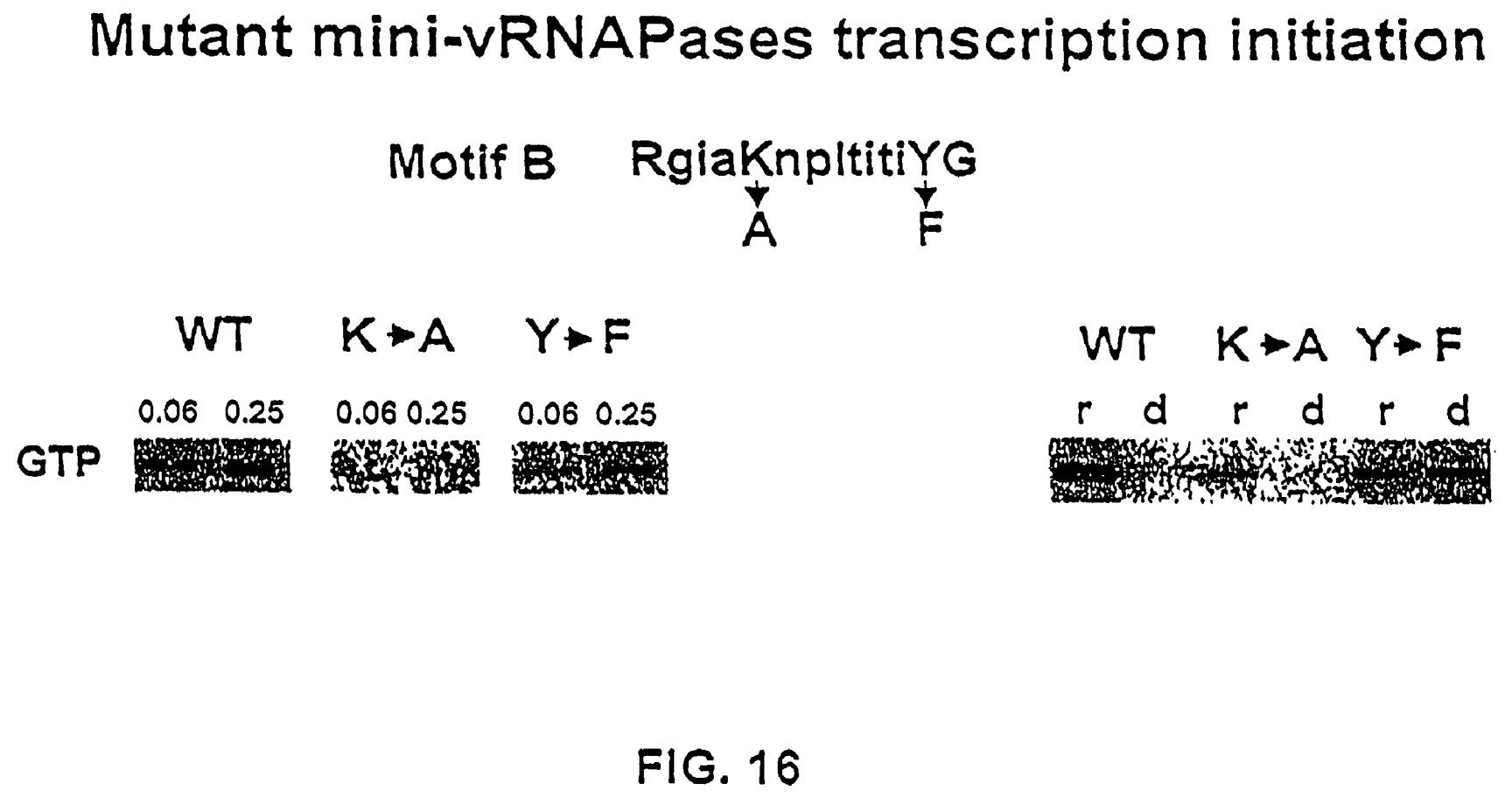

The initiation properties of the three enzymes were compared using catalytic autolabeling (FIG. 16). The K670A enzyme displays significantly reduced activity with the GTP derivative. The Y678F enzyme, in contrast to wild-type polymerase, incorporates dATP as efficiently as rATP in a single round of phosphodiester bond formation.

Therefore, the behavior of the K670A and Y678F mutant enzymes indicates that Motif B is involved in catalysis, with the lysine probably required for NTP binding and the tyrosine responsible for dNTP discrimination. These results suggest that, despite its lack of extensive sequence similarity, vRNAP is a Class II T7-like RNA polymerase. Results of recent experiments revealed the location of the two carboxylates (aspartates) involved in catalysis.

Example 7

Figure 17:
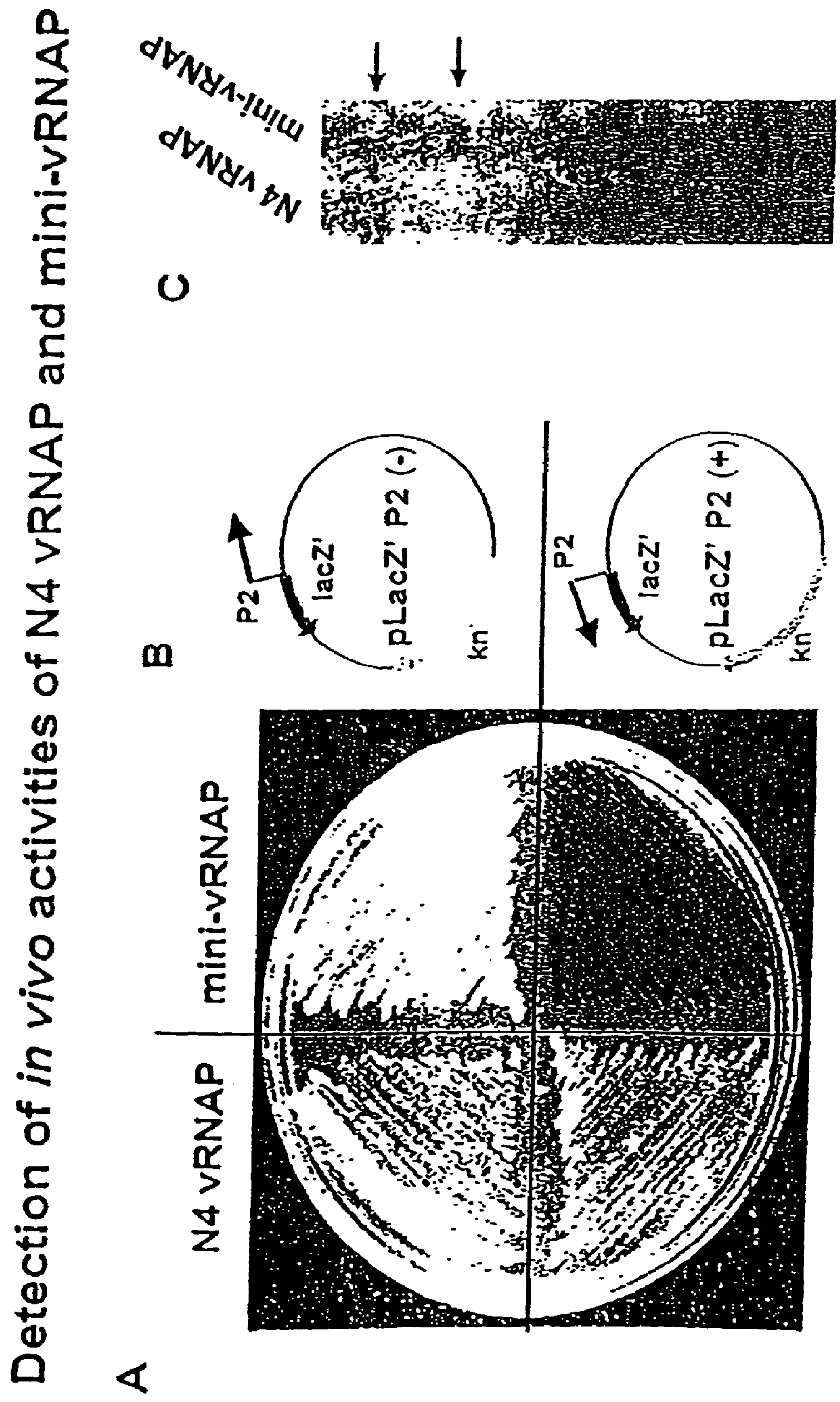
FIG. 17A, FIG. 17B, and FIG. 17C—Detection of in vivo activities of N4 vRNAP and mini-vRNAP. Transcription of β-galactosidase α-peptide by fill size and mini-vRNAP was assayed on inducing-Xgal media (FIG. 17A). Plasmid (PACYC) templates were constructed with a reporter gene (αpeptide of β-galactosidase) under the control of vRNAP promoter P2 cloned in either of two orientations (FIG. 17B). Induction of mini-vRNAP led to production and accumulation of detectable levels of the protein, whereas full-length vRNAP was degraded (FIG. 17C).

Development of an In Vivo System Using Mini-vRNAP and N4 vRNAP Promoters for in Vivo Expression of RNAs and Proteins Plasmid templates were constructed with a reporter gene (α-peptide of β-galactosidase) cloned under the control of vRNAP promoter P2 present in either of two orientations (FIG. 17B). The reporter construct was generated by cloning a cassette into plasmid pACYC177, which was obtained from New England Biolabs. The cassette contains an approximately 30 bp long fragment originating from pT7Ac (purchased from United States Biochemical), a N4 promoter, and sequence encoding the alpha fragment of lacZ (lacZ'). The N4 promoter and lacZ' were generated by oligonucleotide annealing and PCR amplification, respectively. This cassette replaces the pACY177 sequence located between the cleavage sites for restriction enzymes ApaLI and BamHI. These reporter plasmids and recombinant full-length or mini-vRNAP expressing plasmids were introduced into *E. coli* DH5α (ΔM15), a strain that encodes the β-galactosidase σ-peptide. Expression of the reporter gene α-peptide) in this strain results in the synthesis of active β-galactosidase and consequent production of blue colonies on X-gal plates. Transcription of α-peptide by full-length and mini-vRNAP was assayed on inducing-Xgal media and shown in FIG. 17A. Induction of full-length polymerase results in small colonies with no β-galactosidase activity. This is not surprising since full-length vRNAP is degraded in these cells (FIG. 17C). In contrast, induction of mini-vRNAP led to detectable levels of the protein (FIG. 17C) and to β-galactosidase activity only from the plasmid containing promoter P2 in the proper orientation (FIG. 17A). These results indicate that this system will be suitable for in vivo expression of RNAs and proteins under mini-N4 vRNAP promoter control.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 8

Rolling Circle Transcription of Model ssDNA Transcription Substrates

Each oligonucleotides (50 picomoles), comprising a sense P2 promoter sequence (or, in control reactions, an anti-sense sequence to the P2 promoter or no promoter) at its 5'-end, which was phosphorylated, and up to 52 additional nucleotides corresponding to a model target sequence (e.g., for the human beta actin gene) in its 3'-portion, was ligated in a reaction mixture containing 0.2 mM ATP, 1 mM DTT, and 50 micrograms per ml of BSA for 2 hours at 60° C. using 200 units of ThermoPhage™ RNA Ligase II (Prokaria, Rejkjavik, Iceland, #Rlig122) in 1× ThermoPhage RNA Ligase II Buffer comprising 50 mM MOPS, pH 7.5, 5 mM $MgCl_2$, and 10 mM KCl. Then, linear oligos were removed by digestion with Exonuclease I (EPICENTRE Technologies, Madison, Wis.), the Exo I was heat-inactivated, and the circular ssDNA oligos were ethanol precipitated using standard techniques.

One picomole of circular ssDNA oligonucleotide, prepared as just described, was then incubated for four hours at 37° C. in a 60-microliter reaction mixture comprising one microgram of N4 mini-vRNAP (EPICENTRE Technologies, Madison, Wis.), 1 mM each NTP, 1 mM DTT, and 5 micromolar *E. coli* SSB Protein (EPICENTRE Technologies, Madison, Wis.), in 1× Transcription Buffer comprising 40 mM Tris HCl, pH 7.5, 10 mM NaCl, 6 mM $MgCl_2$, and 1 mM spermidine. The resulting mini-vRNAP transcription products were then analyzed by electrophoresis in a 1% agarose gel containing 0.22 M formaldehyde. Transcription products, including products having a length many-fold greater than the starting oligonucleotide, were observed on the gel using the transcription substrate having a sense P2 promoter sequence, indicating efficient rolling circle transcription. No transcription products were observed if the oligo did not contain a P2 promoter, if an anti-sense sequence to the P2 promoter was used instead of the sense P2 promoter, or if an unligated linear oligo with a sense P2 promoter was used.

Example 9

Use of Target-Dependent Transcription Using Bipartite Target Probes Comprising a P2 Promoter to Detect the Human β-Globin Gene Sequence in which a Single Nucleotide Mutation Results in Sickle Cell Anemia Bipartite target probes were designed to anneal to the gene encoding human hemoglobin β chain. The ligation junction of the adjacent probes when annealed to the denatured globin gene is the site of a single-base difference responsible for the sickle-cell phenotype (an A to T transversion leading to Gluà-Val change in the β-globin). The probe can be circularized by DNA ligase only when annealed to the wild-type globin allele, but not when the ligation junction is annealed to a target nucleotide comprising a single-base mismatch that results in the sickle-cell phenotype.

Oligonucleotide target probes were obtained from Integrated DNA Technologies, Coralville, Iowa and were 5' phosphorylated during synthesis. All human β-globin bipartite target probes consisted of two target-complementary arms in the 5' and 3' terminal regions connected by a spacer of a specific size that contained a P2 promoter sequence, as well as (optional) binding sites for amplification primers, restriction sites, signal sequences, etc. The 5' arm length was from 11 to 18 nucleotides and was designed to anneal immediately upstream of the single-base mismatch that results in the sickle-cell phenotype. The 3' arm was from 14 to 20 nucleotides long and was complementary to the region immediately downstream of this mutation. In most probes the 3'-terminal base was complementary to the nucleotide that differed in the wild type and mutant alleles of the β-globin gene. This was done to improve allele discrimination, since base mismatches at the 3' terminus are more inhibitory to ligation than those at 5' terminus (Luo et al., Nucleic Acids Res., 24:3071-3078, 1996). The length of the spacer region should allow circularization of the oligo while its 5' and 3' terminal arms are annealed to the target and cannot be shorter then 1.26-times the combined length of target-complementary arms.

The sequence of one of the human β-globin bipartite target probes is given below.

The target-complementary sequences are underlined. The P2 promoter hairpin sequence is in italics.

5'Phos-GTCCTCAGTCCCAAAAGAAGCGGAGCT-TCT(24)CCGTCTGAAGAGGA3' (SEC) ID NO:42)

67 bases, 25 are complementary to the target)

Bipartite target probes for detection of a beta-globin gene sequence were designed with a goal to be optimal for (i) target recognition specificity and thermostable ligase activity under hybridization and ligation reaction conditions and (ii) N4 mini-vRNAP-catalyzed rolling circle transcription. Thus, the probe was designed so that the P2 promoter hairpin was the only stable secondary structure at 37° C., and the target-complementary portions of the target probes were long enough to hybridize preferentially to the target sequence at a hybridization temperature that would still provide sufficient thermostable ligase activity. At the same time the overall length of the probe was kept to a minimum (under 100 nucleotides) to unsure efficient rolling circle (RC) transcription.

The β-globin bipartite target probes were incubated with subcloned plasmid DNA containing the wild-type β-globin gene sequence, digested with Apa LI restriction endonuclease. Target probes were annealed and ligated to the target sequence as follows: 2.5 micrograms of plasmid DNA comprising the target sequence were denatured and hybridized to 2 to 50 picomoles of each target probe in 20 mM Tris-HCl (pH 8.3 at 25° C.), 25 mM KCl, 10 mM MgCl2, 0.5 mM NAD, 0.01% Triton X-100 at 94° C. for 1.5 minutes in the total volume of 50 ul. Target probes annealed to the target sequence were ligated using 50 Units of Ampligase® Thermostable Ligase (EPICENTRE Technologies, Madison, Wis.) by thermocycling for 20 to 50 cycles of 94° C. for 30 seconds and 40° C. for 6 minutes. The unligated probe was then removed by digestion with 40 units of *E. coli* Exonuclease I (EPICENTRE) for 30 minutes at 37° C. Ligation reactions were ethanol-precipitated or used directly as substrates for the N4 mini-vRNAP transcription.

Transcription reactions were analyzed as follows: 10-25% of the ligation reaction was used as template in the transcription reaction. The 20 ul reactions contained 1 mM each NTP, 1 mM DTT, 5 uM EcoSSB Protein (EPICENTRE), 1 U/ul RNasin (Promega, Fitchburg, Wis.), and 8 pmol N4 mini-vRNAP (EPICENTRE) in 1× transcription buffer comprising 40 mM Tris HCl, pH 7.5, 10 mM NaCl, 6 mM MgCl2, and 1 mM spermidine. Reactions were incubated at 37° C. for 2 to 6 hours. The transcription reactions were treated with 2 Units DNAse I for 30 minutes at 37° C. Samples were heat denatured in formamide loading buffer with 0.1% SDS and were analyzed by denaturing 1% agarose gel electrophoresis in 1×TAE buffer.

Upon hybridization with the target sequence, a bipartite probe oligo circularizes and serves as efficient template for N4 mini-vRNAP-catalyzed rolling circle transcription, yielding high molecular weight RNA products. The unligated linear probe yields only a 11-18-nucleotide transcript (and no signal sequence would be obtained).

As expected, high molecular weight RNA transcription products were observed only in reactions in which the wild type β-globin target probes were incubated under hybridization and ligation conditions in the presence of the wild-type β-globin sequence. No high molecular weight transcription product was observed in the absence of the wild-type β-globin sequence, in the absence of ligase, or in the presence of only one target probe.

Various modifications and variations of the described method and system of the invention will be apparent to those skilled in the art without departing from the scope and spirit of the invention. It is understood, however, that examples and embodiments of the present invention set forth above are illustrative and not intended to confine the invention. The invention embraces all modified forms of the examples and embodiments as come within the scope of the following claims.

We claim:

1. A method of making RNA comprising:

(a) obtaining a N4 virion RNA polymerase consisting of a transcriptionally active mini-vRNAP, wherein said mini-vRNAP consists of a sequence at least 95% identical to SEQ ID NOS: 4, 6, or 8;

(b) obtaining a single-stranded DNA oligonucleotide wherein said single-stranded DNA oligonucleotide contains a N4 virion RNA polymerase promoter sequence;

(c) admixing said N4 virion RNA polymerase and said single-stranded DNA oligonucleotide; and (d) culturing said N4 virion RNA polymerase and said single-stranded DNA oligonucleotide under conditions effective to allow RNA synthesis.

* * * * *

SEQUENCE LISTING

```
<160> NUMBER OF SEQ ID NOS: 49

<210> SEQ ID NO 1
<211> LENGTH: 10506
<212> TYPE: DNA
<213> ORGANISM: Artificial Sequence
<220> FEATURE:
<223> OTHER INFORMATION: Synthetic
```

-continued

<400> SEQUENCE: 1

```
atgtcagtat ttgatagact ggctgggttc gcagacagcg taaccaatgc aaagcaagtt     60
gacgtctcta ctgcaaccgc ccagaagaaa gctgaacaag gtgtcactac tcctcttgtt    120
tctcctgatg ctgcttatca aatgcaagct gcccgtactg gtaatgttgg ggctaatgca    180
tttgaaccag ggacagtgca atcagatttc atgaatctga ccccaatgca aatcatgaat    240
aagtatgggg ttgagcaagg cttacaactt atcaatgctc gtgctgatgc agggaaccag    300
gtattcaatg attcagttac tacaagaact cctggggaag aactggggga tattgctact    360
ggtgttggcc ttggttttgt taataccctt gggggcattg gtgctcttgg ggcaggctta    420
ctcaacgatg atgcaggtgc tgttgttgct caacaattga gtaagtttaa tgatgctgtt    480
catgctaccc aaagccaggc attacaagat aaacgtaagc tctttgctgc tcgtaactta    540
atgaatgaag tagagagtga acgtcagtat caaacagata agaaagaagg cactaatgac    600
atagtagctt ccttatctaa atttggacgt gattttgtag gttcaattga gaatgctgct    660
caaactgact ctattatttc tgatgggtta gcagaagggg taggttctct attaggtgct    720
ggtcctgtat taaggggtgc atctttactg ggtaaagcag ttgttccagc aaatactctt    780
cgtagtgctg cattggctgg tgctattgat gcaggtactg gtactcagtc actggctcgt    840
attgcctcta ctgtaggtag agctgcaccg ggtatggttg gtgttggtgc aatggaagct    900
ggtggtgcat accaacaaac tgctgatgaa attatgaaga tgagtcttaa agacttagag    960
aagtctcctg tttatcagca acatattaaa gatggtatgt cccctgaaca ggctcgtcgt   1020
cagactgcat ctgaaactgg tcttactgct gctgctattc aattacctat tgctgctgca   1080
accggtcctc tggtatcccg ttttgagatg gctcctttcc gtgctggctc tttaggtgct   1140
gtaggtatga accttgcccg tgaaacagtg gaagaaggtg ttcagggtgc tacaggccaa   1200
ctggctcaga atattgcaca gcaacaaaac attgataaga accaagacct gcttaaaggt   1260
gtcggtacac aggctggttt aggtgctctt tatggctttg gttctgctgg tgttgtacag   1320
gctccggctg gtgctgctcg tttagcaggt gctgcaactg ctcctgtatt gcgtaccaca   1380
atggctggtg ttaaagctgc tggtagtgta gcaggtaagg ttgtttctcc tattaagaat   1440
actttagtag ctcgtggtga acgggttatg aagcagaatg aagaagcatc tcctgttgct   1500
gatgactatg ttgcacaggc agcacaagaa gctatggctc aagcaccaga agcagaagtt   1560
actattcgtg atgctgttga agcaactgat gctactccag aacagaaagt tgcagcacac   1620
cagtatgttt ctgacttaat gaatgctact cgttttaatc ctgaaaatta tcaggaagca   1680
ccagagcata ttcgtaatgc tgtagctggt tctactgacc aagtacaggt tattcagaag   1740
ttagcagact tagttaacac attagatgaa tctaatcctc aagcactgat ggaagctgca   1800
tcttatatgt atgatgctgt ttcagagttt gagcagttca ttaaccgtga ccctgctgca   1860
ctggatagca ttcctaaaga ttctccggct attgagttac tcaaccgtta tacgaatctg   1920
acagctaata ttcagaacac accaaaagta attggtgcac tgaatgttat taatcgaatg   1980
attaatgaat ctgctcagaa tggttctttg aatgtgactg aagaatccag tccacaggaa   2040
atgcagaacg tagcattagc tgctgaagta gcccctgaaa agctcaatcc agagtctgta   2100
aatgttgttc ttaaacatgc tgctgatggt cgtattaaac tgaataatcg ccagattgct   2160
gccctccaga atgctgctgc aatcctgaag ggggcacggg aatatgatgc agaagctgcc   2220
cgtcttggat tacgtcctca agacattgtg agtaaacaga ttaaaacgga tgagagcaga   2280
actcaggaag gacaatactc tgcgttgcaa catgcgaata ggattcggtc tgcgtataac   2340
```

-continued

```
tctggtaatt tcgagttggc ctccgcttac ctgaacgact ttatgcagtt cgcccagcac   2400
atgcagaata aggttggagc gttgaatgag catcttgtta cggggaatgc ggataagaat   2460
aagtctgtcc actaccaagc tcttactgct gacagagaat gggttcgtag ccgtaccgga   2520
ttgggggtca atccctatga cactaagtcg gttaaatttg cccagcaagt tgctcttgaa   2580
gcgaaaacgg tagcggatat tgctaatgcc ctcgcttcgg cttacccgga actgaaggtc   2640
agtcatataa aagttactcc attggattca cgtcttaacg ctcctgctgc tgaggtggtc   2700
aaggcattcc gtcaaggcaa tcgagacgtt gcttcttctc aaccgaaagc tgactccgtg   2760
aatcaggtta aagaaactcc tgttacaaaa caggaaccag ttacatctac tgtacagact   2820
aagactcctg ttagtgaatc tgttaaaaca gaacctacta ctaaagagtc tagcccacag   2880
gctataaaag aacctgtgaa ccagtctgaa aaacaggatg ttaaccttac taatgaggac   2940
aacatcaagc aacctactga atctgttaaa gaaactgaaa cttctacaaa agaaagtaca   3000
gttacagaag aattaaaaga aggtattgat gctgtttacc cttcattggt aggtactgct   3060
gattctaaag cagagggtat taagaactat ttcaaattgt cctttacctt accagaagaa   3120
cagaaatccc gtactgttgg ttcagaagca cctctaaaag atgtagccca agctctgtct   3180
tctcgtgctc gttatgaact ctttactgag aaagaaactg ctaaccctgc ttttaatggg   3240
gaagttatta agcgatacaa agaactcatg gaacatgggg aaggtattgc tgatattctt   3300
cgctcccgtc tggctaagtt ccttaacact aaggatgttg gtaaacgttt tgctcaaggt   3360
acagaagcca accgttgggt aggtggtaag ttacttaaca ttgttgagca ggatggggat   3420
acctttaagt acaacgaaca attgctacag actgctgtat tagcaggtct tcaatggaga   3480
cttactgcta ccagcaatac tgctatcaaa gatgcaaaag atgttgctgc tattactggt   3540
attgaccaag ctctgctgcc agaaggttta gtagagcaat ttgatactgg tatgacactc   3600
actgaagcag ttagttccct ggctcagaaa attgagtctt actggggatt atctcgtaat   3660
ccaaatgctc cattgggcta taccaaaggc atccctacag caatggctgc tgaaattctg   3720
gctgcatttg tagagtctac tgatgttgta gagaacatcg tggatatgtc agaaattgac   3780
ccagataaca agaagactat tggtctgtac accattactg aactggattc cttcgaccca   3840
attaatagct tccctactgc tattgaagaa gctgttttag tgaatcctac agagaagatg   3900
ttctttggtg atgacattcc tcctgtagct aatactcagc ttcgtaaccc tgctgttcgt   3960
aatactccag aacagaaggc tgcattgaaa gcagagcagg ctacagagtt ctatgtacac   4020
accccaatgg ttcaattcta tgagacgtta ggtaaagacc gtattctcga actgatgggt   4080
gctggtactc tgaataaaga gttacttaat gataaccatg ctaaatctct ggaaggtaag   4140
aaccgttcag tagaggactc ttacaaccaa ctgttctccg tcattgagca ggtaagagca   4200
cagagcgaag acatctctac tgtacctatt cactatgcat acaatatgac ccgtgttggt   4260
cgtatgcaga tgttaggtaa atacaatcct caatcagcca aactggttcg tgaggccatc   4320
ttacctacta aagctacttt ggatttatcg aaccagaaca atgaagactt ctctgcattc   4380
cagttaggtc tggctcaggc attggacatt aaagtccata ctatgactcg tgaggttatg   4440
tctgacgagt tgactaaatt actggaaggt aatctgaaac cagccattga tatgatggtt   4500
gagtttaata ccactggttc cttaccagaa aacgcagttg atgttctgaa tacagcatta   4560
ggagatagga agtcattcgt agcattgatg gctcttatgg agtattcccg ttacttagta   4620
gcagaggata aatctgcatt tgtaactcca ctgtatgtag aagcagatgg tgttactaat   4680
```

-continued

```
ggtccaatca atgccatgat gctaatgaca ggcggtctgt ttactcctga ctggattcgt   4740
aatattgcca aagggggctt gttcattggt tctccaaata agaccatgaa tgagcatcgc   4800
tctactgctg acaataatga tttatatcaa gcatccacta atgctttgat ggaatcgttg   4860
ggtaagttac gtagtaacta tgcctctaat atgcctattc agtctcagat agacagtctt   4920
ctttctctga tggatttgtt tttaccggat attaatcttg gtgagaatgg tgctttagaa   4980
cttaaacgtg gtattgctaa gaacccactg actattacca tctatggttc tggtgctcgt   5040
ggtattgcag gtaagctggt tagttctgtt actgatgcca tctatgagcg tatgtctgat   5100
gtactgaaag ctcgtgctaa agacccaaat atctctgctg ctatggcaat gtttggtaag   5160
caagctgctt cagaagcaca tgctgaagaa cttcttgccc gtttcctgaa agatatggaa   5220
acactgactt ctactgttcc tgttaaacgt aaaggtgtac tggaactaca atccacaggt   5280
acaggagcca aaggaaaaat caatcctaag acctatacca ttaagggcga gcaactgaag   5340
gcacttcagg aaaatatgct gcacttcttt gtagaaccac tacgtaatgg tattactcag   5400
actgtaggtg aaagtctggt gtactctact gaacaattac agaaagctac tcagattcaa   5460
tctgtagtgc tggaagatat gttcaaacag cgagtacaag agaagctggc agagaaggct   5520
aaagacccaa catggaagaa aggtgatttc cttactcaga aagaactgaa tgatattcag   5580
gcttctctga ataacttagc ccctatgatt gagactggtt ctcagacttt ctacattgct   5640
ggttcagaaa atgcagaagt agcaaatcag gtattagcta ctaaccttga tgaccgtatg   5700
cgtgtaccaa tgagtatcta tgctccagca caggccggtg tagcaggtat tccatttatg   5760
actattggta ctggtgatgg catgatgatg caaactcttt ccactatgaa aggtgcacca   5820
aagaataccc tcaaaatctt tgatggtatg aacattggtt tgaatgacat cactgatgcc   5880
agtcgtaaag ctaatgaagc tgtttacact tcttggcagg gtaaccctat taagaatgtt   5940
tatgaatcat atgctaagtt catgaagaat gtagatttca gcaagctgtc ccctgaagca   6000
ttggaagcaa ttggtaaatc tgctctggaa tatgaccaac gtgagaatgc tactgtagat   6060
gatattgcta acgctgcatc tctgattgaa cgtaacttac gtaatattgc actgggtgta   6120
gatattcgtc ataaggtgct ggataaggta aatctgtcca ttgaccagat ggctgctgta   6180
ggtgctcctt atcagaacaa cggtaagatt gacctcagca atatgacccc tgaacaacag   6240
gctgatgaac tgaataaact tttccgtgaa gagttagaag cccgtaaaca aaaagtcgct   6300
aaggctaggg ctgaagtcaa agaagaaact gtttctgaaa aagaaccagt gaatccagac   6360
tttggtatgg taggccgtga gcataaggca tctggtgttc gtatcctgtc tgctactgct   6420
attcgtaatc tggctaagat tagtaatctg ccatctactc aggcagctac tcttgcggag   6480
attcagaaat cactggcagc taaagactat aagattatct acggtacacc tactcaggtt   6540
gcagagtatg ctcgtcagaa gaatgttact gaattgactt ctcaggaaat ggaagaagct   6600
caggcaggta atatttatgg ctggactaac ttcgatgata agaccattta tctggttagc   6660
ccatctatgg aaaccctcat tcatgaactg gttcatgcct ctaccttcga ggaagtttat   6720
tccttctatc agggtaatga agtaagccct acttctaagc aggctattga gaaccttgaa   6780
ggtctgatgg aacagttccg ttctctggat atttccaaag attctccaga aatgagagaa   6840
gcatatgctg atgctattgc aactatcgaa ggtcatttga gtaatggatt tgttgaccca   6900
gctatctcta aagctgctgc tcttaatgag tttatggctt gggggttagc taaccgtgct   6960
cttgctgcta aacagaagag aacatcttca ctggttcaaa tggtgaaaga tgtttatcag   7020
gctattaaga aattgatttg ggacgtaaa caagctcctg cattgggaga agatatgttc   7080
```

-continued

```
tccaatctgc tgtttaactc tgcaattctg atgcgtagcc aacctacaac tcaggcagta   7140
gctaaagatg gcacactgtt ccatagcaaa gcatatggta ataatgaacg tctgtctcag   7200
ttgaaccaga ctttcgataa actggtaact gattaccttc gtactgaccc agttacagaa   7260
gtagaacgtc gtggcaatgt ggctaatgca ttaatgagtg ctactcgact ggttcgtgat   7320
gttcagtctc atggcttcaa tatgactgct caggaacagt ctgtattcca gatggttact   7380
gctgcattag caactgaagc tgcgattgac ccacatgcta tggctcgtgc tcaggaactt   7440
tatacccatg taatgaaaca ccttacggta gagcatttca tggctgaccc tgatagtact   7500
aaccctgctg accgttacta tgctcaacag aaatatgaca ccatctctgg tgctaatctg   7560
gttgaagtag atgccaaagg tagaaccagt ctgttaccta cattcctggg tctggctatg   7620
gttaatgaag aactacgttc aatcattaaa gaaatgcctg tacctaaagc agataagaaa   7680
ttagggaatg atatagatac tctgcttacc aatgcaggta ctcaggtaat ggaatctctg   7740
aaccgtcgta tggctggtga ccagaaagct actaatgttc aggacagtat tgatgctttg   7800
tcagaaacaa tcatggctgc tgctttgaaa cgagagtcct tctatgatgc tgtagcaacc   7860
cctaccggta acttcattga ccgtgctaat cagtacgtaa cggatagcat tgaacggtta   7920
tctgaaactg ttattgagaa ggcagataag gtaattgcta acccttctaa tatagctgct   7980
aaaggtgttg ctcatctggc taaactgact gctgctattg catctgaaaa acagggtgaa   8040
atagtggctc agggtgttat gactgctatg aaccagggta aagtatggca acctttccat   8100
gacttagtta atgacattgt tggccgtact aagactaatg ccaatgtcta tgacttaatc   8160
aaattggtta agagccagat ttctcaagac cgtcagcaat tccgtgagca tttacctaca   8220
gtcattgctg gtaagttctc tcgtaaattg actgataccg aatggtctgc aatgcatact   8280
ggtttaggta aaacagattt agctgttcta cgtgaaacta tgagcatggc tgaaattaga   8340
gatttactct cttcatccaa gaaagtgaaa gatgaaatct ctactctgga aaaagagatt   8400
cagaaccaag caggtagaaa ctggaatctg gttcagaaga aatctaagca actggctcaa   8460
tacatgatta tgggggaagt aggtaataac ctccttcgta atgcccatgc tattagtcgt   8520
ttgttaggtg aacgtattac taatggtcct gtggcagatg tagctgctat tgataagctc   8580
attactttgt actctctgga attgatgaat aagtctgacc gtgacctttt gtcagaattg   8640
gctcaatcag aagtggaagg tatggagttc tccattgctt atatggttgg tcaacgtact   8700
gaagagatgc gtaaagctaa aggtgataac cgtactctgc tgaatcactt taaaggctat   8760
atccctgtag agaaccagca aggtgtgaat ttgattattg ctgacgataa agagtttgct   8820
aagttaaata gccaatcctt tactcgtatt ggtacttatc aggggagcac tggtttccgt   8880
actggttcta aaggttatta cttcagccca gtagctgccc gtgcccctta ctctcagggt   8940
attcttcaga acgttcgtaa tactgctggt ggtgtggata ttggtactgg ctttacgtta   9000
ggcactatgg ttgctgggcg tattactgac aaaccaaccg tagagcgtat taccaaagct   9060
ctggctaaag gtgagcgtgg gcgtgaacca ctgatgccaa tttataacag caaaggtcag   9120
gtagttgctt atgaacaatc cgttgaccct aatatgttga agcacctaaa ccaagacaat   9180
cactttgcta agatggttgg tgtatggcgt ggtcgtcagg tggaagaggc taaagcacaa   9240
cgttttaatg acattctcat tgagcaatta catgctatgt atgagaaaga cattaaagac   9300
tccagtgcta ataaatctca atatgtaaac ctgttaggta aaattgatga cccagtactg   9360
gctgatgcga ttaacctgat gaacattgag actcgtcata aggccgaaga actcttcggt   9420
```

-continued aaagatgagt tatgggttcg tagggatatg ctgaatgatg cacttggcta tcgtgctgca 9480
tctattggtg atgtgtggac cggtaactct cgttggtcac ctagcaccct tgatactgtt 9540
aagaagatgt tcctcggtgc attcggtaat aaggcatatc atgtagtaat gaatgctgaa 9600
aataccattc agaacttagt gaaggacgct aagacagtaa ttgttgttaa atctgttgta 9660
gtaccggcag ttaacttcct tgctaacatc taccagatga ttggacgtgg tgttcctgtt 9720
aaagatattg ctgtgaacat tcctcgtaag acgtcagaga ttaatcagta tattaaatct 9780
cgtttacgtc agattgatgc ggaagcagag ctacgtgctg ctgaaggtaa ccctaatctg 9840
gttcgtaaac ttaaaactga gattcaatct attactgata gtcatcgtcg tatgagtatc 9900
tggcctttga ttgaagcagg tgagttctct tctattgctg atgctggtat tagtcgtgat 9960
gacctgttag tagctgaagg taagattcat gagtacatgg aaaaacttgc taataaactt 10020
ccagaaaaag tacgtaatgc tggccgttac gctcttattg ctaaggacac tgctctgttc 10080
cagggtatcc agaaaacagt agagtattca gactttattg ctaaagccat catctatgat 10140
gatttagtga aacgtaagaa aaaatcttct tctgaagcat taggtcaggt aactgaagag 10200
tttattaact atgacagatt gcctggtcgt ttccgtggct atatggaaag tatgggtctg 10260
atgtggttct acaactttaa aattcgttcc attaaagttg ctatgagcat gattagaaac 10320
aacccagtac attctctgat tgctacagta gtacctgctc ctaccatgtt tggtaacgta 10380
ggtctaccaa ttcaggacaa catgctaacc atgctggctg aaggaagact ggattactca 10440
ttaggcttcg gacaaggatt aagagcacct accctcaatc cttggttcaa ccttactcac 10500
taataa 10506

<210> SEQ ID NO 2
<211> LENGTH: 3500
<212> TYPE: PRT
<213> ORGANISM: Artificial Sequence
<220> FEATURE:
<223> OTHER INFORMATION: Synthetic

<400> SEQUENCE: 2

Met Ser Val Phe Asp Arg Leu Ala Gly Phe Ala Asp Ser Val Thr Asn
1 5 10 15

Ala Lys Gln Val Asp Val Ser Thr Ala Thr Ala Gln Lys Lys Ala Glu
20 25 30

Gln Gly Val Thr Thr Pro Leu Val Ser Pro Asp Ala Ala Tyr Gln Met
35 40 45

Gln Ala Ala Arg Thr Gly Asn Val Gly Ala Asn Ala Phe Glu Pro Gly
50 55 60

Thr Val Gln Ser Asp Phe Met Asn Leu Thr Pro Met Gln Ile Met Asn
65 70 75 80

Lys Tyr Gly Val Glu Gln Gly Leu Gln Leu Ile Asn Ala Arg Ala Asp
85 90 95

Ala Gly Asn Gln Val Phe Asn Asp Ser Val Thr Thr Arg Thr Pro Gly
100 105 110

Glu Glu Leu Gly Asp Ile Ala Thr Gly Val Gly Leu Gly Phe Val Asn
115 120 125

Thr Leu Gly Gly Ile Gly Ala Leu Gly Ala Gly Leu Leu Asn Asp Asp
130 135 140

Ala Gly Ala Val Val Ala Gln Gln Leu Ser Lys Phe Asn Asp Ala Val
145 150 155 160

His Ala Thr Gln Ser Gln Ala Leu Gln Asp Lys Arg Lys Leu Phe Ala

-continued

```
                165                 170                 175

Ala Arg Asn Leu Met Asn Glu Val Glu Ser Glu Arg Gln Tyr Gln Thr
            180                 185                 190

Asp Lys Lys Glu Gly Thr Asn Asp Ile Val Ala Ser Leu Ser Lys Phe
        195                 200                 205

Gly Arg Asp Phe Val Gly Ser Ile Glu Asn Ala Ala Gln Thr Asp Ser
    210                 215                 220

Ile Ile Ser Asp Gly Leu Ala Glu Gly Val Gly Ser Leu Leu Gly Ala
225                 230                 235                 240

Gly Pro Val Leu Arg Gly Ala Ser Leu Leu Gly Lys Ala Val Val Pro
                245                 250                 255

Ala Asn Thr Leu Arg Ser Ala Ala Leu Ala Gly Ala Ile Asp Ala Gly
            260                 265                 270

Thr Gly Thr Gln Ser Leu Ala Arg Ile Ala Ser Thr Val Gly Arg Ala
        275                 280                 285

Ala Pro Gly Met Val Gly Val Gly Ala Met Glu Ala Gly Gly Ala Tyr
    290                 295                 300

Gln Gln Thr Ala Asp Glu Ile Met Lys Met Ser Leu Lys Asp Leu Glu
305                 310                 315                 320

Lys Ser Pro Val Tyr Gln Gln His Ile Lys Asp Gly Met Ser Pro Glu
                325                 330                 335

Gln Ala Arg Arg Gln Thr Ala Ser Glu Thr Gly Leu Thr Ala Ala Ala
            340                 345                 350

Ile Gln Leu Pro Ile Ala Ala Ala Thr Gly Pro Leu Val Ser Arg Phe
        355                 360                 365

Glu Met Ala Pro Phe Arg Ala Gly Ser Leu Gly Ala Val Gly Met Asn
    370                 375                 380

Leu Ala Arg Glu Thr Val Glu Glu Gly Val Gln Gly Ala Thr Gly Gln
385                 390                 395                 400

Leu Ala Gln Asn Ile Ala Gln Gln Gln Asn Ile Asp Lys Asn Gln Asp
                405                 410                 415

Leu Leu Lys Gly Val Gly Thr Gln Ala Gly Leu Gly Ala Leu Tyr Gly
            420                 425                 430

Phe Gly Ser Ala Gly Val Val Gln Ala Pro Ala Gly Ala Ala Arg Leu
        435                 440                 445

Ala Gly Ala Ala Thr Ala Pro Val Leu Arg Thr Thr Met Ala Gly Val
    450                 455                 460

Lys Ala Ala Gly Ser Val Ala Gly Lys Val Val Ser Pro Ile Lys Asn
465                 470                 475                 480

Thr Leu Val Ala Arg Gly Glu Arg Val Met Lys Gln Asn Glu Glu Ala
                485                 490                 495

Ser Pro Val Ala Asp Asp Tyr Val Ala Gln Ala Ala Gln Glu Ala Met
            500                 505                 510

Ala Gln Ala Pro Glu Ala Glu Val Thr Ile Arg Asp Ala Val Glu Ala
        515                 520                 525

Thr Asp Ala Thr Pro Glu Gln Lys Val Ala Ala His Gln Tyr Val Ser
    530                 535                 540

Asp Leu Met Asn Ala Thr Arg Phe Asn Pro Glu Asn Tyr Gln Glu Ala
545                 550                 555                 560

Pro Glu His Ile Arg Asn Ala Val Ala Gly Ser Thr Asp Gln Val Gln
                565                 570                 575

Val Ile Gln Lys Leu Ala Asp Leu Val Asn Thr Leu Asp Glu Ser Asn
            580                 585                 590
```

-continued

```
Pro Gln Ala Leu Met Glu Ala Ala Ser Tyr Met Tyr Asp Ala Val Ser
        595                 600                 605

Glu Phe Glu Gln Phe Ile Asn Arg Asp Pro Ala Ala Leu Asp Ser Ile
    610                 615                 620

Pro Lys Asp Ser Pro Ala Ile Glu Leu Leu Asn Arg Tyr Thr Asn Leu
625                 630                 635                 640

Thr Ala Asn Ile Gln Asn Thr Pro Lys Val Ile Gly Ala Leu Asn Val
                645                 650                 655

Ile Asn Arg Met Ile Asn Glu Ser Ala Gln Asn Gly Ser Leu Asn Val
            660                 665                 670

Thr Glu Glu Ser Ser Pro Gln Glu Met Gln Asn Val Ala Leu Ala Ala
        675                 680                 685

Glu Val Ala Pro Glu Lys Leu Asn Pro Glu Ser Val Asn Val Val Leu
    690                 695                 700

Lys His Ala Ala Asp Gly Arg Ile Lys Leu Asn Asn Arg Gln Ile Ala
705                 710                 715                 720

Ala Leu Gln Asn Ala Ala Ala Ile Leu Lys Gly Ala Arg Glu Tyr Asp
                725                 730                 735

Ala Glu Ala Ala Arg Leu Gly Leu Arg Pro Gln Asp Ile Val Ser Lys
            740                 745                 750

Gln Ile Lys Thr Asp Glu Ser Arg Thr Gln Glu Gly Gln Tyr Ser Ala
        755                 760                 765

Leu Gln His Ala Asn Arg Ile Arg Ser Ala Tyr Asn Ser Gly Asn Phe
    770                 775                 780

Glu Leu Ala Ser Ala Tyr Leu Asn Asp Phe Met Gln Phe Ala Gln His
785                 790                 795                 800

Met Gln Asn Lys Val Gly Ala Leu Asn Glu His Leu Val Thr Gly Asn
                805                 810                 815

Ala Asp Lys Asn Lys Ser Val His Tyr Gln Ala Leu Thr Ala Asp Arg
            820                 825                 830

Glu Trp Val Arg Ser Arg Thr Gly Leu Gly Val Asn Pro Tyr Asp Thr
        835                 840                 845

Lys Ser Val Lys Phe Ala Gln Gln Val Ala Leu Glu Ala Lys Thr Val
    850                 855                 860

Ala Asp Ile Ala Asn Ala Leu Ala Ser Ala Tyr Pro Glu Leu Lys Val
865                 870                 875                 880

Ser His Ile Lys Val Thr Pro Leu Asp Ser Arg Leu Asn Ala Pro Ala
                885                 890                 895

Ala Glu Val Val Lys Ala Phe Arg Gln Gly Asn Arg Asp Val Ala Ser
            900                 905                 910

Ser Gln Pro Lys Ala Asp Ser Val Asn Gln Val Lys Glu Thr Pro Val
        915                 920                 925

Thr Lys Gln Glu Pro Val Thr Ser Thr Val Gln Thr Lys Thr Pro Val
    930                 935                 940

Ser Glu Ser Val Lys Thr Glu Pro Thr Thr Lys Glu Ser Ser Pro Gln
945                 950                 955                 960

Ala Ile Lys Glu Pro Val Asn Gln Ser Glu Lys Gln Asp Val Asn Leu
                965                 970                 975

Thr Asn Glu Asp Asn Ile Lys Gln Pro Thr Glu Ser Val Lys Glu Thr
            980                 985                 990

Glu Thr Ser Thr Lys Glu Ser Thr  Val Thr Glu Glu Leu  Lys Glu Gly
        995                 1000                1005
```

-continued

```
Ile Asp  Ala Val Tyr Pro Ser  Leu Val Gly Thr Ala  Asp Ser Lys
    1010                 1015                 1020

Ala Glu  Gly Ile Lys Asn Tyr  Phe Lys Leu Ser Phe  Thr Leu Pro
    1025                 1030                 1035

Glu Glu  Gln Lys Ser Arg Thr  Val Gly Ser Glu Ala  Pro Leu Lys
    1040                 1045                 1050

Asp Val  Ala Gln Ala Leu Ser  Ser Arg Ala Arg Tyr  Glu Leu Phe
    1055                 1060                 1065

Thr Glu  Lys Glu Thr Ala Asn  Pro Ala Phe Asn Gly  Glu Val Ile
    1070                 1075                 1080

Lys Arg  Tyr Lys Glu Leu Met  Glu His Gly Glu Gly  Ile Ala Asp
    1085                 1090                 1095

Ile Leu  Arg Ser Arg Leu Ala  Lys Phe Leu Asn Thr  Lys Asp Val
    1100                 1105                 1110

Gly Lys  Arg Phe Ala Gln Gly  Thr Glu Ala Asn Arg  Trp Val Gly
    1115                 1120                 1125

Gly Lys  Leu Leu Asn Ile Val  Glu Gln Asp Gly Asp  Thr Phe Lys
    1130                 1135                 1140

Tyr Asn  Glu Gln Leu Leu Gln  Thr Ala Val Leu Ala  Gly Leu Gln
    1145                 1150                 1155

Trp Arg  Leu Thr Ala Thr Ser  Asn Thr Ala Ile Lys  Asp Ala Lys
    1160                 1165                 1170

Asp Val  Ala Ala Ile Thr Gly  Ile Asp Gln Ala Leu  Leu Pro Glu
    1175                 1180                 1185

Gly Leu  Val Glu Gln Phe Asp  Thr Gly Met Thr Leu  Thr Glu Ala
    1190                 1195                 1200

Val Ser  Ser Leu Ala Gln Lys  Ile Glu Ser Tyr Trp  Gly Leu Ser
    1205                 1210                 1215

Arg Asn  Pro Asn Ala Pro Leu  Gly Tyr Thr Lys Gly  Ile Pro Thr
    1220                 1225                 1230

Ala Met  Ala Ala Glu Ile Leu  Ala Ala Phe Val Glu  Ser Thr Asp
    1235                 1240                 1245

Val Val  Glu Asn Ile Val Asp  Met Ser Glu Ile Asp  Pro Asp Asn
    1250                 1255                 1260

Lys Lys  Thr Ile Gly Leu Tyr  Thr Ile Thr Glu Leu  Asp Ser Phe
    1265                 1270                 1275

Asp Pro  Ile Asn Ser Phe Pro  Thr Ala Ile Glu Glu  Ala Val Leu
    1280                 1285                 1290

Val Asn  Pro Thr Glu Lys Met  Phe Phe Gly Asp Asp  Ile Pro Pro
    1295                 1300                 1305

Val Ala  Asn Thr Gln Leu Arg  Asn Pro Ala Val Arg  Asn Thr Pro
    1310                 1315                 1320

Glu Gln  Lys Ala Ala Leu Lys  Ala Glu Gln Ala Thr  Glu Phe Tyr
    1325                 1330                 1335

Val His  Thr Pro Met Val Gln  Phe Tyr Glu Thr Leu  Gly Lys Asp
    1340                 1345                 1350

Arg Ile  Leu Glu Leu Met Gly  Ala Gly Thr Leu Asn  Lys Glu Leu
    1355                 1360                 1365

Leu Asn  Asp Asn His Ala Lys  Ser Leu Glu Gly Lys  Asn Arg Ser
    1370                 1375                 1380

Val Glu  Asp Ser Tyr Asn Gln  Leu Phe Ser Val Ile  Glu Gln Val
    1385                 1390                 1395

Arg Ala  Gln Ser Glu Asp Ile  Ser Thr Val Pro Ile  His Tyr Ala
```

-continued

```
    1400                1405                1410

Tyr Asn  Met Thr Arg Val Gly  Arg Met Gln Met Leu  Gly Lys Tyr
    1415                1420                1425

Asn Pro  Gln Ser Ala Lys Leu  Val Arg Glu Ala Ile  Leu Pro Thr
    1430                1435                1440

Lys Ala  Thr Leu Asp Leu Ser  Asn Gln Asn Asn Glu  Asp Phe Ser
    1445                1450                1455

Ala Phe  Gln Leu Gly Leu Ala  Gln Ala Leu Asp Ile  Lys Val His
    1460                1465                1470

Thr Met  Thr Arg Glu Val Met  Ser Asp Glu Leu Thr  Lys Leu Leu
    1475                1480                1485

Glu Gly  Asn Leu Lys Pro Ala  Ile Asp Met Met Val  Glu Phe Asn
    1490                1495                1500

Thr Thr  Gly Ser Leu Pro Glu  Asn Ala Val Asp Val  Leu Asn Thr
    1505                1510                1515

Ala Leu  Gly Asp Arg Lys Ser  Phe Val Ala Leu Met  Ala Leu Met
    1520                1525                1530

Glu Tyr  Ser Arg Tyr Leu Val  Ala Glu Asp Lys Ser  Ala Phe Val
    1535                1540                1545

Thr Pro  Leu Tyr Val Glu Ala  Asp Gly Val Thr Asn  Gly Pro Ile
    1550                1555                1560

Asn Ala  Met Met Leu Met Thr  Gly Gly Leu Phe Thr  Pro Asp Trp
    1565                1570                1575

Ile Arg  Asn Ile Ala Lys Gly  Gly Leu Phe Ile Gly  Ser Pro Asn
    1580                1585                1590

Lys Thr  Met Asn Glu His Arg  Ser Thr Ala Asp Asn  Asn Asp Leu
    1595                1600                1605

Tyr Gln  Ala Ser Thr Asn Ala  Leu Met Glu Ser Leu  Gly Lys Leu
    1610                1615                1620

Arg Ser  Asn Tyr Ala Ser Asn  Met Pro Ile Gln Ser  Gln Ile Asp
    1625                1630                1635

Ser Leu  Leu Ser Leu Met Asp  Leu Phe Leu Pro Asp  Ile Asn Leu
    1640                1645                1650

Gly Glu  Asn Gly Ala Leu Glu  Leu Lys Arg Gly Ile  Ala Lys Asn
    1655                1660                1665

Pro Leu  Thr Ile Thr Ile Tyr  Gly Ser Gly Ala Arg  Gly Ile Ala
    1670                1675                1680

Gly Lys  Leu Val Ser Ser Val  Thr Asp Ala Ile Tyr  Glu Arg Met
    1685                1690                1695

Ser Asp  Val Leu Lys Ala Arg  Ala Lys Asp Pro Asn  Ile Ser Ala
    1700                1705                1710

Ala Met  Ala Met Phe Gly Lys  Gln Ala Ala Ser Glu  Ala His Ala
    1715                1720                1725

Glu Glu  Leu Leu Ala Arg Phe  Leu Lys Asp Met Glu  Thr Leu Thr
    1730                1735                1740

Ser Thr  Val Pro Val Lys Arg  Lys Gly Val Leu Glu  Leu Gln Ser
    1745                1750                1755

Thr Gly  Thr Gly Ala Lys Gly  Lys Ile Asn Pro Lys  Thr Tyr Thr
    1760                1765                1770

Ile Lys  Gly Glu Gln Leu Lys  Ala Leu Gln Glu Asn  Met Leu His
    1775                1780                1785

Phe Phe  Val Glu Pro Leu Arg  Asn Gly Ile Thr Gln  Thr Val Gly
    1790                1795                1800
```

```
Glu Ser  Leu Val Tyr Ser Thr  Glu Gln Leu Gln Lys  Ala Thr Gln
    1805                 1810                 1815

Ile Gln  Ser Val Val Leu Glu  Asp Met Phe Lys Gln  Arg Val Gln
    1820                 1825                 1830

Glu Lys  Leu Ala Glu Lys Ala  Lys Asp Pro Thr Trp  Lys Lys Gly
    1835                 1840                 1845

Asp Phe  Leu Thr Gln Lys Glu  Leu Asn Asp Ile Gln  Ala Ser Leu
    1850                 1855                 1860

Asn Asn  Leu Ala Pro Met Ile  Glu Thr Gly Ser Gln  Thr Phe Tyr
    1865                 1870                 1875

Ile Ala  Gly Ser Glu Asn Ala  Glu Val Ala Asn Gln  Val Leu Ala
    1880                 1885                 1890

Thr Asn  Leu Asp Asp Arg Met  Arg Val Pro Met Ser  Ile Tyr Ala
    1895                 1900                 1905

Pro Ala  Gln Ala Gly Val Ala  Gly Ile Pro Phe Met  Thr Ile Gly
    1910                 1915                 1920

Thr Gly  Asp Gly Met Met Met  Gln Thr Leu Ser Thr  Met Lys Gly
    1925                 1930                 1935

Ala Pro  Lys Asn Thr Leu Lys  Ile Phe Asp Gly Met  Asn Ile Gly
    1940                 1945                 1950

Leu Asn  Asp Ile Thr Asp Ala  Ser Arg Lys Ala Asn  Glu Ala Val
    1955                 1960                 1965

Tyr Thr  Ser Trp Gln Gly Asn  Pro Ile Lys Asn Val  Tyr Glu Ser
    1970                 1975                 1980

Tyr Ala  Lys Phe Met Lys Asn  Val Asp Phe Ser Lys  Leu Ser Pro
    1985                 1990                 1995

Glu Ala  Leu Glu Ala Ile Gly  Lys Ser Ala Leu Glu  Tyr Asp Gln
    2000                 2005                 2010

Arg Glu  Asn Ala Thr Val Asp  Asp Ile Ala Asn Ala  Ala Ser Leu
    2015                 2020                 2025

Ile Glu  Arg Asn Leu Arg Asn  Ile Ala Leu Gly Val  Asp Ile Arg
    2030                 2035                 2040

His Lys  Val Leu Asp Lys Val  Asn Leu Ser Ile Asp  Gln Met Ala
    2045                 2050                 2055

Ala Val  Gly Ala Pro Tyr Gln  Asn Asn Gly Lys Ile  Asp Leu Ser
    2060                 2065                 2070

Asn Met  Thr Pro Glu Gln Gln  Ala Asp Glu Leu Asn  Lys Leu Phe
    2075                 2080                 2085

Arg Glu  Glu Leu Glu Ala Arg  Lys Gln Lys Val Ala  Lys Ala Arg
    2090                 2095                 2100

Ala Glu  Val Lys Glu Glu Thr  Val Ser Glu Lys Glu  Pro Val Asn
    2105                 2110                 2115

Pro Asp  Phe Gly Met Val Gly  Arg Glu His Lys Ala  Ser Gly Val
    2120                 2125                 2130

Arg Ile  Leu Ser Ala Thr Ala  Ile Arg Asn Leu Ala  Lys Ile Ser
    2135                 2140                 2145

Asn Leu  Pro Ser Thr Gln Ala  Ala Thr Leu Ala Glu  Ile Gln Lys
    2150                 2155                 2160

Ser Leu  Ala Ala Lys Asp Tyr  Lys Ile Ile Tyr Gly  Thr Pro Thr
    2165                 2170                 2175

Gln Val  Ala Glu Tyr Ala Arg  Gln Lys Asn Val Thr  Glu Leu Thr
    2180                 2185                 2190
```

-continued

```
Ser Gln  Glu Met Glu Glu Ala  Gln Ala Gly Asn Ile  Tyr Gly Trp
    2195                 2200                 2205

Thr Asn  Phe Asp Asp Lys Thr  Ile Tyr Leu Val Ser  Pro Ser Met
    2210                 2215                 2220

Glu Thr  Leu Ile His Glu Leu  Val His Ala Ser Thr  Phe Glu Glu
    2225                 2230                 2235

Val Tyr  Ser Phe Tyr Gln Gly  Asn Glu Val Ser Pro  Thr Ser Lys
    2240                 2245                 2250

Gln Ala  Ile Glu Asn Leu Glu  Gly Leu Met Glu Gln  Phe Arg Ser
    2255                 2260                 2265

Leu Asp  Ile Ser Lys Asp Ser  Pro Glu Met Arg Glu  Ala Tyr Ala
    2270                 2275                 2280

Asp Ala  Ile Ala Thr Ile Glu  Gly His Leu Ser Asn  Gly Phe Val
    2285                 2290                 2295

Asp Pro  Ala Ile Ser Lys Ala  Ala Ala Leu Asn Glu  Phe Met Ala
    2300                 2305                 2310

Trp Gly  Leu Ala Asn Arg Ala  Leu Ala Ala Lys Gln  Lys Arg Thr
    2315                 2320                 2325

Ser Ser  Leu Val Gln Met Val  Lys Asp Val Tyr Gln  Ala Ile Lys
    2330                 2335                 2340

Lys Leu  Ile Trp Gly Arg Lys  Gln Ala Pro Ala Leu  Gly Glu Asp
    2345                 2350                 2355

Met Phe  Ser Asn Leu Leu Phe  Asn Ser Ala Ile Leu  Met Arg Ser
    2360                 2365                 2370

Gln Pro  Thr Thr Gln Ala Val  Ala Lys Asp Gly Thr  Leu Phe His
    2375                 2380                 2385

Ser Lys  Ala Tyr Gly Asn Asn  Glu Arg Leu Ser Gln  Leu Asn Gln
    2390                 2395                 2400

Thr Phe  Asp Lys Leu Val Thr  Asp Tyr Leu Arg Thr  Asp Pro Val
    2405                 2410                 2415

Thr Glu  Val Glu Arg Arg Gly  Asn Val Ala Asn Ala  Leu Met Ser
    2420                 2425                 2430

Ala Thr  Arg Leu Val Arg Asp  Val Gln Ser His Gly  Phe Asn Met
    2435                 2440                 2445

Thr Ala  Gln Glu Gln Ser Val  Phe Gln Met Val Thr  Ala Ala Leu
    2450                 2455                 2460

Ala Thr  Glu Ala Ala Ile Asp  Pro His Ala Met Ala  Arg Ala Gln
    2465                 2470                 2475

Glu Leu  Tyr Thr His Val Met  Lys His Leu Thr Val  Glu His Phe
    2480                 2485                 2490

Met Ala  Asp Pro Asp Ser Thr  Asn Pro Ala Asp Arg  Tyr Tyr Ala
    2495                 2500                 2505

Gln Gln  Lys Tyr Asp Thr Ile  Ser Gly Ala Asn Leu  Val Glu Val
    2510                 2515                 2520

Asp Ala  Lys Gly Arg Thr Ser  Leu Leu Pro Thr Phe  Leu Gly Leu
    2525                 2530                 2535

Ala Met  Val Asn Glu Glu Leu  Arg Ser Ile Ile Lys  Glu Met Pro
    2540                 2545                 2550

Val Pro  Lys Ala Asp Lys Lys  Leu Gly Asn Asp Ile  Asp Thr Leu
    2555                 2560                 2565

Leu Thr  Asn Ala Gly Thr Gln  Val Met Glu Ser Leu  Asn Arg Arg
    2570                 2575                 2580

Met Ala  Gly Asp Gln Lys Ala  Thr Asn Val Gln Asp  Ser Ile Asp
```

-continued

```
    2585                2590                2595

Ala Leu Ser Glu Thr Ile Met Ala Ala Ala Leu Lys Arg Glu Ser
    2600                2605                2610

Phe Tyr Asp Ala Val Ala Thr Pro Thr Gly Asn Phe Ile Asp Arg
    2615                2620                2625

Ala Asn Gln Tyr Val Thr Asp Ser Ile Glu Arg Leu Ser Glu Thr
    2630                2635                2640

Val Ile Glu Lys Ala Asp Lys Val Ile Ala Asn Pro Ser Asn Ile
    2645                2650                2655

Ala Ala Lys Gly Val Ala His Leu Ala Lys Leu Thr Ala Ala Ile
    2660                2665                2670

Ala Ser Glu Lys Gln Gly Glu Ile Val Ala Gln Gly Val Met Thr
    2675                2680                2685

Ala Met Asn Gln Gly Lys Val Trp Gln Pro Phe His Asp Leu Val
    2690                2695                2700

Asn Asp Ile Val Gly Arg Thr Lys Thr Asn Ala Asn Val Tyr Asp
    2705                2710                2715

Leu Ile Lys Leu Val Lys Ser Gln Ile Ser Gln Asp Arg Gln Gln
    2720                2725                2730

Phe Arg Glu His Leu Pro Thr Val Ile Ala Gly Lys Phe Ser Arg
    2735                2740                2745

Lys Leu Thr Asp Thr Glu Trp Ser Ala Met His Thr Gly Leu Gly
    2750                2755                2760

Lys Thr Asp Leu Ala Val Leu Arg Glu Thr Met Ser Met Ala Glu
    2765                2770                2775

Ile Arg Asp Leu Leu Ser Ser Ser Lys Lys Val Lys Asp Glu Ile
    2780                2785                2790

Ser Thr Leu Glu Lys Glu Ile Gln Asn Gln Ala Gly Arg Asn Trp
    2795                2800                2805

Asn Leu Val Gln Lys Lys Ser Lys Gln Leu Ala Gln Tyr Met Ile
    2810                2815                2820

Met Gly Glu Val Gly Asn Asn Leu Leu Arg Asn Ala His Ala Ile
    2825                2830                2835

Ser Arg Leu Leu Gly Glu Arg Ile Thr Asn Gly Pro Val Ala Asp
    2840                2845                2850

Val Ala Ala Ile Asp Lys Leu Ile Thr Leu Tyr Ser Leu Glu Leu
    2855                2860                2865

Met Asn Lys Ser Asp Arg Asp Leu Leu Ser Glu Leu Ala Gln Ser
    2870                2875                2880

Glu Val Glu Gly Met Glu Phe Ser Ile Ala Tyr Met Val Gly Gln
    2885                2890                2895

Arg Thr Glu Glu Met Arg Lys Ala Lys Gly Asp Asn Arg Thr Leu
    2900                2905                2910

Leu Asn His Phe Lys Gly Tyr Ile Pro Val Glu Asn Gln Gln Gly
    2915                2920                2925

Val Asn Leu Ile Ile Ala Asp Asp Lys Glu Phe Ala Lys Leu Asn
    2930                2935                2940

Ser Gln Ser Phe Thr Arg Ile Gly Thr Tyr Gln Gly Ser Thr Gly
    2945                2950                2955

Phe Arg Thr Gly Ser Lys Gly Tyr Tyr Phe Ser Pro Val Ala Ala
    2960                2965                2970

Arg Ala Pro Tyr Ser Gln Gly Ile Leu Gln Asn Val Arg Asn Thr
    2975                2980                2985
```

```
Ala Gly Gly Val Asp Ile Gly Thr Gly Phe Thr Leu Gly Thr Met
    2990                2995                3000

Val Ala Gly Arg Ile Thr Asp Lys Pro Thr Val Glu Arg Ile Thr
    3005                3010                3015

Lys Ala Leu Ala Lys Gly Glu Arg Gly Arg Glu Pro Leu Met Pro
    3020                3025                3030

Ile Tyr Asn Ser Lys Gly Gln Val Val Ala Tyr Glu Gln Ser Val
    3035                3040                3045

Asp Pro Asn Met Leu Lys His Leu Asn Gln Asp Asn His Phe Ala
    3050                3055                3060

Lys Met Val Gly Val Trp Arg Gly Arg Gln Val Glu Glu Ala Lys
    3065                3070                3075

Ala Gln Arg Phe Asn Asp Ile Leu Ile Glu Gln Leu His Ala Met
    3080                3085                3090

Tyr Glu Lys Asp Ile Lys Asp Ser Ser Ala Asn Lys Ser Gln Tyr
    3095                3100                3105

Val Asn Leu Leu Gly Lys Ile Asp Asp Pro Val Leu Ala Asp Ala
    3110                3115                3120

Ile Asn Leu Met Asn Ile Glu Thr Arg His Lys Ala Glu Glu Leu
    3125                3130                3135

Phe Gly Lys Asp Glu Leu Trp Val Arg Arg Asp Met Leu Asn Asp
    3140                3145                3150

Ala Leu Gly Tyr Arg Ala Ala Ser Ile Gly Asp Val Trp Thr Gly
    3155                3160                3165

Asn Ser Arg Trp Ser Pro Ser Thr Leu Asp Thr Val Lys Lys Met
    3170                3175                3180

Phe Leu Gly Ala Phe Gly Asn Lys Ala Tyr His Val Val Met Asn
    3185                3190                3195

Ala Glu Asn Thr Ile Gln Asn Leu Val Lys Asp Ala Lys Thr Val
    3200                3205                3210

Ile Val Val Lys Ser Val Val Val Pro Ala Val Asn Phe Leu Ala
    3215                3220                3225

Asn Ile Tyr Gln Met Ile Gly Arg Gly Val Pro Val Lys Asp Ile
    3230                3235                3240

Ala Val Asn Ile Pro Arg Lys Thr Ser Glu Ile Asn Gln Tyr Ile
    3245                3250                3255

Lys Ser Arg Leu Arg Gln Ile Asp Ala Glu Ala Glu Leu Arg Ala
    3260                3265                3270

Ala Glu Gly Asn Pro Asn Leu Val Arg Lys Leu Lys Thr Glu Ile
    3275                3280                3285

Gln Ser Ile Thr Asp Ser His Arg Arg Met Ser Ile Trp Pro Leu
    3290                3295                3300

Ile Glu Ala Gly Glu Phe Ser Ser Ile Ala Asp Ala Gly Ile Ser
    3305                3310                3315

Arg Asp Asp Leu Leu Val Ala Glu Gly Lys Ile His Glu Tyr Met
    3320                3325                3330

Glu Lys Leu Ala Asn Lys Leu Pro Glu Lys Val Arg Asn Ala Gly
    3335                3340                3345

Arg Tyr Ala Leu Ile Ala Lys Asp Thr Ala Leu Phe Gln Gly Ile
    3350                3355                3360

Gln Lys Thr Val Glu Tyr Ser Asp Phe Ile Ala Lys Ala Ile Ile
    3365                3370                3375
```

-continued

```
Tyr Asp  Asp Leu Val Lys Arg  Lys Lys Lys Ser Ser  Ser Glu Ala
    3380                 3385                 3390

Leu Gly  Gln Val Thr Glu Glu  Phe Ile Asn Tyr Asp  Arg Leu Pro
    3395                 3400                 3405

Gly Arg  Phe Arg Gly Tyr Met  Glu Ser Met Gly Leu  Met Trp Phe
    3410                 3415                 3420

Tyr Asn  Phe Lys Ile Arg Ser  Ile Lys Val Ala Met  Ser Met Ile
    3425                 3430                 3435

Arg Asn  Asn Pro Val His Ser  Leu Ile Ala Thr Val  Val Pro Ala
    3440                 3445                 3450

Pro Thr  Met Phe Gly Asn Val  Gly Leu Pro Ile Gln  Asp Asn Met
    3455                 3460                 3465

Leu Thr  Met Leu Ala Glu Gly  Arg Leu Asp Tyr Ser  Leu Gly Phe
    3470                 3475                 3480

Gly Gln  Gly Leu Arg Ala Pro  Thr Leu Asn Pro Trp  Phe Asn Leu
    3485                 3490                 3495

Thr His
    3500
```

<210> SEQ ID NO 3
<211> LENGTH: 3318
<212> TYPE: DNA
<213> ORGANISM: Artificial Sequence
<220> FEATURE:
<223> OTHER INFORMATION: Synthetic

<400> SEQUENCE: 3

```
gaaagtacag ttacagaaga attaaaagaa ggtattgatg ctgtttaccc ttcattggta     60

ggtactgctg attctaaagc agagggtatt aagaactatt tcaaattgtc ctttacctta    120

ccagaagaac agaaatcccg tactgttggt tcagaagcac ctctaaaaga tgtagcccaa    180

gctctgtctt ctcgtgctcg ttatgaactc tttactgaga aagaaactgc taaccctgct    240

tttaatgggg aagttattaa gcgatacaaa gaactcatgg aacatgggga aggtattgct    300

gatattcttc gctcccgtct ggctaagttc cttaacacta aggatgttgg taaacgtttt    360

gctcaaggta cagaagccaa ccgttgggta ggtggtaagt tacttaacat tgttgagcag    420

gatggggata cctttaagta caacgaacaa ttgctacaga ctgctgtatt agcaggtctt    480

caatggagac ttactgctac cagcaatact gctatcaaag atgcaaaaga tgttgctgct    540

attactggta ttgaccaagc tctgctgcca gaaggtttag tagagcaatt tgatactggt    600

atgacactca ctgaagcagt tagttccctg gctcagaaaa ttgagtctta ctggggatta    660

tctcgtaatc caaatgctcc attgggctat accaaaggca tccctacagc aatggctgct    720

gaaattctgg ctgcatttgt agagtctact gatgttgtag agaacatcgt ggatatgtca    780

gaaattgacc cagataacaa gaagactatt ggtctgtaca ccattactga actggattcc    840

ttcgacccaa ttaatagctt ccctactgct attgaagaag ctgttttagt gaatcctaca    900

gagaagatgt tctttggtga tgacattcct cctgtagcta atactcagct tcgtaaccct    960

gctgttcgta atactccaga acagaaggct gcattgaaag cagagcaggc tacagagttc   1020

tatgtacaca ccccaatggt tcaattctat gagacgttag gtaaagaccg tattctcgaa   1080

ctgatgggtg ctggtactct gaataaagag ttacttaatg ataaccatgc taaatctctg   1140

gaaggtaaga accgttcagt agaggactct tacaaccaac tgttctccgt cattgagcag   1200

gtaagagcac agagcgaaga catctctact gtacctattc actatgcata caatatgacc   1260
```

-continued

```
cgtgttggtc gtatgcagat gttaggtaaa tacaatcctc aatcagccaa actggttcgt   1320

gaggccatct tacctactaa agctactttg gatttatcga accagaacaa tgaagacttc   1380

tctgcattcc agttaggtct ggctcaggca ttggacatta aagtccatac tatgactcgt   1440

gaggttatgt ctgacgagtt gactaaatta ctggaaggta atctgaaacc agccattgat   1500

atgatggttg agtttaatac cactggttcc ttaccagaaa acgcagttga tgttctgaat   1560

acagcattag gagataggaa gtcattcgta gcattgatgg ctcttatgga gtattcccgt   1620

tacttagtag cagaggataa atctgcattt gtaactccac tgtatgtaga agcagatggt   1680

gttactaatg gtccaatcaa tgccatgatg ctaatgacag gcggtctgtt tactcctgac   1740

tggattcgta atattgccaa agggggcttg ttcattggtt ctccaaataa gaccatgaat   1800

gagcatcgct ctactgctga caataatgat ttatatcaag catccactaa tgctttgatg   1860

gaatcgttgg gtaagttacg tagtaactat gcctctaata tgcctattca gtctcagata   1920

gacagtcttc tttctctgat ggatttgttt ttaccggata ttaatcttgg tgagaatggt   1980

gctttagaac ttaaacgtgg tattgctaag aacccactga ctattaccat ctatggttct   2040

ggtgctcgtg gtattgcagg taagctggtt agttctgtta ctgatgccat ctatgagcgt   2100

atgtctgatg tactgaaagc tcgtgctaaa gacccaaata tctctgctgc tatggcaatg   2160

tttggtaagc aagctgcttc agaagcacat gctgaagaac ttcttgcccg tttcctgaaa   2220

gatatggaaa cactgacttc tactgttcct gttaaacgta aaggtgtact ggaactacaa   2280

tccacaggta caggagccaa aggaaaaatc aatcctaaga cctataccat taagggcgag   2340

caactgaagg cacttcagga aaatatgctg cacttctttg tagaaccact acgtaatggt   2400

attactcaga ctgtaggtga aagtctggtg tactctactg aacaattaca gaaagctact   2460

cagattcaat ctgtagtgct ggaagatatg ttcaaacagc gagtacaaga gaagctggca   2520

gagaaggcta aagacccaac atggaagaaa ggtgatttcc ttactcagaa agaactgaat   2580

gatattcagg cttctctgaa taacttagcc cctatgattg agactggttc tcagactttc   2640

tacattgctg gttcagaaaa tgcagaagta gcaaatcagg tattagctac taaccttgat   2700

gaccgtatgc gtgtaccaat gagtatctat gctccagcac aggccggtgt agcaggtatt   2760

ccatttatga ctattggtac tggtgatggc atgatgatgc aaactctttc cactatgaaa   2820

ggtgcaccaa agaataccct caaaatcttt gatggtatga acattggttt gaatgacatc   2880

actgatgcca gtcgtaaagc taatgaagct gtttacactt cttggcaggg taaccctatt   2940

aagaatgttt atgaatcata tgctaagttc atgaagaatg tagatttcag caagctgtcc   3000

cctgaagcat tggaagcaat tggtaaatct gctctggaat atgaccaacg tgagaatgct   3060

actgtagatg atattgctaa cgctgcatct ctgattgaac gtaacttacg taatattgca   3120

ctgggtgtag atattcgtca taaggtgctg gataaggtaa atctgtccat tgaccagatg   3180

gctgctgtag gtgctcctta tcagaacaac ggtaagattg acctcagcaa tatgacccct   3240

gaacaacagg ctgatgaact gaataaactt ttccgtgaag agttagaagc ccgtaaacaa   3300

aaagtcgcta aggctagg                                                 3318
```

```
<210> SEQ ID NO 4
<211> LENGTH: 1107
<212> TYPE: PRT
<213> ORGANISM: Artificial Sequence
<220> FEATURE:
<223> OTHER INFORMATION: Synthetic

<400> SEQUENCE: 4
```

-continued

```
Met Glu Ser Thr Val Thr Glu Glu Leu Lys Glu Gly Ile Asp Ala Val
1               5                   10                  15

Tyr Pro Ser Leu Val Gly Thr Ala Asp Ser Lys Ala Glu Gly Ile Lys
            20                  25                  30

Asn Tyr Phe Lys Leu Ser Phe Thr Leu Pro Glu Glu Gln Lys Ser Arg
        35                  40                  45

Thr Val Gly Ser Glu Ala Pro Leu Lys Asp Val Ala Gln Ala Leu Ser
    50                  55                  60

Ser Arg Ala Arg Tyr Glu Leu Phe Thr Glu Lys Glu Thr Ala Asn Pro
65                  70                  75                  80

Ala Phe Asn Gly Glu Val Ile Lys Arg Tyr Lys Glu Leu Met Glu His
                85                  90                  95

Gly Glu Gly Ile Ala Asp Ile Leu Arg Ser Arg Leu Ala Lys Phe Leu
            100                 105                 110

Asn Thr Lys Asp Val Gly Lys Arg Phe Ala Gln Gly Thr Glu Ala Asn
        115                 120                 125

Arg Trp Val Gly Gly Lys Leu Leu Asn Ile Val Glu Gln Asp Gly Asp
    130                 135                 140

Thr Phe Lys Tyr Asn Glu Gln Leu Leu Gln Thr Ala Val Leu Ala Gly
145                 150                 155                 160

Leu Gln Trp Arg Leu Thr Ala Thr Ser Asn Thr Ala Ile Lys Asp Ala
                165                 170                 175

Lys Asp Val Ala Ala Ile Thr Gly Ile Asp Gln Ala Leu Leu Pro Glu
            180                 185                 190

Gly Leu Val Glu Gln Phe Asp Thr Gly Met Thr Leu Thr Glu Ala Val
        195                 200                 205

Ser Ser Leu Ala Gln Lys Ile Glu Ser Tyr Trp Gly Leu Ser Arg Asn
    210                 215                 220

Pro Asn Ala Pro Leu Gly Tyr Thr Lys Gly Ile Pro Thr Ala Met Ala
225                 230                 235                 240

Ala Glu Ile Leu Ala Ala Phe Val Glu Ser Thr Asp Val Val Glu Asn
                245                 250                 255

Ile Val Asp Met Ser Glu Ile Asp Pro Asp Asn Lys Lys Thr Ile Gly
            260                 265                 270

Leu Tyr Thr Ile Thr Glu Leu Asp Ser Phe Asp Pro Ile Asn Ser Phe
        275                 280                 285

Pro Thr Ala Ile Glu Glu Ala Val Leu Val Asn Pro Thr Glu Lys Met
    290                 295                 300

Phe Phe Gly Asp Asp Ile Pro Pro Val Ala Asn Thr Gln Leu Arg Asn
305                 310                 315                 320

Pro Ala Val Arg Asn Thr Pro Glu Gln Lys Ala Ala Leu Lys Ala Glu
                325                 330                 335

Gln Ala Thr Glu Phe Tyr Val His Thr Pro Met Val Gln Phe Tyr Glu
            340                 345                 350

Thr Leu Gly Lys Asp Arg Ile Leu Glu Leu Met Gly Ala Gly Thr Leu
        355                 360                 365

Asn Lys Glu Leu Leu Asn Asp Asn His Ala Lys Ser Leu Glu Gly Lys
    370                 375                 380

Asn Arg Ser Val Glu Asp Ser Tyr Asn Gln Leu Phe Ser Val Ile Glu
385                 390                 395                 400

Gln Val Arg Ala Gln Ser Glu Asp Ile Ser Thr Val Pro Ile His Tyr
                405                 410                 415
```

-continued

```
Ala Tyr Asn Met Thr Arg Val Gly Arg Met Gln Met Leu Gly Lys Tyr
            420                 425                 430

Asn Pro Gln Ser Ala Lys Leu Val Arg Glu Ala Ile Leu Pro Thr Lys
        435                 440                 445

Ala Thr Leu Asp Leu Ser Asn Gln Asn Asn Glu Asp Phe Ser Ala Phe
    450                 455                 460

Gln Leu Gly Leu Ala Gln Ala Leu Asp Ile Lys Val His Thr Met Thr
465                 470                 475                 480

Arg Glu Val Met Ser Asp Glu Leu Thr Lys Leu Leu Glu Gly Asn Leu
                485                 490                 495

Lys Pro Ala Ile Asp Met Met Val Glu Phe Asn Thr Thr Gly Ser Leu
            500                 505                 510

Pro Glu Asn Ala Val Asp Val Leu Asn Thr Ala Leu Gly Asp Arg Lys
        515                 520                 525

Ser Phe Val Ala Leu Met Ala Leu Met Glu Tyr Ser Arg Tyr Leu Val
    530                 535                 540

Ala Glu Asp Lys Ser Ala Phe Val Thr Pro Leu Tyr Val Glu Ala Asp
545                 550                 555                 560

Gly Val Thr Asn Gly Pro Ile Asn Ala Met Met Leu Met Thr Gly Gly
                565                 570                 575

Leu Phe Thr Pro Asp Trp Ile Arg Asn Ile Ala Lys Gly Gly Leu Phe
            580                 585                 590

Ile Gly Ser Pro Asn Lys Thr Met Asn Glu His Arg Ser Thr Ala Asp
        595                 600                 605

Asn Asn Asp Leu Tyr Gln Ala Ser Thr Asn Ala Leu Met Glu Ser Leu
    610                 615                 620

Gly Lys Leu Arg Ser Asn Tyr Ala Ser Asn Met Pro Ile Gln Ser Gln
625                 630                 635                 640

Ile Asp Ser Leu Leu Ser Leu Met Asp Leu Phe Leu Pro Asp Ile Asn
                645                 650                 655

Leu Gly Glu Asn Gly Ala Leu Glu Leu Lys Arg Gly Ile Ala Lys Asn
            660                 665                 670

Pro Leu Thr Ile Thr Ile Tyr Gly Ser Gly Ala Arg Gly Ile Ala Gly
        675                 680                 685

Lys Leu Val Ser Ser Val Thr Asp Ala Ile Tyr Glu Arg Met Ser Asp
    690                 695                 700

Val Leu Lys Ala Arg Ala Lys Asp Pro Asn Ile Ser Ala Ala Met Ala
705                 710                 715                 720

Met Phe Gly Lys Gln Ala Ala Ser Glu Ala His Ala Glu Glu Leu Leu
                725                 730                 735

Ala Arg Phe Leu Lys Asp Met Glu Thr Leu Thr Ser Thr Val Pro Val
            740                 745                 750

Lys Arg Lys Gly Val Leu Glu Leu Gln Ser Thr Gly Thr Gly Ala Lys
        755                 760                 765

Gly Lys Ile Asn Pro Lys Thr Tyr Thr Ile Lys Gly Glu Gln Leu Lys
    770                 775                 780

Ala Leu Gln Glu Asn Met Leu His Phe Phe Val Glu Pro Leu Arg Asn
785                 790                 795                 800

Gly Ile Thr Gln Thr Val Gly Glu Ser Leu Val Tyr Ser Thr Glu Gln
                805                 810                 815

Leu Gln Lys Ala Thr Gln Ile Gln Ser Val Val Leu Glu Asp Met Phe
            820                 825                 830

Lys Gln Arg Val Gln Glu Lys Leu Ala Glu Lys Ala Lys Asp Pro Thr
```

-continued

```
        835                 840                 845

Trp Lys Lys Gly Asp Phe Leu Thr Gln Lys Glu Leu Asn Asp Ile Gln
    850                 855                 860

Ala Ser Leu Asn Asn Leu Ala Pro Met Ile Glu Thr Gly Ser Gln Thr
865                 870                 875                 880

Phe Tyr Ile Ala Gly Ser Glu Asn Ala Glu Val Ala Asn Gln Val Leu
                885                 890                 895

Ala Thr Asn Leu Asp Asp Arg Met Arg Val Pro Met Ser Ile Tyr Ala
            900                 905                 910

Pro Ala Gln Ala Gly Val Ala Gly Ile Pro Phe Met Thr Ile Gly Thr
        915                 920                 925

Gly Asp Gly Met Met Met Gln Thr Leu Ser Thr Met Lys Gly Ala Pro
    930                 935                 940

Lys Asn Thr Leu Lys Ile Phe Asp Gly Met Asn Ile Gly Leu Asn Asp
945                 950                 955                 960

Ile Thr Asp Ala Ser Arg Lys Ala Asn Glu Ala Val Tyr Thr Ser Trp
                965                 970                 975

Gln Gly Asn Pro Ile Lys Asn Val Tyr Glu Ser Tyr Ala Lys Phe Met
            980                 985                 990

Lys Asn Val Asp Phe Ser Lys Leu  Ser Pro Glu Ala Leu  Glu Ala Ile
        995                 1000                 1005

Gly Lys  Ser Ala Leu Glu Tyr  Asp Gln Arg Glu Asn  Ala Thr Val
    1010                 1015                 1020

Asp Asp  Ile Ala Asn Ala Ala  Ser Leu Ile Glu Arg  Asn Leu Arg
    1025                 1030                 1035

Asn Ile  Ala Leu Gly Val Asp  Ile Arg His Lys Val  Leu Asp Lys
    1040                 1045                 1050

Val Asn  Leu Ser Ile Asp Gln  Met Ala Ala Val Gly  Ala Pro Tyr
    1055                 1060                 1065

Gln Asn  Asn Gly Lys Ile Asp  Leu Ser Asn Met Thr  Pro Glu Gln
    1070                 1075                 1080

Gln Ala  Asp Glu Leu Asn Lys  Leu Phe Arg Glu Glu  Leu Glu Ala
    1085                 1090                 1095

Arg Lys  Gln Lys Val Ala Lys  Ala Arg
    1100                 1105
```

```
<210> SEQ ID NO 5
<211> LENGTH: 3432
<212> TYPE: DNA
<213> ORGANISM: Artificial Sequence
<220> FEATURE:
<223> OTHER INFORMATION: Synthetic

<400> SEQUENCE: 5

atggggggtt ctcatcatca tcatcatcat ggtatggcta gcatgactgg tggacagcaa      60

atgggtcggg atctgtacga cgatgacgat aaggatccga gctcgagatc tgaaagtaca     120

gttacagaag aattaaaaga aggtattgat gctgtttacc cttcattggt aggtactgct     180

gattctaaag cagagggtat taagaactat ttcaaattgt cctttacctt accagaagaa     240

cagaaatccc gtactgttgg ttcagaagca cctctaaaag atgtagccca agctctgtct     300

tctcgtgctc gttatgaact ctttactgag aaagaaactg ctaaccctgc ttttaatggg     360

gaagttatta agcgatacaa agaactcatg gaacatgggg aaggtattgc tgatattctt     420

cgctcccgtc tggctaagtt ccttaacact aaggatgttg gtaaacgttt tgctcaaggt     480
```

-continued

```
acagaagcca accgttgggt aggtggtaag ttacttaaca ttgttgagca ggatggggat    540
acctttaagt acaacgaaca attgctacag actgctgtat tagcaggtct tcaatggaga    600
cttactgcta ccagcaatac tgctatcaaa gatgcaaaag atgttgctgc tattactggt    660
attgaccaag ctctgctgcc agaaggttta gtagagcaat ttgatactgg tatgacactc    720
actgaagcag ttagttccct ggctcagaaa attgagtctt actggggatt atctcgtaat    780
ccaaatgctc cattgggcta taccaaaggc atccctacag caatggctgc tgaaattctg    840
gctgcatttg tagagtctac tgatgttgta gagaacatcg tggatatgtc agaaattgac    900
ccagataaca agaagactat tggtctgtac accattactg aactggattc cttcgaccca    960
attaatagct tccctactgc tattgaagaa gctgttttag tgaatcctac agagaagatg   1020
ttctttggtg atgacattcc tcctgtagct aatactcagc ttcgtaaccc tgctgttcgt   1080
aatactccag aacagaaggc tgcattgaaa gcagagcagg ctacagagtt ctatgtacac   1140
accccaatgg ttcaattcta tgagacgtta ggtaaagacc gtattctcga actgatgggt   1200
gctggtactc tgaataaaga gttacttaat gataaccatg ctaaatctct ggaaggtaag   1260
aaccgttcag tagaggactc ttacaaccaa ctgttctccg tcattgagca ggtaagagca   1320
cagagcgaag acatctctac tgtacctatt cactatgcat acaatatgac ccgtgttggt   1380
cgtatgcaga tgttaggtaa atacaatcct caatcagcca aactggttcg tgaggccatc   1440
ttacctacta aagctacttt ggatttatcg aaccagaaca atgaagactt ctctgcattc   1500
cagttaggtc tggctcaggc attggacatt aaagtccata ctatgactcg tgaggttatg   1560
tctgacgagt tgactaaatt actggaaggt aatctgaaac cagccattga tatgatggtt   1620
gagtttaata ccactggttc cttaccagaa aacgcagttg atgttctgaa tacagcatta   1680
ggagatagga agtcattcgt agcattgatg gctcttatgg agtattcccg ttacttagta   1740
gcagaggata aatctgcatt tgtaactcca ctgtatgtag aagcagatgg tgttactaat   1800
ggtccaatca atgccatgat gctaatgaca ggcggtctgt ttactcctga ctggattcgt   1860
aatattgcca aagggggctt gttcattggt tctccaaata agaccatgaa tgagcatcgc   1920
tctactgctg acaataatga tttatatcaa gcatccacta atgctttgat ggaatcgttg   1980
ggtaagttac gtagtaacta tgcctctaat atgcctattc agtctcagat agacagtctt   2040
ctttctctga tggatttgtt tttaccggat attaatcttg gtgagaatgg tgctttagaa   2100
cttaaacgtg gtattgctaa gaacccactg actattacca tctatggttc tggtgctcgt   2160
ggtattgcag gtaagctggt tagttctgtt actgatgcca tctatgagcg tatgtctgat   2220
gtactgaaag ctcgtgctaa agacccaaat atctctgctg ctatggcaat gtttggtaag   2280
caagctgctt cagaagcaca tgctgaagaa cttcttgccc gtttcctgaa agatatggaa   2340
acactgactt ctactgttcc tgttaaacgt aaaggtgtac tggaactaca atccacaggt   2400
acaggagcca aaggaaaaat caatcctaag acctatacca ttaagggcga gcaactgaag   2460
gcacttcagg aaaatatgct gcacttcttt gtagaaccac tacgtaatgg tattactcag   2520
actgtaggtg aaagtctggt gtactctact gaacaattac agaaagctac tcagattcaa   2580
tctgtagtgc tggaagatat gttcaaacag cgagtacaag agaagctggc agagaaggct   2640
aaagacccaa catggaagaa aggtgatttc cttactcaga aagaactgaa tgatattcag   2700
gcttctctga ataacttagc ccctatgatt gagactggtt ctcagacttt ctacattgct   2760
ggttcagaaa atgcagaagt agcaaatcag gtattagcta ctaaccttga tgaccgtatg   2820
cgtgtaccaa tgagtatcta tgctccagca caggccggtg tagcaggtat tccatttatg   2880
```

-continued

```
actattggta ctggtgatgg catgatgatg caaactcttt ccactatgaa aggtgcacca   2940

aagaataccc tcaaaatctt tgatggtatg aacattggtt tgaatgacat cactgatgcc   3000

agtcgtaaag ctaatgaagc tgtttacact tcttggcagg gtaaccctat taagaatgtt   3060

tatgaatcat atgctaagtt catgaagaat gtagatttca gcaagctgtc ccctgaagca   3120

ttggaagcaa ttggtaaatc tgctctggaa tatgaccaac gtgagaatgc tactgtagat   3180

gatattgcta acgctgcatc tctgattgaa cgtaacttac gtaatattgc actgggtgta   3240

gatattcgtc ataaggtgct ggataaggta aatctgtcca ttgaccagat ggctgctgta   3300

ggtgctcctt atcagaacaa cggtaagatt gacctcagca atatgacccc tgaacaacag   3360

gctgatgaac tgaataaact tttccgtgaa gagttagaag cccgtaaaca aaaagtcgct   3420

aaggctaggt aa                                                         3432
```

```
<210> SEQ ID NO 6
<211> LENGTH: 1143
<212> TYPE: PRT
<213> ORGANISM: Artificial Sequence
<220> FEATURE:
<223> OTHER INFORMATION: Synthetic

<400> SEQUENCE: 6

Met Gly Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Ser Ser Arg Ser Glu Ser Thr Val Thr Glu Glu Leu Lys Glu Gly
        35                  40                  45

Ile Asp Ala Val Tyr Pro Ser Leu Val Gly Thr Ala Asp Ser Lys Ala
    50                  55                  60

Glu Gly Ile Lys Asn Tyr Phe Lys Leu Ser Phe Thr Leu Pro Glu Glu
65                  70                  75                  80

Gln Lys Ser Arg Thr Val Gly Ser Glu Ala Pro Leu Lys Asp Val Ala
                85                  90                  95

Gln Ala Leu Ser Ser Arg Ala Arg Tyr Glu Leu Phe Thr Glu Lys Glu
            100                 105                 110

Thr Ala Asn Pro Ala Phe Asn Gly Glu Val Ile Lys Arg Tyr Lys Glu
        115                 120                 125

Leu Met Glu His Gly Glu Gly Ile Ala Asp Ile Leu Arg Ser Arg Leu
    130                 135                 140

Ala Lys Phe Leu Asn Thr Lys Asp Val Gly Lys Arg Phe Ala Gln Gly
145                 150                 155                 160

Thr Glu Ala Asn Arg Trp Val Gly Gly Lys Leu Leu Asn Ile Val Glu
                165                 170                 175

Gln Asp Gly Asp Thr Phe Lys Tyr Asn Glu Gln Leu Leu Gln Thr Ala
            180                 185                 190

Val Leu Ala Gly Leu Gln Trp Arg Leu Thr Ala Thr Ser Asn Thr Ala
        195                 200                 205

Ile Lys Asp Ala Lys Asp Val Ala Ala Ile Thr Gly Ile Asp Gln Ala
    210                 215                 220

Leu Leu Pro Glu Gly Leu Val Glu Gln Phe Asp Thr Gly Met Thr Leu
225                 230                 235                 240

Thr Glu Ala Val Ser Ser Leu Ala Gln Lys Ile Glu Ser Tyr Trp Gly
                245                 250                 255
```

-continued

```
Leu Ser Arg Asn Pro Asn Ala Pro Leu Gly Tyr Thr Lys Gly Ile Pro
            260                 265                 270

Thr Ala Met Ala Ala Glu Ile Leu Ala Ala Phe Val Glu Ser Thr Asp
        275                 280                 285

Val Val Glu Asn Ile Val Asp Met Ser Glu Ile Asp Pro Asp Asn Lys
    290                 295                 300

Lys Thr Ile Gly Leu Tyr Thr Ile Thr Glu Leu Asp Ser Phe Asp Pro
305                 310                 315                 320

Ile Asn Ser Phe Pro Thr Ala Ile Glu Glu Ala Val Leu Val Asn Pro
                325                 330                 335

Thr Glu Lys Met Phe Phe Gly Asp Asp Ile Pro Pro Val Ala Asn Thr
            340                 345                 350

Gln Leu Arg Asn Pro Ala Val Arg Asn Thr Pro Glu Gln Lys Ala Ala
        355                 360                 365

Leu Lys Ala Glu Gln Ala Thr Glu Phe Tyr Val His Thr Pro Met Val
    370                 375                 380

Gln Phe Tyr Glu Thr Leu Gly Lys Asp Arg Ile Leu Glu Leu Met Gly
385                 390                 395                 400

Ala Gly Thr Leu Asn Lys Glu Leu Leu Asn Asp Asn His Ala Lys Ser
                405                 410                 415

Leu Glu Gly Lys Asn Arg Ser Val Glu Asp Ser Tyr Asn Gln Leu Phe
            420                 425                 430

Ser Val Ile Glu Gln Val Arg Ala Gln Ser Glu Asp Ile Ser Thr Val
        435                 440                 445

Pro Ile His Tyr Ala Tyr Asn Met Thr Arg Val Gly Arg Met Gln Met
    450                 455                 460

Leu Gly Lys Tyr Asn Pro Gln Ser Ala Lys Leu Val Arg Glu Ala Ile
465                 470                 475                 480

Leu Pro Thr Lys Ala Thr Leu Asp Leu Ser Asn Gln Asn Asn Glu Asp
                485                 490                 495

Phe Ser Ala Phe Gln Leu Gly Leu Ala Gln Ala Leu Asp Ile Lys Val
            500                 505                 510

His Thr Met Thr Arg Glu Val Met Ser Asp Glu Leu Thr Lys Leu Leu
        515                 520                 525

Glu Gly Asn Leu Lys Pro Ala Ile Asp Met Met Val Glu Phe Asn Thr
    530                 535                 540

Thr Gly Ser Leu Pro Glu Asn Ala Val Asp Val Leu Asn Thr Ala Leu
545                 550                 555                 560

Gly Asp Arg Lys Ser Phe Val Ala Leu Met Ala Leu Met Glu Tyr Ser
                565                 570                 575

Arg Tyr Leu Val Ala Glu Asp Lys Ser Ala Phe Val Thr Pro Leu Tyr
            580                 585                 590

Val Glu Ala Asp Gly Val Thr Asn Gly Pro Ile Asn Ala Met Met Leu
        595                 600                 605

Met Thr Gly Gly Leu Phe Thr Pro Asp Trp Ile Arg Asn Ile Ala Lys
    610                 615                 620

Gly Gly Leu Phe Ile Gly Ser Pro Asn Lys Thr Met Asn Glu His Arg
625                 630                 635                 640

Ser Thr Ala Asp Asn Asn Asp Leu Tyr Gln Ala Ser Thr Asn Ala Leu
                645                 650                 655

Met Glu Ser Leu Gly Lys Leu Arg Ser Asn Tyr Ala Ser Asn Met Pro
            660                 665                 670

Ile Gln Ser Gln Ile Asp Ser Leu Leu Ser Leu Met Asp Leu Phe Leu
```

-continued

```
        675                 680                 685

Pro Asp Ile Asn Leu Gly Glu Asn Gly Ala Leu Glu Leu Lys Arg Gly
    690                 695                 700

Ile Ala Lys Asn Pro Leu Thr Ile Thr Ile Tyr Gly Ser Gly Ala Arg
705                 710                 715                 720

Gly Ile Ala Gly Lys Leu Val Ser Ser Val Thr Asp Ala Ile Tyr Glu
                725                 730                 735

Arg Met Ser Asp Val Leu Lys Ala Arg Ala Lys Asp Pro Asn Ile Ser
            740                 745                 750

Ala Ala Met Ala Met Phe Gly Lys Gln Ala Ala Ser Glu Ala His Ala
        755                 760                 765

Glu Glu Leu Leu Ala Arg Phe Leu Lys Asp Met Glu Thr Leu Thr Ser
    770                 775                 780

Thr Val Pro Val Lys Arg Lys Gly Val Leu Glu Leu Gln Ser Thr Gly
785                 790                 795                 800

Thr Gly Ala Lys Gly Lys Ile Asn Pro Lys Thr Tyr Thr Ile Lys Gly
                805                 810                 815

Glu Gln Leu Lys Ala Leu Gln Glu Asn Met Leu His Phe Phe Val Glu
            820                 825                 830

Pro Leu Arg Asn Gly Ile Thr Gln Thr Val Gly Glu Ser Leu Val Tyr
        835                 840                 845

Ser Thr Glu Gln Leu Gln Lys Ala Thr Gln Ile Gln Ser Val Val Leu
    850                 855                 860

Glu Asp Met Phe Lys Gln Arg Val Gln Glu Lys Leu Ala Glu Lys Ala
865                 870                 875                 880

Lys Asp Pro Thr Trp Lys Lys Gly Asp Phe Leu Thr Gln Lys Glu Leu
                885                 890                 895

Asn Asp Ile Gln Ala Ser Leu Asn Asn Leu Ala Pro Met Ile Glu Thr
            900                 905                 910

Gly Ser Gln Thr Phe Tyr Ile Ala Gly Ser Glu Asn Ala Glu Val Ala
        915                 920                 925

Asn Gln Val Leu Ala Thr Asn Leu Asp Asp Arg Met Arg Val Pro Met
    930                 935                 940

Ser Ile Tyr Ala Pro Ala Gln Ala Gly Val Ala Gly Ile Pro Phe Met
945                 950                 955                 960

Thr Ile Gly Thr Gly Asp Gly Met Met Met Gln Thr Leu Ser Thr Met
                965                 970                 975

Lys Gly Ala Pro Lys Asn Thr Leu Lys Ile Phe Asp Gly Met Asn Ile
            980                 985                 990

Gly Leu Asn Asp Ile Thr Asp Ala  Ser Arg Lys Ala Asn  Glu Ala Val
        995                 1000                1005

Tyr Thr  Ser Trp Gln Gly Asn  Pro Ile Lys Asn Val  Tyr Glu Ser
    1010                1015                1020

Tyr Ala  Lys Phe Met Lys Asn  Val Asp Phe Ser Lys  Leu Ser Pro
    1025                1030                1035

Glu Ala  Leu Glu Ala Ile Gly  Lys Ser Ala Leu Glu  Tyr Asp Gln
    1040                1045                1050

Arg Glu  Asn Ala Thr Val Asp  Asp Ile Ala Asn Ala  Ala Ser Leu
    1055                1060                1065

Ile Glu  Arg Asn Leu Arg Asn  Ile Ala Leu Gly Val  Asp Ile Arg
    1070                1075                1080

His Lys  Val Leu Asp Lys Val  Asn Leu Ser Ile Asp  Gln Met Ala
    1085                1090                1095
```

```
Ala Val  Gly Ala Pro Tyr Gln  Asn Asn Gly Lys Ile  Asp Leu Ser
    1100                 1105                 1110

Asn Met  Thr Pro Glu Gln Gln  Ala Asp Glu Leu Asn  Lys Leu Phe
    1115                 1120                 1125

Arg Glu  Glu Leu Glu Ala Arg  Lys Gln Lys Val Ala  Lys Ala Arg
    1130                 1135                 1140


<210> SEQ ID NO 7
<211> LENGTH: 3432
<212> TYPE: DNA
<213> ORGANISM: Artificial Sequence
<220> FEATURE:
<223> OTHER INFORMATION: Synthetic

<400> SEQUENCE: 7

atggggggtt ctcatcatca tcatcatcat ggtatggcta gcatgactgg tggacagcaa     60

atgggtcggg atctgtacga cgatgacgat aaggatccga gctcgagatc tgaaagtaca    120

gttacagaag aattaaaaga aggtattgat gctgtttacc cttcattggt aggtactgct    180

gattctaaag cagagggtat taagaactat ttcaaattgt cctttacctt accagaagaa    240

cagaaatccc gtactgttgg ttcagaagca cctctaaaag atgtagccca agctctgtct    300

tctcgtgctc gttatgaact ctttactgag aaagaaactg ctaaccctgc ttttaatggg    360

gaagttatta agcgatacaa agaactcatg gaacatgggg aaggtattgc tgatattctt    420

cgctcccgtc tggctaagtt ccttaacact aaggatgttg gtaaacgttt tgctcaaggt    480

acagaagcca accgttgggt aggtggtaag ttacttaaca ttgttgagca ggatggggat    540

acctttaagt acaacgaaca attgctacag actgctgtat tagcaggtct tcaatggaga    600

cttactgcta ccagcaatac tgctatcaaa gatgcaaaag atgttgctgc tattactggt    660

attgaccaag ctctgctgcc agaaggttta gtagagcaat ttgatactgg tatgacactc    720

actgaagcag ttagttccct ggctcagaaa attgagtctt actggggatt atctcgtaat    780

ccaaatgctc cattgggcta taccaaaggc atccctacag caatggctgc tgaaattctg    840

gctgcatttg tagagtctac tgatgttgta gagaacatcg tggatatgtc agaaattgac    900

ccagataaca agaagactat tggtctgtac accattactg aactggattc cttcgaccca    960

attaatagct tccctactgc tattgaagaa gctgttttag tgaatcctac agagaagatg   1020

ttctttggtg atgacattcc tcctgtagct aatactcagc ttcgtaaccc tgctgttcgt   1080

aatactccag aacagaaggc tgcattgaaa gcagagcagg ctacagagtt ctatgtacac   1140

accccaatgg ttcaattcta tgagacgtta ggtaaagacc gtattctcga actgatgggt   1200

gctggtactc tgaataaaga gttacttaat gataaccatg ctaaatctct ggaaggtaag   1260

aaccgttcag tagaggactc ttacaaccaa ctgttctccg tcattgagca ggtaagagca   1320

cagagcgaag acatctctac tgtacctatt cactatgcat acaatatgac ccgtgttggt   1380

cgtatgcaga tgttaggtaa atacaatcct caatcagcca aactggttcg tgaggccatc   1440

ttacctacta aagctacttt ggatttatcg aaccagaaca atgaagactt ctctgcattc   1500

cagttaggtc tggctcaggc attggacatt aaagtccata ctatgactcg tgaggttatg   1560

tctgacgagt tgactaaatt actggaaggt aatctgaaac cagccattga tatgatggtt   1620

gagtttaata ccactggttc cttaccagaa aacgcagttg atgttctgaa tacagcatta   1680

ggagatagga agtcattcgt agcattgatg gctcttatgg agtattcccg ttacttagta   1740

gcagaggata aatctgcatt tgtaactcca ctgtatgtag aagcagatgg tgttactaat   1800
```

-continued

```
ggtccaatca atgccatgat gctaatgaca ggcggtctgt ttactcctga ctggattcgt   1860

aatattgcca aagggggctt gttcattggt tctccaaata agaccatgaa tgagcatcgc   1920

tctactgctg acaataatga tttatatcaa gcatccacta atgctttgat ggaatcgttg   1980

ggtaagttac gtagtaacta tgcctctaat atgcctattc agtctcagat agacagtctt   2040

ctttctctga tggatttgtt tttaccggat attaatcttg gtgagaatgg tgctttagaa   2100

cttaaacgtg gtattgctaa gaacccactg actattacca tcttcggttc tggtgctcgt   2160

ggtattgcag gtaagctggt tagttctgtt actgatgcca tctatgagcg tatgtctgat   2220

gtactgaaag ctcgtgctaa agacccaaat atctctgctg ctatggcaat gtttggtaag   2280

caagctgctt cagaagcaca tgctgaagaa cttcttgccc gtttcctgaa agatatggaa   2340

acactgactt ctactgttcc tgttaaacgt aaaggtgtac tggaactaca atccacaggt   2400

acaggagcca aaggaaaaat caatcctaag acctatacca ttaagggcga gcaactgaag   2460

gcacttcagg aaaatatgct gcacttcttt gtagaaccac tacgtaatgg tattactcag   2520

actgtaggtg aaagtctggt gtactctact gaacaattac agaaagctac tcagattcaa   2580

tctgtagtgc tggaagatat gttcaaacag cgagtacaag agaagctggc agagaaggct   2640

aaagacccaa catggaagaa aggtgatttc cttactcaga aagaactgaa tgatattcag   2700

gcttctctga ataacttagc ccctatgatt gagactggtt ctcagacttt ctacattgct   2760

ggttcagaaa atgcagaagt agcaaatcag gtattagcta ctaaccttga tgaccgtatg   2820

cgtgtaccaa tgagtatcta tgctccagca caggccggtg tagcaggtat tccatttatg   2880

actattggta ctggtgatgg catgatgatg caaactcttt ccactatgaa aggtgcacca   2940

aagaataccc tcaaaatctt tgatggtatg aacattggtt tgaatgacat cactgatgcc   3000

agtcgtaaag ctaatgaagc tgtttacact tcttggcagg gtaaccctat taagaatgtt   3060

tatgaatcat atgctaagtt catgaagaat gtagatttca gcaagctgtc ccctgaagca   3120

ttggaagcaa ttggtaaatc tgctctggaa tatgaccaac gtgagaatgc tactgtagat   3180

gatattgcta acgctgcatc tctgattgaa cgtaacttac gtaatattgc actgggtgta   3240

gatattcgtc ataaggtgct ggataaggta aatctgtcca ttgaccagat ggctgctgta   3300

ggtgctcctt atcagaacaa cggtaagatt gacctcagca atatgacccc tgaacaacag   3360

gctgatgaac tgaataaact tttccgtgaa gagttagaag cccgtaaaca aaaagtcgct   3420

aaggctaggt aa                                                       3432
```

<210> SEQ ID NO 8
<211> LENGTH: 1143
<212> TYPE: PRT
<213> ORGANISM: Artificial Sequence
<220> FEATURE:
<223> OTHER INFORMATION: Synthetic

<400> SEQUENCE: 8

```
Met Gly Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Ser Ser Arg Ser Glu Ser Thr Val Thr Glu Glu Leu Lys Glu Gly
        35                  40                  45

Ile Asp Ala Val Tyr Pro Ser Leu Val Gly Thr Ala Asp Ser Lys Ala
    50                  55                  60
```

-continued

```
Glu Gly Ile Lys Asn Tyr Phe Lys Leu Ser Phe Thr Leu Pro Glu Glu
65                  70                  75                  80

Gln Lys Ser Arg Thr Val Gly Ser Glu Ala Pro Leu Lys Asp Val Ala
                85                  90                  95

Gln Ala Leu Ser Ser Arg Ala Arg Tyr Glu Leu Phe Thr Glu Lys Glu
            100                 105                 110

Thr Ala Asn Pro Ala Phe Asn Gly Glu Val Ile Lys Arg Tyr Lys Glu
        115                 120                 125

Leu Met Glu His Gly Glu Gly Ile Ala Asp Ile Leu Arg Ser Arg Leu
    130                 135                 140

Ala Lys Phe Leu Asn Thr Lys Asp Val Gly Lys Arg Phe Ala Gln Gly
145                 150                 155                 160

Thr Glu Ala Asn Arg Trp Val Gly Gly Lys Leu Leu Asn Ile Val Glu
                165                 170                 175

Gln Asp Gly Asp Thr Phe Lys Tyr Asn Glu Gln Leu Leu Gln Thr Ala
            180                 185                 190

Val Leu Ala Gly Leu Gln Trp Arg Leu Thr Ala Thr Ser Asn Thr Ala
        195                 200                 205

Ile Lys Asp Ala Lys Asp Val Ala Ala Ile Thr Gly Ile Asp Gln Ala
    210                 215                 220

Leu Leu Pro Glu Gly Leu Val Glu Gln Phe Asp Thr Gly Met Thr Leu
225                 230                 235                 240

Thr Glu Ala Val Ser Ser Leu Ala Gln Lys Ile Glu Ser Tyr Trp Gly
                245                 250                 255

Leu Ser Arg Asn Pro Asn Ala Pro Leu Gly Tyr Thr Lys Gly Ile Pro
            260                 265                 270

Thr Ala Met Ala Ala Glu Ile Leu Ala Ala Phe Val Glu Ser Thr Asp
        275                 280                 285

Val Val Glu Asn Ile Val Asp Met Ser Glu Ile Asp Pro Asp Asn Lys
    290                 295                 300

Lys Thr Ile Gly Leu Tyr Thr Ile Thr Glu Leu Asp Ser Phe Asp Pro
305                 310                 315                 320

Ile Asn Ser Phe Pro Thr Ala Ile Glu Glu Ala Val Leu Val Asn Pro
                325                 330                 335

Thr Glu Lys Met Phe Phe Gly Asp Asp Ile Pro Pro Val Ala Asn Thr
            340                 345                 350

Gln Leu Arg Asn Pro Ala Val Arg Asn Thr Pro Glu Gln Lys Ala Ala
        355                 360                 365

Leu Lys Ala Glu Gln Ala Thr Glu Phe Tyr Val His Thr Pro Met Val
    370                 375                 380

Gln Phe Tyr Glu Thr Leu Gly Lys Asp Arg Ile Leu Glu Leu Met Gly
385                 390                 395                 400

Ala Gly Thr Leu Asn Lys Glu Leu Leu Asn Asp Asn His Ala Lys Ser
                405                 410                 415

Leu Glu Gly Lys Asn Arg Ser Val Glu Asp Ser Tyr Asn Gln Leu Phe
            420                 425                 430

Ser Val Ile Glu Gln Val Arg Ala Gln Ser Glu Asp Ile Ser Thr Val
        435                 440                 445

Pro Ile His Tyr Ala Tyr Asn Met Thr Arg Val Gly Arg Met Gln Met
    450                 455                 460

Leu Gly Lys Tyr Asn Pro Gln Ser Ala Lys Leu Val Arg Glu Ala Ile
465                 470                 475                 480

Leu Pro Thr Lys Ala Thr Leu Asp Leu Ser Asn Gln Asn Asn Glu Asp
```

-continued

```
                485                 490                 495

Phe Ser Ala Phe Gln Leu Gly Leu Ala Gln Ala Leu Asp Ile Lys Val
            500                 505                 510

His Thr Met Thr Arg Glu Val Met Ser Asp Glu Leu Thr Lys Leu Leu
        515                 520                 525

Glu Gly Asn Leu Lys Pro Ala Ile Asp Met Met Val Glu Phe Asn Thr
    530                 535                 540

Thr Gly Ser Leu Pro Glu Asn Ala Val Asp Val Leu Asn Thr Ala Leu
545                 550                 555                 560

Gly Asp Arg Lys Ser Phe Val Ala Leu Met Ala Leu Met Glu Tyr Ser
                565                 570                 575

Arg Tyr Leu Val Ala Glu Asp Lys Ser Ala Phe Val Thr Pro Leu Tyr
            580                 585                 590

Val Glu Ala Asp Gly Val Thr Asn Gly Pro Ile Asn Ala Met Met Leu
        595                 600                 605

Met Thr Gly Gly Leu Phe Thr Pro Asp Trp Ile Arg Asn Ile Ala Lys
    610                 615                 620

Gly Gly Leu Phe Ile Gly Ser Pro Asn Lys Thr Met Asn Glu His Arg
625                 630                 635                 640

Ser Thr Ala Asp Asn Asn Asp Leu Tyr Gln Ala Ser Thr Asn Ala Leu
                645                 650                 655

Met Glu Ser Leu Gly Lys Leu Arg Ser Asn Tyr Ala Ser Asn Met Pro
            660                 665                 670

Ile Gln Ser Gln Ile Asp Ser Leu Leu Ser Leu Met Asp Leu Phe Leu
        675                 680                 685

Pro Asp Ile Asn Leu Gly Glu Asn Gly Ala Leu Glu Leu Lys Arg Gly
    690                 695                 700

Ile Ala Lys Asn Pro Leu Thr Ile Thr Ile Phe Gly Ser Gly Ala Arg
705                 710                 715                 720

Gly Ile Ala Gly Lys Leu Val Ser Ser Val Thr Asp Ala Ile Tyr Glu
                725                 730                 735

Arg Met Ser Asp Val Leu Lys Ala Arg Ala Lys Asp Pro Asn Ile Ser
            740                 745                 750

Ala Ala Met Ala Met Phe Gly Lys Gln Ala Ala Ser Glu Ala His Ala
        755                 760                 765

Glu Glu Leu Leu Ala Arg Phe Leu Lys Asp Met Glu Thr Leu Thr Ser
    770                 775                 780

Thr Val Pro Val Lys Arg Lys Gly Val Leu Glu Leu Gln Ser Thr Gly
785                 790                 795                 800

Thr Gly Ala Lys Gly Lys Ile Asn Pro Lys Thr Tyr Thr Ile Lys Gly
                805                 810                 815

Glu Gln Leu Lys Ala Leu Gln Glu Asn Met Leu His Phe Phe Val Glu
            820                 825                 830

Pro Leu Arg Asn Gly Ile Thr Gln Thr Val Gly Glu Ser Leu Val Tyr
        835                 840                 845

Ser Thr Glu Gln Leu Gln Lys Ala Thr Gln Ile Gln Ser Val Val Leu
    850                 855                 860

Glu Asp Met Phe Lys Gln Arg Val Gln Glu Lys Leu Ala Glu Lys Ala
865                 870                 875                 880

Lys Asp Pro Thr Trp Lys Lys Gly Asp Phe Leu Thr Gln Lys Glu Leu
                885                 890                 895

Asn Asp Ile Gln Ala Ser Leu Asn Asn Leu Ala Pro Met Ile Glu Thr
            900                 905                 910
```

```
Gly Ser Gln Thr Phe Tyr Ile Ala Gly Ser Glu Asn Ala Glu Val Ala
        915                 920                 925

Asn Gln Val Leu Ala Thr Asn Leu Asp Asp Arg Met Arg Val Pro Met
    930                 935                 940

Ser Ile Tyr Ala Pro Ala Gln Ala Gly Val Ala Gly Ile Pro Phe Met
945                 950                 955                 960

Thr Ile Gly Thr Gly Asp Gly Met Met Met Gln Thr Leu Ser Thr Met
                965                 970                 975

Lys Gly Ala Pro Lys Asn Thr Leu Lys Ile Phe Asp Gly Met Asn Ile
            980                 985                 990

Gly Leu Asn Asp Ile Thr Asp Ala  Ser Arg Lys Ala Asn  Glu Ala Val
        995                 1000                1005

Tyr Thr  Ser Trp Gln Gly Asn  Pro Ile Lys Asn Val  Tyr Glu Ser
    1010                 1015                 1020

Tyr Ala  Lys Phe Met Lys Asn  Val Asp Phe Ser Lys  Leu Ser Pro
    1025                 1030                 1035

Glu Ala  Leu Glu Ala Ile Gly  Lys Ser Ala Leu Glu  Tyr Asp Gln
    1040                 1045                 1050

Arg Glu  Asn Ala Thr Val Asp  Asp Ile Ala Asn Ala  Ala Ser Leu
    1055                 1060                 1065

Ile Glu  Arg Asn Leu Arg Asn  Ile Ala Leu Gly Val  Asp Ile Arg
    1070                 1075                 1080

His Lys  Val Leu Asp Lys Val  Asn Leu Ser Ile Asp  Gln Met Ala
    1085                 1090                 1095

Ala Val  Gly Ala Pro Tyr Gln  Asn Asn Gly Lys Ile  Asp Leu Ser
    1100                 1105                 1110

Asn Met  Thr Pro Glu Gln Gln  Ala Asp Glu Leu Asn  Lys Leu Phe
    1115                 1120                 1125

Arg Glu  Glu Leu Glu Ala Arg  Lys Gln Lys Val Ala  Lys Ala Arg
    1130                 1135                 1140
```

<210> SEQ ID NO 9
<211> LENGTH: 69
<212> TYPE: DNA
<213> ORGANISM: Artificial Sequence
<220> FEATURE:
<223> OTHER INFORMATION: Synthetic

<400> SEQUENCE: 9

```
tcccagacaa aaggttaaga tttcatacag gattggatgc attacttcat ccaaaagaag     60

cggagcttc                                                             69
```

<210> SEQ ID NO 10
<211> LENGTH: 69
<212> TYPE: DNA
<213> ORGANISM: Artificial Sequence
<220> FEATURE:
<223> OTHER INFORMATION: Synthetic

<400> SEQUENCE: 10

```
tgggagagaa aaggttaaga tttgatagag gattggatgg attagttgat ggaaaagaag     60

cggagcttc                                                             69
```

<210> SEQ ID NO 11
<211> LENGTH: 69
<212> TYPE: DNA
<213> ORGANISM: Artificial Sequence
<220> FEATURE:
<223> OTHER INFORMATION: Synthetic

<400> SEQUENCE: 11
tccctgtctt ttggttttgt tttctttctg gtttggttgc ttttcttctt ccaaaagaag 60
cggagcttc 69

<210> SEQ ID NO 12
<211> LENGTH: 69
<212> TYPE: DNA
<213> ORGANISM: Artificial Sequence
<220> FEATURE:
<223> OTHER INFORMATION: Synthetic

<400> SEQUENCE: 12
tcccacacaa aaccttaaca tttcatacac cattccatcc attacttcat ccaaaagaag 60
cggagcttc 69

<210> SEQ ID NO 13
<211> LENGTH: 69
<212> TYPE: DNA
<213> ORGANISM: Artificial Sequence
<220> FEATURE:
<223> OTHER INFORMATION: Synthetic

<400> SEQUENCE: 13
acccagacaa aaggaaaaga aaacaaacag gaaaggaagc aaaacaacaa ccaaaagaag 60
cggagcttc 69

<210> SEQ ID NO 14
<211> LENGTH: 10617
<212> TYPE: DNA
<213> ORGANISM: Artificial Sequence
<220> FEATURE:
<223> OTHER INFORMATION: Synthetic

<400> SEQUENCE: 14
atggggggtt ctcatcatca tcatcatcat ggtatggcta gcatgactgg tggacagcaa 60
atgggtcggg atctgtacga cgatgacgat aaggatccga gctcgagatc tatgtcagta 120
tttgatagac tggctgggtt cgcagacagc gtaaccaatg caaagcaagt tgacgtctct 180
actgcaaccg cccagaagaa agctgaacaa ggtgtcacta ctcctcttgt ttctcctgat 240
gctgcttatc aaatgcaagc tgcccgtact ggtaatgttg ggctaatgc atttgaacca 300 gggacagtgc aatcagattt catgaatctg accccaatgc aaatcatgaa taagtatggg 360
gttgagcaag gcttacaact tatcaatgct cgtgctgatg cagggaacca ggtattcaat 420
gattcagtta ctacaagaac tcctggggaa gaactggggg atattgctac tggtgttggc 480
cttggttttg ttaataccct tgggggcatt ggtgctcttg ggcaggcttt actcaacgat 540
gatgcaggtg ctgttgttgc tcaacaattg agtaagttta atgatgctgt tcatgctacc 600
caaagccagg cattacaaga taaacgtaag ctctttgctg ctcgtaactt aatgaatgaa 660
gtagagagtg aacgtcagta tcaaacagat aagaaagaag gcactaatga catagtagct 720
tccttatcta aatttggacg tgattttgta ggttcaattg agaatgctgc tcaaactgac 780
tctattattt ctgatgggtt agcagaaggg gtaggttctc tattaggtgc tggtcctgta 840
ttaaggggtg catctttact gggtaaagca gttgttccag caaatactct tcgtagtgct 900
gcattggctg gtgctattga tgcaggtact ggtactcagt cactggctcg tattgcctct 960

-continued

```
actgtaggta gagctgcacc gggtatggtt ggtgttggtg caatggaagc tggtggtgca   1020
taccaacaaa ctgctgatga aattatgaag atgagtctta aagacttaga gaagtctcct   1080
gtttatcagc aacatattaa agatggtatg tcccctgaac aggctcgtcg tcagactgca   1140
tctgaaactg gtcttactgc tgctgctatt caattaccta ttgctgctgc aaccggtcct   1200
ctggtatccc gttttgagat ggctcctttc cgtgctggct ctttaggtgc tgtaggtatg   1260
aaccttgccc gtgaaacagt ggaagaaggt gttcagggtg ctacaggcca actggctcag   1320
aatattgcac agcaacaaaa cattgataag aaccaagacc tgcttaaagg tgtcggtaca   1380
caggctggtt taggtgctct ttatggcttt ggttctgctg gtgttgtaca ggctccggct   1440
ggtgctgctc gtttagcagg tgctgcaact gctcctgtat tgcgtaccac aatggctggt   1500
gttaaagctg ctggtagtgt agcaggtaag gttgtttctc ctattaagaa tactttagta   1560
gctcgtggtg aacgggttat gaagcagaat gaagaagcat ctcctgttgc tgatgactat   1620
gttgcacagg cagcacaaga agctatggct caagcaccag aagcagaagt tactattcgt   1680
gatgctgttg aagcaactga tgctactcca gaacagaaag ttgcagcaca ccagtatgtt   1740
tctgacttaa tgaatgctac tcgttttaat cctgaaaatt atcaggaagc accagagcat   1800
attcgtaatg ctgtagctgg ttctactgac caagtacagg ttattcagaa gttagcagac   1860
ttagttaaca cattagatga atctaatcct caagcactga tggaagctgc atcttatatg   1920
tatgatgctg tttcagagtt tgagcagttc attaaccgtg accctgctgc actggatagc   1980
attcctaaag attctccggc tattgagtta ctcaaccgtt atacgaatct gacagctaat   2040
attcagaaca caccaaaagt aattggtgca ctgaatgtta ttaatcgaat gattaatgaa   2100
tctgctcaga atggttcttt gaatgtgact gaagaatcca gtccacagga aatgcagaac   2160
gtagcattag ctgctgaagt agcccctgaa aagctcaatc cagagtctgt aaatgttgtt   2220
cttaaacatg ctgctgatgg tcgtattaaa ctgaataatc gccagattgc tgccctccag   2280
aatgctgctg caatcctgaa gggggcacgg gaatatgatg cagaagctgc ccgtcttgga   2340
ttacgtcctc aagacattgt gagtaaacag attaaaacgg atgagagcag aactcaggaa   2400
ggacaatact ctgcgttgca acatgcgaat aggattcggt ctgcgtataa ctctggtaat   2460
ttcgagttgg cctccgctta cctgaacgac tttatgcagt tcgcccagca catgcagaat   2520
aaggttggag cgttgaatga gcatcttgtt acggggaatg cggataagaa taagtctgtc   2580
cactaccaag ctcttactgc tgacagagaa tgggttcgta gccgtaccgg attgggggtc   2640
aatccctatg acactaagtc ggttaaattt gcccagcaag ttgctcttga agcgaaaacg   2700
gtagcggata ttgctaatgc cctcgcttcg gcttacccgg aactgaaggt cagtcatata   2760
aaagttactc cattggattc acgtcttaac gctcctgctg ctgaggtggt caaggcattc   2820
cgtcaaggca atcgagacgt tgcttcttct caaccgaaag ctgactccgt gaatcaggtt   2880
aaagaaactc ctgttacaaa acaggaacca gttacatcta ctgtacagac taagactcct   2940
gttagtgaat ctgttaaaac agaacctact actaaagagt ctagcccaca ggctataaaa   3000
gaacctgtga accagtctga aaaacaggat gttaacctta ctaatgagga caacatcaag   3060
caacctactg aatctgttaa agaaactgaa acttctacaa aagaaagtac agttacagaa   3120
gaattaaaag aaggtattga tgctgtttac ccttcattgg taggtactgc tgattctaaa   3180
gcagagggta ttaagaacta tttcaaattg tcctttacct taccagaaga acagaaatcc   3240
cgtactgttg gttcagaagc acctctaaaa gatgtagccc aagctctgtc ttctcgtgct   3300
cgttatgaac tctttactga gaaagaaact gctaaccctg cttttaatgg ggaagttatt   3360
```

-continued

```
aagcgataca aagaactcat ggaacatggg gaaggtattg ctgatattct tcgctcccgt   3420
ctggctaagt tccttaacac taaggatgtt ggtaaacgtt ttgctcaagg tacagaagcc   3480
aaccgttggg taggtggtaa gttacttaac attgttgagc aggatgggga tacctttaag   3540
tacaacgaac aattgctaca gactgctgta ttagcaggtc ttcaatggag acttactgct   3600
accagcaata ctgctatcaa agatgcaaaa gatgttgctg ctattactgg tattgaccaa   3660
gctctgctgc cagaaggttt agtagagcaa tttgatactg gtatgacact cactgaagca   3720
gttagttccc tggctcagaa aattgagtct tactggggat tatctcgtaa tccaaatgct   3780
ccattgggct ataccaaagg catccctaca gcaatggctg ctgaaattct ggctgcattt   3840
gtagagtcta ctgatgttgt agagaacatc gtggatatgt cagaaattga cccagataac   3900
aagaagacta ttggtctgta caccattact gaactggatt ccttcgaccc aattaatagc   3960
ttccctactg ctattgaaga agctgtttta gtgaatccta cagagaagat gttctttggt   4020
gatgacattc ctcctgtagc taatactcag cttcgtaacc ctgctgttcg taatactcca   4080
gaacagaagg ctgcattgaa agcagagcag gctacagagt tctatgtaca caccccaatg   4140
gttcaattct atgagacgtt aggtaaagac cgtattctcg aactgatggg tgctggtact   4200
ctgaataaag agttacttaa tgataaccat gctaaatctc tggaaggtaa gaaccgttca   4260
gtagaggact cttacaacca actgttctcc gtcattgagc aggtaagagc acagagcgaa   4320
gacatctcta ctgtacctat tcactatgca tacaatatga cccgtgttgg tcgtatgcag   4380
atgttaggta aatacaatcc tcaatcagcc aaactggttc gtgaggccat cttacctact   4440
aaagctactt tggatttatc gaaccagaac aatgaagact tctctgcatt ccagttaggt   4500
ctggctcagg cattggacat taaagtccat actatgactc gtgaggttat gtctgacgag   4560
ttgactaaat tactggaagg taatctgaaa ccagccattg atatgatggt tgagtttaat   4620
accactggtt ccttaccaga aaacgcagtt gatgttctga atacagcatt aggagatagg   4680
aagtcattcg tagcattgat ggctcttatg gagtattccc gttacttagt agcagaggat   4740
aaatctgcat ttgtaactcc actgtatgta gaagcagatg gtgttactaa tggtccaatc   4800
aatgccatga tgctaatgac aggcggtctg tttactcctg actggattcg taatattgcc   4860
aaagggggct tgttcattgg ttctccaaat aagaccatga atgagcatcg ctctactgct   4920
gacaataatg atttatatca agcatccact aatgctttga tggaatcgtt gggtaagtta   4980
cgtagtaact atgcctctaa tatgcctatt cagtctcaga tagacagtct tctttctctg   5040
atggatttgt ttttaccgga tattaatctt ggtgagaatg gtgctttaga acttaaacgt   5100
ggtattgcta agaacccact gactattacc atctatggtt ctggtgctcg tggtattgca   5160
ggtaagctgg ttagttctgt tactgatgcc atctatgagc gtatgtctga tgtactgaaa   5220
gctcgtgcta aagacccaaa tatctctgct gctatggcaa tgtttggtaa gcaagctgct   5280
tcagaagcac atgctgaaga acttcttgcc cgtttcctga aagatatgga aacactgact   5340
tctactgttc ctgttaaacg taaaggtgta ctggaactac aatccacagg tacaggagcc   5400
aaaggaaaaa tcaatcctaa gacctatacc attaagggcg agcaactgaa ggcacttcag   5460
gaaaatatgc tgcacttctt tgtagaacca ctacgtaatg gtattactca gactgtaggt   5520
gaaagtctgg tgtactctac tgaacaatta cagaaagcta ctcagattca atctgtagtg   5580
ctggaagata tgttcaaaca gcgagtacaa gagaagctgg cagagaaggc taaagaccca   5640
acatggaaga aaggtgattt ccttactcag aaagaactga atgatattca ggcttctctg   5700
```

-continued

```
aataacttag cccctatgat tgagactggt tctcagactt tctacattgc tggttcagaa   5760
aatgcagaag tagcaaatca ggtattagct actaaccttg atgaccgtat gcgtgtacca   5820
atgagtatct atgctccagc acaggccggt gtagcaggta ttccatttat gactattggt   5880
actggtgatg gcatgatgat gcaaactctt tccactatga aaggtgcacc aaagaatacc   5940
ctcaaaatct ttgatggtat gaacattggt ttgaatgaca tcactgatgc cagtcgtaaa   6000
gctaatgaag ctgtttacac ttcttggcag ggtaacccta ttaagaatgt ttatgaatca   6060
tatgctaagt tcatgaagaa tgtagatttc agcaagctgt cccctgaagc attggaagca   6120
attggtaaat ctgctctgga atatgaccaa cgtgagaatg ctactgtaga tgatattgct   6180
aacgctgcat ctctgattga acgtaactta cgtaatattg cactgggtgt agatattcgt   6240
cataaggtgc tggataaggt aaatctgtcc attgaccaga tggctgctgt aggtgctcct   6300
tatcagaaca acggtaagat tgacctcagc aatatgaccc ctgaacaaca ggctgatgaa   6360
ctgaataaac ttttccgtga agagttagaa gcccgtaaac aaaaagtcgc taaggctagg   6420
gctgaagtca aagaagaaac tgtttctgaa aaagaaccag tgaatccaga ctttggtatg   6480
gtaggccgtg agcataaggc atctggtgtt cgtatcctgt ctgctactgc tattcgtaat   6540
ctggctaaga ttagtaatct gccatctact caggcagcta ctcttgcgga gattcagaaa   6600
tcactggcag ctaaagacta taagattatc tacggtacac ctactcaggt tgcagagtat   6660
gctcgtcaga agaatgttac tgaattgact tctcaggaaa tggaagaagc tcaggcaggt   6720
aatatttatg gctggactaa cttcgatgat aagaccattt atctggttag cccatctatg   6780
gaaaccctca ttcatgaact ggttcatgcc tctaccttcg aggaagttta ttccttctat   6840
cagggtaatg aagtaagccc tacttctaag caggctattg agaaccttga aggtctgatg   6900
gaacagttcc gttctctgga tatttccaaa gattctccag aaatgagaga agcatatgct   6960
gatgctattg caactatcga aggtcatttg agtaatggat ttgttgaccc agctatctct   7020
aaagctgctg ctcttaatga gtttatggct tgggggttag ctaaccgtgc tcttgctgct   7080
aaacagaaga gaacatcttc actggttcaa atggtgaaag atgtttatca ggctattaag   7140
aaattgattt ggggacgtaa acaagctcct gcattgggag aagatatgtt ctccaatctg   7200
ctgtttaact ctgcaattct gatgcgtagc caacctacaa ctcaggcagt agctaaagat   7260
ggcacactgt tccatagcaa agcatatggt aataatgaac gtctgtctca gttgaaccag   7320
actttcgata aactggtaac tgattacctt cgtactgacc cagttacaga agtagaacgt   7380
cgtggcaatg tggctaatgc attaatgagt gctactcgac tggttcgtga tgttcagtct   7440
catggcttca atatgactgc tcaggaacag tctgtattcc agatggttac tgctgcatta   7500
gcaactgaag ctgcgattga cccacatgct atggctcgtg ctcaggaact ttatacccat   7560
gtaatgaaac accttacggt agagcatttc atggctgacc ctgatagtac taaccctgct   7620
gaccgttact atgctcaaca gaaatatgac accatctctg gtgctaatct ggttgaagta   7680
gatgccaaag gtagaaccag tctgttacct acattcctgg gtctggctat ggttaatgaa   7740
gaactacgtt caatcattaa agaaatgcct gtacctaaag cagataagaa attagggaat   7800
gatatagata ctctgcttac caatgcaggt actcaggtaa tggaatctct gaaccgtcgt   7860
atggctggtg accagaaagc tactaatgtt caggacagta ttgatgcttt gtcagaaaca   7920
atcatggctg ctgctttgaa acgagagtcc ttctatgatg ctgtagcaac ccctaccggt   7980
aacttcattg accgtgctaa tcagtacgta acggatagca ttgaacggtt atctgaaact   8040
gttattgaga aggcagataa ggtaattgct aacccttcta atatagctgc taaaggtgtt   8100
```

-continued

```
gctcatctgg ctaaactgac tgctgctatt gcatctgaaa aacagggtga aatagtggct   8160
cagggtgtta tgactgctat gaaccagggt aaagtatggc aacctttcca tgacttagtt   8220
aatgacattg ttggccgtac taagactaat gccaatgtct atgacttaat caaattggtt   8280
aagagccaga tttctcaaga ccgtcagcaa ttccgtgagc atttacctac agtcattgct   8340
ggtaagttct ctcgtaaatt gactgatacc gaatggtctg caatgcatac tggtttaggt   8400
aaaacagatt tagctgttct acgtgaaact atgagcatgg ctgaaattag agatttactc   8460
tcttcatcca agaaagtgaa agatgaaatc tctactctgg aaaaagagat tcagaaccaa   8520
gcaggtagaa actggaatct ggttcagaag aaatctaagc aactggctca atacatgatt   8580
atgggggaag taggtaataa cctccttcgt aatgcccatg ctattagtcg tttgttaggt   8640
gaacgtatta ctaatggtcc tgtggcagat gtagctgcta ttgataagct cattactttg   8700
tactctctgg aattgatgaa taagtctgac cgtgaccttt tgtcagaatt ggctcaatca   8760
gaagtggaag gtatggagtt ctccattgct tatatggttg gtcaacgtac tgaagagatg   8820
cgtaaagcta aaggtgataa ccgtactctg ctgaatcact ttaaaggcta tatccctgta   8880
gagaaccagc aaggtgtgaa tttgattatt gctgacgata aagagtttgc taagttaaat   8940
agccaatcct ttactcgtat tggtacttat caggggagca ctggtttccg tactggttct   9000
aaaggttatt acttcagccc agtagctgcc cgtgcccctt actctcaggg tattcttcag   9060
aacgttcgta atactgctgg tggtgtggat attggtactg gctttacgtt aggcactatg   9120
gttgctgggc gtattactga caaaccaacc gtagagcgta ttaccaaagc tctggctaaa   9180
ggtgagcgtg ggcgtgaacc actgatgcca atttataaca gcaaaggtca ggtagttgct   9240
tatgaacaat ccgttgaccc taatatgttg aagcacctaa accaagacaa tcactttgct   9300
aagatggttg gtgtatggcg tggtcgtcag gtggaagagg ctaaagcaca acgttttaat   9360
gacattctca ttgagcaatt acatgctatg tatgagaaag acattaaaga ctccagtgct   9420
aataaatctc aatatgtaaa cctgttaggt aaaattgatg acccagtact ggctgatgcg   9480
attaacctga tgaacattga gactcgtcat aaggccgaag aactcttcgg taaagatgag   9540
ttatgggttc gtagggatat gctgaatgat gcacttggct atcgtgctgc atctattggt   9600
gatgtgtgga ccggtaactc tcgttggtca cctagcaccc ttgatactgt taagaagatg   9660
ttcctcggtg cattcggtaa taaggcatat catgtagtaa tgaatgctga aaataccatt   9720
cagaacttag tgaaggacgc taagacagta attgttgtta aatctgttgt agtaccggca   9780
gttaacttcc ttgctaacat ctaccagatg attggacgtg gtgttcctgt taaagatatt   9840
gctgtgaaca ttcctcgtaa gacgtcagag attaatcagt atattaaatc tcgtttacgt   9900
cagattgatg cggaagcaga gctacgtgct gctgaaggta accctaatct ggttcgtaaa   9960
cttaaaactg agattcaatc tattactgat agtcatcgtc gtatgagtat ctggcctttg  10020
attgaagcag gtgagttctc ttctattgct gatgctggta ttagtcgtga tgacctgtta  10080
gtagctgaag gtaagattca tgagtacatg gaaaaacttg ctaataaact tccagaaaaa  10140
gtacgtaatg ctggccgtta cgctcttatt gctaaggaca ctgctctgtt ccagggtatc  10200
cagaaaacag tagagtattc agactttatt gctaaagcca tcatctatga tgatttagtg  10260
aaacgtaaga aaaaatcttc ttctgaagca ttaggtcagg taactgaaga gtttattaac  10320
tatgacagat tgcctggtcg tttccgtggc tatatggaaa gtatgggtct gatgtggttc  10380
tacaacttta aaattcgttc cattaaagtt gctatgagca tgattagaaa caacccagta  10440
```

-continued

```
cattctctga ttgctacagt agtacctgct cctaccatgt ttggtaacgt aggtctacca  10500

attcaggaca acatgctaac catgctggct gaaggaagac tggattactc attaggcttc  10560

ggacaaggat taagagcacc taccctcaat ccttggttca accttactca ctaataa     10617
```

<210> SEQ ID NO 15
<211> LENGTH: 3537
<212> TYPE: PRT
<213> ORGANISM: Artificial Sequence
<220> FEATURE:
<223> OTHER INFORMATION: Synthetic

<400> SEQUENCE: 15

```
Met Gly Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Ser Ser Arg Ser Met Ser Val Phe Asp Arg Leu Ala Gly Phe Ala
        35                  40                  45

Asp Ser Val Thr Asn Ala Lys Gln Val Asp Val Ser Thr Ala Thr Ala
    50                  55                  60

Gln Lys Lys Ala Glu Gln Gly Val Thr Thr Pro Leu Val Ser Pro Asp
65                  70                  75                  80

Ala Ala Tyr Gln Met Gln Ala Ala Arg Thr Gly Asn Val Gly Ala Asn
                85                  90                  95

Ala Phe Glu Pro Gly Thr Val Gln Ser Asp Phe Met Asn Leu Thr Pro
            100                 105                 110

Met Gln Ile Met Asn Lys Tyr Gly Val Glu Gln Gly Leu Gln Leu Ile
        115                 120                 125

Asn Ala Arg Ala Asp Ala Gly Asn Gln Val Phe Asn Asp Ser Val Thr
    130                 135                 140

Thr Arg Thr Pro Gly Glu Glu Leu Gly Asp Ile Ala Thr Gly Val Gly
145                 150                 155                 160

Leu Gly Phe Val Asn Thr Leu Gly Gly Ile Gly Ala Leu Gly Ala Gly
                165                 170                 175

Leu Leu Asn Asp Asp Ala Gly Ala Val Val Ala Gln Gln Leu Ser Lys
            180                 185                 190

Phe Asn Asp Ala Val His Ala Thr Gln Ser Gln Ala Leu Gln Asp Lys
        195                 200                 205

Arg Lys Leu Phe Ala Ala Arg Asn Leu Met Asn Glu Val Glu Ser Glu
    210                 215                 220

Arg Gln Tyr Gln Thr Asp Lys Lys Glu Gly Thr Asn Asp Ile Val Ala
225                 230                 235                 240

Ser Leu Ser Lys Phe Gly Arg Asp Phe Val Gly Ser Ile Glu Asn Ala
                245                 250                 255

Ala Gln Thr Asp Ser Ile Ile Ser Asp Gly Leu Ala Glu Gly Val Gly
            260                 265                 270

Ser Leu Leu Gly Ala Gly Pro Val Leu Arg Gly Ala Ser Leu Leu Gly
        275                 280                 285

Lys Ala Val Val Pro Ala Asn Thr Leu Arg Ser Ala Ala Leu Ala Gly
    290                 295                 300

Ala Ile Asp Ala Gly Thr Gly Thr Gln Ser Leu Ala Arg Ile Ala Ser
305                 310                 315                 320

Thr Val Gly Arg Ala Ala Pro Gly Met Val Gly Val Gly Ala Met Glu
                325                 330                 335
```

-continued

```
Ala Gly Gly Ala Tyr Gln Gln Thr Ala Asp Glu Ile Met Lys Met Ser
            340                 345                 350

Leu Lys Asp Leu Glu Lys Ser Pro Val Tyr Gln Gln His Ile Lys Asp
        355                 360                 365

Gly Met Ser Pro Glu Gln Ala Arg Arg Gln Thr Ala Ser Glu Thr Gly
    370                 375                 380

Leu Thr Ala Ala Ala Ile Gln Leu Pro Ile Ala Ala Ala Thr Gly Pro
385                 390                 395                 400

Leu Val Ser Arg Phe Glu Met Ala Pro Phe Arg Ala Gly Ser Leu Gly
                405                 410                 415

Ala Val Gly Met Asn Leu Ala Arg Glu Thr Val Glu Glu Gly Val Gln
            420                 425                 430

Gly Ala Thr Gly Gln Leu Ala Gln Asn Ile Ala Gln Gln Gln Asn Ile
        435                 440                 445

Asp Lys Asn Gln Asp Leu Leu Lys Gly Val Gly Thr Gln Ala Gly Leu
    450                 455                 460

Gly Ala Leu Tyr Gly Phe Gly Ser Ala Gly Val Val Gln Ala Pro Ala
465                 470                 475                 480

Gly Ala Ala Arg Leu Ala Gly Ala Ala Thr Ala Pro Val Leu Arg Thr
                485                 490                 495

Thr Met Ala Gly Val Lys Ala Ala Gly Ser Val Ala Gly Lys Val Val
            500                 505                 510

Ser Pro Ile Lys Asn Thr Leu Val Ala Arg Gly Glu Arg Val Met Lys
        515                 520                 525

Gln Asn Glu Glu Ala Ser Pro Val Ala Asp Asp Tyr Val Ala Gln Ala
    530                 535                 540

Ala Gln Glu Ala Met Ala Gln Ala Pro Glu Ala Glu Val Thr Ile Arg
545                 550                 555                 560

Asp Ala Val Glu Ala Thr Asp Ala Thr Pro Glu Gln Lys Val Ala Ala
                565                 570                 575

His Gln Tyr Val Ser Asp Leu Met Asn Ala Thr Arg Phe Asn Pro Glu
            580                 585                 590

Asn Tyr Gln Glu Ala Pro Glu His Ile Arg Asn Ala Val Ala Gly Ser
        595                 600                 605

Thr Asp Gln Val Gln Val Ile Gln Lys Leu Ala Asp Leu Val Asn Thr
    610                 615                 620

Leu Asp Glu Ser Asn Pro Gln Ala Leu Met Glu Ala Ala Ser Tyr Met
625                 630                 635                 640

Tyr Asp Ala Val Ser Glu Phe Glu Gln Phe Ile Asn Arg Asp Pro Ala
                645                 650                 655

Ala Leu Asp Ser Ile Pro Lys Asp Ser Pro Ala Ile Glu Leu Leu Asn
            660                 665                 670

Arg Tyr Thr Asn Leu Thr Ala Asn Ile Gln Asn Thr Pro Lys Val Ile
        675                 680                 685

Gly Ala Leu Asn Val Ile Asn Arg Met Ile Asn Glu Ser Ala Gln Asn
    690                 695                 700

Gly Ser Leu Asn Val Thr Glu Glu Ser Ser Pro Gln Glu Met Gln Asn
705                 710                 715                 720

Val Ala Leu Ala Ala Glu Val Ala Pro Glu Lys Leu Asn Pro Glu Ser
                725                 730                 735

Val Asn Val Val Leu Lys His Ala Ala Asp Gly Arg Ile Lys Leu Asn
            740                 745                 750

Asn Arg Gln Ile Ala Ala Leu Gln Asn Ala Ala Ala Ile Leu Lys Gly
```

-continued

```
        755                 760                 765

Ala Arg Glu Tyr Asp Ala Glu Ala Ala Arg Leu Gly Leu Arg Pro Gln
    770                 775                 780

Asp Ile Val Ser Lys Gln Ile Lys Thr Asp Glu Ser Arg Thr Gln Glu
785                 790                 795                 800

Gly Gln Tyr Ser Ala Leu Gln His Ala Asn Arg Ile Arg Ser Ala Tyr
                805                 810                 815

Asn Ser Gly Asn Phe Glu Leu Ala Ser Ala Tyr Leu Asn Asp Phe Met
            820                 825                 830

Gln Phe Ala Gln His Met Gln Asn Lys Val Gly Ala Leu Asn Glu His
        835                 840                 845

Leu Val Thr Gly Asn Ala Asp Lys Asn Lys Ser Val His Tyr Gln Ala
    850                 855                 860

Leu Thr Ala Asp Arg Glu Trp Val Arg Ser Arg Thr Gly Leu Gly Val
865                 870                 875                 880

Asn Pro Tyr Asp Thr Lys Ser Val Lys Phe Ala Gln Gln Val Ala Leu
                885                 890                 895

Glu Ala Lys Thr Val Ala Asp Ile Ala Asn Ala Leu Ala Ser Ala Tyr
            900                 905                 910

Pro Glu Leu Lys Val Ser His Ile Lys Val Thr Pro Leu Asp Ser Arg
        915                 920                 925

Leu Asn Ala Pro Ala Ala Glu Val Val Lys Ala Phe Arg Gln Gly Asn
    930                 935                 940

Arg Asp Val Ala Ser Ser Gln Pro Lys Ala Asp Ser Val Asn Gln Val
945                 950                 955                 960

Lys Glu Thr Pro Val Thr Lys Gln Glu Pro Val Thr Ser Thr Val Gln
                965                 970                 975

Thr Lys Thr Pro Val Ser Glu Ser Val Lys Thr Glu Pro Thr Thr Lys
            980                 985                 990

Glu Ser Ser Pro Gln Ala Ile Lys  Glu Pro Val Asn Gln  Ser Glu Lys
        995                 1000                1005

Gln Asp  Val Asn Leu Thr Asn  Glu Asp Asn Ile Lys  Gln Pro Thr
    1010                1015                1020

Glu Ser  Val Lys Glu Thr Glu  Thr Ser Thr Lys Glu  Ser Thr Val
    1025                1030                1035

Thr Glu  Glu Leu Lys Glu Gly  Ile Asp Ala Val Tyr  Pro Ser Leu
    1040                1045                1050

Val Gly  Thr Ala Asp Ser Lys  Ala Glu Gly Ile Lys  Asn Tyr Phe
    1055                1060                1065

Lys Leu  Ser Phe Thr Leu Pro  Glu Glu Gln Lys Ser  Arg Thr Val
    1070                1075                1080

Gly Ser  Glu Ala Pro Leu Lys  Asp Val Ala Gln Ala  Leu Ser Ser
    1085                1090                1095

Arg Ala  Arg Tyr Glu Leu Phe  Thr Glu Lys Glu Thr  Ala Asn Pro
    1100                1105                1110

Ala Phe  Asn Gly Glu Val Ile  Lys Arg Tyr Lys Glu  Leu Met Glu
    1115                1120                1125

His Gly  Glu Gly Ile Ala Asp  Ile Leu Arg Ser Arg  Leu Ala Lys
    1130                1135                1140

Phe Leu  Asn Thr Lys Asp Val  Gly Lys Arg Phe Ala  Gln Gly Thr
    1145                1150                1155

Glu Ala  Asn Arg Trp Val Gly  Gly Lys Leu Leu Asn  Ile Val Glu
    1160                1165                1170
```

-continued

```
Gln Asp  Gly Asp Thr Phe Lys  Tyr Asn Glu Gln Leu  Leu Gln Thr
    1175                 1180                 1185

Ala Val  Leu Ala Gly Leu Gln  Trp Arg Leu Thr Ala  Thr Ser Asn
    1190                 1195                 1200

Thr Ala  Ile Lys Asp Ala Lys  Asp Val Ala Ala Ile  Thr Gly Ile
    1205                 1210                 1215

Asp Gln  Ala Leu Leu Pro Glu  Gly Leu Val Glu Gln  Phe Asp Thr
    1220                 1225                 1230

Gly Met  Thr Leu Thr Glu Ala  Val Ser Ser Leu Ala  Gln Lys Ile
    1235                 1240                 1245

Glu Ser  Tyr Trp Gly Leu Ser  Arg Asn Pro Asn Ala  Pro Leu Gly
    1250                 1255                 1260

Tyr Thr  Lys Gly Ile Pro Thr  Ala Met Ala Ala Glu  Ile Leu Ala
    1265                 1270                 1275

Ala Phe  Val Glu Ser Thr Asp  Val Val Glu Asn Ile  Val Asp Met
    1280                 1285                 1290

Ser Glu  Ile Asp Pro Asp Asn  Lys Lys Thr Ile Gly  Leu Tyr Thr
    1295                 1300                 1305

Ile Thr  Glu Leu Asp Ser Phe  Asp Pro Ile Asn Ser  Phe Pro Thr
    1310                 1315                 1320

Ala Ile  Glu Glu Ala Val Leu  Val Asn Pro Thr Glu  Lys Met Phe
    1325                 1330                 1335

Phe Gly  Asp Asp Ile Pro Pro  Val Ala Asn Thr Gln  Leu Arg Asn
    1340                 1345                 1350

Pro Ala  Val Arg Asn Thr Pro  Glu Gln Lys Ala Ala  Leu Lys Ala
    1355                 1360                 1365

Glu Gln  Ala Thr Glu Phe Tyr  Val His Thr Pro Met  Val Gln Phe
    1370                 1375                 1380

Tyr Glu  Thr Leu Gly Lys Asp  Arg Ile Leu Glu Leu  Met Gly Ala
    1385                 1390                 1395

Gly Thr  Leu Asn Lys Glu Leu  Leu Asn Asp Asn His  Ala Lys Ser
    1400                 1405                 1410

Leu Glu  Gly Lys Asn Arg Ser  Val Glu Asp Ser Tyr  Asn Gln Leu
    1415                 1420                 1425

Phe Ser  Val Ile Glu Gln Val  Arg Ala Gln Ser Glu  Asp Ile Ser
    1430                 1435                 1440

Thr Val  Pro Ile His Tyr Ala  Tyr Asn Met Thr Arg  Val Gly Arg
    1445                 1450                 1455

Met Gln  Met Leu Gly Lys Tyr  Asn Pro Gln Ser Ala  Lys Leu Val
    1460                 1465                 1470

Arg Glu  Ala Ile Leu Pro Thr  Lys Ala Thr Leu Asp  Leu Ser Asn
    1475                 1480                 1485

Gln Asn  Asn Glu Asp Phe Ser  Ala Phe Gln Leu Gly  Leu Ala Gln
    1490                 1495                 1500

Ala Leu  Asp Ile Lys Val His  Thr Met Thr Arg Glu  Val Met Ser
    1505                 1510                 1515

Asp Glu  Leu Thr Lys Leu Leu  Glu Gly Asn Leu Lys  Pro Ala Ile
    1520                 1525                 1530

Asp Met  Met Val Glu Phe Asn  Thr Thr Gly Ser Leu  Pro Glu Asn
    1535                 1540                 1545

Ala Val  Asp Val Leu Asn Thr  Ala Leu Gly Asp Arg  Lys Ser Phe
    1550                 1555                 1560
```

-continued

```
Val Ala  Leu Met Ala Leu Met  Glu Tyr Ser Arg Tyr  Leu Val Ala
    1565                 1570                 1575

Glu Asp  Lys Ser Ala Phe Val  Thr Pro Leu Tyr Val  Glu Ala Asp
    1580                 1585                 1590

Gly Val  Thr Asn Gly Pro Ile  Asn Ala Met Met Leu  Met Thr Gly
    1595                 1600                 1605

Gly Leu  Phe Thr Pro Asp Trp  Ile Arg Asn Ile Ala  Lys Gly Gly
    1610                 1615                 1620

Leu Phe  Ile Gly Ser Pro Asn  Lys Thr Met Asn Glu  His Arg Ser
    1625                 1630                 1635

Thr Ala  Asp Asn Asn Asp Leu  Tyr Gln Ala Ser Thr  Asn Ala Leu
    1640                 1645                 1650

Met Glu  Ser Leu Gly Lys Leu  Arg Ser Asn Tyr Ala  Ser Asn Met
    1655                 1660                 1665

Pro Ile  Gln Ser Gln Ile Asp  Ser Leu Leu Ser Leu  Met Asp Leu
    1670                 1675                 1680

Phe Leu  Pro Asp Ile Asn Leu  Gly Glu Asn Gly Ala  Leu Glu Leu
    1685                 1690                 1695

Lys Arg  Gly Ile Ala Lys Asn  Pro Leu Thr Ile Thr  Ile Tyr Gly
    1700                 1705                 1710

Ser Gly  Ala Arg Gly Ile Ala  Gly Lys Leu Val Ser  Ser Val Thr
    1715                 1720                 1725

Asp Ala  Ile Tyr Glu Arg Met  Ser Asp Val Leu Lys  Ala Arg Ala
    1730                 1735                 1740

Lys Asp  Pro Asn Ile Ser Ala  Ala Met Ala Met Phe  Gly Lys Gln
    1745                 1750                 1755

Ala Ala  Ser Glu Ala His Ala  Glu Glu Leu Leu Ala  Arg Phe Leu
    1760                 1765                 1770

Lys Asp  Met Glu Thr Leu Thr  Ser Thr Val Pro Val  Lys Arg Lys
    1775                 1780                 1785

Gly Val  Leu Glu Leu Gln Ser  Thr Gly Thr Gly Ala  Lys Gly Lys
    1790                 1795                 1800

Ile Asn  Pro Lys Thr Tyr Thr  Ile Lys Gly Glu Gln  Leu Lys Ala
    1805                 1810                 1815

Leu Gln  Glu Asn Met Leu His  Phe Phe Val Glu Pro  Leu Arg Asn
    1820                 1825                 1830

Gly Ile  Thr Gln Thr Val Gly  Glu Ser Leu Val Tyr  Ser Thr Glu
    1835                 1840                 1845

Gln Leu  Gln Lys Ala Thr Gln  Ile Gln Ser Val Val  Leu Glu Asp
    1850                 1855                 1860

Met Phe  Lys Gln Arg Val Gln  Glu Lys Leu Ala Glu  Lys Ala Lys
    1865                 1870                 1875

Asp Pro  Thr Trp Lys Lys Gly  Asp Phe Leu Thr Gln  Lys Glu Leu
    1880                 1885                 1890

Asn Asp  Ile Gln Ala Ser Leu  Asn Asn Leu Ala Pro  Met Ile Glu
    1895                 1900                 1905

Thr Gly  Ser Gln Thr Phe Tyr  Ile Ala Gly Ser Glu  Asn Ala Glu
    1910                 1915                 1920

Val Ala  Asn Gln Val Leu Ala  Thr Asn Leu Asp Asp  Arg Met Arg
    1925                 1930                 1935

Val Pro  Met Ser Ile Tyr Ala  Pro Ala Gln Ala Gly  Val Ala Gly
    1940                 1945                 1950

Ile Pro  Phe Met Thr Ile Gly  Thr Gly Asp Gly Met  Met Met Gln
```

-continued

```
    1955                1960                1965

Thr Leu  Ser Thr Met Lys Gly  Ala Pro Lys Asn Thr  Leu Lys Ile
    1970                1975                1980

Phe Asp  Gly Met Asn Ile Gly  Leu Asn Asp Ile Thr  Asp Ala Ser
    1985                1990                1995

Arg Lys  Ala Asn Glu Ala Val  Tyr Thr Ser Trp Gln  Gly Asn Pro
    2000                2005                2010

Ile Lys  Asn Val Tyr Glu Ser  Tyr Ala Lys Phe Met  Lys Asn Val
    2015                2020                2025

Asp Phe  Ser Lys Leu Ser Pro  Glu Ala Leu Glu Ala  Ile Gly Lys
    2030                2035                2040

Ser Ala  Leu Glu Tyr Asp Gln  Arg Glu Asn Ala Thr  Val Asp Asp
    2045                2050                2055

Ile Ala  Asn Ala Ala Ser Leu  Ile Glu Arg Asn Leu  Arg Asn Ile
    2060                2065                2070

Ala Leu  Gly Val Asp Ile Arg  His Lys Val Leu Asp  Lys Val Asn
    2075                2080                2085

Leu Ser  Ile Asp Gln Met Ala  Ala Val Gly Ala Pro  Tyr Gln Asn
    2090                2095                2100

Asn Gly  Lys Ile Asp Leu Ser  Asn Met Thr Pro Glu  Gln Gln Ala
    2105                2110                2115

Asp Glu  Leu Asn Lys Leu Phe  Arg Glu Glu Leu Glu  Ala Arg Lys
    2120                2125                2130

Gln Lys  Val Ala Lys Ala Arg  Ala Glu Val Lys Glu  Glu Thr Val
    2135                2140                2145

Ser Glu  Lys Glu Pro Val Asn  Pro Asp Phe Gly Met  Val Gly Arg
    2150                2155                2160

Glu His  Lys Ala Ser Gly Val  Arg Ile Leu Ser Ala  Thr Ala Ile
    2165                2170                2175

Arg Asn  Leu Ala Lys Ile Ser  Asn Leu Pro Ser Thr  Gln Ala Ala
    2180                2185                2190

Thr Leu  Ala Glu Ile Gln Lys  Ser Leu Ala Ala Lys  Asp Tyr Lys
    2195                2200                2205

Ile Ile  Tyr Gly Thr Pro Thr  Gln Val Ala Glu Tyr  Ala Arg Gln
    2210                2215                2220

Lys Asn  Val Thr Glu Leu Thr  Ser Gln Glu Met Glu  Glu Ala Gln
    2225                2230                2235

Ala Gly  Asn Ile Tyr Gly Trp  Thr Asn Phe Asp Asp  Lys Thr Ile
    2240                2245                2250

Tyr Leu  Val Ser Pro Ser Met  Glu Thr Leu Ile His  Glu Leu Val
    2255                2260                2265

His Ala  Ser Thr Phe Glu Glu  Val Tyr Ser Phe Tyr  Gln Gly Asn
    2270                2275                2280

Glu Val  Ser Pro Thr Ser Lys  Gln Ala Ile Glu Asn  Leu Glu Gly
    2285                2290                2295

Leu Met  Glu Gln Phe Arg Ser  Leu Asp Ile Ser Lys  Asp Ser Pro
    2300                2305                2310

Glu Met  Arg Glu Ala Tyr Ala  Asp Ala Ile Ala Thr  Ile Glu Gly
    2315                2320                2325

His Leu  Ser Asn Gly Phe Val  Asp Pro Ala Ile Ser  Lys Ala Ala
    2330                2335                2340

Ala Leu  Asn Glu Phe Met Ala  Trp Gly Leu Ala Asn  Arg Ala Leu
    2345                2350                2355
```

-continued

```
Ala Ala Lys Gln Lys Arg Thr Ser Ser Leu Val Gln Met Val Lys
    2360                2365                2370

Asp Val Tyr Gln Ala Ile Lys Lys Leu Ile Trp Gly Arg Lys Gln
    2375                2380                2385

Ala Pro Ala Leu Gly Glu Asp Met Phe Ser Asn Leu Leu Phe Asn
    2390                2395                2400

Ser Ala Ile Leu Met Arg Ser Gln Pro Thr Thr Gln Ala Val Ala
    2405                2410                2415

Lys Asp Gly Thr Leu Phe His Ser Lys Ala Tyr Gly Asn Asn Glu
    2420                2425                2430

Arg Leu Ser Gln Leu Asn Gln Thr Phe Asp Lys Leu Val Thr Asp
    2435                2440                2445

Tyr Leu Arg Thr Asp Pro Val Thr Glu Val Glu Arg Arg Gly Asn
    2450                2455                2460

Val Ala Asn Ala Leu Met Ser Ala Thr Arg Leu Val Arg Asp Val
    2465                2470                2475

Gln Ser His Gly Phe Asn Met Thr Ala Gln Glu Gln Ser Val Phe
    2480                2485                2490

Gln Met Val Thr Ala Ala Leu Ala Thr Glu Ala Ala Ile Asp Pro
    2495                2500                2505

His Ala Met Ala Arg Ala Gln Glu Leu Tyr Thr His Val Met Lys
    2510                2515                2520

His Leu Thr Val Glu His Phe Met Ala Asp Pro Asp Ser Thr Asn
    2525                2530                2535

Pro Ala Asp Arg Tyr Tyr Ala Gln Gln Lys Tyr Asp Thr Ile Ser
    2540                2545                2550

Gly Ala Asn Leu Val Glu Val Asp Ala Lys Gly Arg Thr Ser Leu
    2555                2560                2565

Leu Pro Thr Phe Leu Gly Leu Ala Met Val Asn Glu Glu Leu Arg
    2570                2575                2580

Ser Ile Ile Lys Glu Met Pro Val Pro Lys Ala Asp Lys Lys Leu
    2585                2590                2595

Gly Asn Asp Ile Asp Thr Leu Leu Thr Asn Ala Gly Thr Gln Val
    2600                2605                2610

Met Glu Ser Leu Asn Arg Arg Met Ala Gly Asp Gln Lys Ala Thr
    2615                2620                2625

Asn Val Gln Asp Ser Ile Asp Ala Leu Ser Glu Thr Ile Met Ala
    2630                2635                2640

Ala Ala Leu Lys Arg Glu Ser Phe Tyr Asp Ala Val Ala Thr Pro
    2645                2650                2655

Thr Gly Asn Phe Ile Asp Arg Ala Asn Gln Tyr Val Thr Asp Ser
    2660                2665                2670

Ile Glu Arg Leu Ser Glu Thr Val Ile Glu Lys Ala Asp Lys Val
    2675                2680                2685

Ile Ala Asn Pro Ser Asn Ile Ala Ala Lys Gly Val Ala His Leu
    2690                2695                2700

Ala Lys Leu Thr Ala Ala Ile Ala Ser Glu Lys Gln Gly Glu Ile
    2705                2710                2715

Val Ala Gln Gly Val Met Thr Ala Met Asn Gln Gly Lys Val Trp
    2720                2725                2730

Gln Pro Phe His Asp Leu Val Asn Asp Ile Val Gly Arg Thr Lys
    2735                2740                2745
```

-continued

```
Thr Asn  Ala Asn Val Tyr Asp  Leu Ile Lys Leu Val  Lys Ser Gln
    2750                 2755                 2760

Ile Ser  Gln Asp Arg Gln Gln  Phe Arg Glu His Leu  Pro Thr Val
    2765                 2770                 2775

Ile Ala  Gly Lys Phe Ser Arg  Lys Leu Thr Asp Thr  Glu Trp Ser
    2780                 2785                 2790

Ala Met  His Thr Gly Leu Gly  Lys Thr Asp Leu Ala  Val Leu Arg
    2795                 2800                 2805

Glu Thr  Met Ser Met Ala Glu  Ile Arg Asp Leu Leu  Ser Ser Ser
    2810                 2815                 2820

Lys Lys  Val Lys Asp Glu Ile  Ser Thr Leu Glu Lys  Glu Ile Gln
    2825                 2830                 2835

Asn Gln  Ala Gly Arg Asn Trp  Asn Leu Val Gln Lys  Lys Ser Lys
    2840                 2845                 2850

Gln Leu  Ala Gln Tyr Met Ile  Met Gly Glu Val Gly  Asn Asn Leu
    2855                 2860                 2865

Leu Arg  Asn Ala His Ala Ile  Ser Arg Leu Leu Gly  Glu Arg Ile
    2870                 2875                 2880

Thr Asn  Gly Pro Val Ala Asp  Val Ala Ala Ile Asp  Lys Leu Ile
    2885                 2890                 2895

Thr Leu  Tyr Ser Leu Glu Leu  Met Asn Lys Ser Asp  Arg Asp Leu
    2900                 2905                 2910

Leu Ser  Glu Leu Ala Gln Ser  Glu Val Glu Gly Met  Glu Phe Ser
    2915                 2920                 2925

Ile Ala  Tyr Met Val Gly Gln  Arg Thr Glu Glu Met  Arg Lys Ala
    2930                 2935                 2940

Lys Gly  Asp Asn Arg Thr Leu  Leu Asn His Phe Lys  Gly Tyr Ile
    2945                 2950                 2955

Pro Val  Glu Asn Gln Gln Gly  Val Asn Leu Ile Ile  Ala Asp Asp
    2960                 2965                 2970

Lys Glu  Phe Ala Lys Leu Asn  Ser Gln Ser Phe Thr  Arg Ile Gly
    2975                 2980                 2985

Thr Tyr  Gln Gly Ser Thr Gly  Phe Arg Thr Gly Ser  Lys Gly Tyr
    2990                 2995                 3000

Tyr Phe  Ser Pro Val Ala Ala  Arg Ala Pro Tyr Ser  Gln Gly Ile
    3005                 3010                 3015

Leu Gln  Asn Val Arg Asn Thr  Ala Gly Gly Val Asp  Ile Gly Thr
    3020                 3025                 3030

Gly Phe  Thr Leu Gly Thr Met  Val Ala Gly Arg Ile  Thr Asp Lys
    3035                 3040                 3045

Pro Thr  Val Glu Arg Ile Thr  Lys Ala Leu Ala Lys  Gly Glu Arg
    3050                 3055                 3060

Gly Arg  Glu Pro Leu Met Pro  Ile Tyr Asn Ser Lys  Gly Gln Val
    3065                 3070                 3075

Val Ala  Tyr Glu Gln Ser Val  Asp Pro Asn Met Leu  Lys His Leu
    3080                 3085                 3090

Asn Gln  Asp Asn His Phe Ala  Lys Met Val Gly Val  Trp Arg Gly
    3095                 3100                 3105

Arg Gln  Val Glu Glu Ala Lys  Ala Gln Arg Phe Asn  Asp Ile Leu
    3110                 3115                 3120

Ile Glu  Gln Leu His Ala Met  Tyr Glu Lys Asp Ile  Lys Asp Ser
    3125                 3130                 3135

Ser Ala  Asn Lys Ser Gln Tyr  Val Asn Leu Leu Gly  Lys Ile Asp
```

-continued

```
    3140                3145                3150

Asp Pro  Val Leu Ala Asp Ala  Ile Asn Leu Met Asn  Ile Glu Thr
    3155                3160                3165

Arg His  Lys Ala Glu Glu Leu  Phe Gly Lys Asp Glu  Leu Trp Val
    3170                3175                3180

Arg Arg  Asp Met Leu Asn Asp  Ala Leu Gly Tyr Arg  Ala Ala Ser
    3185                3190                3195

Ile Gly  Asp Val Trp Thr Gly  Asn Ser Arg Trp Ser  Pro Ser Thr
    3200                3205                3210

Leu Asp  Thr Val Lys Lys Met  Phe Leu Gly Ala Phe  Gly Asn Lys
    3215                3220                3225

Ala Tyr  His Val Val Met Asn  Ala Glu Asn Thr Ile  Gln Asn Leu
    3230                3235                3240

Val Lys  Asp Ala Lys Thr Val  Ile Val Val Lys Ser  Val Val Val
    3245                3250                3255

Pro Ala  Val Asn Phe Leu Ala  Asn Ile Tyr Gln Met  Ile Gly Arg
    3260                3265                3270

Gly Val  Pro Val Lys Asp Ile  Ala Val Asn Ile Pro  Arg Lys Thr
    3275                3280                3285

Ser Glu  Ile Asn Gln Tyr Ile  Lys Ser Arg Leu Arg  Gln Ile Asp
    3290                3295                3300

Ala Glu  Ala Glu Leu Arg Ala  Ala Glu Gly Asn Pro  Asn Leu Val
    3305                3310                3315

Arg Lys  Leu Lys Thr Glu Ile  Gln Ser Ile Thr Asp  Ser His Arg
    3320                3325                3330

Arg Met  Ser Ile Trp Pro Leu  Ile Glu Ala Gly Glu  Phe Ser Ser
    3335                3340                3345

Ile Ala  Asp Ala Gly Ile Ser  Arg Asp Asp Leu Leu  Val Ala Glu
    3350                3355                3360

Gly Lys  Ile His Glu Tyr Met  Glu Lys Leu Ala Asn  Lys Leu Pro
    3365                3370                3375

Glu Lys  Val Arg Asn Ala Gly  Arg Tyr Ala Leu Ile  Ala Lys Asp
    3380                3385                3390

Thr Ala  Leu Phe Gln Gly Ile  Gln Lys Thr Val Glu  Tyr Ser Asp
    3395                3400                3405

Phe Ile  Ala Lys Ala Ile Ile  Tyr Asp Asp Leu Val  Lys Arg Lys
    3410                3415                3420

Lys Lys  Ser Ser Ser Glu Ala  Leu Gly Gln Val Thr  Glu Glu Phe
    3425                3430                3435

Ile Asn  Tyr Asp Arg Leu Pro  Gly Arg Phe Arg Gly  Tyr Met Glu
    3440                3445                3450

Ser Met  Gly Leu Met Trp Phe  Tyr Asn Phe Lys Ile  Arg Ser Ile
    3455                3460                3465

Lys Val  Ala Met Ser Met Ile  Arg Asn Asn Pro Val  His Ser Leu
    3470                3475                3480

Ile Ala  Thr Val Val Pro Ala  Pro Thr Met Phe Gly  Asn Val Gly
    3485                3490                3495

Leu Pro  Ile Gln Asp Asn Met  Leu Thr Met Leu Ala  Glu Gly Arg
    3500                3505                3510

Leu Asp  Tyr Ser Leu Gly Phe  Gly Gln Gly Leu Arg  Ala Pro Thr
    3515                3520                3525

Leu Asn  Pro Trp Phe Asn Leu  Thr His
    3530                3535
```

<210> SEQ ID NO 16
<211> LENGTH: 32
<212> TYPE: DNA
<213> ORGANISM: Artificial Sequence
<220> FEATURE:
<223> OTHER INFORMATION: Synthetic

<400> SEQUENCE: 16
ggcattactt catccaaaag aagcggagct tc 32

<210> SEQ ID NO 17
<211> LENGTH: 37
<212> TYPE: DNA
<213> ORGANISM: Artificial Sequence
<220> FEATURE:
<223> OTHER INFORMATION: Synthetic

<400> SEQUENCE: 17
ggccatccat tacttcatcc aaaagaagcg gagcttc 37

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
ggatccaaaa gaagcggagc ttc 23

<210> SEQ ID NO 19
<211> LENGTH: 32
<212> TYPE: DNA
<213> ORGANISM: Artificial Sequence
<220> FEATURE:
<223> OTHER INFORMATION: Synthetic

<400> SEQUENCE: 19
ggcattactt catccaaaag aagctgagct tc 32

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
ggcattactt catccaaaag aagcggagc 29

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ggaggctcct cggagtctcc tttt 24

<210> SEQ ID NO 22
<211> LENGTH: 25
<212> TYPE: DNA
<213> ORGANISM: Artificial Sequence
<220> FEATURE:

<223> OTHER INFORMATION: Synthetic

<400> SEQUENCE: 22
ggactacctt cgggtagtcc ttttt 25

<210> SEQ ID NO 23
<211> LENGTH: 33
<212> TYPE: DNA
<213> ORGANISM: Artificial Sequence
<220> FEATURE:
<223> OTHER INFORMATION: Synthetic

<400> SEQUENCE: 23
agaagggggc tactaagccc tcttcttatt ttt 33

<210> SEQ ID NO 24
<211> LENGTH: 19
<212> TYPE: DNA
<213> ORGANISM: Artificial Sequence
<220> FEATURE:
<223> OTHER INFORMATION: Synthetic

<400> SEQUENCE: 24
aagctgctcc gcagctttt 19

<210> SEQ ID NO 25
<211> LENGTH: 35
<212> TYPE: DNA
<213> ORGANISM: Artificial Sequence
<220> FEATURE:
<223> OTHER INFORMATION: Synthetic

<400> SEQUENCE: 25
aaggctatcc ctacgggggt agcctttatt ttttt 35

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
gccctccttg tgagggcttt tt 22

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
tccataagtt gcgaagcaac 20

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
tccaaaagaa gcggagcttc tt 22

-continued

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
accaaaagct gcggagcagc 20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
tccaaaagaa gcggagcttc 20

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
atccaaaaga agcggagctt c 21

<210> SEQ ID NO 32
<211> LENGTH: 19
<212> TYPE: DNA
<213> ORGANISM: Artificial Sequence
<220> FEATURE:
<223> OTHER INFORMATION: Synthetic

<400> SEQUENCE: 32
atccaaaaga agcggagct 19

<210> SEQ ID NO 33
<211> LENGTH: 18
<212> TYPE: DNA
<213> ORGANISM: Artificial Sequence
<220> FEATURE:
<223> OTHER INFORMATION: Synthetic

<400> SEQUENCE: 33
atccaaaaga agcggagc 18

<210> SEQ ID NO 34
<211> LENGTH: 17
<212> TYPE: DNA
<213> ORGANISM: Artificial Sequence
<220> FEATURE:
<223> OTHER INFORMATION: Synthetic

<400> SEQUENCE: 34
atccaaaaga agcggag 17

<210> SEQ ID NO 35
<211> LENGTH: 16
<212> TYPE: DNA
<213> ORGANISM: Artificial Sequence
<220> FEATURE:
<223> OTHER INFORMATION: Synthetic

<400> SEQUENCE: 35
atccaaaaga agcgga 16

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
atccaaaaga agcggagctt ctt 23

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atccaaaaga agcggagctt cttt 24

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
atccaaaaga agcggagctt ctttt 25

<210> SEQ ID NO 39
<211> LENGTH: 26
<212> TYPE: DNA
<213> ORGANISM: Artificial Sequence
<220> FEATURE:
<223> OTHER INFORMATION: Synthetic

<400> SEQUENCE: 39
atccaaaaga agcggagctt cttttg 26

<210> SEQ ID NO 40
<211> LENGTH: 14
<212> TYPE: PRT
<213> ORGANISM: Artificial Sequence
<220> FEATURE:
<223> OTHER INFORMATION: Synthetic

<400> SEQUENCE: 40

Arg Gly Ile Ala Lys Asn Pro Leu Thr Ile Thr Ile Tyr Gly
1 5 10

<210> SEQ ID NO 41
<211> LENGTH: 14
<212> TYPE: PRT
<213> ORGANISM: Artificial Sequence
<220> FEATURE:
<223> OTHER INFORMATION: Synthetic

<400> SEQUENCE: 41

Arg Gly Ile Ala Ala Asn Pro Leu Thr Ile Thr Ile Phe Gly
1 5 10

<210> SEQ ID NO 42
<211> LENGTH: 67
<212> TYPE: DNA
<213> ORGANISM: Artificial Sequence
<220> FEATURE:
<223> OTHER INFORMATION: Synthetic

<400> SEQUENCE: 42
gtcctcagtc ccaaaagaag cggagcttct tttttttttt tttttttttt tttccgtctg 60
aagagga 67

<210> SEQ ID NO 43
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n is a or t
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (13)..(13)
<223> OTHER INFORMATION: n is a or g
<220> FEATURE:
<221> NAME/KEY: misc_feature
<222> LOCATION: (17)..(18)
<223> OTHER INFORMATION: n is a, c, g, or t

<400> SEQUENCE: 43
ccanaagnng cgnagcnnc 19

<210> SEQ ID NO 44
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Asp or Thr
<220> FEATURE:
<221> NAME/KEY: misc_feature
<222> LOCATION: (2)..(3)
<223> OTHER INFORMATION: Xaa can be any naturally occurring amino acid

<400> SEQUENCE: 44

Xaa Xaa Xaa Gly Arg
1 5

<210> SEQ ID NO 45
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(11)
<223> OTHER INFORMATION: Xaa can be any naturally occurring amino acid
<220> FEATURE:
<221> NAME/KEY: MISC_FEATURE -continued

```
<222> LOCATION: (12)..(12)
<223> OTHER INFORMATION: Xaa can be any naturally occurring amino acid,
      and may be present or absent

<400> SEQUENCE: 45

Arg Xaa Xaa Xaa Lys Xaa Xaa Xaa Xaa Xaa Xaa Xaa Tyr Gly
1               5                   10


<210> SEQ ID NO 46
<211> LENGTH: 6
<212> TYPE: PRT
<213> ORGANISM: Artificial Sequence
<220> FEATURE:
<223> OTHER INFORMATION: Synthetic

<400> SEQUENCE: 46

His His His His His His
1               5


<210> SEQ ID NO 47
<211> LENGTH: 8
<212> TYPE: PRT
<213> ORGANISM: Artificial Sequence
<220> FEATURE:
<223> OTHER INFORMATION: Synthetic

<400> SEQUENCE: 47

Asp Tyr Lys Asp Asp Asp Asp Lys
1               5


<210> SEQ ID NO 48
<211> LENGTH: 11
<212> TYPE: PRT
<213> ORGANISM: Artificial Sequence
<220> FEATURE:
<223> OTHER INFORMATION: Synthetic

<400> SEQUENCE: 48

His Ala Tyr Pro Tyr Asp Val Pro Asp Tyr Ala
1               5                   10


<210> SEQ ID NO 49
<211> LENGTH: 10
<212> TYPE: PRT
<213> ORGANISM: Artificial Sequence
<220> FEATURE:
<223> OTHER INFORMATION: Synthetic

<400> SEQUENCE: 49

Glu Gln Lys Leu Ile Ser Glu Glu Asp Leu
1               5                   10
```